(12) United States Patent
Tu et al.

(10) Patent No.: US 9,914,703 B2
(45) Date of Patent: Mar. 13, 2018

(54) PYRIDIC KETONE DERIVATIVES, METHOD OF PREPARING SAME, AND PHARMACEUTICAL APPLICATION THEREOF

(71) Applicants: Shanghai Hengrui Pharmaceutical Co., Ltd., Shanghai (CN); Jiangsu Hengrui Medicine Co., Ltd., Lianyungang, Jiangsu (CN)

(72) Inventors: Wangyang Tu, Shanghai (CN); Haitang Zhang, Shanghai (CN); Guoji Xu, Shanghai (CN); Jiangtao Chi, Shanghai (CN)

(73) Assignees: Shanghai Hengrui Pharmaceutical Co., Ltd., Shanghai (CN); Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 15/030,125

(22) PCT Filed: Sep. 5, 2014

(86) PCT No.: PCT/CN2014/085976
§ 371 (c)(1),
(2) Date: Apr. 18, 2016

(87) PCT Pub. No.: WO2015/058589
PCT Pub. Date: Apr. 30, 2015

(65) Prior Publication Data
US 2016/0244410 A1   Aug. 25, 2016

(30) Foreign Application Priority Data

Oct. 25, 2013   (CN) .......................... 2013 1 0512377

(51) Int. Cl.
| | |
|---|---|
| *A61K 31/443* | (2006.01) |
| *C07D 213/82* | (2006.01) |
| *C07D 405/12* | (2006.01) |
| *C07D 471/04* | (2006.01) |
| *A61K 31/4412* | (2006.01) |
| *A61K 31/444* | (2006.01) |
| *A61K 45/06* | (2006.01) |

(52) U.S. Cl.
CPC .......... *C07D 213/82* (2013.01); *A61K 31/443* (2013.01); *A61K 31/444* (2013.01); *A61K 31/4412* (2013.01); *A61K 45/06* (2013.01); *C07D 405/12* (2013.01); *C07D 471/04* (2013.01)

(58) Field of Classification Search
CPC ... A61K 31/443; A61K 31/444; C07D 213/82
USPC ....................................................... 514/335
See application file for complete search history.

(56) References Cited

U.S. PATENT DOCUMENTS

| | | | |
|---|---|---|---|
| 8,492,427 B2 | 7/2013 | Gancia et al. | |
| 2007/0197617 A1 | 8/2007 | Chen et al. | |
| 2010/0063053 A1 | 3/2010 | Marlow et al. | |
| 2012/0238599 A1* | 9/2012 | Lee ..................... | C07D 213/82 |
| | | | 213/82 |

FOREIGN PATENT DOCUMENTS

| | | |
|---|---|---|
| CN | 101006086 A | 7/2007 |
| CN | 101912400 A | 12/2010 |
| CN | 102134218 | 7/2011 |
| CN | 102137843 A | 7/2011 |
| WO | 2005121142 A1 | 12/2005 |
| WO | 2007096259 A1 | 8/2007 |
| WO | 2010003022 A1 | 1/2010 |
| WO | 2010145197 A1 | 12/2010 |
| WO | 2012162293 A1 | 11/2012 |
| WO | 2013136249 A1 | 9/2013 |

OTHER PUBLICATIONS

Grimaldi et al, Current Opinion—Oncology, Mar. 2014, vol. 26(2), pp. 1-8.*
Hartz et al., "Design, Synthesis, and Biological Evaluation of 1, 2, 3, 7-Tetrahydro-6H-purin-6-one and 3,7-Dihydro-1H-purine-2,6-dione Derivatives as Corticotropin-Releasing Factor Receptor Antagonists", J. Med. Chem., vol. 47, pp. 741-4754 (2004).
Duguet et al., "Heterocyclic Lithium Amides as Chiral Ligands for an Enantioselective Hydroxyallcylation with n-BuLi," Journal of Organic Chemistry, vol. 73, pp. 5397-5409 (2008).
Ito et al., "Studies toward the total synthesis of nakiterpiosin: construction of the CDE ring system by a transannular Diels-Alder strategy," Tetrahedron Letters, vol. 48, pp. 5465-5469 (2007).
Lafleur et al., "Structure-Based Optimization of Potent and Selective Inhibitors of the Tyrosine Kinase Erythropoietin Producing Human Hepatocellular Carcinoma Receptor B4 (EphB4)," Journal of Medicinal Chemistry, vol. 52, pp. 5433-6446 (2009).

(Continued)

*Primary Examiner* — Kathrien A Cruz
(74) *Attorney, Agent, or Firm* — Panitch Schwarze Belisario & Nadel LLP

(57) ABSTRACT

Pyridone derivatives, methods of preparing the pyridone derivatives, and methods of using the pyridone derivatives are provided. In particular, pyridone derivatives of formula (I), and pharmaceutical salts thereof are provided. The pyridone derivatives are useful as mitogen-activated protein kinase kinase (MEK) inhibitors, and can be used as therapeutic agents for treating cancer.

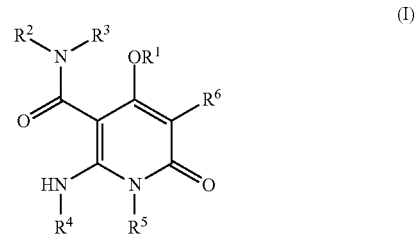

(I)

22 Claims, No Drawings

(56) References Cited

OTHER PUBLICATIONS

International Search Report issued Dec. 16, 2014 in International Application No. PCT/CN2014/085976.

* cited by examiner

PYRIDIC KETONE DERIVATIVES, METHOD OF PREPARING SAME, AND PHARMACEUTICAL APPLICATION THEREOF

CROSS-REFERENCE TO RELATED APPLICATION

This application is a Section 371 of International Application No. PCT/CN2014/085976, filed Sep. 5, 2014, which was published in the Chinese language on Apr. 30, 2015, under International Publication No. WO 2015/058589 A1, and the disclosure of which is incorporated herein by reference.

FIELD OF THE INVENTION

The present invention relates to novel pyridone derivatives, preparation method thereof, pharmaceutical compositions containing the same, and their use as MEK inhibitors, and especially as therapeutic agents for cancer.

BACKGROUND OF THE INVENTION

Statistical data from the Health Ministry of China in 2008 indicated that there were approximately 2.127 million new cases of neoplasm in China every year, of which there were about 1.06 million new cases of malignant neoplasm. Meanwhile, there were about 2.685 million existing patients with neoplasm, of which there were about 1.485 million existing patients with malignant neoplasm. Health Minister CHEN Zhu indicated in the 21$^{st}$ World Cancer Congress that Chinese cancer mortality has increased by 80% in the past 30 years, the annual deaths caused by cancer were 1.8 million, and cancer had become the leading cause of death for Chinese residents. According to the survey "China Health Statistics Yearbook 2012," the mortality rate of malignant neoplasm is increasing. The top five types of malignant neoplasm are lung cancer, liver cancer, stomach cancer, esophageal cancer, and colorectal cancer respectively, wherein the mortality of lung cancer and liver cancer increased the fastest, and these two cancers ranked as having the highest mortality of malignant neoplasm diseases.

In the past half-century, many achievements have been made in the field of tumor therapy. With thorough studies of tumor genetics and biology, multiple intracellular key signaling pathways associated with tumors have been found. Cancer cells transduce the extracellular signal to intracellular transduction and regulate activities, such as continual self-proliferation and apoptosis, via these intracellular pathways, to maintain malignant phenotypes and, on the other hand, to generate resistance against treatments by regulating specific genes and protein products thereof. Abnormity of the MAPK kinase pathway, which leads to uncontrolled cell proliferation and retardant differentiation, is closely related to tumorigenesis. As a result, the MAPK kinase signaling pathway has become a preferred target for cancer drug development.

Serine/threonine mitogen-activated protein kinases (MAPKs, also called extracellular signal-regulated kinases, ERKs) are activated by a tyrosine kinase receptor (e.g. EGF receptor) and/or a cytokine receptor related with the heterotrimer of G protein. MAPKs can interact with intracellular signals triggered by different second messengers, then phosphorylate and regulate the activity of various enzymes and transcription factors (such as NF-κB, Rsk 90, phospholipase A2, c-Myc, CREB, Ets-1, AP-1 and c-jun, etc.). In the MAPK pathways involved in normal and abnormal cell growth, the Ras/Raf/MEK/ERK kinase pathway is one of the most well-researched and most important pathways. Over ten years ago, scientists found that the protein kinase family ERKs is involved in promoting proliferation. The MEK family, the upstream kinase of ERK, was quickly identified in subsequent studies. Then it was found that Raf can activate MEKs. Raf is upstream of Ras, which belongs to the G protein family and binds to activated GTP, which can indirectly activate Raf. Ras gene mutation is found in approximately 30% of malignant neoplasm patients, and Ras gene mutation rate is even up to 90% in pancreatic cancer. B-Raf mutation rate is 50%-70% in melanoma, 35% in ovarian cancer, 30% in thyroid cancer, and 10% in colon cancer. Likewise, MEKs can be activated by MEK kinase (also known as MEKK) which is independent of Raf.

MEKs, also known as MAP kinase kinases (MAPKK or ERK kinase), are bispecific kinases. MEKs can phosphorylate serine/threonine residues and tyrosine residues of MAPK (p44$^{MAPK}$(ERK1) and p42$^{MAPK}$(ERK2)) (phosphorylation sites of ERK1 are T202 and Y204, phosphorylation sites of ERK2 are T183 and Y185). The MEK family includes five genes: MEK1, MEK2, MEK3, MEK4, and MEK5. The N-terminus of MEKs is a negative regulatory region, and the C-terminal catalytic domain has the functions of binding with ERKs and activating ERKs. Tests have found that the knockout of regulatory regions of MEK1 would lead to intrinsic activity inhibition of MEK1 and ERK.

MEK1, with a molecular weight of about 44 kDa and 393 amino acids in total, is mainly expressed in adult tissues, especially in brain tissue. A trace of MEK1 expression can also be detected during embryonic development. The activity of MEK1 is triggered by S218 and S222 phosphorylation. Studies found that in NIH3T3 cells, the activity of MEK1 is increased when the two residues are phosphorylated into aspartic acid or glutamic acid, and colony formation is increased as well. The intrinsic activity of MEK1 promotes cell aging and expression of p53 and p16$^{INK4a}$ in primary cell culture. However, the role of MEK1 is the opposite in immortalized cells and p16$^{INK4a}$ or p53-deficient cells. MEK2, with a molecular weight of about 45 kDa, has 79% sequence similarity with MEK1, and its activity is triggered by S226 and S222 phosphorylation. The phosphorylation catalytic activity of MEK1 and MEK2 are different for disparate MAPK isoforms, ERK1 and ERK2. MEK3, MEK4 and MEK5 do not play a role by acting on ERKs.

Currently there are many compounds for specifically inhibiting Raf and MEK via the MAPK signaling pathway in clinical trials and the marketing stage. Whereas sorafenib (Bay 43-9006), marketed in 2006, is a non-specific serine/threonine and tyrosine kinase inhibitor that targets Raf, MEK, VEGFR2/3, Flt-3, PDGFR, c-Kit etc., B-Raf specific inhibitors, such as dabrafenib (GSK2118436) and vemurafenib (PLX4032), showed good clinical results, but the duration is not long enough. Meanwhile, clinical studies indicated that the symptoms of most patients who received PLX4032 effective treatment recurred, and it was suggested that long-term treatment with B-Raf inhibitors may cause acquired drug resistance and make patients insensitive to B-Raf inhibitors. In order to overcome the resistance of patients, MEK inhibitors are often combined with B-Raf inhibitors in clinical therapeutics. The specific MEK1/2 inhibitor Trametinib (GSK-1120212), developed by Glaxo-SmithKline (GSK), has now entered the pre-registration stage. Other MEK1/2 inhibitors, such as Selumetinib (AZD-6422), Pimasertib hydrochloride (AS-703026), and TAK- 733 etc. have entered the clinical trial stage. However, no interaction data between these MEK inhibitors and ERK1 or ERK2 has been disclosed.

A series of patent applications of disclosing MEK inhibitors have been published, including WO2007096259, WO2010003022 and WO2012162293 etc.

In order to achieve better oncotherapy purposes, and to better meet the market demands, we hope to develop a new generation of MAPKs signaling pathway inhibitors, especially MEK inhibitors, with high efficiency and low toxicity. The present disclosure provides novel structural MEK inhibitors, and it is found that the compounds having such structures have low CYP450 inhibition, good activity, and exhibit excellent anti-proliferation activity of cancer cells.

SUMMARY OF THE INVENTION

The present invention is directed to a compound of formula (I), a tautomer, mesomer, racemate, enantiomer, or diastereomer thereof, or a mixture thereof, or a pharmaceutically acceptable salt thereof:

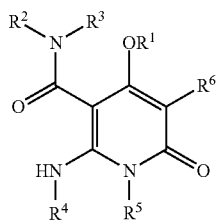

wherein:

$R^1$ is selected from the group consisting of cycloalkyl, heterocyclyl, aryl, and heteroaryl, wherein the cycloalkyl, heterocyclyl, aryl, and heteroaryl are each independently and optionally substituted with one or more groups selected from the group consisting of halogen, cyano, nitro, alkyl, haloalkyl, hydroxyalkyl, alkenyl, alkynyl, cycloalkyl, heterocyclyl, aryl, heteroaryl, —OR$^7$, —C(O)OR$^7$, —OC(O)R$^7$, —O(CH$_2$)$_n$C(O)OR$^7$, —C(O)R$^7$, —C(O)NHR$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$;

$R^2$ and $R^3$ are each independently selected from the group consisting of hydrogen and alkyl, wherein the alkyl is optionally substituted with one or more groups selected from the group consisting of halogen, cyano, nitro, alkenyl, alkynyl, heterocyclyl, aryl, heteroaryl, —OR$^7$, —C(O)OR$^7$, —OC(O)R$^7$, —O(CH$_2$)$_n$C(O)OR$^7$, —C(O)R$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$;

$R^4$ is selected from the group consisting of aryl and heteroaryl, wherein the aryl and heteroaryl are each independently and optionally substituted with one or more groups selected from the group consisting of halogen, cyano, hydroxy, nitro, alkyl, haloalkyl, hydroxyalkyl, alkenyl, alkynyl, heterocyclyl, aryl, heteroaryl, —OR$^7$, —C(O)OR$^7$, —OC(O)R$^7$, —O(CH$_2$)$_n$C(O)OR$^7$, —C(O)R$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$;

$R^5$ is selected from the group consisting of hydrogen, alkyl, alkenyl, and alkynyl, wherein the alkyl, alkenyl, and alkynyl are each independently and optionally substituted with one or more groups selected from the group consisting of halogen, hydroxy, alkoxy, cyano, and haloalkyl;

$R^6$ is selected from the group consisting of hydrogen, halogen, and alkyl, wherein the alkyl is optionally substituted with one or more groups selected from the group consisting of halogen, hydroxy, cyano, nitro, alkoxy, cycloalkyl, heterocyclyl, aryl, and heteroaryl;

$R^7$ is selected from the group consisting of hydrogen, alkyl, cycloalkyl, heterocyclyl, aryl, and heteroaryl, wherein the alkyl, cycloalkyl, heterocyclyl, aryl, and heteroaryl are each independently and optionally substituted with one or more groups selected from the group consisting of alkyl, halogen, hydroxy, alkoxy, cycloalkyl, heterocyclyl, aryl, heteroaryl, carboxyl, and alkoxycarbonyl;

$R^8$ and $R^9$ are each independently selected from the group consisting of hydrogen, alkyl, cycloalkyl, heterocyclyl, aryl, and heteroaryl, wherein the alkyl, cycloalkyl, heterocyclyl, aryl, and heteroaryl are each independently and optionally substituted with one or more groups selected from the group consisting of alkyl, halogen, hydroxy, alkoxy, cycloalkyl, heterocyclyl, aryl, heteroaryl, carboxyl, and alkoxycarbonyl;

alternatively, $R^8$ and $R^9$ together with the nitrogen atom to which they are attached form a heterocyclyl, wherein the heterocyclyl contains one or more hetero atoms selected from the group consisting of N, O, and S(O)$_m$, and the heterocyclyl is optionally further substituted with one or more groups selected from the group consisting of alkyl, halogen, hydroxy, alkoxy, cycloalkyl, heterocyclyl, aryl, heteroaryl, carboxyl, and alkoxycarbonyl;

m is 0, 1, or 2; and n is 0, 1, or 2.

In a preferred embodiment of the invention, in the compound of formula (I) or a tautomer, mesomer, racemate, enantiomer, or diastereomer thereof, or mixture thereof, or a pharmaceutically acceptable salt thereof, wherein $R^1$ is selected from the group consisting of aryl and heteroaryl, wherein the aryl and heteroaryl are each optionally substituted with one or more groups selected from the group consisting of halogen, cyano, nitro, alkyl, haloalkyl, hydroxyalkyl, alkenyl, alkynyl, cycloalkyl, heterocyclyl, aryl, heteroaryl, —OR$^7$, —C(O)OR$^7$, —OC(O)R$^7$, —O(CH$_2$)$_n$C(O)OR$^7$, —C(O)R$^7$, —C(O)NHR$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$, and R$^7$, R$^8$, R$^9$, m, and n are as defined in formula (I).

In another preferred embodiment of the invention, in the compound of formula (I) or a tautomer, mesomer, racemate, enantiomer, or diastereomer thereof, or mixture thereof, or a pharmaceutically acceptable salt thereof, wherein $R^1$ is selected from the group consisting of phenyl and pyridyl, wherein the phenyl and pyridyl are each optionally substituted with one or more groups selected from the group consisting of alkyl, halogen, haloalkyl, —OR$^7$, —C(O)NHR$^7$, —NHC(O)R$^7$, —NHC(O)OR$^7$, and —NHS(O)$_m$R$^7$, and R$^7$ and m are as defined in formula (I).

In another preferred embodiment of the invention, in the compound of formula (I) or a tautomer, mesomer, racemate, enantiomer, or diastereomer thereof, or mixture thereof, or a pharmaceutically acceptable salt thereof, wherein $R^2$ is hydrogen, $R^3$ is selected from the group consisting of hydrogen and alkyl, wherein the alkyl is optionally substituted with one or more groups selected from the group consisting of halogen, cyano, nitro, alkyl, alkenyl, alkynyl, heterocyclyl, aryl, heteroaryl, —OR$^7$, —C(O)OR$^7$, —OC(O)R$^7$, —O(CH$_2$)$_n$C(O)OR$^7$, —C(O)R$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$, and R$^7$, R$^8$, R$^9$, m and n are as defined in formula (I).

In another preferred embodiment of the invention, in the compound of formula (I) or a tautomer, mesomer, racemate, enantiomer, or diastereomer thereof, or mixture thereof, or a pharmaceutically acceptable salt thereof, wherein $R^4$ is aryl, wherein the aryl is optionally substituted with one or more halogens.

In another preferred embodiment of the invention, in the compound of formula (I) or a tautomer, mesomer, racemate, enantiomer, or diastereomer thereof, or mixture thereof, or a pharmaceutically acceptable salt thereof, wherein $R^5$ is alkyl, wherein the alkyl is optionally substituted with one or more groups selected from the group consisting of halogen, hydroxy, alkoxy, cyano, and haloalkyl.

In another preferred embodiment of the invention, in the compound of formula (I) or a tautomer, mesomer, racemate, enantiomer, or diastereomer thereof, or mixture thereof, or a pharmaceutically acceptable salt thereof, wherein $R^6$ is selected from the group consisting of hydrogen and halogen.

In another preferred embodiment of the invention, a compound of formula (I) or a tautomer, mesomer, racemate, enantiomer, or diastereomer thereof, or mixture thereof, or a pharmaceutically acceptable salt thereof, is a compound of formula (II) or a tautomer, mesomer, racemate, enantiomer, or diastereomer thereof, or mixture thereof, or a pharmaceutically acceptable salt thereof:

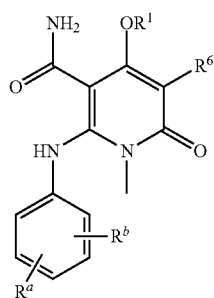

(II)

$R^a$ and $R^b$ are each selected from the group consisting of hydrogen, halogen, alkyl, and haloalkyl;

$R^1$ is selected from the group consisting of phenyl and pyridinyl, wherein the phenyl and pyridyl are each optionally substituted with one or more groups selected from the group consisting of alkyl, halogen, haloalkyl, —$OR^7$, —$C(O)NHR^7$, —$NHC(O)R^7$, —$NHC(O)OR^7$, and —$NHS(O)_mR^7$;

$R^6$ is selected from the group consisting of hydrogen, halogen, and alkyl, wherein the alkyl is optionally substituted with one or more groups selected from the group consisting of halogen, hydroxy, cyano, nitro, alkoxy, cycloalkyl, heterocyclyl, aryl, and heteroaryl; and $R^7$ is selected from the group consisting of hydrogen, alkyl, cycloalkyl, heterocyclyl, aryl, and heteroaryl, wherein the alkyl, cycloalkyl, heterocyclyl, aryl, and heteroaryl are each optionally substituted with one or more groups selected from the group consisting of alkyl, halogen, hydroxy, alkoxy, cycloalkyl, heterocyclyl, aryl, heteroaryl, carboxyl, and alkoxycarbonyl.

In another preferred embodiment of the invention, in the compound of formula (I) or a tautomer, mesomer, racemate, enantiomer, or diastereomer thereof, or mixture thereof, or a pharmaceutically acceptable salt thereof, wherein $R^7$ is selected from the group consisting of hydrogen, alkyl, cycloalkyl, and heterocyclyl, wherein the alkyl is optionally substituted with one or more groups selected from the group consisting of halogen, hydroxy, and alkoxy.

Typical compounds of the present invention include, but are not limited to the following:

| Example No. | Structure and Name |
|---|---|
| 1 | 4-(3-fluoro-2-methylphenoxy)-2-((2-fluoro-4-iodophenyl)amino)-1-methyl-6-oxo-1,6-dihydropyridine-3-carboxamide |
| 2 | N,1-dimethyl-4-(3-(ethylsulfonamido)-2-methylphenoxy)-2-((2-fluoro-4-iodophenyl)amino)-6-oxo-1,6-dihydropyridine-3-carboxamide |
| 3 | 4-(3-(ethylsulfonamido)-2-methylphenoxy)-2-((2-fluoro-4-iodophenyl)amino)-1-methyl-6-oxo-1,6-dihydropyridine-3-carboxamide |

| Example No. | Structure and Name |
|---|---|
| 4 | 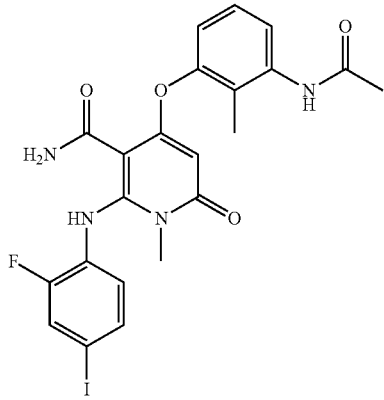 [SMILES: CC(=O)Nc1cccc(Oc2cc(=O)n(C)c(Nc3ccc(I)cc3F)c2C(N)=O)c1C]<br>4-(3-acetamido-2-methylphenoxy)-2-((2-fluoro-4-iodophenyl)amino)-1-methyl-6-oxo-1,6-dihydropyridine-3-carboxamide |
| 5 | 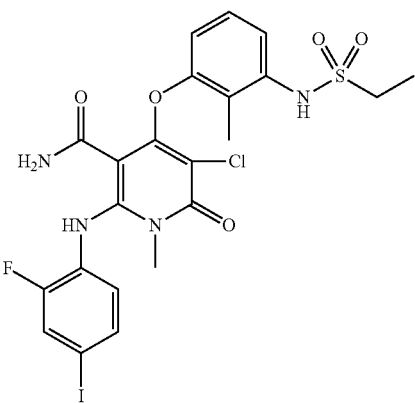 [SMILES: CCS(=O)(=O)Nc1cccc(Oc2c(C(N)=O)c(Nc3ccc(I)cc3F)n(C)c(=O)c2Cl)c1C]<br>4-(3-(ethylsulfonamido)-2-methylphenoxy)-2-((2-fluoro-4-iodophenyl)amino)-1-methyl-5-chloro-6-oxo-1,6-dihydropyridine-3-carboxamide |
| 6 | 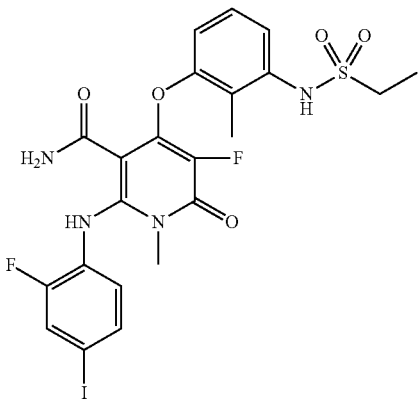 [SMILES: CCS(=O)(=O)Nc1cccc(Oc2c(C(N)=O)c(Nc3ccc(I)cc3F)n(C)c(=O)c2F)c1C]<br>4-(3-(ethylsulfonamido)-2-methylphenoxy)-2-((2-fluoro-4-iodophenyl)amino)-1-methyl-5-fluoro-6-oxo-1,6-dihydropyridine-3-carboxamide |
| 7 | 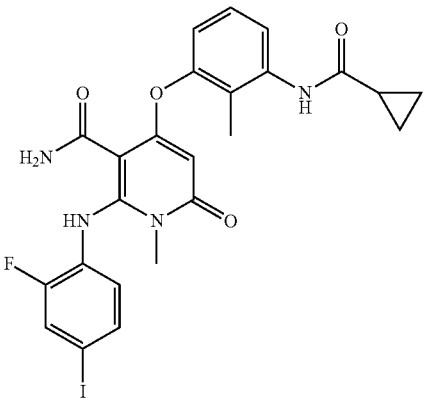 [SMILES: Cc1c(NC(=O)C2CC2)cccc1Oc1cc(=O)n(C)c(Nc2ccc(I)cc2F)c1C(N)=O]<br>4-(3-(cyclopropanecarboxamido)-2-methylphenoxy)-2-((2-fluoro-4-iodophenyl)amino)-1-methyl-6-oxo-1,6-dihydropyridine-3-carboxamide |
| 8 | 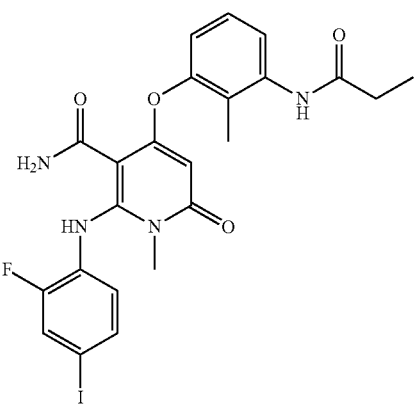 [SMILES: CCC(=O)Nc1cccc(Oc2cc(=O)n(C)c(Nc3ccc(I)cc3F)c2C(N)=O)c1C]<br>4-(3-propionamido-2-methylphenoxy)-2-((2-fluoro-4-iodophenyl)amino)-1-methyl-6-oxo-1,6-dihydropyridine-3-carboxamide |
| 9 | 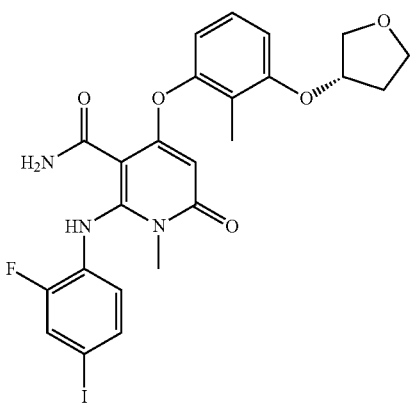 [SMILES: Cc1c(Oc2cc(=O)n(C)c(Nc3ccc(I)cc3F)c2C(N)=O)cccc1O[C@H]1CCOC1]<br>(S)-2-((2-fluoro-4-iodophenyl)amino)-1-methyl-4-(2-methyl-3-((tetrahydrofuran-3-yl)oxy)phenoxy)-6-oxo-1,6-dihydropyridine-3-carboxamide |

| Example No. | Structure and Name |
|---|---|
| 10 | 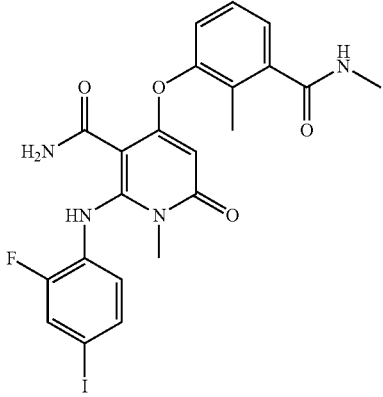 [SMILES: CNC(=O)c1cccc(Oc2cc(=O)n(C)c(Nc3ccc(I)cc3F)c2C(N)=O)c1C]<br>4-(2-methyl-3-(methylcarbamoyl)phenoxy)-2-((2-fluoro-4-iodophenyl)amino)-1-methyl-6-oxo-1,6-dihydropyridine-3-carboxamide |
| 11 | 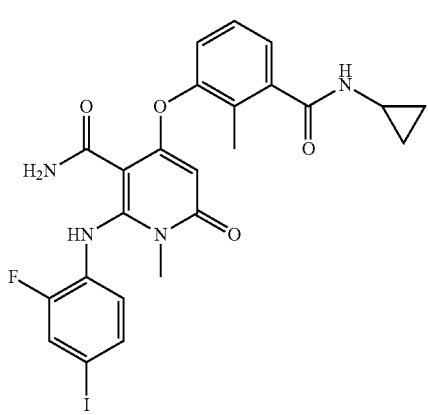 [SMILES: Cc1c(Oc2cc(=O)n(C)c(Nc3ccc(I)cc3F)c2C(N)=O)cccc1C(=O)NC1CC1]<br>4-(3-(cyclopropylcarbamoyl)-2-methylphenoxy)-2-((2-fluoro-4-iodophenyl)amino)-1-methyl-6-oxo-1,6-dihydropyridine-3-carboxamide |
| 12 | 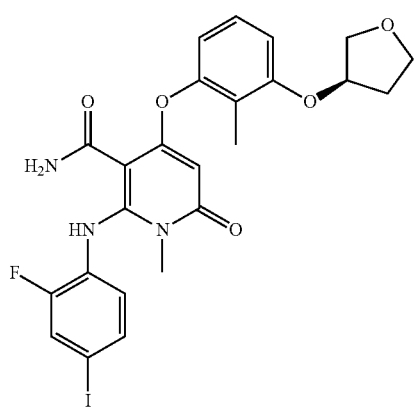 [SMILES: Cc1c(Oc2cc(=O)n(C)c(Nc3ccc(I)cc3F)c2C(N)=O)cccc1O[C@@H]1CCOC1]<br>(R)-2-((2-fluoro-4-iodophenyl)amino)-1-methyl-4-(2-methyl-3-((tetrahydrofuran-3-yl)oxy)phenoxy)-6-oxo-1,6-dihydropyridine-3-carboxamide |
| 13 | 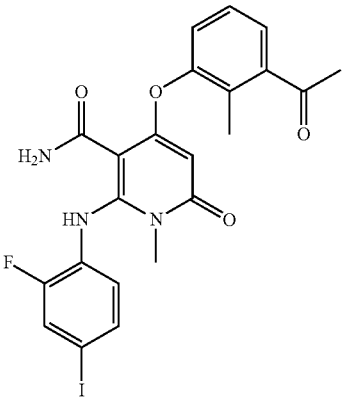 [SMILES: CC(=O)c1cccc(Oc2cc(=O)n(C)c(Nc3ccc(I)cc3F)c2C(N)=O)c1C]<br>4-(3-acetyl-2-methylphenoxy)-2-((2-fluoro-4-iodophenyl)amino)-1-methyl-6-oxo-1,6-dihydropyridine-3-carboxamide |
| 14 | 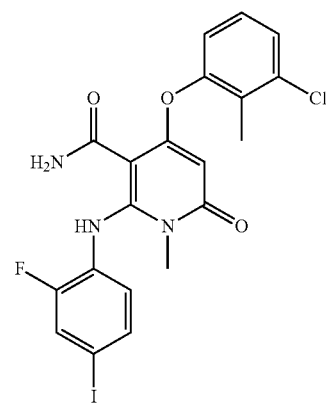 [SMILES: Cc1c(Cl)cccc1Oc1cc(=O)n(C)c(Nc2ccc(I)cc2F)c1C(N)=O]<br>4-(3-chloro-2-methylphenoxy)-2-((2-fluoro-4-iodophenyl)amino)-1-methyl-6-oxo-1,6-dihydropyridine-3-carboxamide |
| 15 | 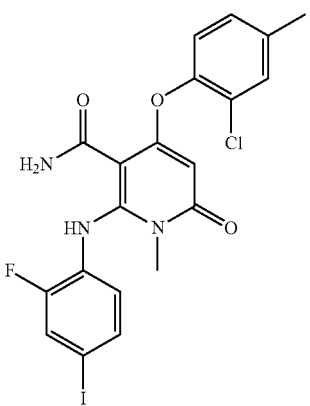 [SMILES: Cc1ccc(Oc2cc(=O)n(C)c(Nc3ccc(I)cc3F)c2C(N)=O)c(Cl)c1]<br>4-(2-chloro-4-methylphenoxy)-2-((2-fluoro-4-iodophenyl)amino)-1-methyl-6-oxo-1,6-dihydropyridine-3-carboxamide |

-continued

| Example No. | Structure and Name |
|---|---|
| 16 | 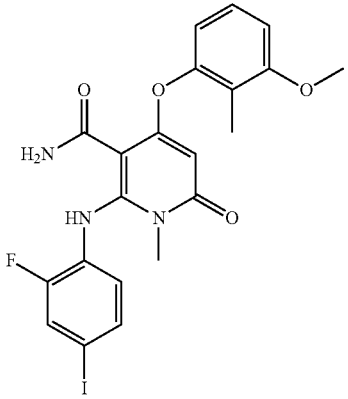 [SMILES: COc1cccc(Oc2cc(=O)n(C)c(Nc3ccc(I)cc3F)c2C(N)=O)c1C]<br>4-(3-methoxy-2-methylphenoxy)-2-((2-fluoro-4-iodophenyl)amino)-1-methyl-6-oxo-1,6-dihydropyridine-3-carboxamide |
| 17 | 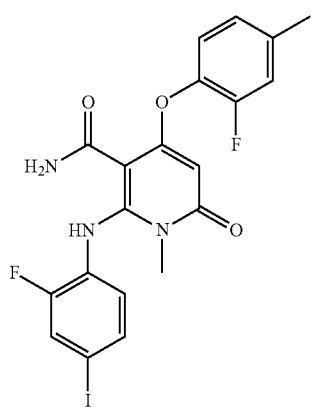<br>4-(2-fluoro-4-methylphenoxy)-2-((2-fluoro-4-iodophenyl)amino)-1-methyl-6-oxo-1,6-dihydropyridine-3-carboxamide |
| 18 | 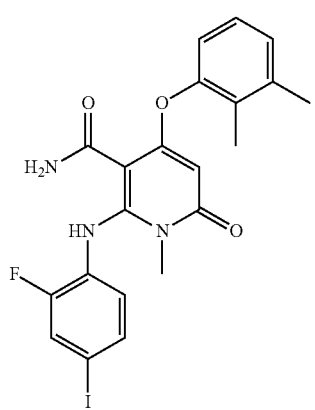 [SMILES: Cc1cccc(Oc2cc(=O)n(C)c(Nc3ccc(I)cc3F)c2C(N)=O)c1C]<br>4-(2,3-dimethylphenoxy)-2-((2-fluoro-4-iodophenyl)amino)-1-methyl-6-oxo-1,6-dihydropyridine-3-carboxamide |

-continued

| Example No. | Structure and Name |
|---|---|
| 19 | 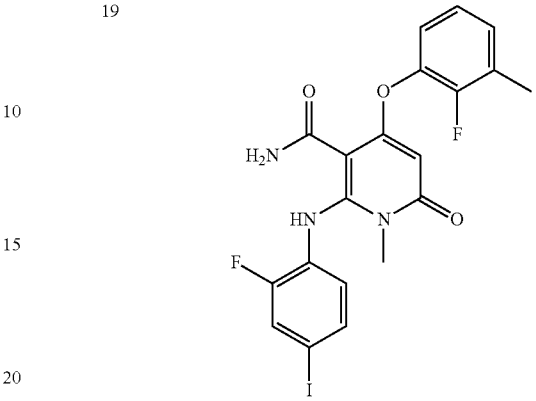<br>4-(2-fluoro-3-methylphenoxy)-2-((2-fluoro-4-iodophenyl)amino)-1-methyl-6-oxo-1,6-dihydropyridine-3-carboxamide |
| 20 | 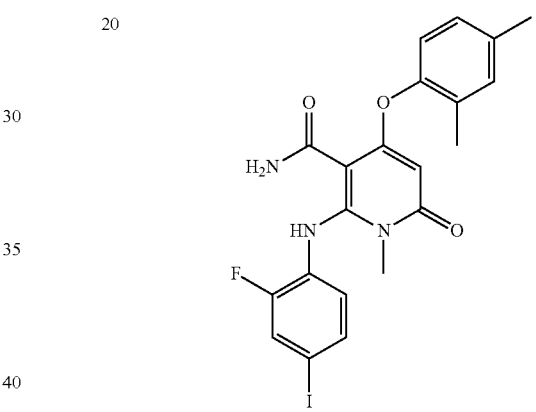<br>4-(2,4-dimethylphenoxy)-2-((2-fluoro-4-iodophenyl)amino)-1-methyl-6-oxo-1,6-dihydropyridine-3-carboxamide |
| 21 | 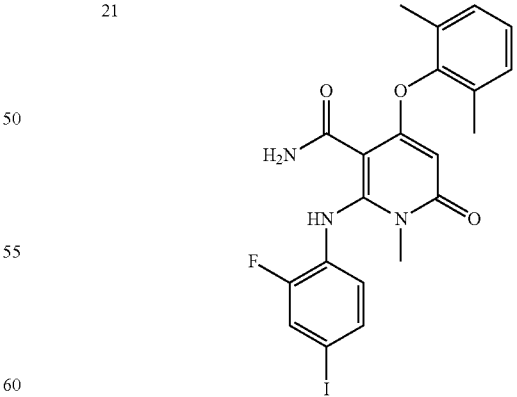<br>4-(2,6-dimethylphenoxy)-2-((2-fluoro-4-iodophenyl)amino)-1-methyl-6-oxo-1,6-dihydropyridine-3-carboxamide |

| Example No. | Structure and Name |
|---|---|
| 22 | 4-(4-fluoro-2-methylphenoxy)-2-((2-fluoro-4-iodophenyl)amino)-1-methyl-6-oxo-1,6-dihydropyridine-3-carboxamide |
| 23 | 4-(2-methylphenoxy)-2-((2-fluoro-4-iodophenyl)amino)-1-methyl-6-oxo-1,6-dihydropyridine-3-carboxamide |
| 24 | 4-(3-hydroxy-2-methylphenoxy)-2-((2-fluoro-4-iodophenyl)amino)-1-methyl-6-oxo-1,6-dihydropyridine-3-carboxamide |
| 25 | 4-(5-fluoro-2-methylphenoxy)-2-((2-fluoro-4-iodophenyl)amino)-1-methyl-6-oxo-1,6-dihydropyridine-3-carboxamide |
| 26 | 5-fluoro-4-(3-fluoro-2-methylphenoxy)-2-((2-fluoro-4-iodophenyl)amino)-1-methyl-6-oxo-1,6-dihydropyridine-3-carboxamide |
| 27 | (R)-N-(2,3-dihydroxypropyl)-4-(3-fluoro-2-methylphenoxy)-2-((2-fluoro-4-iodophenyl)amino)-1-methyl-6-oxo-1,6-dihydropyridine-3-carboxamide |

-continued

| Example No. | Structure and Name |
|---|---|
| 28 | (S)-N-(2,3-dihydroxypropyl)-4-(3-fluoro-2-methylphenoxy)-2-((2-fluoro-4-iodophenyl)amino)-1-methyl-6-oxo-1,6-dihydropyridine-3-carboxamide |
| 29 | (2-((2-fluoro-4-iodophenyl)amino)-1-methyl-4-((2-methylpyridin-3-yl)oxy)-6-oxo-1,6-dihydropyridine-3-carboxamide |
| 30 | 2-((2-fluoro-4-iodophenyl)amino)-1-methyl-4-((5-methylpyridin-3-yl)oxy)-6-oxo-1,6-dihydropyridine-3-carboxamide |

-continued

| Example No. | Structure and Name |
|---|---|
| 31 | 2-((2-fluoro-4-iodophenyl)amino)-1-methyl-4-((6-methylpyridin-3-yl)oxy)-6-oxo-1,6-dihydropyridine-3-carboxamide |
| 32 | 2-((2-fluoro-4-iodophenyl)amino)-1-methyl-4-((2-methylpyridin-4-yl)oxy)-6-oxo-1,6-dihydropyridine-3-carboxamide |
| 33 | 2-((2-fluoro-4-iodophenyl)amino)-1-methyl-4-((4-methylpyridin-3-yl)oxy)-6-oxo-1,6-dihydropyridine-3-carboxamide | or a tautomer, mesomer, racemate, enantiomer, or diastereomer thereof, or mixture thereof, or a pharmaceutically acceptable salt thereof.

In another aspect, the invention is directed to a compound of formula (IA), or a tautomer, mesomer, racemate, enantiomer, or diastereomer thereof, or mixture thereof, or a pharmaceutically acceptable salt thereof, which can be used as an intermediate for preparing a compound of formula (I), or a tautomer, mesomer, racemate, enantiomer, or diastereomer thereof,

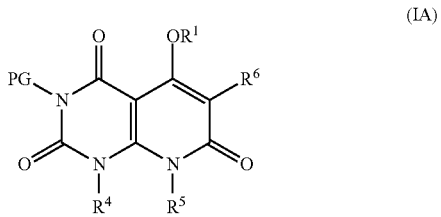

(IA)

wherein:

$R^1$, and $R^4$ to $R^6$ are as defined in formula (I);

PG is selected from the group consisting of alkyl and an amino-protecting group, wherein the amino-protecting group is preferably benzyl; the alkyl and benzyl are each optionally substituted with one or more groups selected from the group consisting of halogen, cyano, nitro, alkyl, cycloalkyl, heterocyclyl, heteroaryl, and —$OR^7$; and $R^7$ is selected from the group consisting of hydrogen, alkyl, cycloalkyl, heterocyclyl, aryl and heteroaryl, wherein the alkyl, cycloalkyl, heterocyclyl, aryl, and heteroaryl are each optionally substituted with one or more groups selected from the group consisting of alkyl, halogen, hydroxy, alkoxy, cycloalkyl, heterocyclyl, aryl, heteroaryl, carboxyl, and alkoxycarbonyl.

Typical compounds of formula (IA) of the present invention include, but are not limited to the following:

| Example No. | Structure and Name |
|---|---|
| 1k | 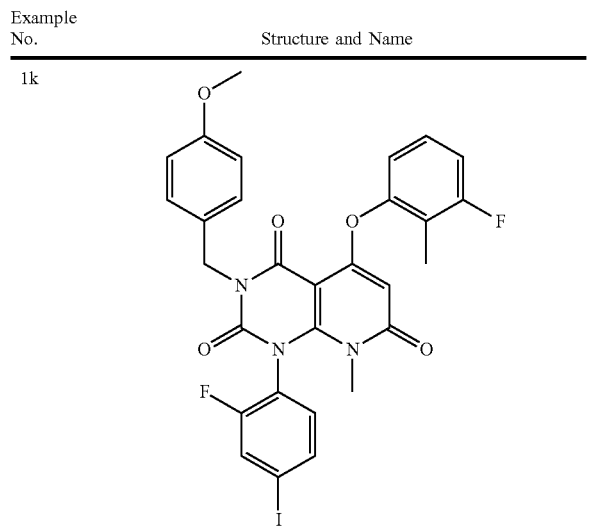<br>5-(3-fluoro-2-methylphenoxy)-1-(2-fluoro-4-iodophenyl)-3-(4-methoxybenzyl)-8-methylpyrido[2,3-d]pyrimidine-2,4,7(1H,3H,8H)-trione |
| 2f | tert-butyl (3-(3,8-dimethyl-1-((2-fluoro-4-iodophenyl)-2,4,7-trioxo-1,2,3,4,7,8-hexahydropyrido[2,3-d]pyrimidin-5-yl)oxy)-2-methylphenyl)carbamate |
| 3a | tert-butyl (3-((1-(2-fluoro-4-iodophenyl)-3-(4-methoxybenzyl)-8-methyl-2,4,7-trioxo-1,2,3,4,7,8-hexahydropyrido[2,3-d]pyrimidin-5-yl)oxy)-2-methylphenyl)carbamate |
| 9c | (S)-1-(2-fluoro-4-iodophenyl)-3-(4-methoxybenzyl)-8-methyl-5-(2-methyl-3-((tetrahydrofuran-3-yl)oxy)phenoxy)pyrido[2,3-d]pyrimidine-2,4,7(1H,3H,8H)-trione |

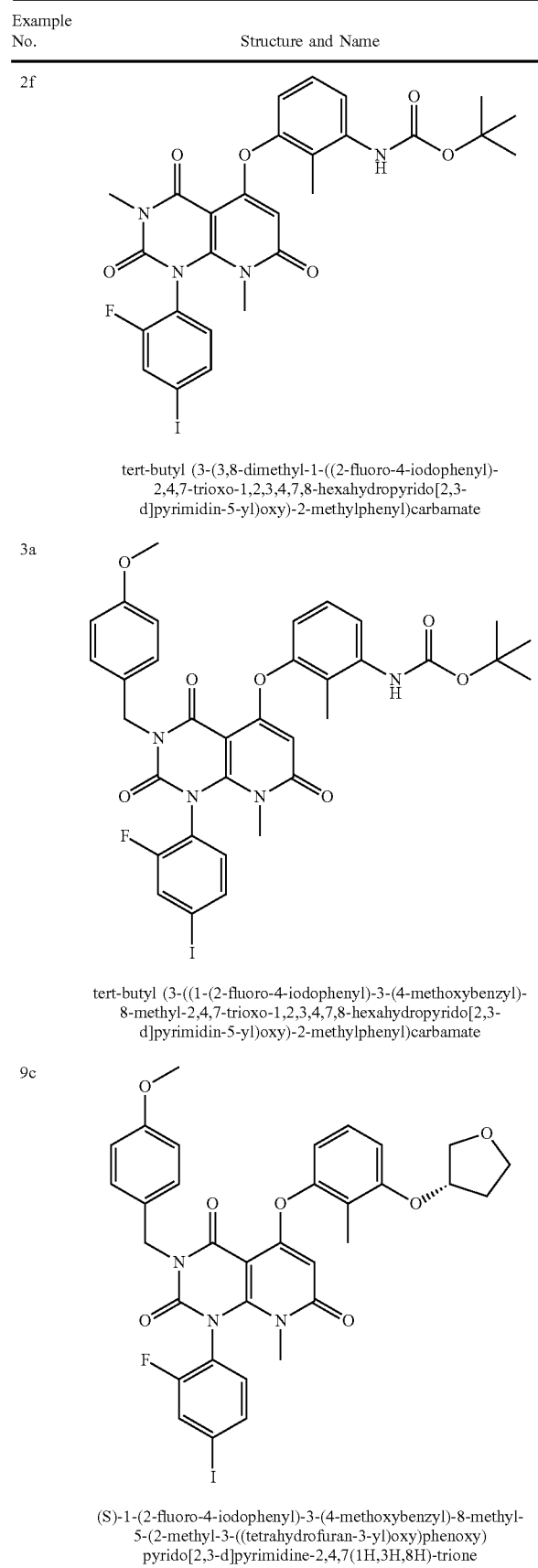

| Example No. | Structure and Name |
|---|---|
| 10a | 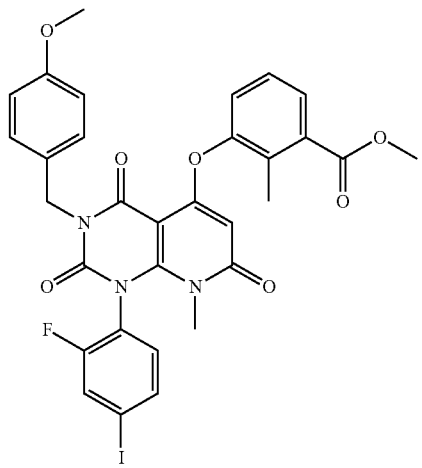 [SMILES: COC(=O)c1cccc(Oc2cc(=O)n(C)c3c2c(=O)n(Cc2ccc(OC)cc2)c(=O)n3-c2ccc(I)cc2F)c1C]<br>methyl 3-((1-(2-fluoro-4-iodophenyl)-3-(4-methoxybenzyl)-8-methyl-2,4,7-trioxo-1,2,3,4,7,8-hexahydropyrido[2,3-d]pyrimidin-5-yl)oxy)-2-methylbenzoate |
| 13c | 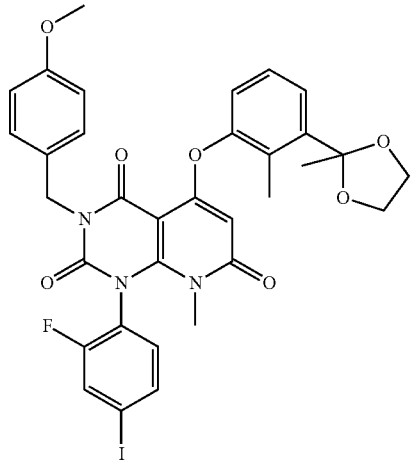<br>1-(2-fluoro-4-iodophenyl)-3-(4-methoxybenzyl)-8-methyl-5-(2-methyl-3-(2-methyl-1,3-dioxolan-2-yl)phenoxy)pyrido[2,3-d]pyrimidine-2,4,7(1H,3H,8H)-trione |
| 12c | 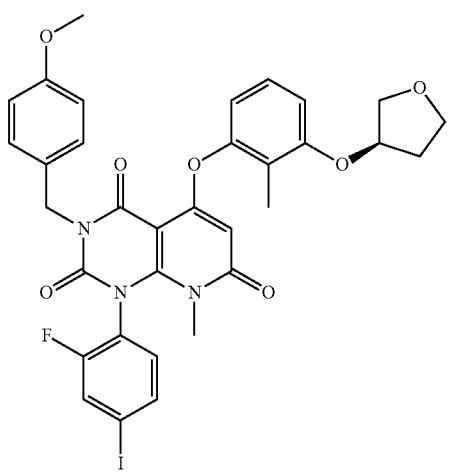 [SMILES: COc1ccc(Cn2c(=O)c3c(Oc4cccc(O[C@@H]5CCOC5)c4C)cc(=O)n(C)c3n(-c3ccc(I)cc3F)c2=O)cc1]<br>(R)-1-(2-fluoro-4-iodophenyl)-3-(4-methoxybenzyl)-8-methyl-5-(2-methyl-3-((tetrahydrofuran-3-yl)oxy)phenoxy)pyrido[2,3-d]pyrimidine-2,4,7(1H,3H,8H)-trione |
| 14a | 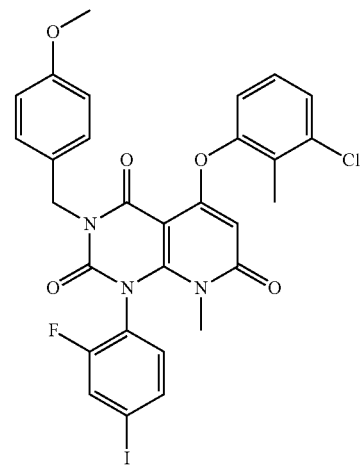 [SMILES: COc1ccc(Cn2c(=O)c3c(Oc4cccc(Cl)c4C)cc(=O)n(C)c3n(-c3ccc(I)cc3F)c2=O)cc1]<br>5-(3-chloro-2-methylphenoxy)-1-(2-fluoro-4-iodophenyl)-3-(4-methoxybenzyl)-8-methylpyrido[2,3-d]pyrimidine-2,4,7(1H,3H,8H)-trione |

| Example No. | Structure and Name |
|---|---|
| 15a | 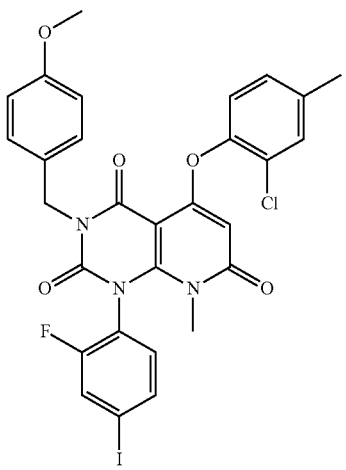 [SMILES: COc1ccc(Cn2c(=O)c3c(Oc4ccc(C)cc4Cl)cc(=O)n(C)c3n(-c3ccc(I)cc3F)c2=O)cc1]<br>5-(2-chloro-4-methylphenoxy)-1-(2-fluoro-4-iodophenyl)-3-(4-methoxybenzyl)-8-methylpyrido[2,3-d]pyrimidine-2,4,7(1H,3H,8H)-trione |
| 16a | 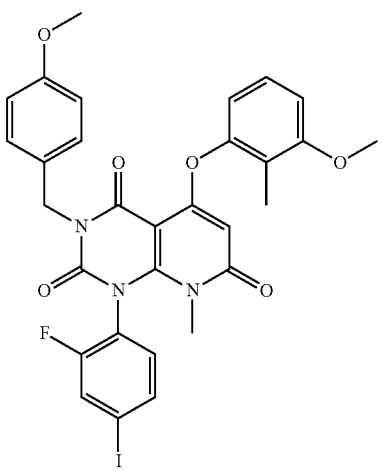 [SMILES: COc1ccc(Cn2c(=O)c3c(Oc4cccc(OC)c4C)cc(=O)n(C)c3n(-c3ccc(I)cc3F)c2=O)cc1]<br>5-(3-methoxy-2-methylphenoxy)-1-(2-fluoro-4-iodophenyl)-3-(4-methoxybenzyl)-8-methylpyrido[2,3-d]pyrimidine-2,4,7(1H,3H,8H)-trione |
| 17a | 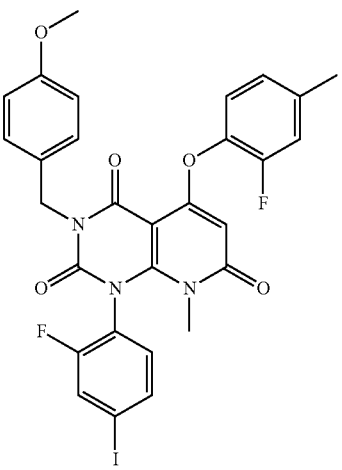 [SMILES: COc1ccc(Cn2c(=O)c3c(Oc4ccc(C)cc4F)cc(=O)n(C)c3n(-c3ccc(I)cc3F)c2=O)cc1]<br>5-(2-fluoro-4-methylphenoxy)-1-(2-fluoro-4-iodophenyl)-3-(4-methoxybenzyl)-8-methylpyrido[2,3-d]pyrimidine-2,4,7(1H,3H,8H)-trione |
| 18a | 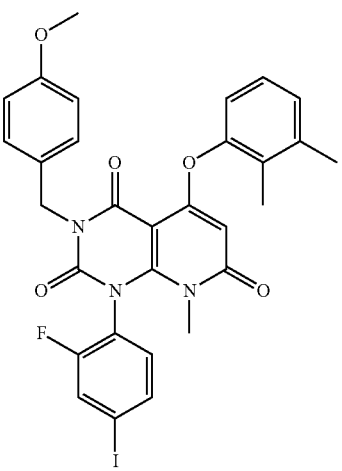 [SMILES: COc1ccc(Cn2c(=O)c3c(Oc4cccc(C)c4C)cc(=O)n(C)c3n(-c3ccc(I)cc3F)c2=O)cc1]<br>5-(2,3-dimethylphenoxy)-1-(2-fluoro-4-iodophenyl)-3-(4-methoxybenzyl)-8-methylpyrido[2,3-d]pyrimidine-2,4,7(1H,3H,8H)-trione |

-continued

| Example No. | Structure and Name |
|---|---|
| 19a | 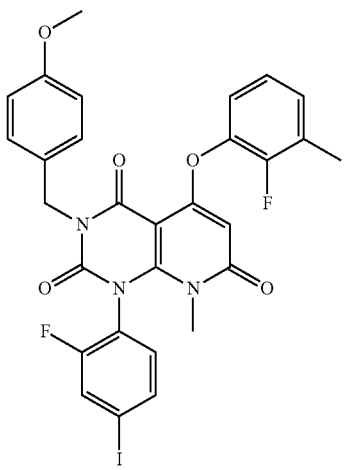<br>5-(2-fluoro-3-methylphenoxy)-1-(2-fluoro-4-iodophenyl)-3-(4-methoxybenzyl)-8-methylpyrido[2,3-d]pyrimidine-2,4,7(1H,3H,8H)-trione |
| 20a | 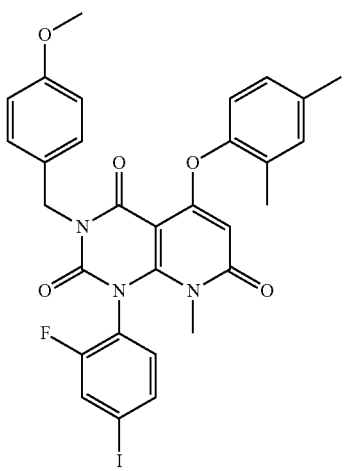 [SMILES: COc1ccc(Cn2c(=O)c3c(Oc4ccc(C)cc4C)cc(=O)n(C)c3n(-c3ccc(I)cc3F)c2=O)cc1]<br>5-(2,4-dimethylphenoxy)-1-(2-fluoro-4-iodophenyl)-3-(4-methoxybenzyl)-8-methylpyrido[2,3-d]pyrimidine-2,4,7(1H,3H,8H)-trione |

-continued

| Example No. | Structure and Name |
|---|---|
| 21a | 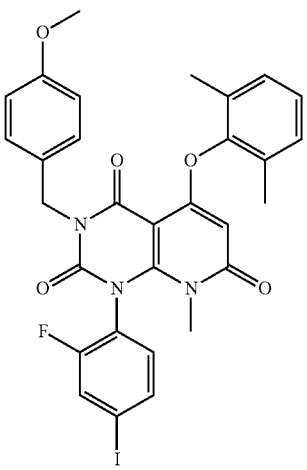 [SMILES: COc1ccc(Cn2c(=O)c3c(Oc4c(C)cccc4C)cc(=O)n(C)c3n(-c3ccc(I)cc3F)c2=O)cc1]<br>5-(2,6-dimethylphenoxy)-1-(2-fluoro-4-iodophenyl)-3-(4-methoxybenzyl)-8-methylpyrido[2,3-d]pyrimidine-2,4,7(1H,3H,8H)-trione |
| 22a | 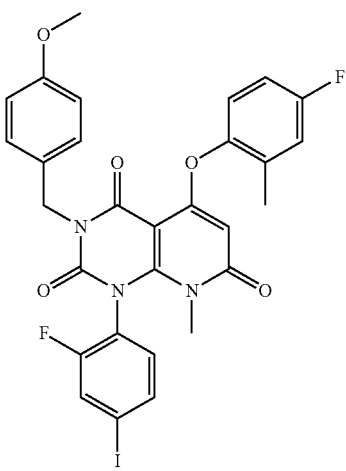 [SMILES: COc1ccc(Cn2c(=O)c3c(Oc4ccc(F)cc4C)cc(=O)n(C)c3n(-c3ccc(I)cc3F)c2=O)cc1]<br>5-(4-fluoro-2-methylphenoxy)-1-(2-fluoro-4-iodophenyl)-3-(4-methoxybenzyl)-8-methylpyrido[2,3-d]pyrimidine-2,4,7(1H,3H,8H)-trione |

| Example No. | Structure and Name |
|---|---|
| 23a | 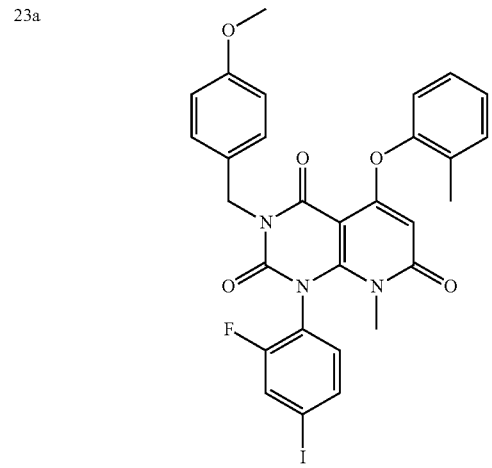<br>5-(2-methylphenoxy)-1-(2-fluoro-4-iodophenyl)-3-(4-methoxybenzyl)-8-methylpyrido[2,3-d]pyrimidine-2,4,7(1H,3H,8H)-trione |
| 24a | 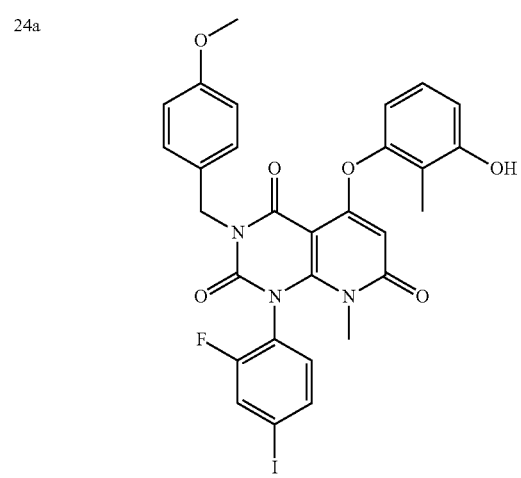<br>5-(3-hydroxy-2-methylphenoxy)-1-(2-fluoro-4-iodophenyl)-3-(4-methoxybenzyl)-8-methylpyrido[2,3-d]pyrimidine-2,4,7(1H,3H,8H)-trione |
| 25a | 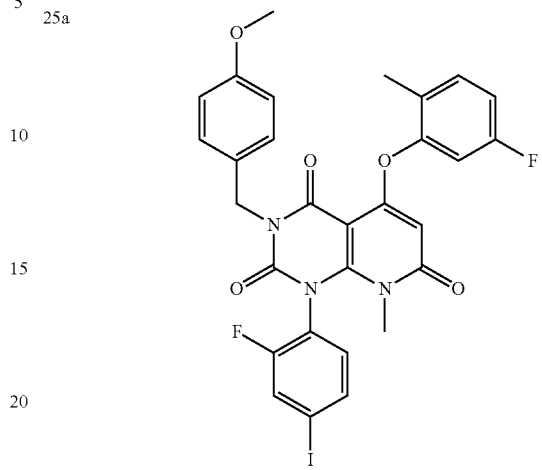<br>5-(5-fluoro-2-methylphenoxy)-1-(2-fluoro-4-iodophenyl)-3-(4-methoxybenzyl)-8-methylpyrido[2,3-d]pyrimidine-2,4,7(1H,3H,8H)-trione |
| 27e | 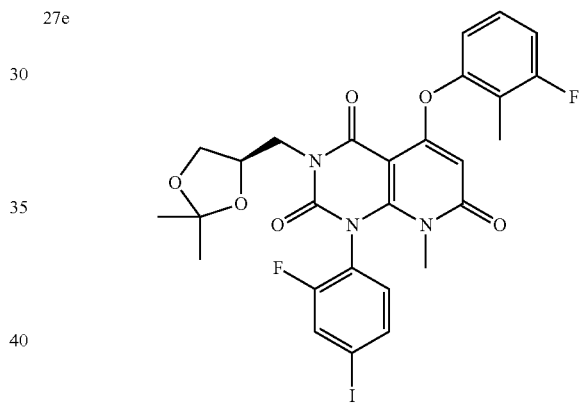<br>(R)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7(1H,3H,8H)-trione |
| 28e | 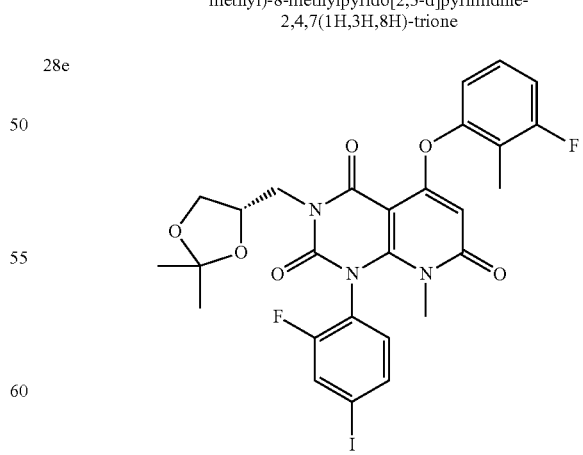<br>(S)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7(1H,3H,8H)-trione |

| Example No. | Structure and Name |
|---|---|
| 29a | 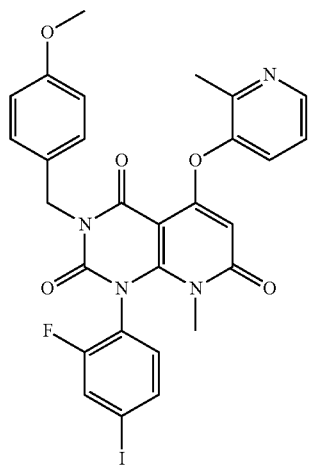 [SMILES: COc1ccc(Cn2c(=O)c3c(Oc4cccnc4C)cc(=O)n(C)c3n(-c3ccc(I)cc3F)c2=O)cc1]<br>5-((2-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione |
| 30a | 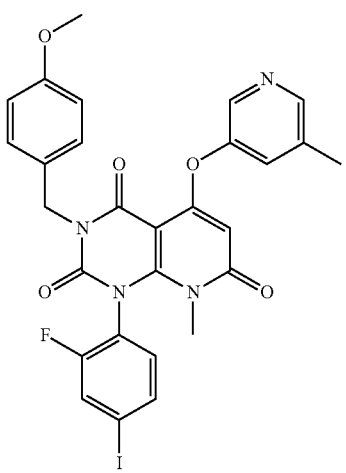 [SMILES: COc1ccc(Cn2c(=O)c3c(Oc4cncc(C)c4)cc(=O)n(C)c3n(-c3ccc(I)cc3F)c2=O)cc1]<br>5-((5-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione |
| 31a | 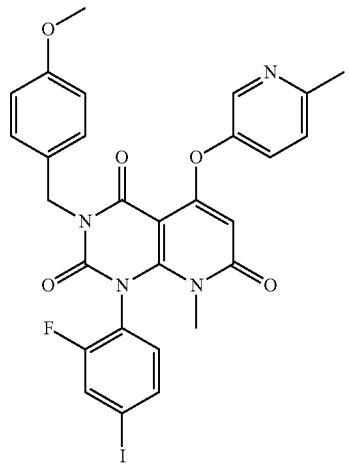 [SMILES: COc1ccc(Cn2c(=O)c3c(Oc4ccc(C)nc4)cc(=O)n(C)c3n(-c3ccc(I)cc3F)c2=O)cc1]<br>5-((6-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione |
| 32a | 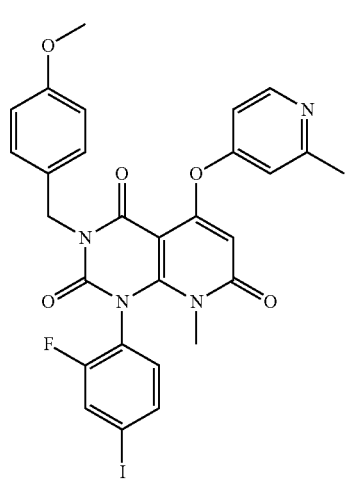 [SMILES: COc1ccc(Cn2c(=O)c3c(Oc4ccnc(C)c4)cc(=O)n(C)c3n(-c3ccc(I)cc3F)c2=O)cc1]<br>5-((2-methylpyridin-4-yl)oxy)-1-(2-fluoro-4-iodophenyl)-3-(4-methoxybenzyl)-8-methylpyrido[2,3-d]pyrimidine-2,4,7(1H,3H,8H)-trione |

| Example No. | Structure and Name |
|---|---|
| 33a | 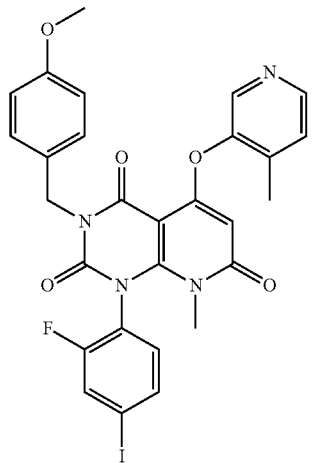 [SMILES: COc1ccc(Cn2c(=O)c3c(Oc4cnccc4C)cc(=O)n(C)c3n(-c3ccc(I)cc3F)c2=O)cc1]<br>5-((4-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione | or a tautomer, mesomer, racemate, enantiomer, or diastereomer thereof, or mixture thereof, or a pharmaceutically acceptable salt thereof.

In another aspect, the invention provides a process of preparing a compound of formula (IA), or a tautomer, mesomer, racemate, enantiomer, or diastereomer thereof, or mixture thereof, or a pharmaceutically acceptable salt thereof, comprising a step of:

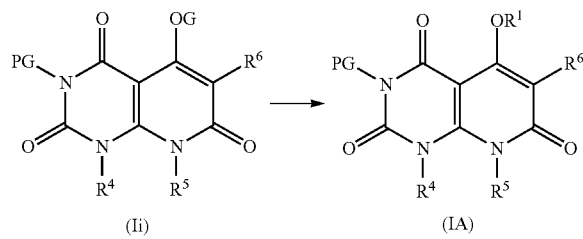

reacting a compound of formula (Ii) with a nucleophile $R^1H$ to obtain a compound of formula (IA);
wherein: $R^1$, and $R^4$ to $R^6$ are as defined in formula (I);
—OG is a leaving group, preferably sulfonyloxy;
PG is selected from the group consisting of alkyl and an amino-protecting group, wherein the amino-protecting group is preferably benzyl; the alkyl and benzyl are each optionally substituted with one or more groups selected from the group consisting of halogen, cyano, nitro, alkyl, cycloalkyl, heterocyclyl, aryl, heteroaryl, and —OR$^7$; and
$R^7$ is selected from the group consisting of hydrogen, alkyl, cycloalkyl, heterocyclyl, aryl, and heteroaryl, wherein the alkyl, cycloalkyl, heterocyclyl, aryl, and heteroaryl are each optionally substituted with one or more groups selected from the group consisting of alkyl, halogen, hydroxy, alkoxy, cycloalkyl, heterocyclyl, aryl, heteroaryl, carboxyl, and alkoxycarbonyl.

In the aforesaid technical solution, the alkaline condition is provided by a reagent including an organic alkali and an inorganic alkali, wherein the organic alkali includes, but is not limited to, triethylamine, pyridine, 2,6-lutidine, sodium methoxide, lithium hexamethyldisilazide, sodium hexamethyldisilazide, n-butyllithium, potassium tert-butoxide, and tetrabutyl ammonium bromide; and the inorganic alkali includes, but is not limited to, sodium hydride, sodium carbonate, sodium bicarbonate, potassium carbonate, potassium bicarbonate, cesium carbonate, lithium hydroxide, sodium hydroxide, and potassium hydroxide; the alkaline reagent is preferably the inorganic alkali, more preferably sodium hydride or cesium carbonate.

In another aspect, the invention provides a process of preparing a compound of formula (I), or a tautomer, mesomer, racemate, enantiomer, or diastereomer thereof, or mixture thereof, or a pharmaceutically acceptable salt thereof, comprising a step of:

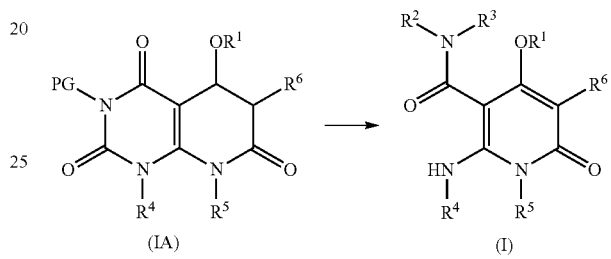

opening a ring of a compound of formula (IA) under an alkaline condition, and optionally removing the amino-protecting group PG to obtain a compound of formula (I);
wherein:
$R^1$ to $R^6$ are as defined in formula (I);
PG is selected from the group consisting of alkyl and an amino-protecting group, wherein the amino-protecting group is preferably benzyl; the alkyl and benzyl are each optionally substituted with one or more groups selected from the group consisting of halogen, cyano, nitro, alkyl, cycloalkyl, heterocyclyl, aryl, heteroaryl, and —OR$^7$; and
$R^7$ is selected from the group consisting of hydrogen, alkyl, cycloalkyl, heterocyclyl, aryl, and heteroaryl, wherein the alkyl, cycloalkyl, heterocyclyl, aryl, and heteroaryl are each optionally substituted with one or more groups selected from the group consisting of alkyl, halogen, hydroxy, alkoxy, cycloalkyl, heterocyclyl, aryl, heteroaryl, carboxyl, and alkoxycarbonyl.

In the aforesaid technical solution, the alkaline condition is provided by a reagent including an organic alkali and an inorganic alkali, wherein the organic alkali includes, but is not limited to, triethylamine, pyridine, 2,6-lutidine, sodium methoxide, lithium hexamethyldisilazide, sodium hexamethyldisilazide, n-butyllithium, potassium tert-butoxide, and tetrabutyl ammonium bromide; and the inorganic alkali includes, but is not limited to, sodium hydride, sodium carbonate, sodium bicarbonate, potassium carbonate, potassium bicarbonate, cesium carbonate, lithium hydroxide, sodium hydroxide, and potassium hydroxide; the alkaline reagent in the ring-opening reaction of the method of the present invention is preferably the inorganic alkali, and more preferably lithium hydroxide, sodium hydroxide, or sodium methoxide.

The present invention also relates to a pharmaceutical composition comprising a therapeutically effective amount of a compound of formula (I), or a tautomer, mesomer, racemate, enantiomer, or diastereomer thereof, or mixture thereof, or a pharmaceutically acceptable salt thereof, and a pharmaceutically acceptable carrier, diluent, or excipient.

The present invention also relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament for inhibiting MEK.

The present invention also relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament for the treatment of an inflammatory disorder, autoimmune disease, cardiovascular disorder, proliferative disease, or nociceptive disorder, wherein the proliferative disease can be cancer (as defined below).

The present invention also relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament for the treatment of cancer, wherein the cancer is selected from the group consisting of melanoma, brain tumor (glioma including astrocytoma and oligodendroglioma, etc.), esophageal cancer, stomach cancer, liver cancer, pancreatic cancer, colorectal cancer (colon cancer, rectal cancer, etc.), lung cancer (non-small cell lung cancer, small cell lung cancer, primary or metastatic squamous cancer, etc.), kidney cancer, breast cancer, ovarian cancer, prostate cancer, skin cancer, neuroblastoma, sarcoma, osteochondroma, osteoma, osteosarcoma, seminoma, testicular cancer, uterine cancer (cervical cancer, endometrial cancer, etc.), head and neck cancer (maxillary bone cancer, laryngeal cancer, nasopharyngeal cancer, tongue cancer, mouth cancer, etc.), multiple myeloma, malignant lymphoma (reticulum cell sarcoma, lymphosarcoma, Hodgkin's lymphoma, etc.), polycythemia vera, leukemia (acute myeloid leukemia, chronic myeloid leukemia, acute lymphoblastic cell leukemia, chronic lymphocytic leukemia, etc.), thyroid cancer, ureter cancer, bladder cancer, gallbladder cancer, cholangiocarcinoma, choriocarcinoma, and pediatric tumor (Ewings sarcoma, Wilms sarcoma, rhabdomyosarcoma, angiosarcoma, fetal testicular cancer, neuroblastoma, retinoblastoma, hepatoblastoma, nephroblastoma, etc.).

The present invention also relates to use of a compound of formula (I), or a tautomer, mesomer, racemate, enantiomer, or diastereomer thereof, or mixture thereof, or a pharmaceutically acceptable salt thereof, or a pharmaceutical composition comprising the same, in the preparation of a medicament for the treatment of cancer, wherein the cancer is preferably colorectal cancer or lung cancer.

The present invention also relates to a method for inhibiting the activity of MEK, comprising a step of administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition containing the same.

Further, the present invention relates to a method for the treatment of an inflammatory disorder, autoimmune disease, cardiovascular disorder, proliferative disease, or nociceptive disorder, comprising a step of administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition containing the same, wherein the proliferative disorder can be cancer (as defined below).

The present invention further relates to a method for treating cancer, comprising a step of administering to a subject in need thereof a therapeutically effective amount of a compound of formula (I), or a tautomer, mesomer, racemate, enantiomer, or diastereomer thereof, or mixture thereof, or a pharmaceutically acceptable salt thereof, or a pharmaceutical composition containing the same, wherein the cancer is selected from the group consisting of melanoma, brain tumor (glioma including astrocytoma and oligodendroglioma, etc.), esophageal cancer, stomach cancer, liver cancer, pancreatic cancer, colorectal cancer (colon cancer, rectal cancer, etc.), lung cancer (non-small cell lung cancer, small cell lung cancer, primary or metastatic squamous cancer etc.), kidney cancer, breast cancer, ovarian cancer, prostate cancer, skin cancer, neuroblastoma, sarcoma, osteochondroma, osteoma, osteosarcoma, seminoma, testicular cancer, uterine cancer (cervical cancer, endometrial cancer, etc.), head and neck cancer (maxillary bone cancer, laryngeal cancer, nasopharyngeal cancer, tongue cancer, mouth cancer, etc.), multiple myeloma, malignant lymphoma (reticulum cell sarcoma, lymphosarcoma, Hodgkin's lymphoma, etc.), polycythemia vera, leukemia (acute myeloid leukemia, chronic myeloid leukemia, acute lymphoblastic leukemia, chronic lymphocytic leukemia, etc.), thyroid cancer, ureter cancer, bladder cancer, gallbladder cancer, cholangiocarcinoma, choriocarcinoma, and pediatric tumor (Ewings sarcoma, Wilms sarcoma, rhabdomyosarcoma, angiosarcoma, fetal testicular cancer, neuroblastoma, retinoblastoma, hepatoblastoma, nephroblastoma, etc.).

The present invention also relates to a compound of formula (I), or a tautomer, mesomer, racemate, enantiomer, diastereomer, or mixture thereof, or a pharmaceutically acceptable salt thereof, or a pharmaceutical composition comprising the same, for use as a medicament for inhibiting the activity of MEK.

The present invention also relates to a compound of formula (I), or a tautomer, mesomer, racemate, enantiomer, or diastereomer thereof, or mixture thereof, or a pharmaceutically acceptable salt thereof, or a pharmaceutical composition comprising the same, for use as a medicament for the treatment of an inflammatory disorder, autoimmune disease, cardiovascular disorder, proliferative disease or nociceptive disorder, wherein the proliferative disease can be cancer.

The present invention also relates to a compound of formula (I), or a tautomer, mesomer, racemate, enantiomer, or diastereomer thereof, or mixture thereof, or a pharmaceutically acceptable salt thereof, or a pharmaceutical composition comprising the same, for use as a medicament for the treatment of cancer, wherein the cancer is selected from the group consisting of melanoma, brain tumor (glioma including astrocytoma and oligodendroglioma, etc.), esophageal cancer, stomach cancer, liver cancer, pancreatic cancer, rectal cancer (colon cancer, colorectal cancer, etc.), lung cancer (non-small cell lung cancer, small cell lung cancer, primary or metastatic squamous cancer, etc.), kidney cancer, breast cancer, ovarian cancer, prostate cancer, skin cancer, neuroblastoma, sarcoma, osteochondroma, osteoma, osteosarcoma, seminoma, testicular cancer, uterine cancer (cervical cancer, endometrial cancer, etc.), head and neck cancer (maxillary bone cancer, laryngeal cancer, nasopharyngeal cancer, tongue cancer, mouth cancer, etc.), multiple myeloma, malignant lymphoma (reticulum cell sarcoma, lymphosarcoma, Hodgkin's lymphoma, etc.) polycythemia vera, leukemia (acute myeloid leukemia, chronic myeloid leukemia, acute lymphoblastic leukemia, chronic lymphocytic leukemia, etc.), thyroid cancer, ureter cancer, bladder cancer, gallbladder cancer, cholangiocarcinoma, choriocarcinoma, and pediatric tumors (Ewings sarcoma, Wilms sarcoma, rhabdomyosarcoma, angiosarcoma, fetal testicular cancer, neuroblastoma, retinoblastoma, hepatoblastoma, nephroblastoma, etc.).

The pharmaceutical composition comprising the active ingredient can be in a form suitable for oral administration, for example, tablets, troches, lozenges, aqueous or oily suspensions, dispersible powders or granules, emulsions, hard or soft capsules, or syrups or elixirs. Compositions intended for oral use are optionally prepared according to known methods, and such compositions can contain one or more agents selected from the group consisting of sweetening agents, flavoring agents, coloring agents, and preserving agents in order to provide pharmaceutically elegant and palatable preparations. Tablets contain the active ingredient in admixture with non-toxic pharmaceutically acceptable excipients which are suitable for the manufacture of tablets. These excipients can be inert excipients, such as calcium carbonate, sodium carbonate, lactose, calcium phosphate, or sodium phosphate; granulating and disintegrating agents, such as microcrystalline cellulose, sodium crosscarmellose, corn starch, or alginic acid; binding agents, such as starch, gelatin, polyvinylpyrrolidone, or acacia; and lubricating agents, such as magnesium stearate, stearic acid, or talc. The tablets can be uncoated or coated by known techniques to mask the taste of the drug or delay disintegration and absorption in the gastrointestinal tract, thereby providing sustained release over a long period. For example, a water soluble taste masking material such as hydroxypropyl methylcellulose or hydroxypropylcellulose, or a material for extending time such as ethyl cellulose or cellulose acetate butyrate can be used.

Oral formulations can also be presented as hard gelatin capsules in which the active ingredient is mixed with an inert solid diluent, such as calcium carbonate, calcium phosphate, or kaolin, or as soft gelatin capsules in which the active ingredient is mixed with a water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, such as sodium carboxymethylcellulose, methylcellulose, hydroxypropylmethylcellulose, sodium alginate, polyvinylpyrrolidone, and gum acacia; dispersing or wetting agents which can be a naturally occurring phosphatide, such as lecithin, or condensation products of an alkylene oxide with fatty acids, such as polyoxyethylene stearate, or condensation products of ethylene oxide with long chain aliphatic alcohols, such as heptadecaethyleneoxy cetanol, or condensation products of ethylene oxide with partial esters derived from fatty acids and hexitols, such as polyoxyethylene sorbitan monooleate, or condensation products of ethylene oxide with partial esters derived from fatty acids and hexitol anhydrides, such as polyethylene sorbitan monooleate. The aqueous suspensions can also contain one or more preservatives, such as ethylparaben or n-propylparaben, one or more coloring agents, one or more flavoring agents, and one or more sweeting agents, such as sucrose, saccharin or aspartame.

Oil suspensions can be formulated by suspending the active ingredient in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. The aforesaid sweetening agents and flavoring agents can be added to provide a palatable preparation. These compositions can be preserved by the addition of an antioxidant such as butylated hydroxyanisole or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring, and coloring agents, can also be included. These compositions can be preserved by the addition of an antioxidant, such as ascorbic acid.

The pharmaceutical compositions can also be in the form of oil-in-water emulsions. The oil phase can be a vegetable oil, such as olive oil or arachis oil, or a mineral oil, such as liquid paraffin or mixtures thereof. Suitable emulsifying agents can be naturally occurring phosphatides, such as soy bean lecithin, and esters or partial esters derived from fatty acids and hexitol anhydrides, such as sorbitan monooleate, and condensation products of the partial esters with ethylene oxide, such as polyoxyethylene sorbitan monooleate. The emulsions can also contain sweetening agents, flavoring agents, preservatives, and antioxidants. Syrups and elixirs can be formulated with sweetening agents, such as glycerol, propylene glycol, sorbitol, or sucrose. Such formulations can also contain a demulcent, a preservative, a coloring agent, and an antioxidant.

The pharmaceutical compositions can be in the form of sterile injectable aqueous solutions. Among the acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. For example, the active ingredient can be firstly dissolved in a mixture of soybean oil and lecithin, then the oil solution is introduced into a mixture of water and glycerol and processed to form a microemulsion. The injectable solutions or microemulsions can be introduced into an individual's bloodstream by local bolus injection. Alternatively, it can be advantageous to administer the solution or microemulsion in such a way as to maintain a constant circulating concentration of the compound of the invention. In order to maintain such a constant concentration, a continuous intravenous delivery device can be utilized. An example of such a device is the Deltec CADD-PLUS™ model 5400 intravenous pump.

The pharmaceutical compositions can be in the form of sterile injectable aqueous or oily suspensions for intramuscular and subcutaneous administration. The suspensions can be formulated according to the known art by using the aforesaid suitable dispersing or wetting agents and suspending agents. The sterile injectable preparation can also be a sterile injectable solution or suspension in a nontoxic parenterally acceptable diluent or solvent, for example, a solution in 1,3-butanediol. In addition, a sterile, or a fixed oil can be conventionally employed as a solvent or a suspending medium. For this purpose, any blend fixed oil for synthesizing mono- or diglycerides can be employed. In addition, fatty acids, such as oleic acid, can be used in the preparation of injections.

The compounds of the invention can also be administered in the form of suppositories for rectal administration. The compositions can be prepared by mixing the active ingredient with a suitable non-irritating excipient which is solid at ordinary temperatures but liquid at the rectal temperature, and will therefore melt in the rectum to release the drug. Such materials include cocoa butter, glycerinated gelatin, hydrogenated vegetable oils, mixtures of polyethylene glycols of various molecular weights, and fatty acid esters of polyethylene glycol.

It is known to those skilled in the art that the dosage of a drug depends on a variety of factors including, but not limited to, the following factors: activity of a particular compound, age of the patient, weight of the patient, general health of the patient, behavior of the patient, diet of the patient, time of administration, route of administration, rate of excretion, drug combination etc. In addition, the best treatment, such as treatment model, daily dose of a compound of formula (I), or the type of pharmaceutically acceptable salt thereof, can be verified by traditional treatment programs.

DETAILED DESCRIPTION OF THE INVENTION

Unless otherwise stated, the terms used in the specification and claims have the meanings described below.

"Alkyl" refers to a saturated aliphatic hydrocarbon group including $C_1$-$C_{20}$ straight chain and branched chain groups. Preferably, an alkyl group is an alkyl having 1 to 10 carbon atoms, and more preferably, an alkyl having 1 to 6 carbon atoms, even more preferably, an alkyl having 1 to 4 carbon atoms, and most preferably methyl. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various isomers with branched chains thereof. More preferably, an alkyl group is a lower alkyl having 1 to 6 carbon atoms. Representative examples include, but are not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. The alkyl group can be substituted or unsubstituted. When substituted, the substituent group(s) can be substituted at any available connection point, and preferably the substituent group(s) is one or more groups independently selected from the group consisting of alkyl, alkenyl, alkynyl, alkoxy, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo group, amino, haloalkyl, hydroxyalkyl, carboxyl, alkoxycarbonyl, $-OR^7$, $-C(O)OR^7$, $-OC(O)R^7$, $-O(CH_2)_nC(O)OR^7$, $-C(O)R^7$, $-C(O)NHR^7$, $-NHC(O)R^7$, $-NHC(O)OR^7$, $-NHS(O)_mR^7$, $-NR^8R^9$, $-OC(O)NR^8R^9$, and $-C(O)NR^8R^9$.

"Alkenyl" refers to an alkyl as defined above that has at least two carbon atoms and at least one carbon-carbon double bond, for example, vinyl, 1-propenyl, 2-propenyl, 1-, 2-, or 3-butenyl, etc, preferably $C_{2-10}$ alkenyl, more preferably $C_{2-6}$ alkenyl, and most preferably $C_{2-4}$ alkenyl. The alkenyl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocyclic alkylthio, oxo group, amino, haloalkyl, hydroxyalkyl, carboxyl, alkoxycarbonyl, $-OR^7$, $-C(O)OR^7$, $-OC(O)R^7$, $-O(CH_2)_nC(O)OR^7$, $-C(O)R^7$, $-C(O)NHR^7$, $-NHC(O)R^7$, $-NHC(O)OR^7$, $-NHS(O)_mR^7$, $-NR^8R^9$, $-OC(O)NR^8R^9$, and $-C(O)NR^8R^9$.

"Alkynyl" refers to an alkyl as defined above that has at least two carbon atoms and at least one carbon-carbon triple bond, for example, ethynyl, 1-propynyl, 2-propynyl, 1-, 2-, or 3-butynyl, etc, preferably $C_{2-10}$ alkynyl, more preferably $C_{2-6}$ alkynyl, and most preferably $C_{2-4}$ alkynyl. The alkynyl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocyclic alkylthio, oxo group, amino, haloalkyl, hydroxyalkyl, carboxyl and alkoxycarbonyl.

"Cycloalkyl" refers to a saturated or partially unsaturated monocyclic or polycyclic hydrocarbon group having 3 to 20 carbon atoms, preferably 3 to 12 carbon atoms, more preferably 3 to 10 carbon atoms, even more preferably 3 to 6 carbon atoms, and most preferably cyclopropyl. Representative examples of monocyclic cycloalkyls include, but are not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, etc, preferably cyclopropyl, or cyclohexenyl. Polycyclic cycloalkyl includes a cycloalkyl having a spiro ring, fused ring, or bridged ring.

The cycloalkyl group can be substituted or unsubstituted. When substituted, preferably the substituent group(s) is one or more groups independently selected from the group consisting of alkyl, alkenyl, alkynyl, alkoxy, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo group, amino, haloalkyl, hydroxyalkyl, carboxyl, alkoxycarbonyl, $-OR^7$, $-C(O)OR^7$, $-OC(O)R^7$, $-O(CH_2)_nC(O)OR^7$, $-C(O)R^7$, $-C(O)NHR^7$, $-NHC(O)R^7$, $-NHC(O)OR^7$, $-NHS(O)_mR^7$, $-NR^8R^9$, $-OC(O)NR^8R^9$, and $-C(O)NR^8R^9$.

"Heterocyclyl" refers to a 3 to 20 membered saturated or partially unsaturated monocyclic or polycyclic hydrocarbon group having one or more heteroatoms selected from the group consisting of N, O, and $S(O)_m$ (wherein m is an integer selected from the group consisting of 0, 1 and 2) as ring atoms, but excluding —O—O—, —O—S— or —S—S— in the ring, with the remaining ring atoms being C. Preferably, a heterocyclyl has 3 to 12 atoms, wherein 1 to 4 atoms are heteroatoms; more preferably 3 to 10 atoms; and most preferably 5 to 6 atoms. Representative examples of monocyclic heterocyclyls include, but are not limited to, pyrrolidyl, piperidyl, piperazinyl, morpholinyl, sulfo-morpholinyl, homopiperazinyl, pyranyl, tetrahydrofuranyl, etc. Polycyclic heterocyclyl includes the heterocyclyl having a spiro ring, fused ring or bridged ring. The heterocyclyl group can be substituted or unsubstituted. When substituted, preferably the substituent group(s) is one or more groups independently selected from the group consisting of alkyl, alkenyl, alkynyl, alkoxy, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, oxo group, amino, haloalkyl, hydroxyalkyl, carboxyl, alkoxycarbonyl, —OR$^7$, —C(O)OR$^7$, —OC(O)R$^7$, —O(CH$_2$)$_n$C(O)OR$^7$, —C(O)R$^7$, —C(O)NHR$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$.

"Aryl" refers to a 6 to 14 membered all-carbon monocyclic ring or polycyclic fused ring (a "fused" ring system means that each ring in the system shares an adjacent pair of carbon atoms with another ring in the system), which has a completely conjugated pi-electron system. Preferably, an aryl is 6 to 10 membered, more preferably phenyl and naphthyl, and most preferably phenyl. The aryl can be fused to the ring of a heteroaryl, heterocyclyl, or cycloalkyl, wherein the ring bound to the parent structure is aryl. Representative examples include, but are not limited to, the following groups:

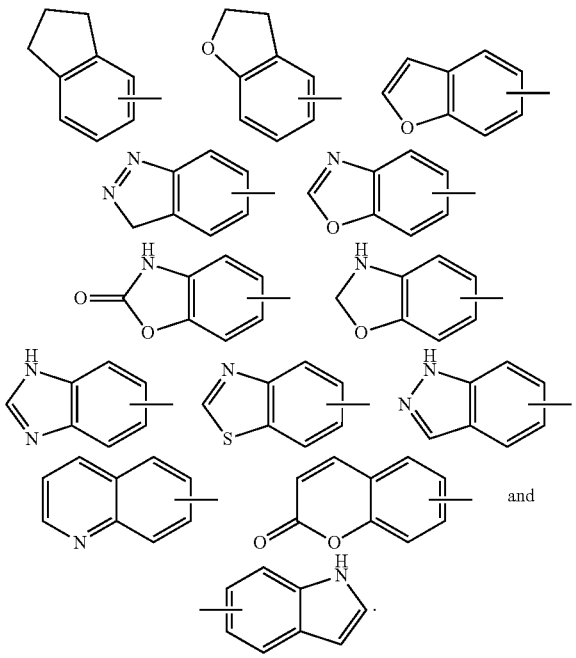

The aryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocyclic alkylthio, —OR$^7$, —C(O)OR$^7$, —OC(O)R$^7$, —O(CH$_2$)$_n$C(O)OR$^7$, —C(O)R$^7$, —C(O)NHR$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$.

"Heteroaryl" refers to a 5 to 14 membered monocyclic ring or polycyclic fused ring, having a completely conjugated pi-electron system and further comprising 1 to 4 heteroatoms selected from the group consisting of oxygen, sulfur, and nitrogen. Preferably, a heteroaryl is 5 to 10 membered, more preferably 5 to 6 membered, and most preferably furyl, thienyl, pyridyl, pyrrolyl, N-alkylpyrrolyl, pyrimidinyl, pyrazinyl, imidazolyl, or tetrazolyl, etc. The heteroaryl can be fused to the ring of an aryl, heterocyclyl, or cycloalkyl, wherein the ring bound to the parent structure is heteroaryl. Representative examples include, but are not limited to, the following groups

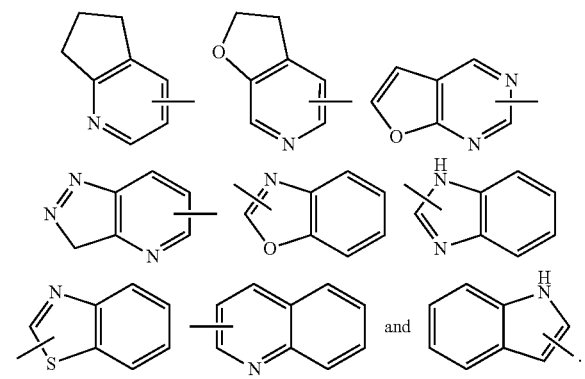

The heteroaryl group can be substituted or unsubstituted. When substituted, the substituent group(s) is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclic alkyl, aryl, heteroaryl, cycloalkoxy, heterocyclic alkoxy, cycloalkylthio, heterocyclic alkylthio, —OR$^7$, —C(O)OR$^7$, —OC(O)R$^7$, —O(CH$_2$)$_n$C(O)OR$^7$, —C(O)R$^7$, —C(O)NHR$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$.

"Alkoxy" refers to both an —O-(alkyl) and an —O-(unsubstituted cycloalkyl) group, wherein the alkyl and cycloalkyl are as defined above. Representative examples include, but are not limited to, methoxy, ethoxy, propoxy, butoxy, cyclopropyloxy, cyclobutyloxy, cyclopentyloxy, cyclohexyloxy, and the like. The alkoxy can be substituted or unsubstituted. When substituted, the substituent is preferably one or more groups independently selected from the group consisting of alkyl, alkenyl, alkynyl, alkoxy, alkylsulfo, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, amino, haloalkyl, hydroxyalkyl, carboxyl, alkoxycarbonyl, —OR$^7$, —C(O)OR$^7$, —OC(O)R, —O(CH$_2$)$_n$C(O)OR$^7$, —C(O)R$^7$, —C(O)NHR$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$.

"Haloalkyl" refers to an alkyl group substituted with one or more halogens, wherein the alkyl is as defined above.

"Hydroxy" refers to an —OH group.

"Hydroxyalkyl" refers to an alkyl group substituted with a hydroxy group, wherein the alkyl is as defined above.

"Halogen" refers to fluoro, chloro, bromo or iodo atoms.

"Amino" refers to an —NH$_2$ group.

"Cyano" refers to a —CN group.

"Nitro" refers to a —NO$_2$ group.

"Oxo group" refers to a ═O group.

"Carboxyl" refers to a —C(O)OH group.

"Alkoxycarbonyl" refers to a —C(O)O(alkyl) or (cycloalkyl) group, wherein the alkyl and cycloalkyl are as defined above.

"Optional" or "optionally" means that the event or circumstance described subsequently can, but need not occur, and the description includes the instances in which the event or circumstance does or does not occur. For example, "the heterocyclic group optionally substituted with an alkyl" means that an alkyl group can be, but need not be, present, and the description includes the case of the heterocyclic group being substituted with an alkyl and the heterocyclic group being not substituted with an alkyl.

"Substituted" refers to one or more hydrogen atoms in the group, preferably up to 5, more preferably 1 to 3 hydrogen atoms, each independently substituted with a corresponding number of substituents. It goes without saying that the substituents exist in their only possible chemical position. The person skilled in the art is able to determine if the substitution is possible or impossible without paying excessive efforts by experiment or theory. For example, the combination of amino or hydroxy group having free hydrogen and carbon atoms having unsaturated bonds (such as olefinic) can be unstable.

A "pharmaceutical composition" refers to a mixture of one or more of the compounds described in the present invention or physiologically/pharmaceutically acceptable salts or prodrugs thereof and other chemical components such as physiologically/pharmaceutically acceptable carriers and excipients. The purpose of a pharmaceutical composition is to facilitate administration of a compound to an organism, which is conducive to the absorption of the active ingredient, thus displaying biological activity.

$R^7$ to $R^9$, m and n are as defined in the above formula (I).

Synthesis Method of the Compound of the Invention

In order to complete the purpose of the invention, the present invention applies the following technical solution:

A process of preparing a compound of formula (I) of the invention, or a tautomer, mesomer, racemate, enantiomer, or diastereomer thereof, or mixture thereof, or a pharmaceutically acceptable salt thereof, comprising the steps of:

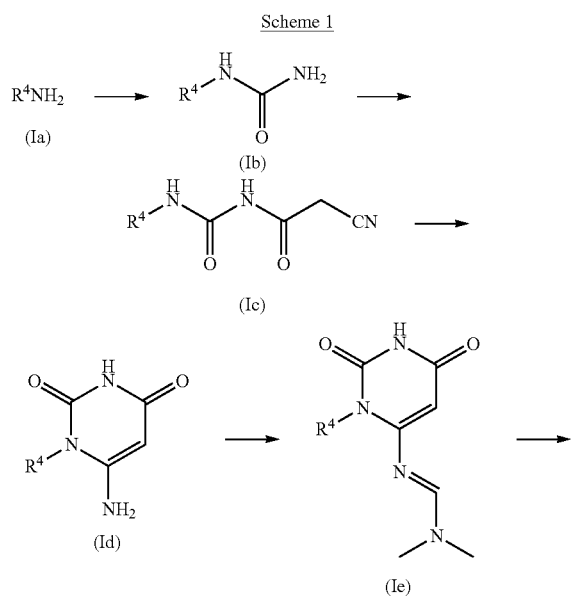

Scheme 1

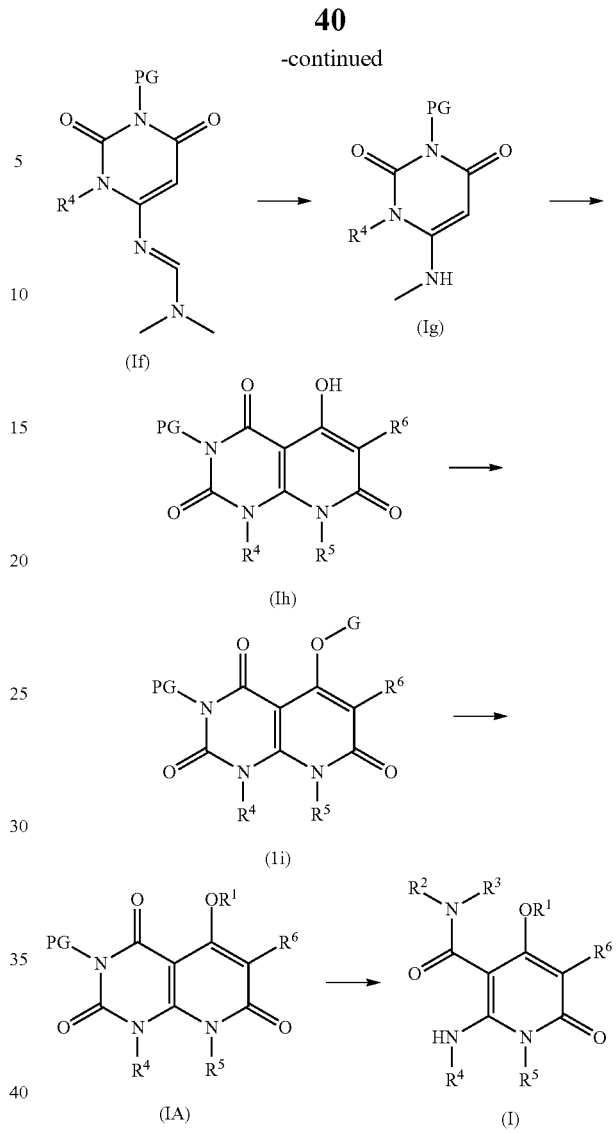

in an ice bath, reacting a compound of formula (Ia) with N,N'-carbonyldiimidazole and ammonia water under an alkaline condition to obtain a compound of formula (Ib); reacting the compound of formula (Ib) with 2-cyanoacetic acid in the presence of methanesulfonyl chloride to obtain a compound of formula (Ic); cyclizing the compound of formula (Ic) under an alkaline condition to obtain a compound of formula (Id); reacting the compound of formula (Id) with an acetal to obtain a compound of formula (Ie); reacting the compound of formula (Ie) with an amino-protecting reagent to obtain a compound of formula (If); reducing the compound of formula (If) in the presence of sodium borohydride to obtain a compound of formula (Ig); heating the compound of formula (Ig) and diethyl malonate to obtain a compound of formula (Ih) via cyclization; reacting the compound of formula (Ih) with a hydroxy-protecting reagent to obtain a compound of formula (Ii); reacting the compound of formula (Ii) with a nucleophile $R^1H$ to obtain a compound of formula (IA); opening a ring of the compound of formula (IA) under an alkaline condition, and optionally removing the amino-protecting group PG to obtain a compound of formula (I);

wherein: $R^1$ to $R^6$ are as defined in formula (I);
—OG is a leaving group, preferably sulfonyloxy;

PG is selected from the group consisting of alkyl and an amino-protecting group, wherein the amino-protecting group is preferably benzyl; the alkyl and benzyl are each optionally substituted with one or more groups selected from the group consisting of halogen, cyano, nitro, alkyl, heterocyclyl, heteroaryl, and —OR$^7$; and R$^7$ is as defined in formula (I).

A process of preparing a compound of formula (II) of the invention, or a tautomer, mesomer, racemate, enantiomer, or diastereomer thereof, or mixture thereof, or a pharmaceutically acceptable salt thereof, comprising the steps of:

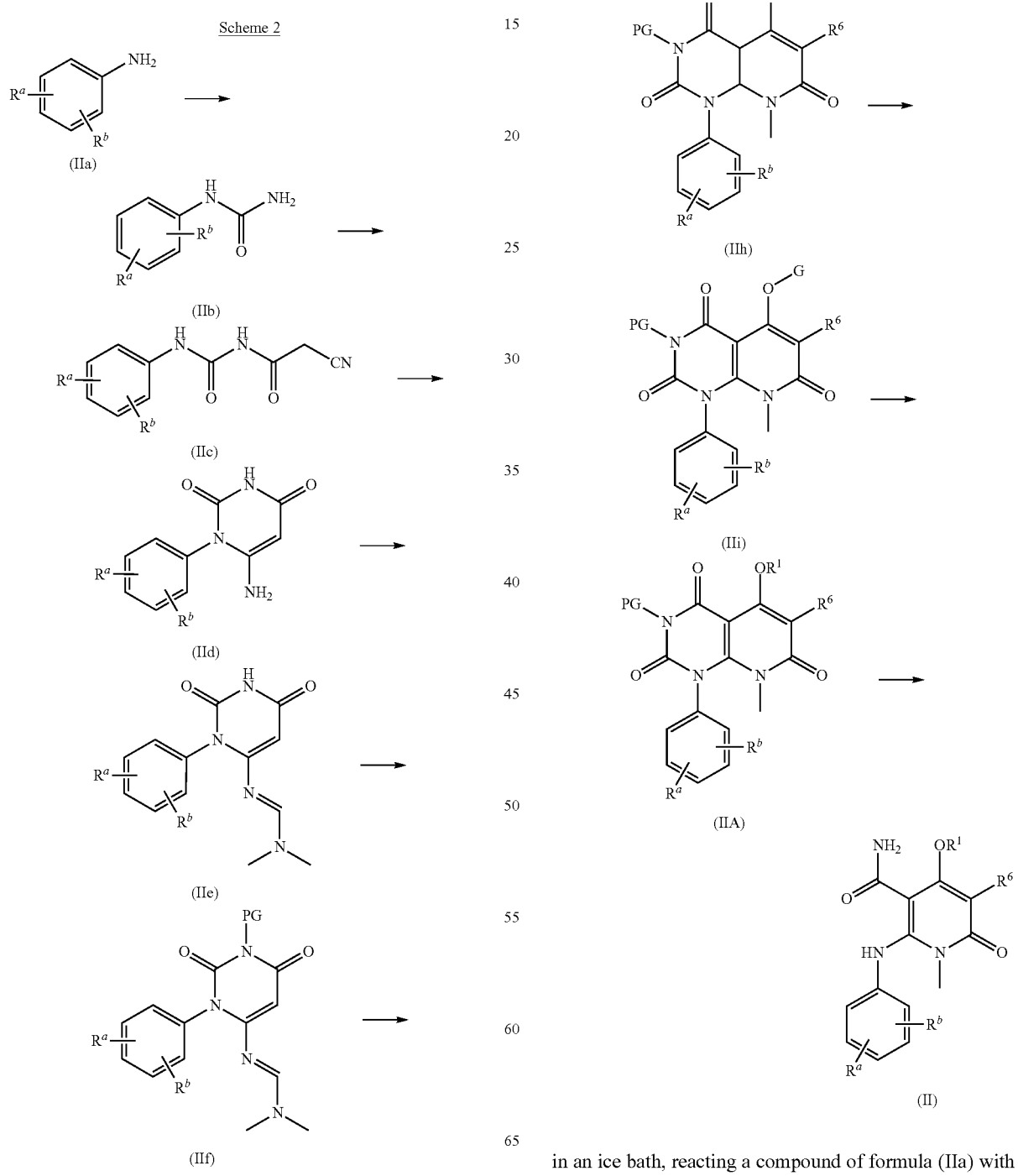

in an ice bath, reacting a compound of formula (IIa) with N,N'-carbonyldiimidazole under an alkaline condition to obtain a compound of formula (IIb); reacting the compound of formula (IIb) with 2-cyanoacetic acid in the presence of methanesulfonyl chloride to obtain a compound of formula (IIc); cyclizing the compound of formula (IIc) under an alkaline condition to obtain a compound of formula (IId); reacting the compound of formula (IId) with an acetal to obtain a compound of formula (IIe); reacting the compound of formula (IIe) with an amino-protecting reagent to obtain a compound of formula (IIf); reducing the compound of formula (IIf) in the presence of sodium borohydride to obtain a compound of formula (IIg); heating the compound of formula (IIg) and diethyl malonate to obtain a compound of formula (IIh) via cyclization; reacting the compound of formula (IIh) with a hydroxy-protecting reagent to obtain a compound of formula (IIi); reacting the compound of formula (IIi) with a nucleophile $R^1H$ to obtain a compound of formula (IIA); opening a ring of the compound of formula (IIA) under an alkaline condition, optionally removing the amino-protecting group PG to obtain a compound of formula (II);

wherein: $R^a$, $R^b$, $R^1$, and $R^6$ are as defined in formula (II);
—OG is a leaving group, preferably sulfonyloxy;
PG is selected from the group consisting of alkyl and an amino-protecting group, wherein the amino-protecting group is preferably benzyl; the alkyl and benzyl are each optionally substituted with one or more groups selected from the group consisting of halogen, cyano, nitro, alkyl, heterocyclyl, heteroaryl, and —$OR^7$; and
$R^7$ is as defined in formula (I).

In the aforesaid schemes, the alkaline condition is provided by a reagent including an organic alkali and an inorganic alkali, wherein the organic alkali includes, but is not limited to, triethylamine, pyridine, 2,6-lutidine, sodium methoxide, lithium hexamethyldisilazide, sodium hexamethyldisilazide, n-butyllithium, potassium tert-butoxide and tetrabutyl ammonium bromide; and the inorganic alkali includes, but is not limited to, sodium hydride, sodium carbonate, sodium bicarbonate, potassium carbonate, potassium bicarbonate, cesium carbonate, lithium hydroxide, sodium hydroxide, and potassium hydroxide; the alkaline reagent in the nucleophilic substitution reaction of the method of the present invention is preferably the inorganic alkali, more preferably sodium hydride or cesium carbonate; the alkaline reagent in the ring-opening reaction of the method of the present invention is preferably the inorganic alkali, more preferably lithium hydroxide or sodium hydride.

PREFERRED EMBODIMENTS

The invention will be further illustrated with reference to the following specific examples. It is to be understood that these examples are merely intended to demonstrate the invention without limiting the scope of the invention.

The experimental methods in the following examples for which no specific conditions are indicated will be carried out according to conventional conditions or recommended conditions of the raw materials and the product manufacturer. The experimental reagents for which no specific sources are indicated will be conventional reagents generally purchased from market.

EXAMPLES

Compound structures were identified by nuclear magnetic resonance (NMR) and/or mass spectrometry (MS). NMR chemical shifts (δ) were given in $10^{-6}$ (ppm). NMR was determined by a Bruker AVANCE-400 machine. The solvents were deuterated-dimethyl sulfoxide (DMSO-$d_6$), deuterated-chloroform (CDCl$_3$), and deuterated-methanol (CD$_3$OD), with tetramethylsilane (TMS) as an internal standard.

MS was determined by a FINNIGAN LCQAd (ESI) mass spectrometer (manufacturer: Thermo, type: Finnigan LCQ advantage MAX).

High performance liquid chromatography (HPLC) was determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average inhibition rate of kinase and IC$_{50}$ were determined by a NovoStar ELIASA (BMG Co., Germany).

For thin-layer silica gel chromatography (TLC), Yantai Huanghai HSGF254 or Qingdao GF254 silica gel plate was used. The dimension of the plates used in TLC was 0.15 mm to 0.2 mm, and the dimension of the plates used in product purification was 0.4 mm to 0.5 mm.

Column chromatography generally used Yantai Huanghai 200 to 300 mesh silica gel as carrier.

The known starting materials of the invention can be prepared by conventional synthesis methods in the prior art, or can be purchased from ABCR GmbH & Co. KG, Acros Organics, Aldrich Chemical Company, Accela ChemBio Inc., or Dari Chemical Company, etc.

Unless otherwise stated, the following reactions were placed under nitrogen atmosphere or argon atmosphere.

The term "argon atmosphere" or "nitrogen atmosphere" means that a reaction flask is equipped with a 1 L argon or nitrogen balloon.

Unless otherwise stated, the solution used in the examples refers to an aqueous solution.

Unless otherwise stated, the reaction temperature in the examples was room temperature in the range of 20° C. to 30° C.

The reaction process was monitored by thin layer chromatography (TLC), and the system of developing solvent included: A: dichloromethane and methanol system, B: n-hexane and ethyl acetate system, C: petroleum ether and ethyl acetate system, D: acetone. The ratio of the volume of the solvent was adjusted according to the polarity of the compounds.

The elution system for purification of the compounds by column chromatography and thin layer chromatography included: A: dichloromethane and methanol system, B: n-hexane and ethyl acetate system, C: dichloromethane and acetone system, D: ethyl acetate and dichloromethane system. The volume of the solvent was adjusted according to the polarity of the compounds, and sometimes a little alkaline reagent, such as triethylamine or acidic reagent, was also added.

Example 1
4-(3-fluoro-2-methylphenoxy)-2-((2-fluoro-4-iodo-phenyl)amino)-1-methyl-6-oxo-1,6-dihydropyridine-3-carboxamide
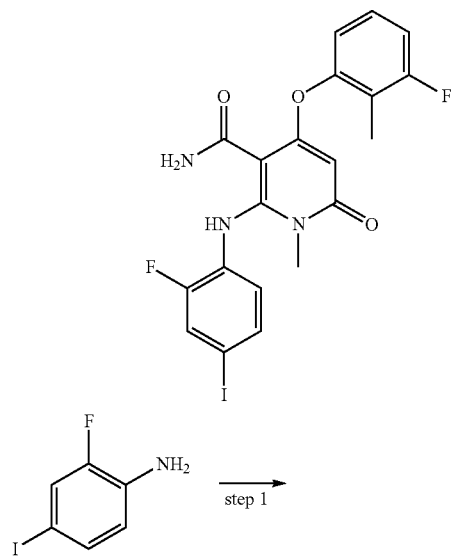
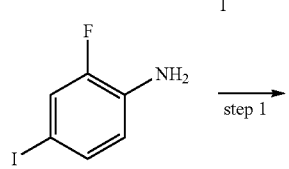
1a
↓ step 1
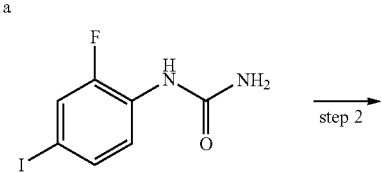
1b
↓ step 2
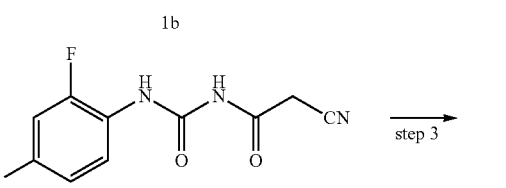
1c
↓ step 3
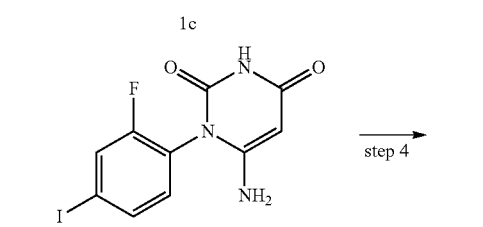
1d
↓ step 4
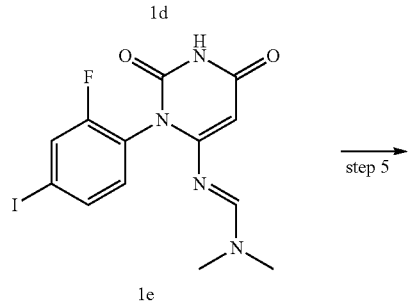
1e
↓ step 5
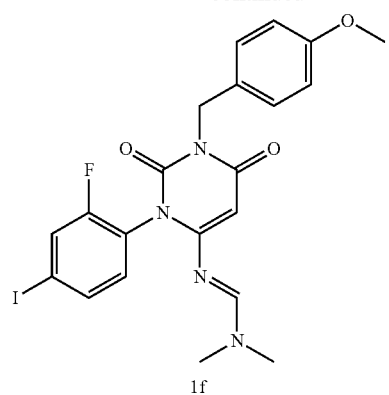
1f
↓ step 6
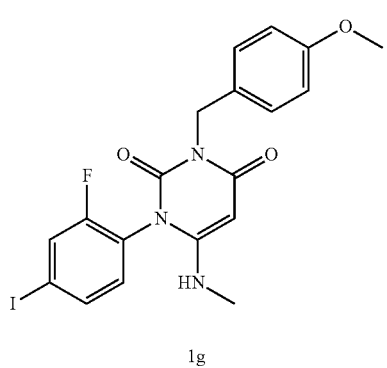
1g
↓ step 7
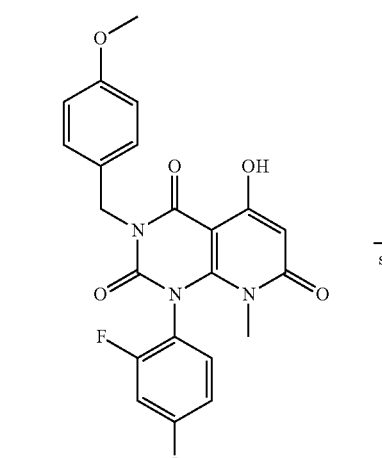
1h
↓ step 8

-continued

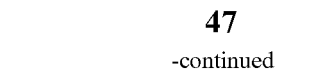

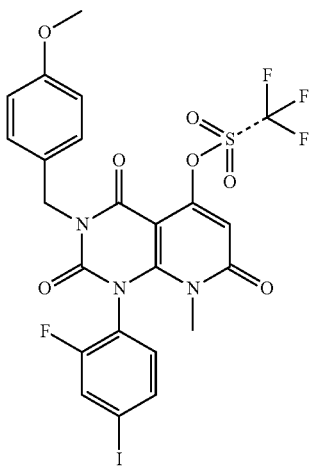

-continued

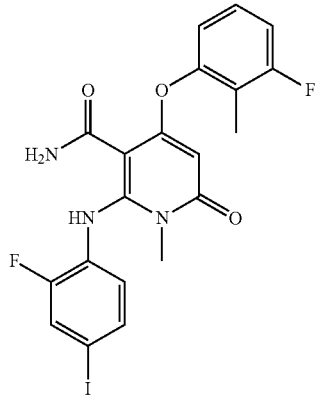

Step 1

1-(2-fluoro-4-iodophenyl)urea 2-fluoro-4-iodoaniline 1a (50.80 g, 214 mmol) was dissolved in 254 mL of trichloromethane, followed by addition of triethylamine (60 mL, 429 mmol). The reaction solution was cooled down to 0° C., and added with N,N'-carbonyldiimidazole (69.50 g, 429 mmol). After stirring for 15 minutes, the reaction solution was warmed up to room temperature and stirred for 4 hours. The reaction solution was cooled down to 0° C., then added with 254 mL of ammonia water and filtered. The filter cake was washed with water (50 mL×2), trichloromethane (20 mL×2), and ethyl acetate (50 mL×2) successively, and dried to obtain the crude title compound 1-(2-fluoro-4-iodophenyl)urea 1b (53 g, white solid), which was used directly in the next step without further purification.

MS m/z (ESI): 281.0 [M+1]

Step 2

2-cyano-N-((2-fluoro-4-iodophenyl)carbamoyl)acetamide

The crude 1-(2-fluoro-4-iodophenyl)urea 1b (113 g, 404 mmol) was dissolved in 450 mL of N,N-dimethylformamide, followed by addition of 2-cyanoacetic acid (41 g, 488 mmol). After cooling down to 0° C., the reaction solution was added with methanesulfonyl chloride (55.44 g, 484 mmol), then warmed up to room temperature and stirred for 2 hours. The reaction solution was added with 780 mL of a mixture of water and isopropanol (V:V=1:2), stirred for 1 hour, and filtered. The filter cake was washed with water (200 mL×2) and ethyl acetate (50 mL) successively, and dried to obtain the crude title compound 2-cyano-N-((2-fluoro-4-iodophenyl)carbamoyl)acetamide 1c (143 g, white solid), which was used directly in the next step without further purification.

MS m/z (ESI): 345.9 [M−1]

Step 3

6-amino-1-(2-fluoro-4-iodophenyl)pyrimidine-2,4(1H,3H)-dione

The crude 2-cyano-N-((2-fluoro-4-iodophenyl)carbamoyl)acetamide 1c (156 g, 430 mmol) was dissolved in 628 mL of water, followed by addition of 2M sodium hydroxide solution (22.6 mL, 42 mmol). The reaction solution was warmed up to 85° C. and stirred for 1 hour. After cooling down to 0° C., the reaction solution was added dropwise with 2M hydrochloric acid to adjust the pH to 3, followed by addition of 300 mL of isopropanol, and filtered. The filter cake was washed with water (200 mL×2) and isopropanol (100 mL×3) successively, and dried to obtain the crude title compound 6-amino-1-(2-fluoro-4-iodophenyl)pyrimidine-2,4(1H,3H)-dione 1d (128 g, white solid), which was used directly in the next step without further purification.

MS m/z (ESI): 348.0 [M+1]

Step 4

(E)-N'-(3-(2-fluoro-4-iodophenyl)-2,6-dioxo-1,2,3,6-tetrahydropyrimidin-4-yl)-N,N-dimethylformimidamide The crude 6-amino-1-(2-fluoro-4-iodophenyl)pyrimidine-2,4(1H,3H)-dione 1d (128 g, 368.80 mmol) was dissolved in 250 mL of N,N-dimethylformamide, followed by addition of N,N-dimethylformamide dimethyl acetal (124 mL, 935 mmol), and stirred for 4.5 hours. The reaction solution was added with 720 mL of a mixture of water and isopropanol (V:V=5:1), stirred for 1 hour, and filtered. The filter cake was washed with water (200 mL×2) and isopropanol (50 mL×2) successively, and dried to obtain the crude title compound (E)-N'-(3-(2-fluoro-4-iodophenyl)-2,6-dioxo-1,2,3,6-tetrahydropyrimidin-4-yl)-N,N-dimethylformimidamide 1e (132 g, white solid), which was used directly in the next step without further purification.

MS m/z (ESI): 403.0 [M+1]

Step 5

(E)-N'-(3-(2-fluoro-4-iodophenyl)-1-(4-methoxybenzyl)-2,6-dioxo-1,2,3,6-tetrahydropyrimidin-4-yl)-N,N-dimethylformimidamide The crude (E)-N'-(3-(2-fluoro-4-iodophenyl)-2,6-dioxo-1,2,3,6-tetrahydropyrimidin-4-yl)-N,N-dimethylformimidamide 1e (20 g, 50 mmol) was dissolved in 150 mL of N,N-dimethylformamide, followed by addition of 1,8-diazabicyclo[5.4.0]undec-7-ene (22.4 mL, 150 mmol) and 4-methoxybenzyl chloride (14.1 mL, 104.30 mmol). The reaction solution was warmed up to 75° C. and stirred for 3 hours. After cooling down to room temperature, the reaction solution was added with 675 mL of a mixture of water and isopropanol (V:V=2:1), stirred for 1 hour and filtered. The filter cake was washed with water (200 mL×2) and isopropanol (50 mL×2) successively, and dried to obtain the crude title compound (E)-N'-(3-(2-fluoro-4-iodophenyl)-1-(4-methoxybenzyl)-2,6-dioxo-1,2,3,6-tetrahydropyrimidin-4-yl)-N,N-dimethylformimidamide 1f (35 g, white solid), which was used directly in the next step without further purification.

MS m/z (ESI): 523.0 [M+1]

Step 6

1-(2-fluoro-4-iodophenyl)-3-(4-methoxybenzyl)-6-(methylamino)pyrimidine-2,4(1H,3H)-dione Sodium borohydride (3.80 g, 100 mmol) was dissolved in 210 mL of a mixture of ethanol and tert-butanol (V:V=1:2), followed by addition of the crude (E)-N'-(3-(2-fluoro-4-iodophenyl)-1-(4-methoxybenzyl)-2,6-dioxo-1,2,3,6-tetrahydropyrimidin-4-yl)-N,N-dimethylformimidamide 1f (35 g, 67 mmol). The reaction solution was warmed up to 65° C. and stirred for 1 hour. Ater cooling down to 0° C., the reaction solution was added with 175 mL of water and 140 mL of 10% citric acid successively, and filtered. The filter cake was washed with water (200 mL×2) and isopropanol (50 mL×2) successively, and dried to obtain the crude title compound 1-(2-fluoro-4-iodophenyl)-3-(4-methoxybenzyl)-6-(methylamino)pyrimidine-2,4(1H,3H)-dione 1g (33 g, white solid), which was used directly in the next step without further purification.

MS m/z (ESI): 482.0 [M+1]

Step 7

1-(2-fluoro-4-iodophenyl)-5-hydroxy-3-(4-methoxybenzyl)-8-methylpyrido[2,3-d]pyrimidine-2,4,7(1H,3H,8H)-trione The crude 1-(2-fluoro-4-iodophenyl)-3-(4-methoxybenzyl)-6-(methylamino) pyrimidine-2,4(1H,3H)-dione 1g (10.80 g, 22.44 mmol) and diethyl malonate (21.20 g, 157.09 mmol) were dissolved in 100 mL of phenyl ether. The reaction solution was warmed up to 230° C. and stirred for 1 hour. After cooling down to room temperature, the reaction solution was concentrated under reduced pressure, and the resulting residue was purified by silica gel column chromatography with elution system B to obtain the title compound 1-(2-fluoro-4-iodophenyl)-5-hydroxy-3-(4-methoxybenzyl)-8-methylpyrido[2,3-d]pyrimidine-2,4,7(1H,3H,8H)-trione 1h (8.97 g, orange solid), yield: 72.9%.

MS m/z (ESI): 550.0 [M+1]

Step 8

1-(2-fluoro-4-iodophenyl)-3-(4-methoxybenzyl)-8-methyl-2,4,7-trioxo-pyrido[2,3-d]pyrimidin-5-yl trifluoromethanesulfonate 1-(2-fluoro-4-iodophenyl)-5-hydroxy-3-(4-methoxybenzyl)-8-methylpyrido[2,3-d]pyrimidine-2,4,7(1H,3H,8H)-trione 1h (8.97 g, 16.33 mmol) was dissolved in 100 mL of dichloromethane, followed by addition of triethylamine (7.00 g, 65.32 mmol). After cooling down to 0° C., the reaction solution was added with trifluoromethanesulfonic anhydride (9.21 g, 32.66 mmol), then warmed up to room temperature and stirred for 3 hours. The reaction solution was concentrated under reduced pressure, and the resulting residue was purified by silica gel column chromatography with elution system B to obtain the title compound 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (4.13 g, yellow solid), yield: 37.1%.

MS m/z (ESI): 682.0 [M+1]

Step 9

5-(3-fluoro-2-methylphenoxy)-1-(2-fluoro-4-iodophenyl)-3-(4-methoxybenzyl)-8-methylpyrido[2,3-d]pyrimidine-2,4,7(1H,3H,8H)-trione 3-fluoro-2-methylphenol (30 mg, 0.24 mmol) was dissolved in 5 mL of tetrahydrofuran, followed by addition of sodium hydride (12 mg, 0.30 mmol). After stirring for 2 hours, the reaction solution was added with 1-(2-fluoro-4-iodophenyl)-3-(4-methoxybenzyl)-8-methyl-2,4,7-trioxopyrido[2,3-d]pyrimidin-5-yl trifluoromethanesulfonate 1j (136 mg, 0.20 mmol), warmed up to 60° C. and stirred for 1 hour. The reaction solution was concentrated under reduced pressure to obtain the title compound 5-(3-fluoro-2-methylphenoxy)-1-(2-fluoro-4-iodophenyl)-3-(4-methoxybenzyl)-8-methylpyrido[2,3-d]pyrimidine-2,4,7 (1H,3H,8H)-trione 1k (131 mg, pale yellow liquid), which was used directly in the next step without further purification.

MS m/z (ESI): 658.1 [M+1]

Step 10

4-(3-fluoro-2-methylphenoxy)-2-((2-fluoro-4-iodophenyl)amino)-N-(4-methoxybenzyl)-1-methyl-6-oxo-1,6-dihydropyridine-3-carboxamide The crude 5-(3-fluoro-2-methylphenoxy)-1-(2-fluoro-4-iodophenyl)-3-(4-methoxybenzyl)-8-methylpyrido[2,3-d] pyrimidine-2,4,7(1H,3H,8H)-trione 1k (131 mg, 0.20 mmol) was dissolved in 6 mL of a mixture of tetrahydrofuran and water (V:V=2:1), followed by addition of lithium hydroxide (168 mg, 4 mmol). The reaction solution was warmed up to 40° C. and stirred for 0.5 hour. After cooling down to room temperature, the reaction solution was stirred for 12 hours, and added with 50 mL of dichloromethane. The organic phase was washed with saturated sodium bicarbonate solution (25 mL×3), dried over anhydrous sodium sulfate, filtered, and the filtrate was concentrated under reduced pressure to obtain the crude title compound 4-(3-fluoro-2-methylphenoxy)-2-((2-fluoro-4-iodophenyl)amino)-N-(4-methoxybenzyl)-1-methyl-6-oxo-1,6-dihydropyridine-3-carboxamide 1m (126 mg, brown solid), which was used directly in the next step without further purification.

MS m/z (ESI): 632.1 [M+1]

Step 11

4-(3-fluoro-2-methylphenoxy)-2-((2-fluoro-4-iodophenyl)amino)-1-methyl-6-oxo-1,6-dihydropyridine-3-carboxamide The crude 4-(3-fluoro-2-methylphenoxy)-2-((2-fluoro-4-iodophenyl)amino)-N-(4-methoxybenzyl)-1-methyl-6-oxo-1,6-dihydropyridine-3-carboxamide 1m (126 mg, 0.20 mmol) was dissolved in 5 mL of anisole, followed by addition of aluminium chloride (133 mg, 1 mmol). The reaction solution was warmed up to 120° C. and stirred for 3.5 hours, added with 10 mL of water and 1 mL of 1 M hydrochloric acid, and extracted with ethyl acetate (20 mL×3). The organic phase was dried over anhydrous sodium sulfate, and filtered. The filtrate was concentrated under reduced pressure, and the resulting residue was purified by preparative separation to obtain the title compound 4-(3-fluoro-2-methylphenoxy)-2-((2-fluoro-4-iodophenyl) amino)-1-methyl-6-oxo-1,6-dihydropyridine-3-carboxamide 1 (33 mg, light brown solid), yield: 32.3%.

MS m/z (ESI): 512.0 [M+1]

$^1$H NMR (400 MHz, DMSO-d$_6$): δ 9.78 (s, 1H), 7.60-7.66 (m, 3H), 7.34-7.44 (m, 2H), 7.18 (t, 1H), 7.10 (d, 1H), 6.67 (t, 1H), 5.04 (s, 1H), 3.15 (s, 3H), 2.06 (s, 3H).

Example 2

N,1-dimethyl-4-(3-(ethylsulfonamido)-2-methylphenoxy)-2-((2-fluoro-4-iodophenyl)amino)-6-oxo-1,6-dihydropyridine-3-carboxamide

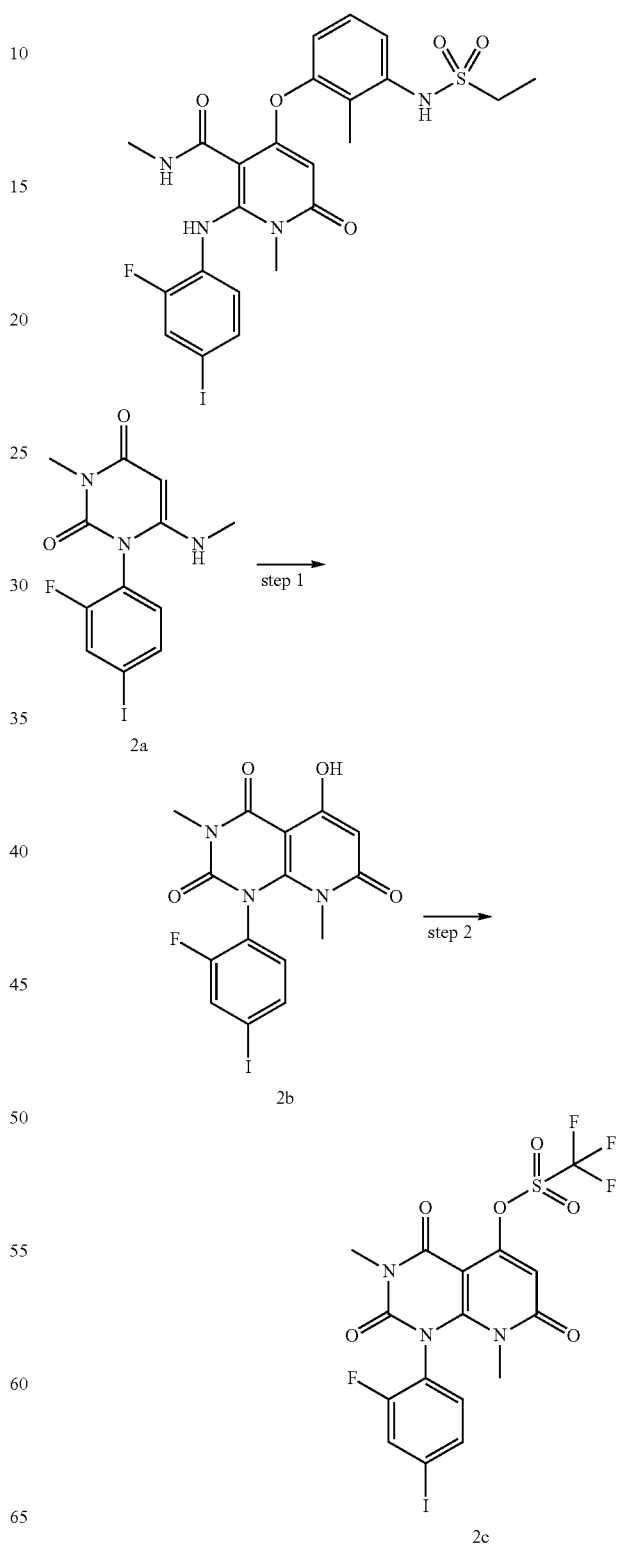

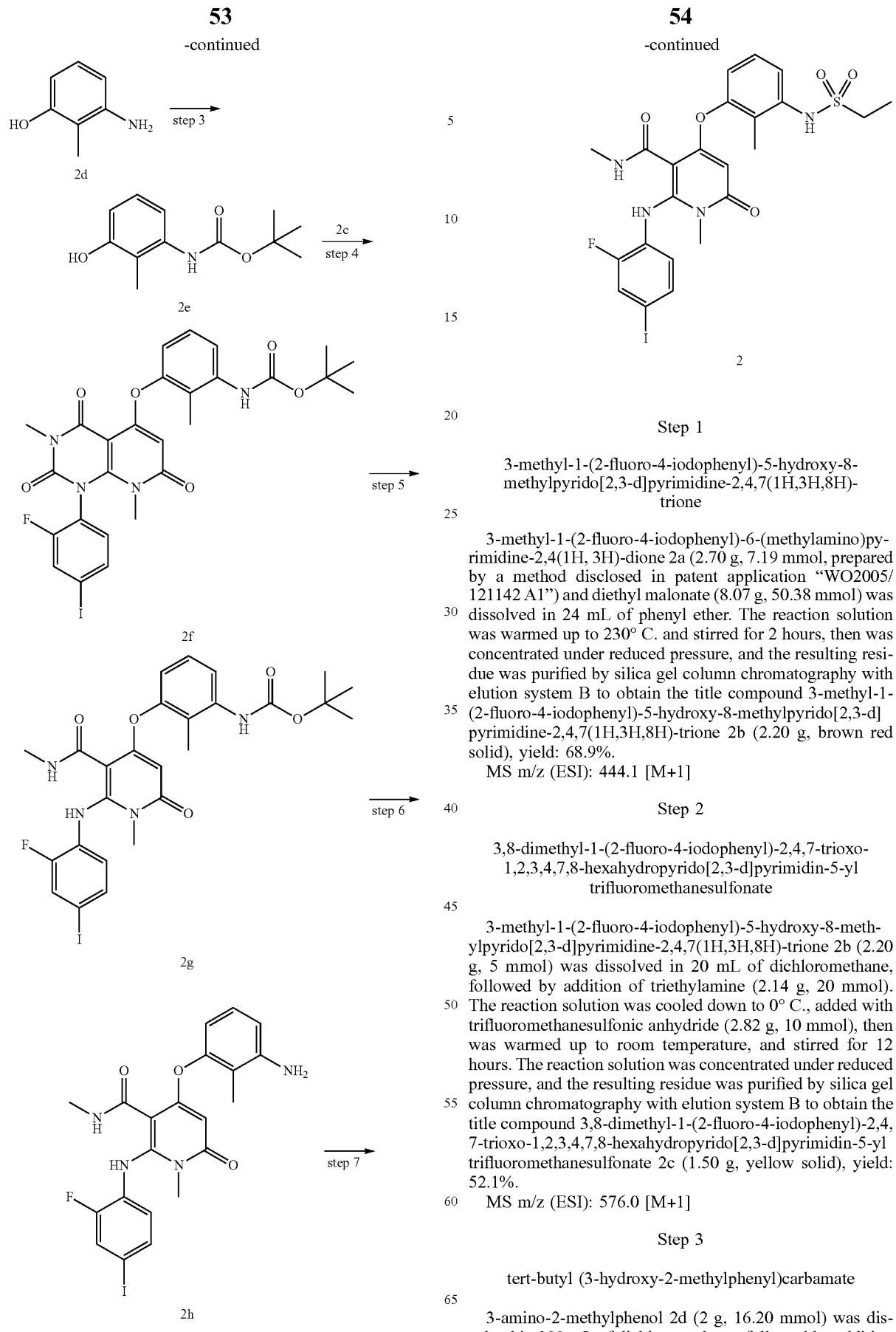

Step 1

3-methyl-1-(2-fluoro-4-iodophenyl)-5-hydroxy-8-methylpyrido[2,3-d]pyrimidine-2,4,7(1H,3H,8H)-trione 3-methyl-1-(2-fluoro-4-iodophenyl)-6-(methylamino)pyrimidine-2,4(1H, 3H)-dione 2a (2.70 g, 7.19 mmol, prepared by a method disclosed in patent application "WO2005/121142 A1") and diethyl malonate (8.07 g, 50.38 mmol) was dissolved in 24 mL of phenyl ether. The reaction solution was warmed up to 230° C. and stirred for 2 hours, then was concentrated under reduced pressure, and the resulting residue was purified by silica gel column chromatography with elution system B to obtain the title compound 3-methyl-1-(2-fluoro-4-iodophenyl)-5-hydroxy-8-methylpyrido[2,3-d]pyrimidine-2,4,7(1H,3H,8H)-trione 2b (2.20 g, brown red solid), yield: 68.9%.

MS m/z (ESI): 444.1 [M+1]

Step 2

3,8-dimethyl-1-(2-fluoro-4-iodophenyl)-2,4,7-trioxo-1,2,3,4,7,8-hexahydropyrido[2,3-d]pyrimidin-5-yl trifluoromethanesulfonate 3-methyl-1-(2-fluoro-4-iodophenyl)-5-hydroxy-8-methylpyrido[2,3-d]pyrimidine-2,4,7(1H,3H,8H)-trione 2b (2.20 g, 5 mmol) was dissolved in 20 mL of dichloromethane, followed by addition of triethylamine (2.14 g, 20 mmol). The reaction solution was cooled down to 0° C., added with trifluoromethanesulfonic anhydride (2.82 g, 10 mmol), then was warmed up to room temperature, and stirred for 12 hours. The reaction solution was concentrated under reduced pressure, and the resulting residue was purified by silica gel column chromatography with elution system B to obtain the title compound 3,8-dimethyl-1-(2-fluoro-4-iodophenyl)-2,4,7-trioxo-1,2,3,4,7,8-hexahydropyrido[2,3-d]pyrimidin-5-yl trifluoromethanesulfonate 2c (1.50 g, yellow solid), yield: 52.1%.

MS m/z (ESI): 576.0 [M+1]

Step 3 tert-butyl (3-hydroxy-2-methylphenyl)carbamate 3-amino-2-methylphenol 2d (2 g, 16.20 mmol) was dissolved in 300 mL of dichloromethane, followed by addition of di-tert-butyl dicarbonate (4.25 g, 19.50 mmol). The reaction solution was warmed up to 70° C. and stirred for 12 hours. The reaction solution was concentrated under reduced pressure, and the resulting residue was purified by silica gel column chromatography with elution system B to obtain the title compound tert-butyl (3-hydroxy-2-methylphenyl)carbamate 2e (3.0 g, white solid) yield: 83.1%.

MS m/z (ESI): 222.2 [M−1]

Step 4 tert-butyl (3-(3,8-dimethyl-(1-(2-fluoro-4-iodophenyl)-2,4,7-trioxo-1,2,3,4,7,8-hexahydropyrido[2,3-d]pyrimidin-5-yl)oxy)-2-methylphenyl)carbamate Tert-butyl (3-hydroxy-2-methylphenyl)carbamate 2e (120 mg, 0.52 mmol) was dissolved in 10 mL of tetrahydrofuran, followed by addition of sodium hydride (25 mg, 0.63 mmol). The reaction solution was stirred for 2 hours, followed by addition of 3,8-dimethyl-1-(2-fluoro-4-iodophenyl)-2,4,7-trioxo-1,2,3,4,7,8-hexahydropyrido[2,3-d]pyrimidin-5-yl trifluoromethanesulfonate 2c (300 mg, 0.53 mmol), then was warmed up to 70° C. and stirred for 2 hours. The reaction solution was concentrated under reduced pressure, added with 50 mL of ethyl acetate and 20 mL of water. The organic phase was dried over anhydrous sodium sulfate, and filtered. The filtrate was concentrated under reduced pressure to obtain the crude title compound tert-butyl (3-(3,8-dimethyl-(1-(2-fluoro-4-iodophenyl)-2,4,7-trioxo-1,2,3,4,7,8-hexahydropyrido[2,3-d]pyrimidin-5-yl)oxy)-2-methylphenyl)carbamate 2f (339 mg, brown liquid), which was used directly in the next step without further purification.

MS m/z (ESI): 649.1 [M+1]

Step 5 tert-butyl (3-(5-(methylcarbamoyl)-(6-((2-fluoro-4-iodophenyl)amino)-1-methyl-2-oxo-1,2-dihydropyridin-4-yl)oxy)-2-methylphenyl)carbamate The crude tert-butyl (3-(3,8-dimethyl-(1-(2-fluoro-4-iodophenyl)-2,4,7-trioxo-1,2,3,4,7,8-hexahydropyrido[2,3-d]pyrimidin-5-yl)oxy)-2-methylphenyl)carbamate 2f (339 mg, 0.52 mmol) was dissolved in 10 mL of tetrahydrofuran, and 2 mL of water was added, followed by addition of lithium hydroxide (218 mg, 5.20 mmol). The reaction solution was warmed up to 40° C. and stirred for 1.5 hours. The reaction solution was concentrated under reduced pressure, added with 50 mL of ethyl acetate, washed with water (10 ml). The organic phase was dried over anhydrous sodium sulfate, and filtered. The filtrate was concentrated under reduced pressure to obtain the crude title compound tert-butyl (3-(5-(methylcarbamoyl)-(6-((2-fluoro-4-iodophenyl)amino)-1-methyl-2-oxo-1,2-dihydropyridin-4-yl)oxy)-2-methylphenyl)carbamate 2g (325 mg, brown solid), which was used directly in the next step without further purification.

MS m/z (ESI): 623.0 [M+1]

Step 6

N,1-dimethyl-4-(3-amino-2-methylphenoxy)-2-((2-fluoro-4-iodophenyl)amino)-6-oxo-1,6-dihydropyridine-3-carboxamide The crude tert-butyl (3-(5-(methylcarbamoyl)-(6-((2-fluoro-4-iodophenyl)amino)-1-methyl-2-oxo-1,2-dihydropyridin-4-yl)oxy)-2-methylphenyl)carbamate 2g (325 mg, 0.52 mmol) was dissolved in 10 mL of dichloromethane, followed by addition of 3 ml of trifluoroacetic acid and stirred for 1 hour. The reaction solution was concentrated under reduced pressure, and added with 100 mL of ethyl acetate. The organic phase was washed with saturated sodium bicarbonate solution (30 mL×2), dried over anhydrous sodium sulfate and filtered. The filtrate was concentrated under reduced pressure to obtain the crude title compound N,1-dimethyl-4-(3-amino-2-methylphenoxy)-2-((2-fluoro-4-iodophenyl)amino)-6-oxo-1,6-dihydropyridine-3-carboxamide 2h (253 mg, brown solid), which was used directly in the next step without further purification.

MS m/z (ESI): 522.9 [M+1]

Step 7

N,1-dimethyl-4-(3-(ethylsulfonamido)-2-methylphenoxy)-2-((2-fluoro-4-iodophenyl)amino)-6-oxo-1,6-dihydropyridine-3-carboxamide The crude N,1-dimethyl-4-(3-amino-2-methylphenoxy)-2-((2-fluoro-4-iodophenyl) amino)-6-oxo-1,6-dihydropyridine-3-carboxamide 2h (175 mg, 0.34 mmol) was dissolved in 10 mL of dichloromethane, followed by addition of 2.5 ml of pyridine. After cooling down to 0° C., the reaction solution was added with ethanesulfonyl chloride (65 mg, 0.50 mmol). The reaction solution was warmed up to room temperature and stirred for 12 hours, then added with 100 mL of ethyl acetate and 30 ml of water. The organic phase was washed with water (20 mL), dried over anhydrous sodium sulfate, and filtered. The filtrate was concentrated under reduced pressure, and the resulting residue was purified by preparative separation to obtain the title compound N,1-dimethyl-4-(3-(ethylsulfonamido)-2-methylphenoxy)-2-((2-fluoro-4-iodophenyl)amino)-6-oxo-1,6-dihydropyridine-3-carboxamide 2 (85 mg, yellow solid), yield: 41.4%.

MS m/z (ESI): 615.1 [M+1]

$^1$H NMR (400 MHz, DMSO-$d_6$) δ 9.26 (s, 1H), 9.23 (s, 1H), 8.03-8.07 (m, 1H), 7.59-7.64 (dd, 1H), 7.40-7.44 (dd, 1H), 7.25-7.35 (m, 2H), 7.07-7.10 (dd, 1H), 6.67-6.72 (t, 1H), 4.95 (s, 1H), 3.22 (s, 3H), 3.10-3.17 (q, 2H), 2.50 (s, 3H), 2.11 (s, 3H), 1.25-1.29 (t, 3H).

Example 3

4-(3-(ethylsulfonamido)-2-methylphenoxy)-2-((2-fluoro-4-iodophenyl)amino)-1-methyl-6-oxo-1,6-dihydropyridine-3-carboxamide

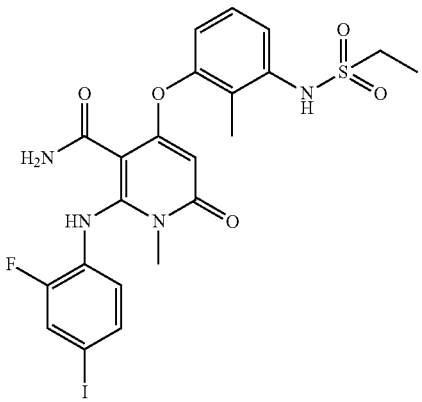

57
-continued
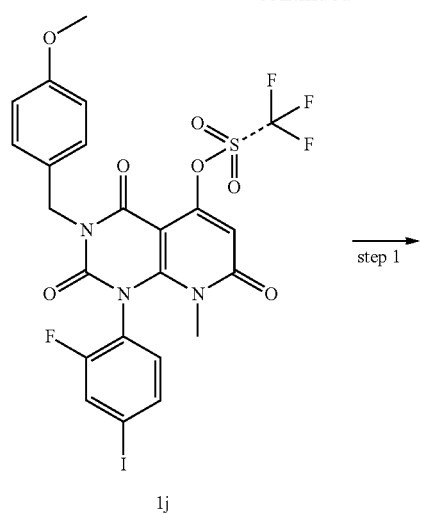
1j
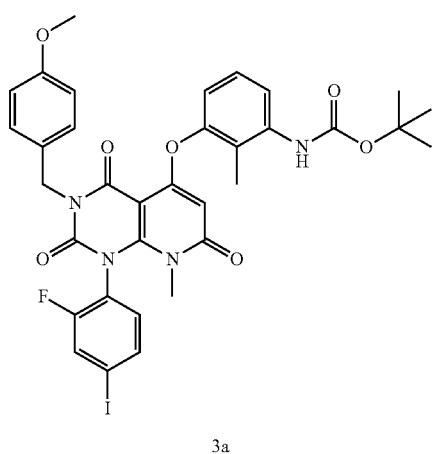
3a
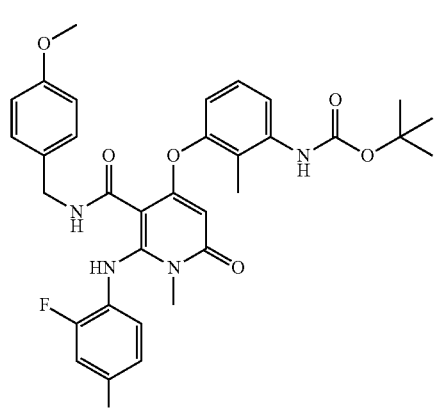
3b
58
-continued
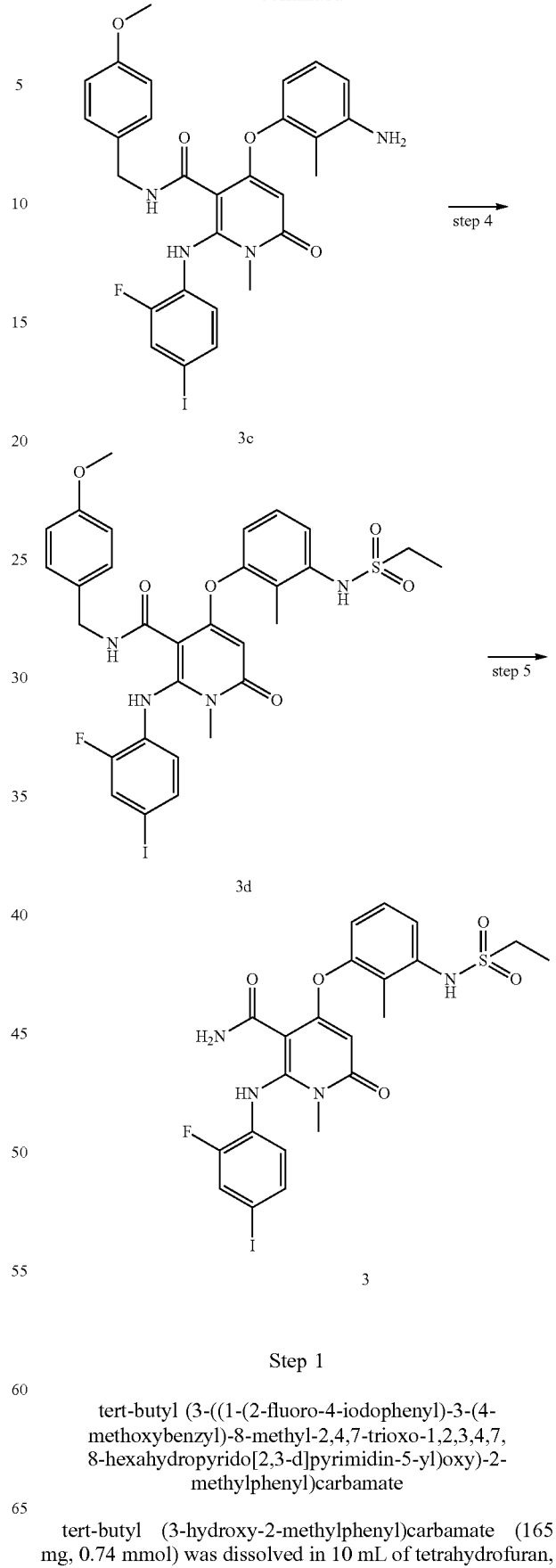
Step 1
tert-butyl (3-((1-(2-fluoro-4-iodophenyl)-3-(4-methoxybenzyl)-8-methyl-2,4,7-trioxo-1,2,3,4,7,8-hexahydropyrido[2,3-d]pyrimidin-5-yl)oxy)-2-methylphenyl)carbamate
tert-butyl (3-hydroxy-2-methylphenyl)carbamate (165 mg, 0.74 mmol) was dissolved in 10 mL of tetrahydrofuran, followed by addition of sodium hydride (37 mg, 0.93 mmol). The reaction solution was stirred for 2 hours, followed by addition of 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (420 mg, 0.62 mmol), then was warmed up to 60° C. After stirring for 0.5 hour, the reaction solution was concentrated under reduced pressure to obtain the crude title compound tert-butyl (3-((1-(2-fluoro-4-iodophenyl)-3-(4-methoxybenzyl)-8-methyl-2,4,7-trioxo-1,2,3,4,7,8-hexahydropyrido[2,3-d]pyrimidin-5-yl)oxy)-2-methylphenyl)carbamate 3a (465 mg, pale yellow liquid), which was used directly in the next step without further purification.

MS m/z (ESI): 755.1 [M+1]

Step 2 tert-butyl (3-((6-((2-fluoro-4-iodophenyl)amino)-5-((4-methoxybenzyl)carbamoyl)-1-methyl-2-oxo-1,2-dihydropyridin-4-yl)oxy)-2-methylphenyl)carbamate The crude tert-butyl (3-((1-(2-fluoro-4-iodophenyl)-3-(4-methoxybenzyl)-8-methyl-2,4,7-trioxo-1,2,3,4,7,8-hexahydropyrido[2,3-d]pyrimidin-5-yl)oxy)-2-methyl phenyl)carbamate 3a (465 mg, 0.62 mmol) was dissolved in 12.5 mL of a mixture of tetrahydrofuran and water (V:V=4:1), followed by addition of lithium hydroxide (517 mg, 12.32 mmol). The reaction solution was warmed up to 40° C. and stirred for 1 hour. After cooling down to room temperature, the reaction solution was stirred for 12 hours, followed by addition of 15 mL of water and 50 mL of dichloromethane. The organic phase was dried over anhydrous sodium sulfate, filtered, and the filtrate was concentrated under reduced pressure to obtain the crude title compound tert-butyl (3-((6-((2-fluoro-4-iodophenyl)amino)-5-((4-methoxybenzyl)carbamoyl)-1-methyl-2-oxo-1,2-dihydropyridin-4-yl)oxy)-2-methylphenyl)carbamate 3b (449 mg, brown solid), which was used directly in the next step without further purification.

MS m/z (ESI): 729.2 [M+1]

Step 3

4-(3-amino-2-methylphenoxy)-2-((2-fluoro-4-iodophenyl)amino)-N-(4-methoxybenzyl)-1-methyl-6-oxo-1,6-dihydropyridine-3-carboxamide The crude tert-butyl (3-((6-((2-fluoro-4-iodophenyl)amino)-5-((4-methoxybenzyl)carbamoyl)-1-methyl-2-oxo-1,2-dihydropyridin-4-yl)oxy)-2-methyl phenyl)carbamate 3b (449 mg, 0.62 mmol) was dissolved in 10 mL of dichloromethane, followed by addition of trifluoroacetic acid (1.40 g, 12.32 mmol). After stirring for 2 hours, the reaction solution was concentrated under reduced pressure, added with 10 mL of dichloromethane and 10 mL of saturated sodium bicarbonate solution. The reaction solution was stirred for 12 hours and extracted with dichloromethane (30 mL×2). The organic phases were combined, dried over anhydrous sodium sulfate, filtered, and the filtrate was concentrated under reduced pressure to obtain the crude title compound 4-(3-amino-2-methylphenoxy)-2-((2-fluoro-4-iodophenyl)amino)-N-(4-methoxybenzyl)-1-methyl-6-oxo-1,6-dihydropyridine-3-carboxamide 3c (387 mg, light brown solid), which was used directly in the next step without further purification.

MS m/z (ESI): 629.0 [M+1]

Step 4

4-(3-(ethylsulfonamido)-2-methylphenoxy)-2-((2-fluoro-4-iodophenyl)amino)-N-(4-methoxybenzyl)-1-methyl-6-oxo-1,6-dihydropyridine-3-carboxamide The crude 4-(3-amino-2-methylphenoxy)-2-((2-fluoro-4-iodophenyl)amino)-N-(4-methoxybenzyl)-1-methyl-6-oxo-1,6-dihydropyridine-3-carboxamide 3c (190 mg, 0.30 mmol) was dissolved in 10 mL of a mixture of dichloromethane and pyridine (V:V=1:1). After cooling down to 0° C., the reaction solution was added with ethanesulfonyl chloride (42 mg, 0.33 mmol), warmed up to room temperature and stirred for 12 hours. 50 mL of dichloromethane was added, the organic phase was washed with water (20 mL), dried over anhydrous sodium sulfate, filtered, and the filtrate was concentrated under reduced pressure to obtain the crude title compound 4-(3-(ethylsulfonamido)-2-methylphenoxy)-2-((2-fluoro-4-iodophenyl)amino)-N-(4-methoxybenzyl)-1-methyl-6-oxo-1,6-dihydropyridine-3-carboxamide 3d (216 mg, brownish black solid), which was used directly in the next step without further purification.

MS m/z (ESI): 720.9 [M+1]

Step 5

4-(3-(ethylsulfonamido)-2-methylphenoxy)-2-((2-fluoro-4-iodophenyl)amino)-1-methyl-6-oxo-1,6-dihydropyridine-3-carboxamide The crude 4-(3-(ethylsulfonamido)-2-methylphenoxy)-2-((2-fluoro-4-iodophenyl)amino)-N-(4-methoxybenzyl)-1-methyl-6-oxo-1,6-dihydropyridine-3-carboxamide 3d (200 mg, 0.28 mmol) was dissolved in 10 mL of anisole, followed by addition of aluminum chloride (185 mg, 1.39 mmol). The reaction solution was warmed up to 120° C. and stirred for 1 hour, followed by addition of 10 mL of water and 1 mL of 1 M hydrochloric acid, and extracted with ethyl acetate (20 mL×3). The organic phase was dried over anhydrous sodium sulfate, and filtered. The filtrate was concentrated under reduced pressure, and the resulting residue was purified by preparative separation to obtain the title compound 4-(3-(ethylsulfonamido)-2-methylphenoxy)-2-((2-fluoro-4-iodophenyl)amino)-1-methyl-6-oxo-1,6-dihydropyridine-3-carboxamide 3 (35 mg, light brown solid), yield: 20.8%.

MS m/z (ESI): 601.0 [M+1]

$^1$H NMR (400 MHz, DMSO-$d_6$): δ 9.88 (s, 1H), 9.27 (s, 1H), 7.58-7.68 (m, 3H), 7.43 (d, 1H), 7.27-7.35 (m, 2H), 7.14 (d, 1H), 6.67 (t, 1H), 4.96 (s, 1H), 3.14 (s, 3H), 3.13 (q, 2H), 2.12 (s, 3H), 1.26 (t, 3H).

Example 4

4-(3-acetamido-2-methylphenoxy)-2-((2-fluoro-4-iodophenyl)amino)-1-methyl-6-oxo-1,6-dihydropyridine-3-carboxamide

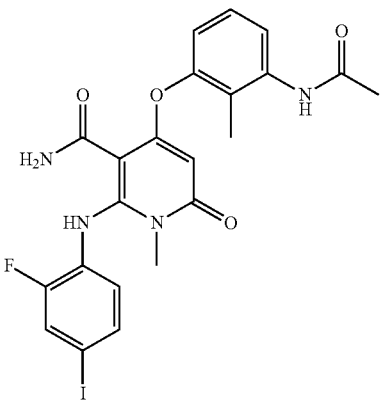

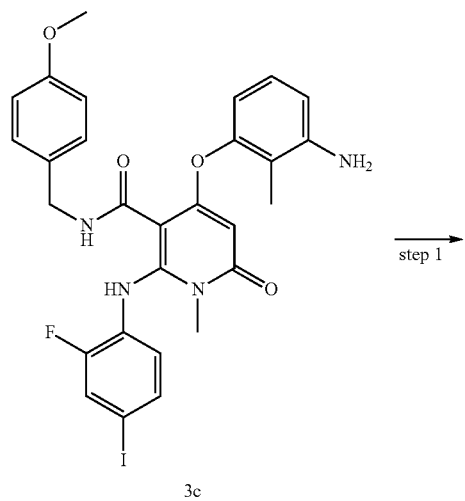

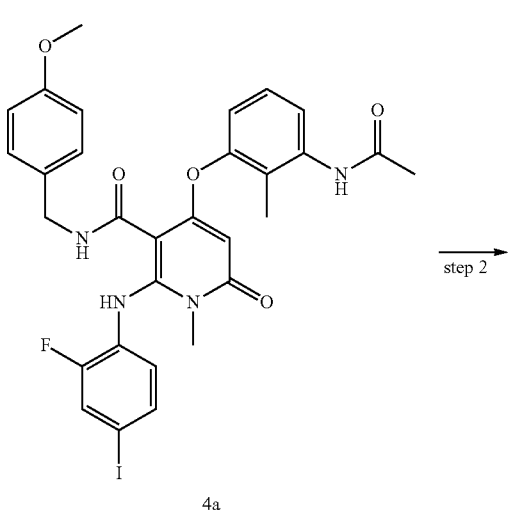

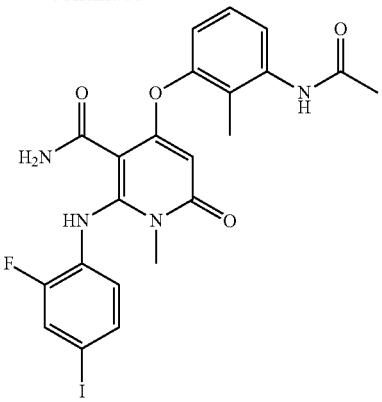

Step 1

4-(3-acetamido-2-methylphenoxy)-2-((2-fluoro-4-iodophenyl)amino)-N-(4-methoxybenzyl)-1-methyl-6-oxo-1,6-dihydropyridine-3-carboxamide The crude 4-(3-amino-2-methylphenoxy)-2-((2-fluoro-4-iodophenyl)amino)-N-(4-methoxybenzyl)-1-methyl-6-oxo-1,6-dihydropyridine-3-carboxamide 3c (190 mg, 0.30 mmol) was dissolved in 10 mL of a mixture of dichloromethane and pyridine (V:V=1:1). After cooling down to 0° C., the reaction solution was added with acetyl chloride (26 mg, 0.33 mmol), then was warmed up to room temperature and stirred for 12 hours, followed by addition of 50 mL of dichloromethane. The organic phase was washed with water (20 mL), dried over anhydrous sodium sulfate, filtered, and the filtrate was concentrated under reduced pressure to obtain the crude title compound 4-(3-acetamido-2-methylphenoxy)-2-((2-fluoro-4-iodophenyl)amino)-N-(4-methoxybenzyl)-1-methyl-6-oxo-1,6-dihydropyridine-3-carboxamide 4a (201 mg, light brown solid), which was used directly in the next step without further purification.

MS m/z (ESI): 671.1 [M+1]

Step 2

4-(3-acetamido-2-methylphenoxy)-2-((2-fluoro-4-iodophenyl)amino)-1-methyl-6-oxo-1,6-dihydropyridine-3-carboxamide The crude 4-(3-acetamido-2-methylphenoxy)-2-((2-fluoro-4-iodophenyl)amino)-N-(4-methoxybenzyl)-1-methyl-6-oxo-1,6-dihydropyridine-3-carboxamide 4a (201 mg, 0.30 mmol) was dissolved in 10 mL of anisole, followed by addition of aluminum chloride (200 mg, 1.50 mmol). The reaction solution was warmed up to 120° C. and stirred for 5 hours, then was concentrated under reduced pressure, and the resulting residue was purified by preparative separation to obtain the title compound 4-(3-acetamido-2-methylphenoxy)-2-((2-fluoro-4-iodophenyl)amino)-1-methyl-6-oxo-1,6-dihydropyridine-3-carboxamide 4 (30 mg, brown solid), yield: 18.2%.

MS m/z (ESI): 551.0 [M+1]

$^1$H NMR (400 MHz, DMSO-$d_6$): δ 9.89 (s, 1H), 9.47 (s, 1H), 7.58-7.68 (m, 3H), 7.42 (t, 2H), 7.29 (t, 1H), 7.06 (d, 1H), 6.67 (t, 1H), 4.96 (s, 1H), 3.14 (s, 3H), 2.07 (s, 3H), 2.02 (s, 3H).

Example 5

4-(3-(ethylsulfonamido)-2-methylphenoxy)-2-((2-fluoro-4-iodophenyl)amino)-1-methyl-5-chloro-6-oxo-1,6-dihydropyridine-3-carboxamide

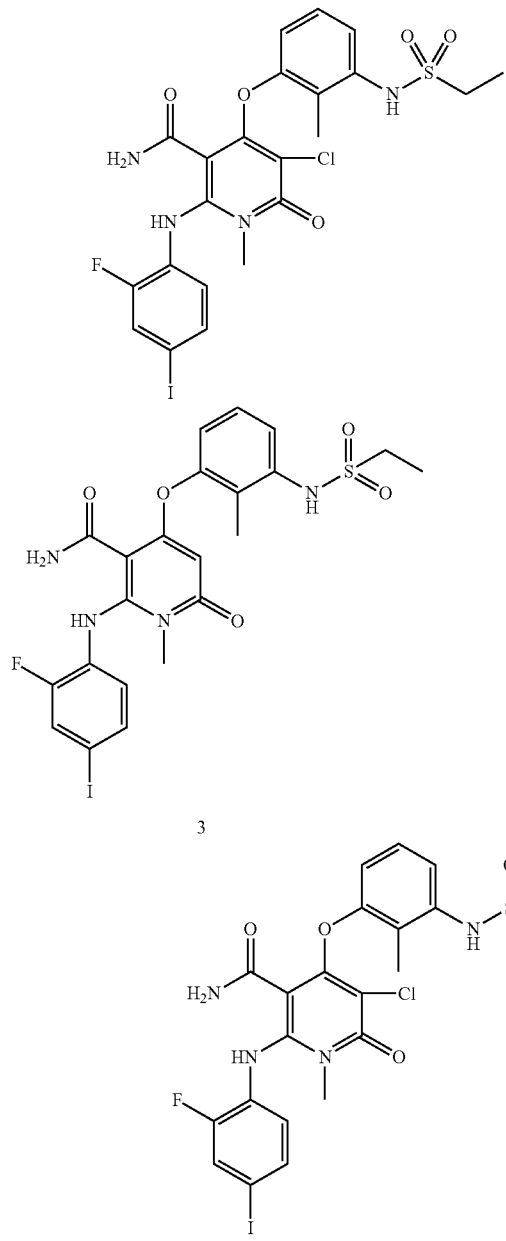

4-(3-(ethylsulfonamido)-2-methylphenoxy)-2-((2-fluoro-4-iodophenyl)amino)-1-methyl-6-oxo-1,6-dihydropyridine-3-carboxamide 3 (30 mg, 0.05 mmol) was dissolved in 9 mL of dichloromethane. After cooling down to 0° C., the reaction solution was added with 3 mL of a solution of N-chlorosuccinimide (7 mg, 0.05 mmol) in dichloromethane, then was warmed up to 40° C. and stirred for 12 hours. The reaction solution was concentrated under reduced pressure, and the resulting residue was purified by preparative separation to obtain the title compound 4-(3-(ethylsulfonamido)-2-methylphenoxy)-2-((2-fluoro-4-iodophenyl)amino)-1-methyl-5-chloro-6-oxo-1,6-dihydropyridine-3-carboxamide 5 (19 mg, white solid), yield: 59.4%.

MS m/z (ESI): 635.0 [M+1]

$^1$H NMR (400 MHz, DMSO-$d_6$): δ 9.17 (s, 1H), 8.96 (s, 1H), 7.60 (dd, 1H), 7.51 (s, 1H), 7.36-7.46 (m, 2H), 6.99-7.09 (m, 2H), 6.74 (t, 1H), 6.58 (d, 1H), 3.36 (s, 3H), 3.09 (q, 2H), 2.30 (s, 3H), 1.26 (t, 3H).

Example 6

4-(3-(ethylsulfonamido)-2-methylphenoxy)-2-((2-fluoro-4-iodophenyl)amino)-1-methyl-5-fluoro-6-oxo-1,6-dihydropyridine-3-carboxamide

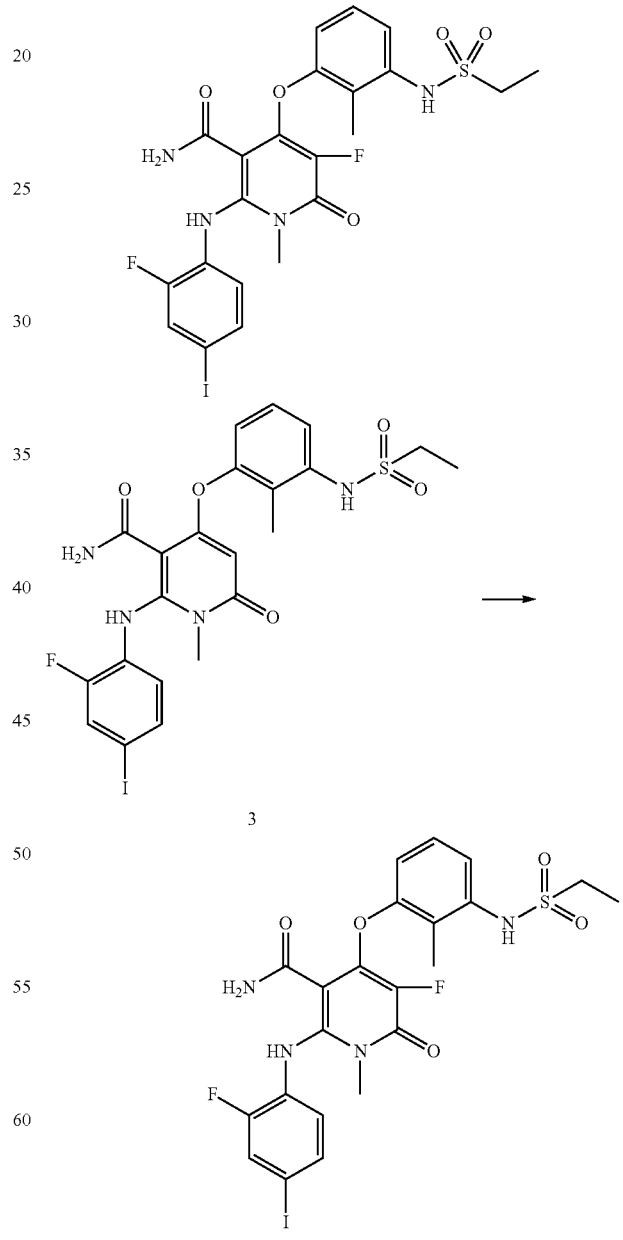

4-(3-(ethylsulfonamido)-2-methylphenoxy)-2-((2-fluoro-4-iodophenyl)amino)-1-methyl-6-oxo-1,6-dihydropyridine-3-carboxamide 3 (12 mg, 0.02 mmol) was dissolved in 10 mL of dichloromethane. After cooling down to 0° C., the reaction solution was added with 3 mL of a solution of 1-chloromethyl-4-fluoro-1,4-diazoniabicyclo[2.2.2]octane bis(tetrafluoroborate) (7 mg, 0.02 mmol) in dichloromethane, then was warmed up to room temperature and stirred for 12 hours. The reaction solution was concentrated under reduced pressure, and the resulting residue was purified by preparative separation to obtain the title compound 4-(3-(ethylsulfonamido)-2-methylphenoxy)-2-((2-fluoro-4-iodophenyl)amino)-1-methyl-5-fluoro-6-oxo-1,6-dihydropyridine-3-carb oxamide 6 (6 mg, light brown solid), yield: 31.5%.

MS m/z (ESI): 619.0 [M+1]

$^1$H NMR (400 MHz, DMSO-d$_6$): δ 9.20 (s, 1H), 8.68 (s, 1H), 7.42-7.66 (m, 3H), 7.30-7.40 (m, 1H), 7.00-7.22 (m, 2H), 6.78-7.88 (m, 1H), 6.58-6.70 (m, 1H), 3.33 (s, 3H), 3.10 (q, 2H), 2.28 (s, 3H), 1.25 (t, 3H).

Example 7

4-(3-(cyclopropanecarboxamido)-2-methylphenoxy)-2-((2-fluoro-4-iodophenyl)amino)-1-methyl-6-oxo-1,6-dihydropyridine-3-carboxamide

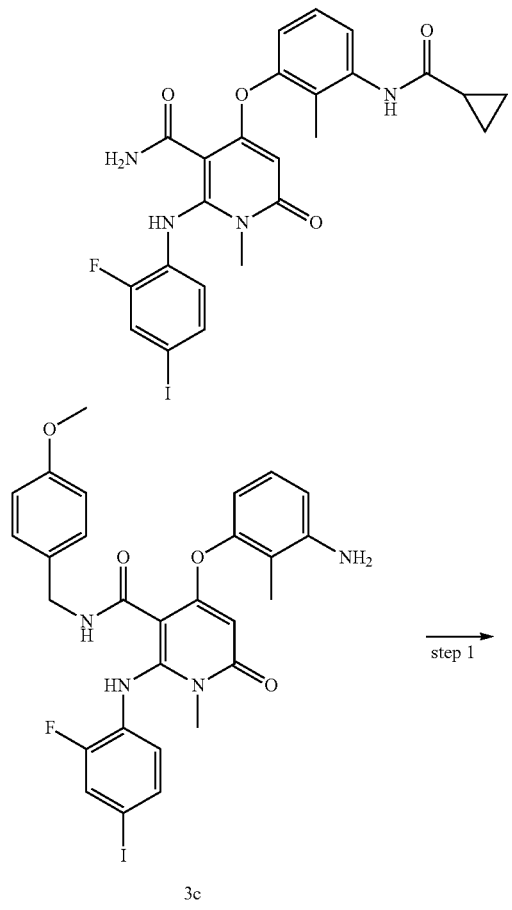

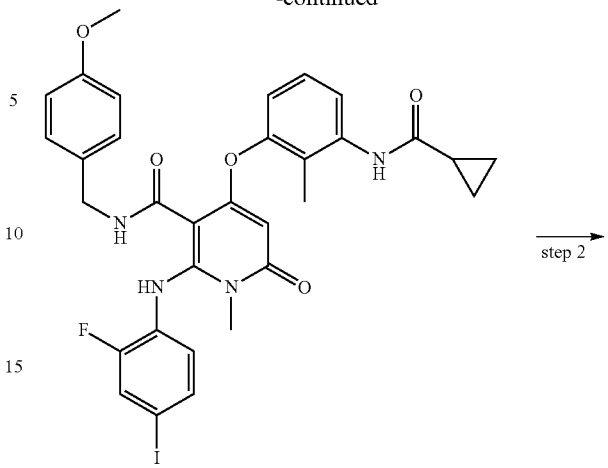

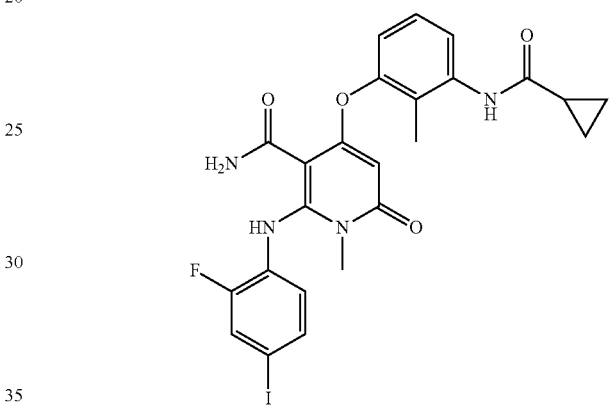

Step 1

4-(3-(cyclopropanecarboxamido)-2-methylphenoxy)-2-((2-fluoro-4-iodophenyl)amino)-N-(4-methoxybenzyl)-1-methyl-6-oxo-1,6-dihydropyridine-3-carboxamide The crude 4-(3-amino-2-methylphenoxy)-2-((2-fluoro-4-iodophenyl)amino)-N-(4-methoxybenzyl)-1-methyl-6-oxo-1,6-dihydropyridine-3-carboxamide 3c (126 mg, 0.20 mmol) was dissolved in 2 mL of a mixture of dichloromethane and pyridine (V:V=1:1). After cooling down to 0° C., the reaction solution was added with cyclopropanecarbonyl chloride (23 mg, 0.22 mmol), then was warmed up to room temperature and stirred for 12 hours. The reaction solution was concentrated under reduced pressure, and added with 50 mL of dichloromethane. The organic phase was washed with water (20 mL), dried over anhydrous sodium sulfate, filtered, and the filtrate was concentrated under reduced pressure to obtain the crude title compound 4-(3-(cyclopropanecarboxamido)-2-methylphenoxy)-2-((2-fluoro-4-iodophenyl)amino)-N-(4-methoxybenzyl)-1-methyl-6-oxo-1,6-dihydropyridine-3-carboxamide 7a (139 mg, light brown solid), which was used directly in the next step without further purification.

MS m/z (ESI): 697.1 [M+1]

Step 2

4-(3-(cyclopropanecarboxamido)-2-methylphenoxy)-
2-((2-fluoro-4-iodophenyl)amino)-1-methyl-6-oxo-1,
6-dihydropyridine-3-carboxamide The crude 4-(3-(cyclopropanecarboxamido)-2-methyl-phenoxy)-2-((2-fluoro-4-iodophenyl)amino)-N-(4-methoxybenzyl)-1-methyl-6-oxo-1,6-dihydropyridine-3-carb oxamide 7a (139 mg, 0.20 mmol) was dissolved in 5 mL of anisole, followed by addition of aluminum chloride (133 mg, 1 mmol). The reaction solution was warmed up to 120° C. and stirred for 1.5 hours, followed by addition of 10 mL water and 1 mL 1 M hydrochloric acid, then was extracted with ethyl acetate (20 mL×3). The organic phase was dried over anhydrous sodium sulfate, and filtered. The filtrate was concentrated under reduced pressure, and the resulting residue was purified by preparative separation method to obtain the title compound 4-(3-(cyclopropanecarboxamido)-2-methylphenoxy)-2-((2-fluoro-4-iodophenyl)amino)-1-methyl-6-oxo-1,6-dihydropyridine-3-carboxamide 7 (49 mg, light brown solid), yield: 42.6%.

MS m/z (ESI): 577.1 [M+1]

$^1$H NMR (400 MHz, DMSO-d$_6$): δ 9.88 (s, 1H), 9.70 (s, 1H), 7.59-7.69 (m, 3H), 7.38-7.46 (m, 2H), 7.28 (t, 1H), 7.05 (d, 1H), 6.66 (t, 1H), 4.96 (s, 1H), 3.14 (s, 3H), 2.01 (s, 3H), 1.83-1.94 (m, 1H), 0.75-0.83 (m, 4H).

Example 8

4-(3-propionamido-2-methylphenoxy)-2-((2-fluoro-
4-iodophenyl)amino)-1-methyl-6-oxo-1,6-dihydro-
pyridine-3-carboxamide

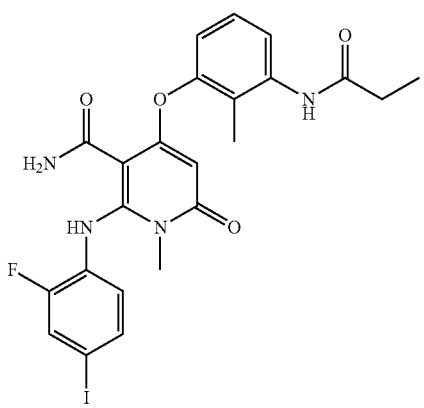

8

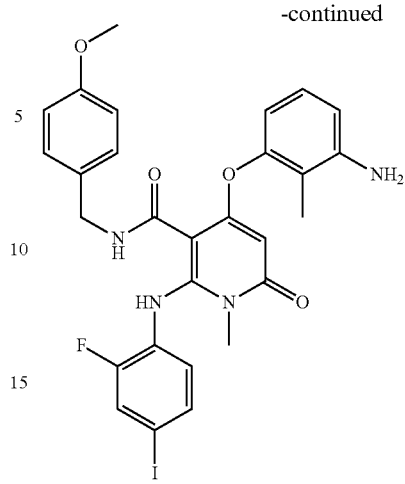

3c

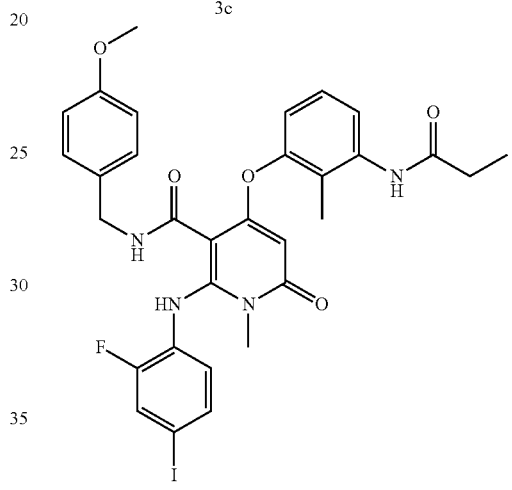

8a

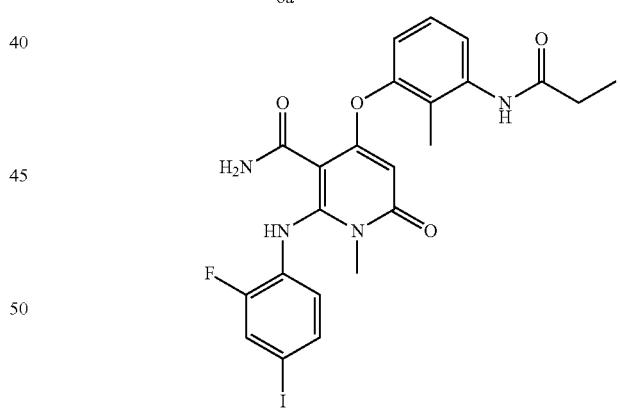

Step 1

4-(3-propionamido-2-methylphenoxy-)-2-((2-fluoro-
4-iodophenyl)amino)-N-(4-methoxybenzyl)-1-
methyl-6-oxo-1,6-dihydropyridine-3-carboxamide The crude 4-(3-amino-2-methylphenoxy)-2-((2-fluoro-4-iodophenyl)amino)-N-(4-methoxybenzyl)-1-methyl-6-oxo-1,6-dihydropyridine-3-carboxamide 3c (126 mg, 0.20 mmol) was dissolved in 2 mL of a mixture of dichloromethane and pyridine (V:V=1:1), followed by addition of propionyl chloride (20 mg, 0.22 mmol). After stirring for 12 hours, the reaction solution was concentrated under reduced pressure, and added with 30 mL of dichloromethane. The organic phase was washed with water (20 mL), dried over anhydrous sodium sulfate, filtered, and the filtrate was concentrated under reduced pressure to obtain the crude title compound 4-(3-propionamido-2-methylphenoxy-)-2-((2-fluoro-4-iodophenyl)amino)-N-(4-methoxybenzyl)-1-methyl-6-oxo-1,6-dihydropyridine-3-carboxamide 8a (137 mg, brown solid), which was used directly in the next step without further purification.

MS m/z (ESI): 685.1 [M+1]

Step 2

4-(3-propionamido-2-methylphenoxy)-2-((2-fluoro-4-iodophenyl)amino)-1-methyl-6-oxo-1,6-dihydropyridine-3-carboxamide The crude 4-(3-propionamido-2-methylphenoxy-)-2-((2-fluoro-4-iodophenyl)amino)-N-(4-methoxybenzyl)-1-methyl-6-oxo-1,6-dihydropyridine-3-carboxamide 8a (137 mg, 0.20 mmol) was dissolved in 5 mL of anisole, followed by addition of aluminum chloride (133 mg, 1 mmol). The reaction solution was warmed up to 120° C. and stirred for 1.5 hours, followed by addition of 10 mL of water and 1 mL of 1 M hydrochloric acid, and then was extracted with ethyl acetate (20 mL×3). The organic phase was dried over anhydrous sodium sulfate, and filtered. The filtrate was concentrated under reduced pressure, and the resulting residue was purified by preparative separation to obtain the title compound 4-(3-propionamido-2-methylphenoxy)-2-((2-fluoro-4-iodophenyl)amino)-1-methyl-6-oxo-1,6-dihydropyridine-3-carboxamide 8 (55 mg, light brown solid), yield: 48.7%.

MS m/z (ESI): 565.1 [M+1]
$^1$H NMR (400 MHz, DMSO-d$_6$): δ 9.89 (s, 1H), 9.39 (s, 1H), 7.59-7.69 (m, 3H), 7.35-7.46 (m, 2H), 7.29 (t, 1H), 7.06 (d, 1H), 6.66 (t, 1H), 4.96 (s, 1H), 3.14 (s, 3H), 2.36 (m, 2H), 1.99 (s, 3H), 1.10 (t, 3H).

Example 9

(S)-2-((2-fluoro-4-iodophenyl)amino)-1-methyl-4-(2-methyl-3-((tetrahydrofuran-3-yl)oxy)phenoxy)-6-oxo-1,6-dihydropyridine-3-carboxamide

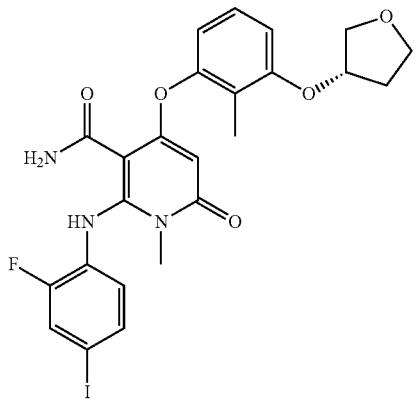

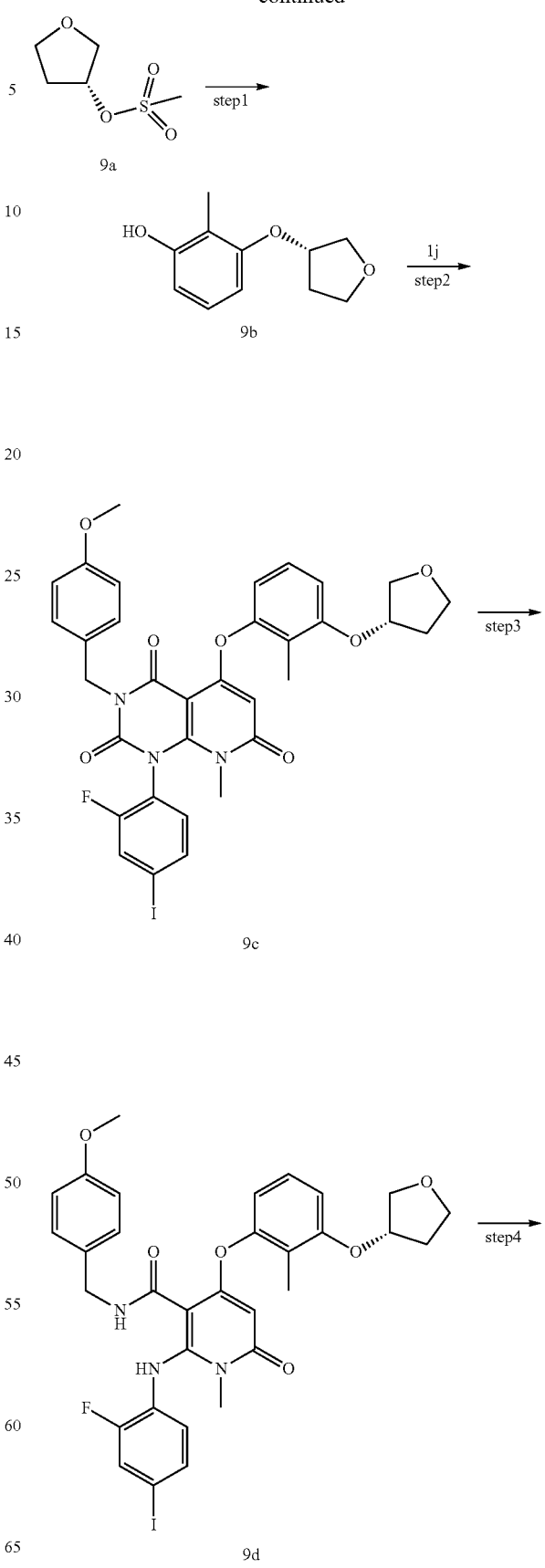

-continued

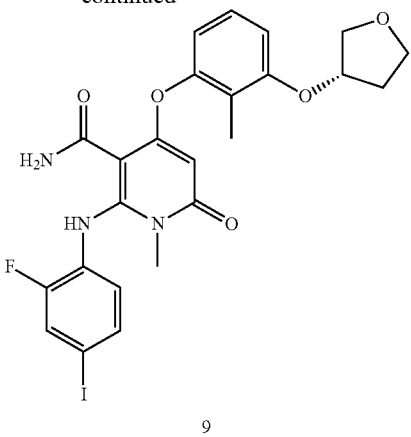

9

Step 1

(S)-2-methyl-3-((tetrahydrofuran-3-yl)oxy)phenol (R)-tetrahydrofuran-3-yl methanesulfonate 9a (373 mg, 3 mmol, prepared by a well known method disclosed in "*Journal of Organic Chemistry*, 73(14), 5397-5409; 2008"), 2-methylbenzene-1,3-diol (500 mg, 3 mmol) and cesium carbonate (977 mg, 3 mmol) were dissolved in 10 mL of dimethylformamide. The reaction solution was warmed up to 80° C. and stirred for 12 hours, followed by addition of 10 mL of water and 50 mL of ethyl acetate, added dropwise with 1 M hydrochloric acid to adjust the pH to 3, and then extracted with dichloromethane (20 mL×3). The organic phases were combined, washed with water (20 mL×3), dried over anhydrous sodium sulfate, and filtered. The filtrate was concentrated under reduced pressure, and the resulting residue was purified by silica gel column chromatography with eluent system B to obtain the title compound (S)-2-methyl-3-((tetrahydrofuran-3-yl)oxy)phenol 9b (290 mg, brown solid), yield: 49.8%.

MS m/z (ESI): 195.1 [M+1]

Step 2

(S)-1-(2-fluoro-4-iodophenyl)-3-(4-methoxybenzyl)-8-methyl-5-(2-methyl-3-((tetrahydrofuran-3-yl)oxy) phenoxy)pyrido[2,3-d]pyrimidine-2,4,7(1H,3H,8H)-trione (S)-2-methyl-3-((tetrahydrofuran-3-yl)oxy)phenol 9b (290 mg, 1.49 mmol) was dissolved in 10 mL of tetrahydrofuran, and sodium hydride (119 mg, 2.98 mmol) was added. After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (300 mg, 0.44 mmol), then warmed up to 60° C. and stirred for 2 hours. The reaction solution was concentrated under reduced pressure to obtain the crude title compound (S)-1-(2-fluoro-4-iodophenyl)-3-(4-methoxybenzyl)-8-methyl-5-(2-methyl-3-((tetrahydrofuran-3-yl)oxy)phenoxy)pyrido[2,3-d]pyrimidine-2,4,7(1H, 3H,8H)-trione 9c (319 mg, pale yellow oil), which was used directly in the next step without further purification.

Step 3

(S)-2-((2-fluoro-4-iodophenyl)amino)-N-(4-methoxybenzyl)-1-methyl-4-(2-methyl-3-((tetrahydrofuran-3-yl)oxy)phenoxy)-6-oxo-1,6-dihydropyridine-3-carboxamide The crude (S)-1-(2-fluoro-4-iodophenyl)-3-(4-methoxybenzyl)-8-methyl-5-(2-methyl-3-((tetrahydrofuran-3-yl) oxy)phenoxy)pyrimidine-2,4,7(1H,3H, 8H)-trione 9c (319 mg, 0.44 mmol) was dissolved in 6 mL of a mixture of tetrahydrofuran and water (V:V=5:1), followed by addition of lithium hydroxide (185 mg, 4.40 mmol). After stirring for 12 hours, the reaction solution was concentrated under reduced pressure, and added with 50 mL of ethyl acetate and 10 mL of water. The organic phase was dried over anhydrous sodium sulfate, filtered, and the filtrate was concentrated under reduced pressure to obtain the crude title compound (S)-2-((2-fluoro-4-iodophenyl)amino)-N-(4-methoxybenzyl)-1-methyl-4-(2-methyl-3-((tetrahydrofuran-3-yl)oxy)phenoxy)-6-oxo-1,6-dihydropyridine-3-carboxamide 9d (130 mg, gray solid), which was used directly in the next step without further purification.

MS m/z (ESI): 700.1 [M+1]

Step 4

(S)-2-((2-fluoro-4-iodophenyl)amino)-1-methyl-4-(2-methyl-3-((tetrahydrofuran-3-yl)oxy)phenoxy)-6-oxo-1,6-dihydropyridine-3-carboxamide The crude (S)-2-((2-fluoro-4-iodophenyl)amino)-N-(4-methoxybenzyl)-1-methyl-4-(2-methyl-3-((tetrahydrofuran-3-yl)oxy)phenoxy)-6-oxo-1,6-dihydropyridine-3-carboxamide 9d (130 mg, 0.20 mmol) was dissolved in 5 mL of anisole, followed by addition of chloride Aluminium (124 mg, 0.93 mmol). The reaction solution was warmed up to 120° C. and stirred for 4 hours, then was concentrated under reduced pressure, and added with 50 mL of ethyl acetate and 10 mL of water. The organic phase was dried over anhydrous sodium sulfate, and filtered. The filtrate was concentrated under reduced pressure, and the resulting residue was purified by preparative separation to obtain the title compound (S)-2-((2-fluoro-4-iodophenyl)amino)-1-methyl-4-(2-methyl-3-((tetrahydrofuran-3-yl)oxy)phenoxy)-6-oxo-1,6-dihydropyridine-3-carboxamide 9 (50 mg, light brown solid), yield: 46.5%.

MS m/z (ESI): 580.1 [M+1]

$^1$H NMR (400 MHz, DMSO-d$_6$) δ 9.90 (s, 1H), 7.62-7.67 (m, 3H), 7.42-7.44 (d, 1H), 7.26-7.31 (t, 1H), 6.93-6.96 (d, 1H), 6.83-6.85 (d, 1H), 6.64-6.69 (t, 1H), 5.10 (br, 1H), 5.00 (s, 1H), 3.76-3.95 (m, 4H), 3.15 (s, 3H), 2.22-2.27 (m, 1H), 2.19-2.03 (m, 4H).

Example 10
4-(2-methyl-3-(methylcarbamoyl)phenoxy)-2-((2-fluoro-4-iodophenyl)amino)-1-methyl-6-oxo-1,6-dihydropyridine-3-carboxamide
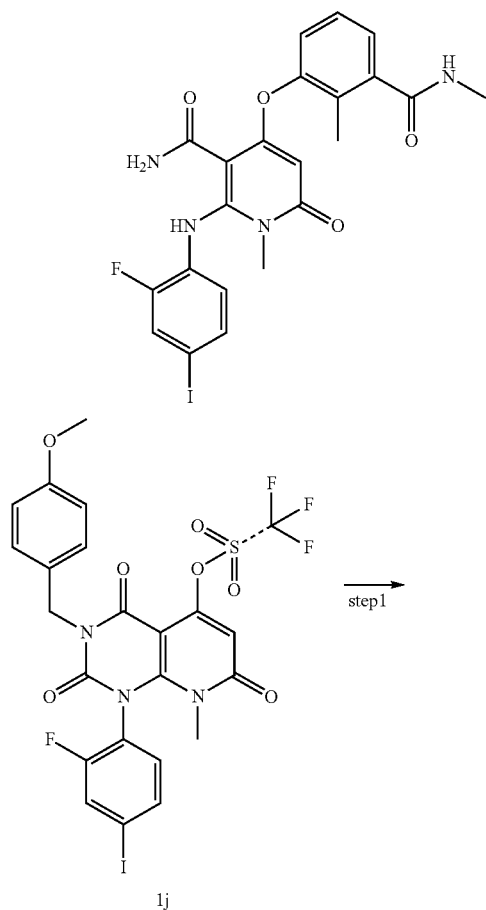
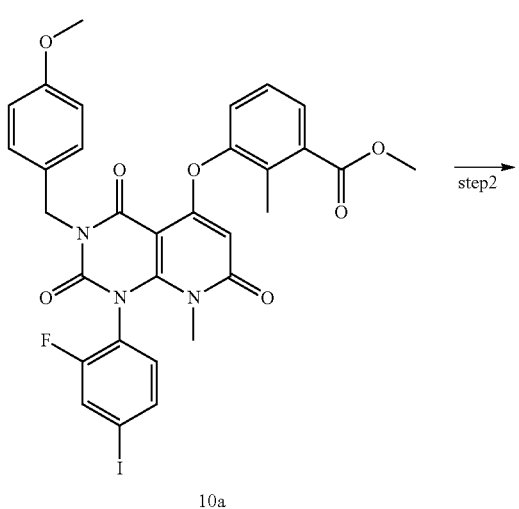
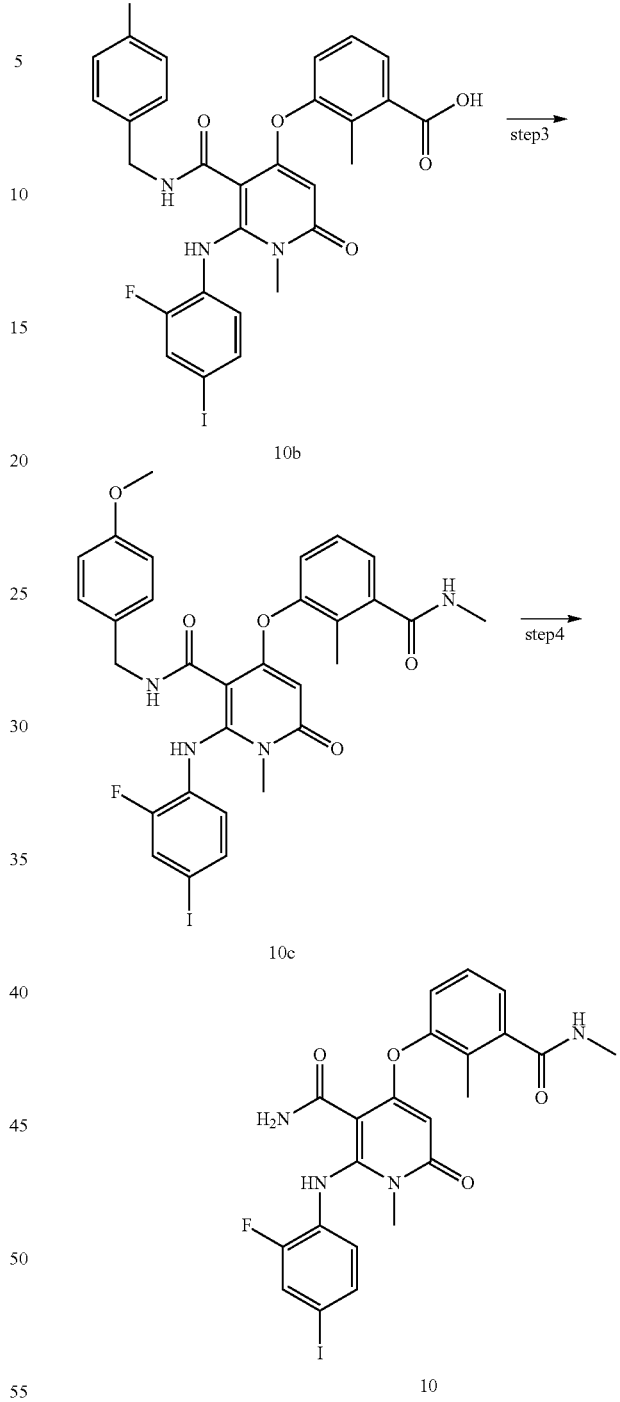
Step 1
methyl 3-((1-(2-fluoro-4-iodophenyl)-3-(4-methoxybenzyl)-8-methyl-2,4,7-trioxo-1,2,3,4,7,8-hexahydropyrido[2,3-d]pyrimidin-5-yl)oxy)-2-methylbenzoate
Methyl 3-hydroxy-2-methylbenzoate (122 mg, 0.73 mmol, prepared by a known method disclosed in "Tetrahedron Letters, 48 (31), 5465-5469; 2007") was dissolved in 10 mL of tetrahydrofuran, followed by addition of sodium hydride (60 mg, 1.50 mmol). After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (500 mg, 0.73 mmol), warmed up to 70° C. and stirred for 2 hours. The reaction solution was concentrated under reduced pressure to obtain the crude title compound methyl 3-((1-(2-fluoro-4-iodophenyl)-3-(4-methoxybenzyl)-8-methyl-2,4,7-trioxo-1,2,3,4,7,8-hexahydropyrido[2,3-d]pyrimidin-5-yl)oxy)-2-methylbenzoate 10a (509 mg, light yellow liquid), which was used directly in the next step without further purification.

MS m/z (ESI): 698.1 [M+1]

Step 2

3-((6-((2-fluoro-4-iodophenyl)amino)-5-((4-methoxybenzyl)carbamoyl)-1-methyl-2-oxo-1,2-dihydropyridin-4-yl)oxy)-2-methylbenzoic acid The crude methyl 3-((1-(2-fluoro-4-iodophenyl)-3-(4-methoxybenzyl)-8-methyl-2,4,7-trioxo-1,2,3,4,7,8-hexahydropyrido[2,3-d]pyrimidin-5-yl)oxy)-2-methylbenzoate 10a (509 mg, 0.73 mmol) was dissolved in 24 mL of a mixture of tetrahydrofuran and water (V:V=5:1), followed by addition of lithium hydroxide (308 mg, 7.34 mmol). After stirring for 12 hours, the reaction was added with 10 mL of water and 50 mL of ethyl acetate. The organic phase was dried over anhydrous sodium sulfate, filtered, and the filtrate was concentrated under reduced pressure to obtain the crude title compound 3-((6-((2-fluoro-4-iodophenyl)amino)-5-((4-methoxybenzyl)carbamoyl)-1-methyl-2-oxo-1,2-dihydropyridin-4-yl)oxy)-2-methylbenzoic acid 10b (500 mg, yellow solid), which was used directly in the next step without further purification.

MS m/z (ESI): 658.1 [M+1]

Step 3

4-(2-methyl-3-(methylcarbamoyl)phenoxy)-2-((2-fluoro-4-iodophenyl)amino)-N-(4-methoxybenzyl)-1-methyl-6-oxo-1,6-dihydropyridine-3-carboxamide The crude 3-((6-((2-fluoro-4-iodophenyl)amino)-5-((4-methoxybenzyl) carbamoyl)-1-methyl-2-oxo-1,2-dihydropyridin-4-yl)oxy)-2-methylbenzoic acid 10b (250 mg, 0.38 mmol) was dissolved in 5 mL of dimethylformamide, followed by addition of 1-ethyl-3-(3-dimethylaminopropyl) carbodiimide hydrochloride (146 mg, 0.76 mmol), 1-hydroxybenzotriazole (103 mg, 0.76 mmol), and 0.5 mL of N,N-diisopropylethylamine successively. After stirring for 10 minutes, the reaction solution was added with methylamine (0.2 mL, 0.38 mmol) and stirred for 12 hours, followed by addition of 20 mL of 10% lithium chloride and 50 mL of ethyl acetate. The organic phase was dried over anhydrous sodium sulfate, filtered, and the filtrate was concentrated under reduced pressure to obtain the crude title compound 4-(2-methyl-3-(methylcarbamoyl)phenoxy)-2-((2-fluoro-4-iodophenyl)amino)-N-(4-methoxybenzyl)-1-methyl-6-oxo-1,6-dihydropyridine-3-carboxamide 10c (200 mg, brown solid), which was used directly in the next step without further purification.

Step 4

4-(2-methyl-3-(methylcarbamoyl)phenoxy)-2-((2-fluoro-4-iodophenyl)amino)-1-methyl-6-oxo-1,6-dihydropyridine-3-carboxamide The crude 4-(2-methyl-3-(methylcarbamoyl)phenoxy)-2-((2-fluoro-4-iodophenyl)amino)-N-(4-methoxybenzyl)-1-methyl-6-oxo-1,6-dihydropyridine-3-carboxamide 10c (200 mg, 0.30 mmol) was dissolved in 5 mL of anisole, followed by addition of aluminum chloride (200 mg, 1.50 mmol). The reaction solution was warmed up to 120° C. and stirred for 3 hours, then was concentrated under reduced pressure, and added with 50 mL of ethyl acetate and 15 mL of water. The organic phase was dried over anhydrous sodium sulfate, and filtered. The filtrate was concentrated under reduced pressure, and the resulting residue was purified by preparative separation to obtain the title compound 4-(2-methyl-3-(methylcarbamoyl)phenoxy)-2-((2-fluoro-4-iodophenyl)amino)-1-methyl-6-oxo-1,6-dihydropyridine-3-carboxamide 10 (35 mg, white solid), yield: 21.3%.

MS m/z (ESI): 551.1 [M+1]

$^1$H NMR (400 MHz, DMSO-d$_6$) δ 9.90 (s, 1H), 8.31-8.33 (m, 1H), 7.63-7.67 (m, 3H), 7.27-7.45 (m, 4H), 6.65-6.70 (t, 1H), 5.01 (s, 1H), 3.15 (s, 3H), 2.76-2.78 (d, 3H), 2.12 (s, 3H).

Example 11

4-(3-(cyclopropylcarbamoyl)-2-methylphenoxy)-2-((2-fluoro-4-iodophenyl)amino)-1-methyl-6-oxo-1,6-dihydropyridine-3-carboxamide

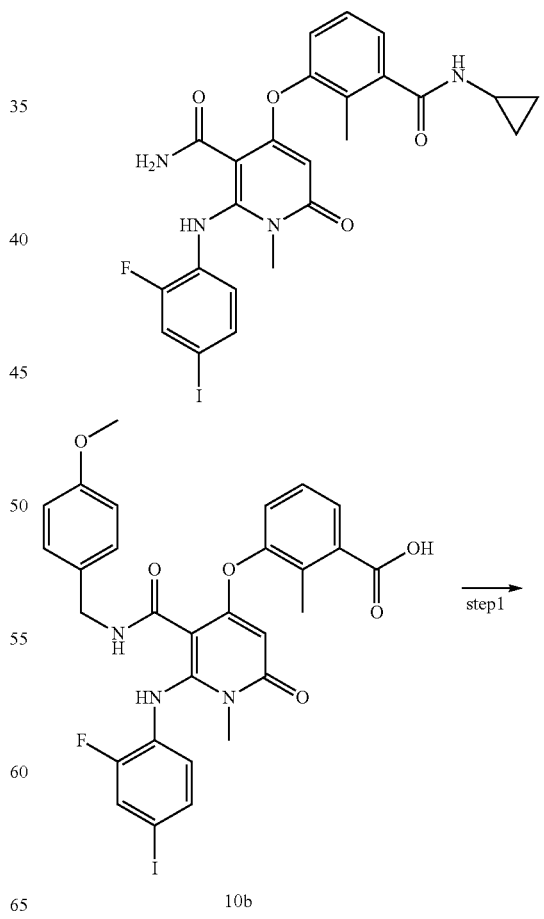

10b

-continued

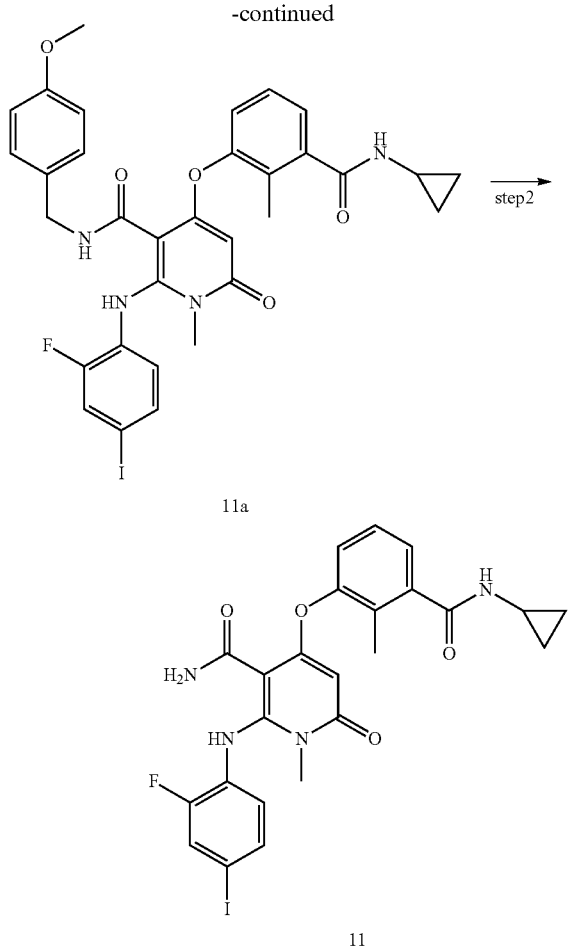

11a

11

Step 1

4-(3-(cyclopropylcarbamoyl)-2-methylphenoxy)-2-((2-fluoro-4-iodophenyl)amino)-N-(4-methoxybenzyl)-1-methyl-6-oxo-1,6-dihydropyridine-3-carboxamide The crude 3-((6-((2-fluoro-4-iodophenyl)amino)-5-((4-methoxybenzyl) carbamoyl)-1-methyl-2-oxo-1,2-dihydropyridin-4-yl)oxy)-2-methylbenzoic acid 10b (250 mg, 0.38 mmol) was dissolved in 5 mL of dimethylformamide, followed by addition of 1-ethyl-3-(3-dimethylaminopropyl) carbodiimide hydrochloride (146 mg, 0.76 mmol), 1-hydroxybenzotriazole (103 mg, 0.76 mmol), and 0.5 mL of N',N'-diisopropylethylamine, successively. After stirring for 10 minutes, the reaction solution was added with cyclopropanemethylamine (22 mg, 0.38 mmol) and stirred for 12 hours, followed by addition of 20 mL of 10% lithium chloride and 50 mL of ethyl acetate. The organic phase was dried over anhydrous sodium sulfate, filtered, and the filtrate was concentrated under reduced pressure to obtain the crude title compound 4-(3-(cyclopropylcarbamoyl)-2-methylphenoxy)-2-((2-fluoro-4-iodophenyl)amino)-N-(4-methoxybenzyl)-1-methyl-6-oxo-1,6-dihydropyridine-3-carboxamide 11a (130 mg, brown solid), which was used directly in the next step without further purification.

Step 2

4-(3-(cyclopropylcarbamoyl)-2-methylphenoxy)-2-((2-fluoro-4-iodophenyl)amino)-1-methyl-6-oxo-1,6-dihydropyridine-3-carboxamide The crude 4-(3-(cyclopropylcarbamoyl)-2-methylphenoxy)-2-((2-fluoro-4-iodophenyl)amino)-N-(4-methoxybenzyl)-1-methyl-6-oxo-1,6-dihydropyridine-3-carboxamide 11a (130 mg, 0.20 mmol) was dissolved in 5 mL of anisole, followed by addition of aluminum chloride (133 mg, 1 mmol). The reaction solution was warmed up to 120° C. and stirred for 3 hours, then was concentrated under reduced pressure, and added with 50 mL of ethyl acetate and 15 mL of water. The organic phase was dried over anhydrous sodium sulfate, and filtered. The filtrate was concentrated under reduced pressure, and the resulting residue was purified by preparative separation to obtain the title compound 4-(3-(cyclopropylcarbamoyl)-2-methylphenoxy)-2-((2-fluoro-4-iodophenyl)amino)-1-methyl-6-oxo-1,6-dihydropyridine-3-carboxamide 11 (40 mg, brown solid), yield: 35.4%.

MS m/z (ESI): 577.1 [M+1]

$^1$H NMR (400 MHz, DMSO-$d_6$) δ 9.90 (s, 1H), 8.43-8.45 (d, 1H), 7.63-7.67 (m, 3H), 7.24-7.45 (m, 4H), 6.65-6.70 (t, 1H), 5.01 (s, 1H), 3.15 (s, 3H), 2.83-2.84 (m, 1H), 2.11 (s, 3H), 0.68-0.71 (m, 2H), 0.52-0.54 (m, 2H).

Example 12

(R)-2-((2-fluoro-4-iodophenyl)amino)-1-methyl-4-(2-methyl-3-((tetrahydrofuran-3-yl)oxy)phenoxy)-6-oxo-1,6-dihydropyridine-3-carboxamide

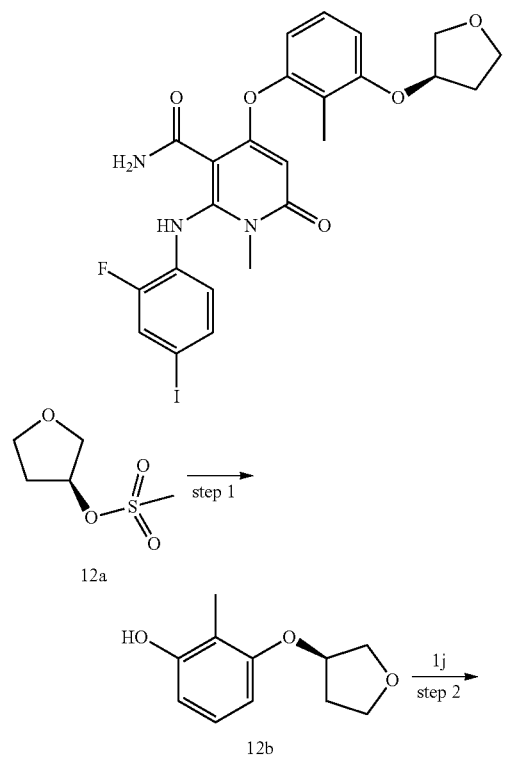

12a

12b

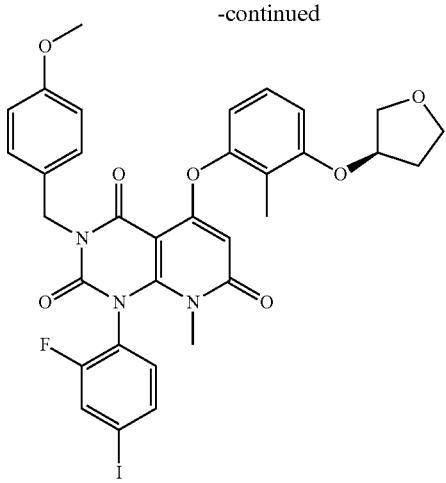

12c

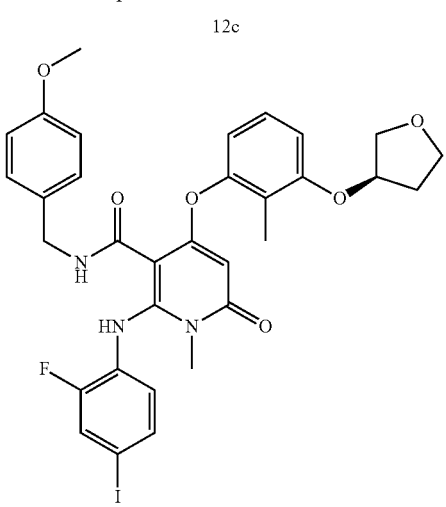

12d

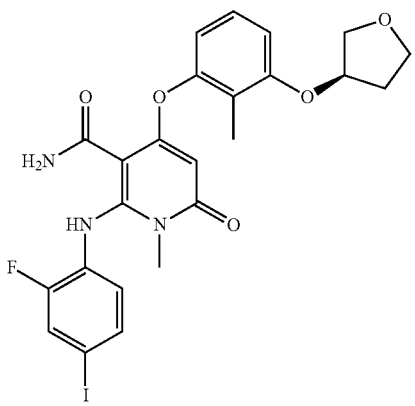

12

Step 1

(R)-2-methyl-3-((tetrahydrofuran-3-yl)oxy)phenol (S)-tetrahydrofuran-3-yl methanesulfonate 12a (1.65 g, 9.93 mmol, prepared by a well known method disclosed in "Journal of Organic Chemistry, 73 (14), 5397-5409; 2008"), 2-methylbenzene-1,3-diol (2.46 g, 19.90 mmol), and cesium carbonate (3.23 g, 9.93 mmol) were dissolved in 250 mL of dimethylformamide. The reaction solution was warmed up to 80° C. and stirred for 12 hours, added dropwise with 1 M hydrochloric acid to adjust the pH to 7, and extracted with dichloromethane (100 mL×3). The organic phases were combined, washed with water (100 mL×3), dried over anhydrous sodium sulfate, and filtered. The filtrate was concentrated under reduced pressure, and the resulting residue was purified by silica gel column chromatography with eluent system B to obtain the title compound (R)-2-methyl-3-((tetrahydrofuran-3-yl)oxy)phenol 12b (1.03 g, off-white solid), yield: 53.3%.

MS m/z (ESI): 195.1 [M+1]

Step 2

(R)-1-(2-fluoro-4-iodophenyl)-3-(4-methoxybenzyl)-8-methyl-5-(2-methyl-3-((tetrahydrofuran-3-yl)oxy)phenoxy)pyrido[2,3-d]pyrimidine-2,4,7(1H,3H,8H)-trione (R)-2-methyl-3-((tetrahydrofuran-3-yl)oxy)phenol 12b (47 mg, 0.24 mmol) was dissolved in 5 mL of tetrahydrofuran, and sodium hydride (12 mg, 0.30 mmol) was added. After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), then warmed up to 60° C. and stirred for 1 hour. The reaction solution was concentrated under reduced pressure to obtain the crude title compound (R)-1-(2-fluoro-4-iodophenyl)-3-(4-methoxybenzyl)-8-methyl-5-(2-methyl-3-((tetrahydrofuran-3-yl)oxy)phenoxy)pyrido[2,3-d]pyrimidine-2,4,7(1H,3H,8H)-trione 12c (145 mg, pale yellow oil), which was used directly in the next step without further purification.

Step 3

(R)-2-((2-fluoro-4-iodophenyl)amino)-N-(4-methoxybenzyl)-1-methyl-4-(2-methyl-3-((tetrahydrofuran-3-yl)oxy)phenoxy)-6-oxo-1,6-dihydropyridine-3-carboxamide The crude (R)-1-(2-fluoro-4-iodophenyl)-3-(4-methoxybenzyl)-8-methyl-5-(2-methyl-3-((tetrahydrofuran-3-yl)oxy)phenoxy)pyrido[2,3-d]pyrimidine-2,4,7(1H,3H,8H)-trione 12c (145 mg, 0.20 mmol) was dissolved in 6 mL of a mixture of tetrahydrofuran and water (V:V=4:1), followed by addition of lithium hydroxide (168 mg, 4 mmol). The reaction solution was warmed up to 40° C. and stirred for 1 hour, then added with 10 mL water, and extracted with dichloromethane (10 mL×3). The organic phases were combined, dried over anhydrous sodium sulfate, filtered, and the filtrate was concentrated under reduced pressure to obtain the crude title compound (R)-2-((2-fluoro-4-iodophenyl)amino)-N-(4-methoxybenzyl)-1-methyl-4-(2-methyl-3-((tetrahydrofuran-3-yl)oxy)phenoxy)-6-oxo-1,6-dihydropyridine-3-carboxamide 12d (140 mg, light brown solid), which was used directly in the next step without further purification.

MS m/z (ESI): 700.0 [M+1]

Step 4

(R)-2-((2-fluoro-4-iodophenyl)amino)-1-methyl-4-(2-methyl-3-((tetrahydrofuran-3-yl)oxy)phenoxy)-6-oxo-1,6-dihydropyridine-3-carboxamide The crude (R)-2-((2-fluoro-4-iodophenyl)amino)-N-(4-methoxybenzyl)-1-methyl-4-(2-methyl-3-((tetrahydrofuran- 3-yl)oxy)phenoxy)-6-oxo-1,6-dihydropyridine-3-carboxamide 12d (140 mg, 0.20 mmol) was dissolved in 5 mL of anisole, followed by addition of aluminum chloride (133 mg, 1 mmol). The reaction solution was warmed up to 120° C. and stirred for 3.5 hours, added with 10 mL of water and 1 mL 1 M hydrochloric acid, and extracted with ethyl acetate (20 mL×3). The organic phase was dried over anhydrous sodium sulfate, and filtered. The filtrate was concentrated under reduced pressure, and the resulting residue was purified by preparative separation to obtain the title compound (R)-2-((2-fluoro-4-iodophenyl)amino)-1-methyl-4-(2-methyl-3-((tetrahydrofuran-3-yl)oxy)phenoxy)-6-oxo-1,6-dihydropyridine-3-carboxamide 12 (35 mg, light brown solid), yield: 30.1%.

MS m/z (ESI): 580.1 [M+1]

$^1$H NMR (400 MHz, DMSO-d$_6$): δ 9.89 (s, 1H), 7.59-7.69 (m, 3H), 7.40-7.47 (m, 1H), 7.29 (t, 1H), 6.95 (d, 1H), 6.84 (d, 1H), 6.67 (t, 1H), 5.07-5.13 (m, 1H), 4.99 (s, 1H), 3.75-3.95 (m, 4H), 3.13 (s, 3H), 2.19-2.29 (m, 1H), 1.97-2.04 (m, 1H), 1.95 (s, 3H).

Example 13

4-(3-acetyl-2-methylphenoxy)-2-((2-fluoro-4-iodophenyl)amino)-1-methyl-6-oxo-1,6-dihydropyridine-3-carboxamide

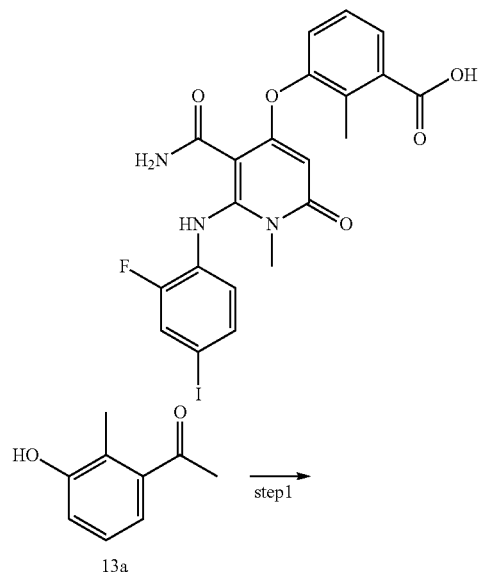

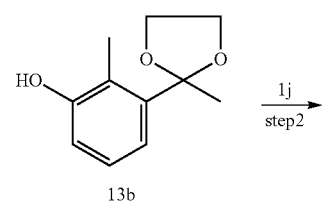

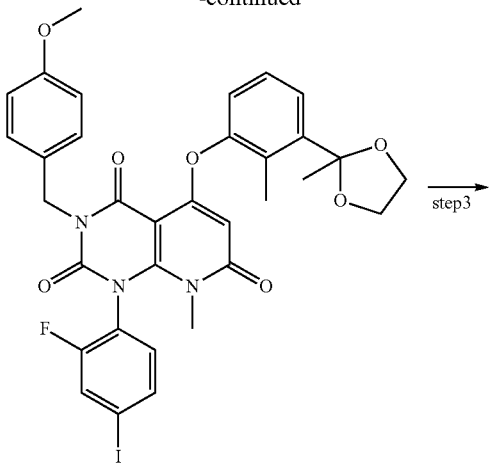

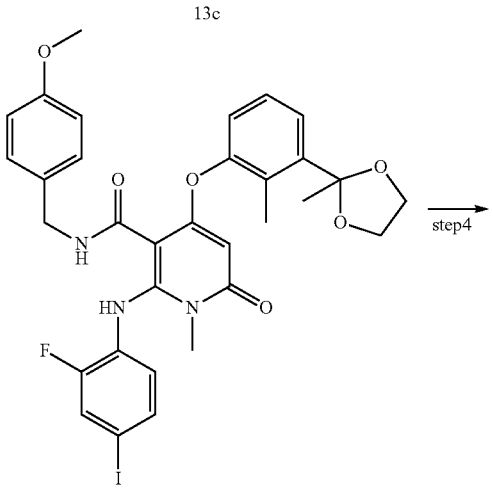

Step 1

2-methyl-3-(2-methyl-1,3-dioxolan-2-yl)phenol 1-(3-hydroxy-2-methylphenyl)ethanone 13a (3 g, 20 mmol, prepared by a well known method disclosed in "*Journal of Medicinal Chemistry*, 52 (20), 6433-6446; 2009") and 30 mL of ethylene glycol were dissolved in 30 mL of toluene. After stirring for 3.5 hours under reflux, the reaction solution was added with 200 mL of ethyl acetate, washed with water (100 mL×3), dried over anhydrous sodium sulfate, and filtered. The filtrate was concentrated under reduced pressure, and the resulting residue was purified by silica gel column chromatography with eluent system B to obtain the title compound 2-methyl-3-(2-methyl-1,3-dioxolan-2-yl)phenol 13b (1.03 g, white solid), yield: 54.1%.

MS m/z (ESI): 195.1 [M+1]

Step 2

1-(2-fluoro-4-iodophenyl)-3-(4-methoxybenzyl)-8-methyl-5-(2-methyl-3-(2-methyl-1,3-dioxolan-2-yl)phenoxy)pyrido[2,3-d]pyrimidine-2,4,7(1H,3H,8H)-trione 2-methyl-3-(2-methyl-1,3-dioxolan-2-yl)phenol 13b (47 mg, 0.24 mmol) was dissolved in 5 mL of tetrahydrofuran, followed by addition of sodium hydride (12 mg, 0.30 mmol). After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), then warmed up to 60° C. and stirred for 1 hour. The reaction solution was concentrated under reduced pressure to obtain the crude title compound 1-(2-fluoro-4-iodophenyl)-3-(4-methoxybenzyl)-8-methyl-5-(2-methyl-3-(2-methyl-1,3-dioxolan-2-yl)phenoxy)pyrido[2,3-d]pyrimidine-2,4,7(1H,3H,8H)-trione 13c (145 mg, pale yellow liquid), which was used directly in the next step without further purification.

MS m/z (ESI): 726.2 [M+1]

Step 3

2-((2-fluoro-4-iodophenyl)amino)-N-(4-methoxybenzyl)-1-methyl-4-(2-methyl-3-(2-methyl-1,3-dioxolan-2-yl)phenoxy)-6-oxo-1,6-dihydropyridine-3-carboxamide The crude 1-(2-fluoro-4-iodophenyl)-3-(4-methoxybenzyl)-8-methyl-5-(2-methyl-3-(2-methyl-1,3-dioxolan-2-yl)phenoxy)pyrido[2,3-d]pyrimidine-2,4,7(1H,3H,8H)-trione 13c (145 mg, 0.20 mmol) was dissolved in 6 mL of a mixture of tetrahydrofuran and water (V:V=4:1), followed by addition of lithium hydroxide (168 mg, 4 mmol). The reaction solution was warmed up to 40° C. and stirred for 1 hour. The reaction solution was added with 50 mL of ethyl acetate, washed with water (25 mL×3), dried over anhydrous sodium sulfate, filtered, and the filtrate was concentrated under reduced pressure to obtain the crude title compound 2-((2-fluoro-4-iodophenyl)amino)-N-(4-methoxybenzyl)-1-methyl-4-(2-methyl-3-(2-methyl-1,3-dioxolan-2-yl)phenoxy)-6-oxo-1,6-dihydropyridine-3-carboxamide 13d (140 mg, light brown solid), which was used directly in the next step without further purification.

MS m/z (ESI): 700.1 [M+1]

Step 4

4-(3-acetyl-2-methylphenoxy)-2-((2-fluoro-4-iodophenyl)amino)-1-methyl-6-oxo-1,6-dihydropyridine-3-carboxamide The crude 2-((2-fluoro-4-iodophenyl)amino)-N-(4-methoxybenzyl)-1-methyl-4-(2-methyl-3-(2-methyl-1,3-dioxolan-2-yl)phenoxy)-6-oxo-1,6-dihydropyridine-3-carboxamide 13d (140 mg, 0.20 mmol) was dissolved in 5 mL of anisole, followed by addition of aluminum chloride (133 mg, 1 mmol). The reaction solution was warmed up to 120° C. and stirred for 3.5 hours, added with 10 mL of water and 1 mL 1 M hydrochloric acid, and extracted with ethyl acetate (20 mL×3). The organic phase was dried over anhydrous sodium sulfate, and filtered. The filtrate was concentrated under reduced pressure, and the resulting residue was purified by preparative separation to obtain the title compound 4-(3-acetyl-2-methylphenoxy)-2-((2-fluoro-4-iodophenyl)amino)-1-methyl-6-oxo-1,6-dihydropyridine-3-carboxamide 13 (7 mg, light brown solid), yield: 6.5%.

MS m/z (ESI): 536.1 [M+1]

$^1$H NMR (400 MHz, DMSO-$d_6$): δ 9.87 (s, 1H), 7.74-7.78 (m, 1H), 7.59-7.69 (m, 3H), 7.39-7.49 (m, 3H), 6.67 (t, 1H), 4.95 (s, 1H), 3.14 (s, 3H), 2.60 (s, 3H), 2.19 (s, 3H).

Example 14

4-(3-chloro-2-methylphenoxy)-2-((2-fluoro-4-iodophenyl)amino)-1-methyl-6-oxo-1,6-dihydropyridine-3-carboxamide

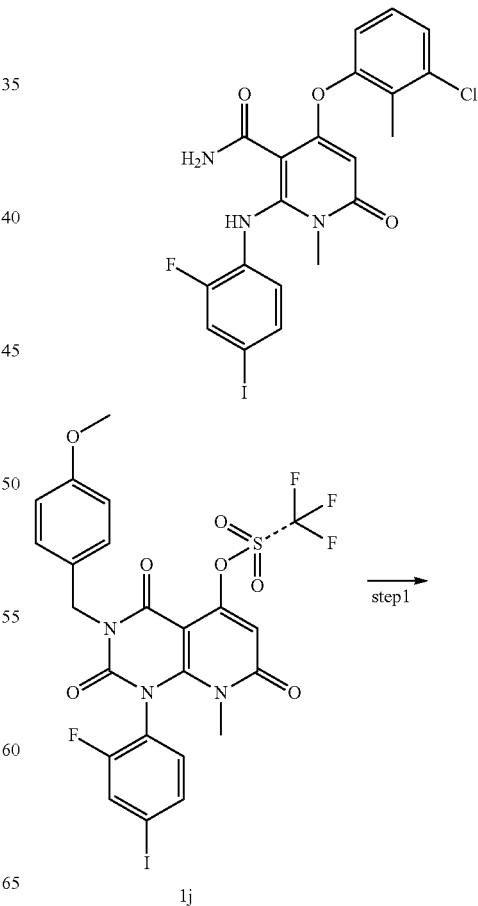

-continued

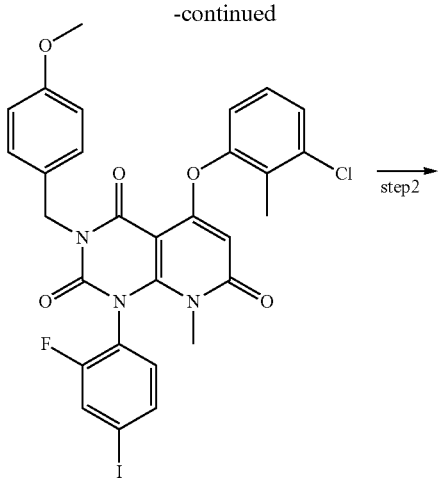

14a

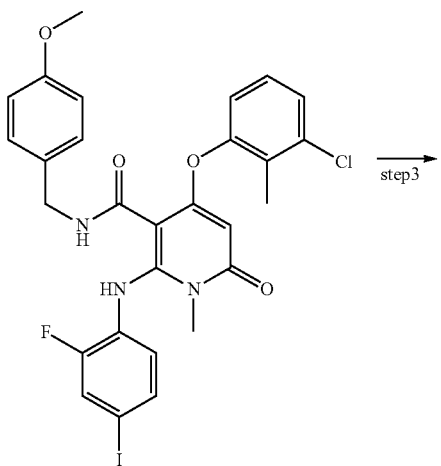

14b

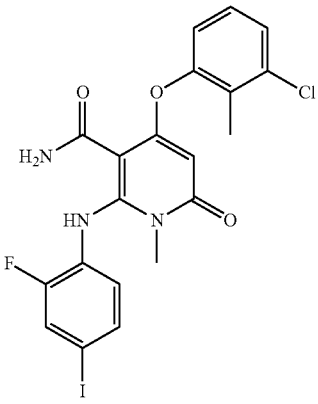

14

Step 1

5-(3-chloro-2-methylphenoxy)-1-(2-fluoro-4-iodophenyl)-3-(4-methoxybenzyl)-8-methylpyrido[2,3-d]pyrimidine-2,4,7(1H,3H,8H)-trione 3-chloro-2-methyl-phenol (26 mg, 0.18 mmol) was dissolved in 5 mL of tetrahydrofuran, followed by addition of sodium hydride (9 mg, 0.23 mmol). After stirring for 1 hour, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (102 mg, 0.15 mmol) and stirred for 12 hours. The reaction solution was concentrated under reduced pressure to obtain the crude title compound 5-(3-chloro-2-methylphenoxy)-1-(2-fluoro-4-iodophenyl)-3-(4-methoxybenzyl)-8-methylpyrido[2,3-d]pyrimidine-2,4,7(1H,3H,8H)-trione 14a (100 mg, pale yellow liquid), which was used directly in the next step without further purification.

MS m/z (ESI): 674.0 [M+1]

Step 2

4-(3-chloro-2-methylphenoxy)-2-((2-fluoro-4-iodophenyl)amino)-N-(4-methoxybenzyl)-1-methyl-6-oxo-1,6-dihydropyridine-3-carboxamide The crude 5-(3-chloro-2-methylphenoxy)-1-(2-fluoro-4-iodophenyl)-3-(4-methoxybenzyl)-8-methylpyrido[2,3-d]pyrimidine-2,4,7(1H,3H,8H)-trione 14a (100 mg, 0.15 mmol) was dissolved in 6 mL of a mixture of tetrahydrofuran and water (V:V=5:1), followed by addition of lithium hydroxide (31 mg, 0.75 mmol). The reaction was stirred for 12 hours, and added with 10 mL of water and 50 mL of ethyl acetate. The organic phase was dried over anhydrous sodium sulfate, filtered, and the filtrate was concentrated under reduced pressure to obtain the crude title compound 4-(3-chloro-2-methylphenoxy)-2-((2-fluoro-4-iodophenyl)amino)-N-(4-methoxybenzyl)-1-methyl-6-oxo-1,6-dihydropyridine-3-carboxamide 14b (106 mg, yellow brown oil), which was used directly in the next step without further purification.

MS m/z (ESI): 648.0 [M+1]

Step 3

4-(3-chloro-2-methylphenoxy)-2-((2-fluoro-4-iodophenyl)amino)-1-methyl-6-oxo-1,6-dihydropyridine-3-carboxamide The crude 4-(3-chloro-2-methylphenoxy)-2-((2-fluoro-4-iodophenyl)amino)-N-(4-methoxybenzyl)-1-methyl-6-oxo-1,6-dihydropyridine-3-carboxamide 14b (106 mg, 0.15 mmol) was dissolved in 5 mL of anisole, followed by addition of aluminum chloride (100 mg, 0.75 mmol). After stirring for 3 hours at 120° C., the reaction solution was concentrated under reduced pressure, added with 50 mL of ethyl acetate and 15 mL of water. The organic phase was washed with 1 M hydrochloric acid (25 mL×3), dried over anhydrous sodium sulfate, and filtered. The filtrate was concentrated under reduced pressure, and the resulting residue was purified by preparative separation to obtain the title compound 4-(3-chloro-2-methylphenoxy)-2-((2-fluoro-4-iodophenyl) amino)-1-methyl-6-oxo-1,6-dihydropyridine-3-carboxamide 14 (21 mg, white solid), yield: 26.5%.

MS m/z (ESI): 528.0 [M+1]

$^1$H NMR (400 MHz, DMSO-d$_6$): δ 9.79 (s, 1H), 7.60-7.68 (m, 3H), 7.41-7.47 (m, 2H), 7.36 (t, 1H), 7.23 (d, 1H), 6.67 (t, 1H), 5.00 (s, 1H), 3.15 (s, 3H), 2.18 (s, 3H).

Example 15

4-(2-chloro-4-methylphenoxy)-2-((2-fluoro-4-iodophenyl)amino)-1-methyl-6-oxo-1,6-dihydropyridine-3-carboxamide

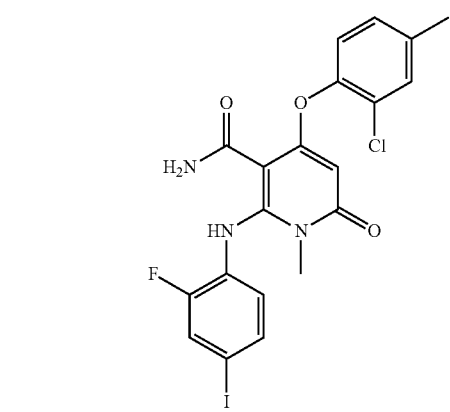

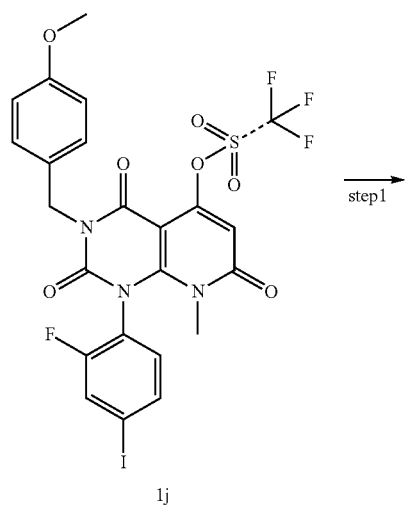

1j

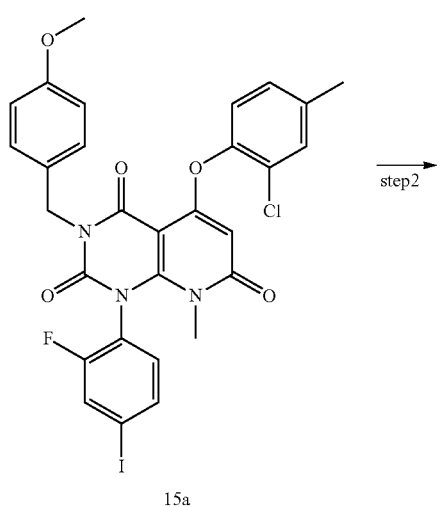

15a

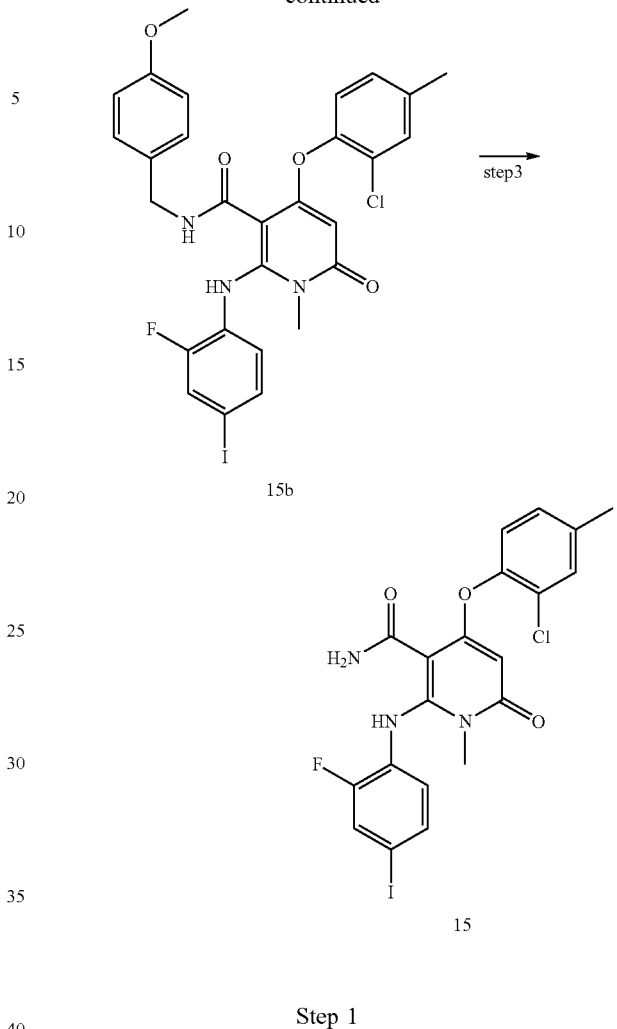

15b

15

Step 1

5-(2-chloro-4-methylphenoxy)-1-(2-fluoro-4-iodophenyl)-3-(4-methoxybenzyl)-8-methylpyrido[2,3-d]pyrimidine-2,4,7(1H,3H,8H)-trione 2-chloro-4-methyl-phenol (34 mg, 0.24 mmol) was dissolved in 5 mL of tetrahydrofuran, followed by addition of sodium hydride (12 mg, 0.30 mmol). After stirring for 2 hours, the reaction solution was added with 1-(2-fluoro-4-iodophenyl)-3-(4-methoxybenzyl)-8-methyl-2,4,7-trioxopyrido[2,3-d]pyrimidin-5-yl trifluoromethanesulfonate 1j (136 mg, 0.20 mmol), and stirred for 12 hours. The reaction solution was concentrated under reduced pressure to obtain the crude title compound 5-(2-chloro-4-methylphenoxy)-1-(2-fluoro-4-iodophenyl)-3-(4-methoxybenzyl)-8-methylpyrido[2,3-d]pyrimidine-2,4,7(1H,3H,8H)-trione 15a (135 mg, pale yellow liquid), which was used directly in the next step without further purification.

MS m/z (ESI): 674.0 [M+1]

Step 2

4-(2-chloro-4-methylphenoxy)-2-((2-fluoro-4-iodophenyl)amino)-N-(4-methoxybenzyl)-1-methyl-6-oxo-1,6-dihydropyridine-3-carboxamide The crude 5-(2-chloro-4-methylphenoxy)-1-(2-fluoro-4-iodophenyl)-3-(4-methoxybenzyl)-8-methylpyrido[2,3-d]

pyrimidine-2,4,7(1H,3H,8H)-trione 15a (135 mg, 0.20 mmol) was dissolved in 6 mL of a mixture of tetrahydrofuran and water (V:V=4:1), followed by addition of lithium hydroxide (168 mg, 4 mmol). The reaction solution was warmed up to 40° C. and stirred for 1 hour, followed by addition of 50 mL of ethyl acetate. The organic phase was washed with 1 M sodium hydroxide solution (25 mL×3), dried over anhydrous sodium sulfate, filtered, and the filtrate was concentrated under reduced pressure to obtain the crude title compound 4-(2-chloro-4-methylphenoxy)-2-((2-fluoro-4-iodophenyl)amino)-N-(4-methoxybenzyl)-1-methyl-6-oxo-1,6-dihydropyridine-3-carboxamide 15b (130 mg, yellow-brown solid), which was used directly in the next step without further purification.

MS m/z (ESI): 648.1 [M+1]

Step 3

4-(2-chloro-4-methylphenoxy)-2-((2-fluoro-4-iodophenyl)amino)-1-methyl-6-oxo-1,6-dihydropyridine-3-carboxamide The crude 4-(2-chloro-4-methylphenoxy)-2-((2-fluoro-4-iodophenyl)amino)-N-(4-methoxybenzyl)-1-methyl-6-oxo-1,6-dihydropyridine-3-carboxamide 15b (130 mg, 0.20 mmol) was dissolved in 5 mL of anisole, followed by addition of aluminum chloride (133 mg, 1 mmol). The reaction solution was warmed up to 120° C. and stirred for 1.5 hours, followed by addition of 10 mL of water and 1 mL of 1 M hydrochloric acid, and extracted with ethyl acetate (20 mL×3). The organic phase was dried over anhydrous sodium sulfate, and filtered. The filtrate was concentrated under reduced pressure, and the resulting residue was purified by preparative separation to obtain the title compound 4-(2-chloro-4-methylphenoxy)-2-((2-fluoro-4-iodophenyl)amino)-1-methyl-6-oxo-1,6-dihydropyridine-3-carboxamide 15 (50 mg, gray-white solid), yield: 47.2%.

MS m/z (ESI): 528.0 [M+1]
$^1$H NMR (400 MHz, DMSO-$d_6$): δ 9.95 (s, 1H), 7.62-7.71 (m, 2H), 7.52-7.58 (m, 1H), 7.48-7.52 (m, 1H), 7.44 (d, 1H), 7.87 (d, 1H), 7.26-7.34 (m, 1H), 6.67 (t, 1H), 4.97 (s, 1H), 3.14 (s, 3H), 2.35 (s, 3H).

Example 16

4-(3-methoxy-2-methylphenoxy)-2-((2-fluoro-4-iodophenyl)amino)-1-methyl-6-oxo-1,6-dihydropyridine-3-carboxamide

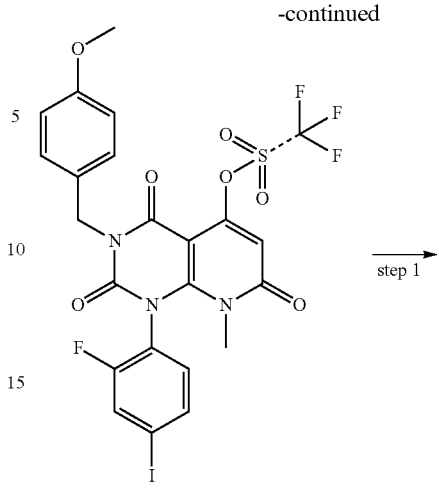

1j step 1

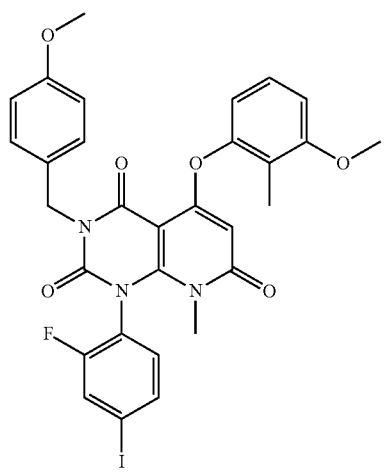

16a step 2

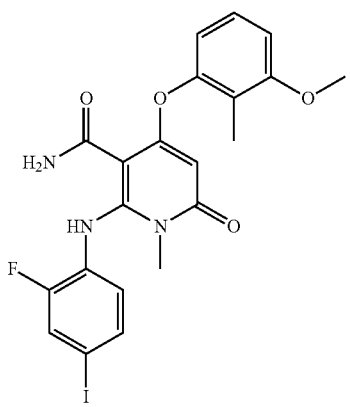

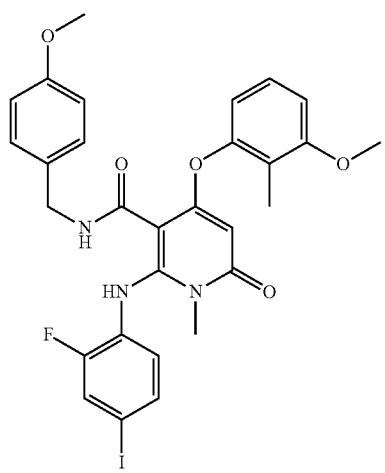

16b step 3

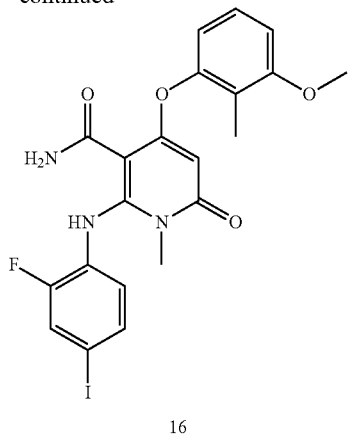

16

Step 1

5-(3-methoxy-2-methylphenoxy)-1-(2-fluoro-4-iodophenyl)-3-(4-methoxybenzyl)-8-methylpyrido[2,3-d]pyrimidine-2,4,7(1H,3H,8H)-trione 3-methoxy-2-methyl-phenol (27 mg, 0.19 mmol) was dissolved in 5 mL of tetrahydrofuran, followed by addition of sodium hydride (7 mg, 0.29 mmol). After stirring for 2 hours, the reaction solution was added with 1-(2-fluoro-4-iodophenyl)-3-(4-methoxybenzyl)-8-methyl-2,4,7-trioxopyrido[2,3-d]pyrimidin-5-yl trifluoromethanesulfonate 1j (130 mg, 0.19 mmol), warmed up to 60° C., and stirred for 1 hour. The reaction solution was concentrated under reduced pressure to obtain the crude title compound 5-(3-methoxy-2-methylphenoxy)-1-(2-fluoro-4-iodophenyl)-3-(4-methoxybenzyl)-8-methylpyrido[2,3-d]pyrimidine-2,4,7(1H,3H,8H)-trione 16a (127 mg, pale yellow liquid), which was used directly in the next step without further purification.

Step 2

4-(3-methoxy-2-methylphenoxy)-2-((2-fluoro-4-iodophenyl)amino)-N-(4-methoxybenzyl)-1-methyl-6-oxo-1,6-dihydropyridine-3-carboxamide The crude 5-(3-methoxy-2-methylphenoxy)-1-(2-fluoro-4-iodophenyl)-3-(4-methoxybenzyl)-8-methylpyrido[2,3-d]pyrimidine-2,4,7(1H,3H,8H)-trione 16a (127 mg, 0.19 mmol) was dissolved in 6 mL of a mixture of tetrahydrofuran and water (V:V=4:1), followed by addition of lithium hydroxide (80 mg, 1.91 mmol). After stirring for 12 hours, the reaction solution was added with 50 mL of ethyl acetate. The organic phase was washed with 1 M sodium hydroxide solution (25 mL×3), dried over anhydrous sodium sulfate, filtered, and the filtrate was concentrated under reduced pressure to obtain the crude title compound 4-(3-methoxy-2-methylphenoxy)-2-((2-fluoro-4-iodophenyl)amino)-N-(4-methoxybenzyl)-1-methyl-6-oxo-1,6-dihydropyridine-3-carboxamide 16b (170 mg, brown oil), which was used directly in the next step without further purification.

MS m/z (ESI): 644.1 [M+1]

Step 3

4-(3-methoxy-2-methylphenoxy)-2-((2-fluoro-4-iodophenyl)amino)-1-methyl-6-oxo-1,6-dihydropyridine-3-carboxamide The crude 4-(3-methoxy-2-methylphenoxy)-2-((2-fluoro-4-iodophenyl)amino)-N-(4-methoxybenzyl)-1-methyl-6-oxo-1,6-dihydropyridine-3-carboxamide 16b (170 mg, 0.19 mmol) was dissolved in 5 mL of anisole, followed by addition of aluminum chloride (127 mg, 0.95 mmol). The reaction solution was warmed up to 120° C. and stirred for 1.5 hours, added with 10 mL of water and 1 mL of 1 M hydrochloric acid, and extracted with ethyl acetate (20 mL×3). The organic phase was dried over anhydrous sodium sulfate, and filtered. The filtrate was concentrated under reduced pressure, and the resulting residue was purified by preparative separation method to obtain the title compound 4-(3-methoxy-2-methylphenoxy)-2-((2-fluoro-4-iodophenyl)amino)-1-methyl-6-oxo-1,6-dihydropyridine-3-carboxamide 16 (28 mg, gray-white solid), yield: 28.0%.

MS m/z (ESI): 524.1 [M+1]

$^1$H NMR (400 MHz, DMSO-$d_6$) δ 9.83 (s, 1H), 7.61-7.67 (m, 3H), 7.42-7.44 (d, 1H), 7.28-7.33 (t, 1H), 6.95-6.98 (d, 1H), 6.82-6.85 (d, 1H), 6.64-6.69 (t, 1H), 4.99 (s, 1H), 3.85 (s, 3H), 3.14 (s, 3H), 1.97 (s, 3H).

Example 17

4-(2-fluoro-4-methylphenoxy)-2-((2-fluoro-4-iodophenyl)amino)-1-methyl-6-oxo-1,6-dihydropyridine-3-carboxamide

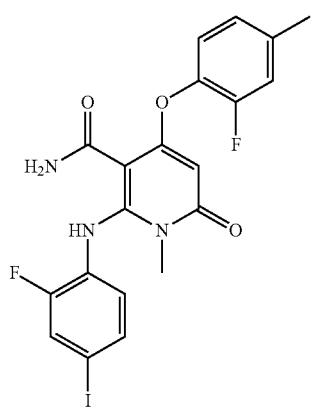

93

-continued

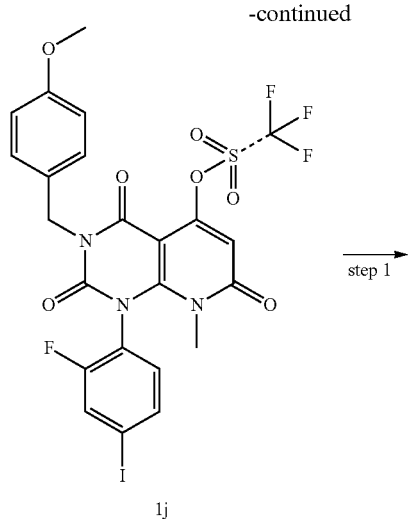

1j

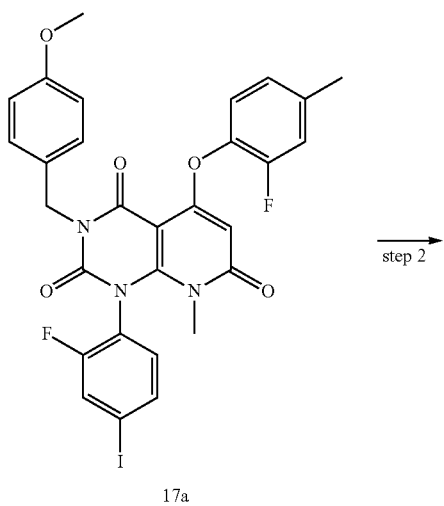

17a

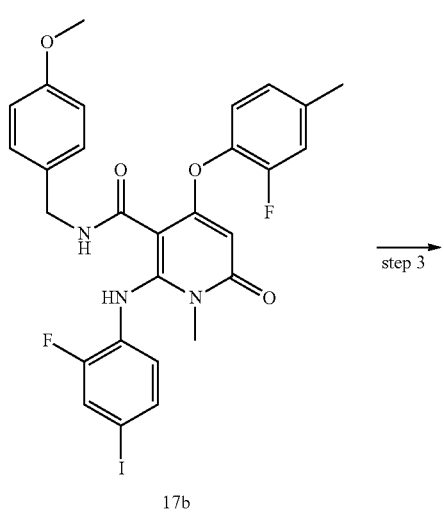

17b

94

-continued

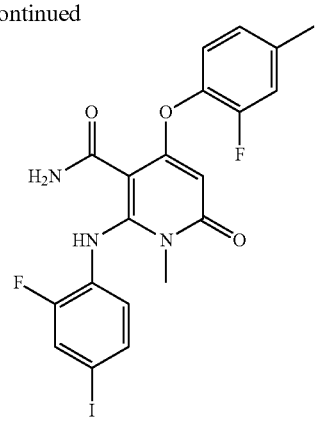

17

Step 1

5-(2-fluoro-4-methylphenoxy)-1-(2-fluoro-4-iodo-phenyl)-3-(4-methoxybenzyl)-8-methylpyrido[2,3-d] pyrimidine-2,4,7(1H,3H,8H)-trione 2-fluoro-4-methyl-phenol (33 mg, 0.26 mmol) was dissolved in 5 mL of tetrahydrofuran, followed by addition of sodium hydride (16 mg, 0.40 mmol). After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), and stirred for 12 hours. The reaction solution was concentrated under reduced pressure to obtain the crude title compound 5-(2-fluoro-4-methylphenoxy)-1-(2-fluoro-4-iodophenyl)-3-(4-methoxybenzyl)-8-methyl-pyrido[2,3-d]pyrimidine-2,4,7(1H,3H,8H)-trione 17a (131 mg, pale yellow liquid), which was used directly in the next step without further purification.

MS m/z (ESI): 658.0 [M+1]

Step 2

4-(2-fluoro-4-methylphenoxy)-2-((2-fluoro-4-iodo-phenyl)amino)-N-(4-methoxybenzyl)-1-methyl-6-oxo-1,6-dihydropyridine-3-carboxamide The crude 5-(2-fluoro-4-methylphenoxy)-1-(2-fluoro-4-iodophenyl)-3-(4-methoxybenzyl)-8-methylpyrido[2,3-d] pyrimidine-2,4,7(1H,3H,8H)-trione 17a (131 mg, 0.20 mmol) was dissolved in 6 mL of a mixture of tetrahydrofuran and water (V:V=4:1), followed by addition of lithium hydroxide (42 mg, 1 mmol). After stirring for 4 hours, the reaction solution was added with 50 mL of ethyl acetate. The organic phase was washed with water (30 mL×1), 0.5 M hydrochloric acid (30 mL×1), and saturated sodium chloride solution (30 mL×1), successively, dried over anhydrous sodium sulfate, filtered, and the filtrate was concentrated under reduced pressure to obtain the crude title compound 4-(2-fluoro-4-methylphenoxy)-2-((2-fluoro-4-iodophenyl) amino)-N-(4-methoxybenzyl)-1-methyl-6-oxo-1,6-dihydro-pyridine-3-carboxamide 17b (126 mg, brown solid), which was used directly in the next step without further purification.

MS m/z (ESI): 632.0 [M+1]

Step 3

4-(2-fluoro-4-methylphenoxy)-2-((2-fluoro-4-iodophenyl)amino)-1-methyl-6-oxo-1,6-dihydropyridine-3-carboxamide The crude 4-(2-fluoro-4-methylphenoxy)-2-((2-fluoro-4-iodophenyl)amino)-N-(4-methoxybenzyl)-1-methyl-6-oxo-1,6-dihydropyridine-3-carboxamide 17b (126 mg, 0.20 mmol) was dissolved in 3 mL of anisole, followed by addition of aluminum chloride (133 mg, 1 mmol). The reaction solution was warmed up to 100° C. and stirred for 1 hour, followed by addition of 60 mL of dichloromethane. The organic phase was washed with water (50 mL×2) and saturated sodium chloride solution (50 mL×1), successively, dried over anhydrous sodium sulfate, and filtered. The filtrate was concentrated under reduced pressure, and the resulting residue was purified by preparative separation to obtain the title compound 4-(2-fluoro-4-methylphenoxy)-2-((2-fluoro-4-iodophenyl)amino)-1-methyl-6-oxo-1,6-dihydropyridine-3-carboxamide 17 (32 mg, off-white solid), yield: 31.4%.

MS m/z (ESI): 512.0 [M+1]

$^1$H NMR (400 MHz, DMSO-d$_6$): δ 9.84 (s, 1H), 7.61-7.66 (m, 3H), 7.41-7.43 (m, 1H), 7.28-7.34 (m, 2H), 7.12-7.15 (m, 1H), 6.64-6.68 (m, 1H), 5.10 (s, 1H), 3.15 (s, 3H), 2.36 (s, 3H).

Example 18

4-(2,3-dimethylphenoxy)-2-((2-fluoro-4-iodophenyl)amino)-1-methyl-6-oxo-1,6-dihydropyridine-3-carboxamide

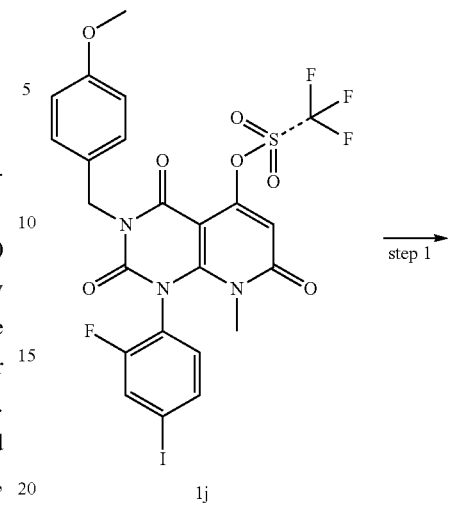

1j

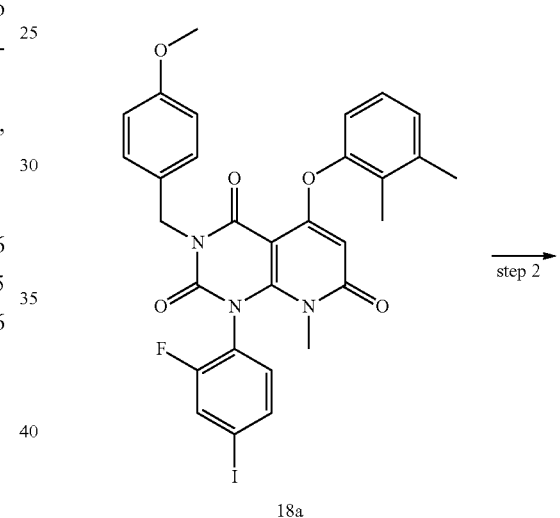

18a

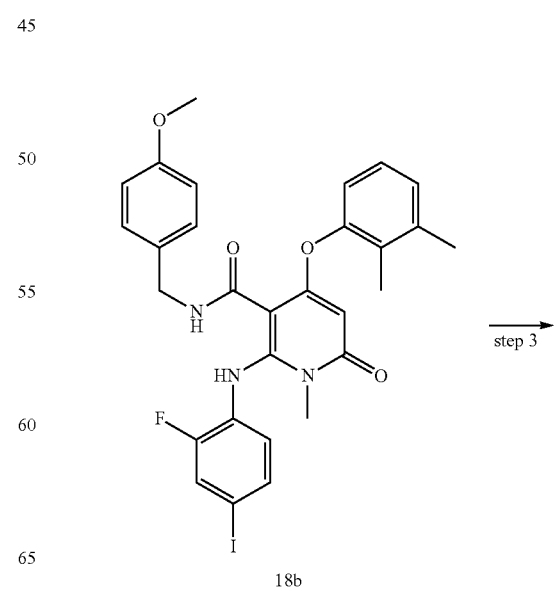

18b

-continued

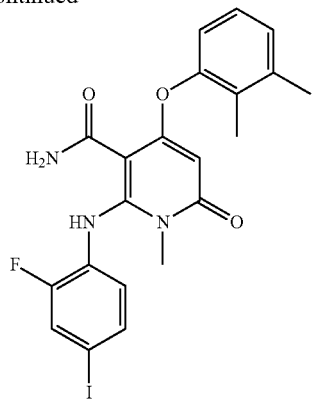

18

Step 1

5-(2,3-dimethylphenoxy)-1-(2-fluoro-4-iodophenyl)-3-(4-methoxybenzyl)-8-methylpyrido[

2,3-d]pyrimidine-2,4,7(1H,3H,8H)-trione 2,3-dimethylphenol (24 mg, 0.19 mmol) was dissolved in 5 mL of tetrahydrofuran, followed by addition of sodium hydride (7 mg, 0.29 mmol). After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (130 mg, 0.19 mmol) and stirred for 12 hours. The reaction solution was concentrated under reduced pressure to obtain the crude title compound 5-(2,3-dimethylphenoxy)-1-(2-fluoro-4-iodophenyl)-3-(4-methoxybenzyl)-8-methylpyrido[2,3-d]pyrimidine-2,4,7(1H,3H,8H)-trione 18a (125 mg, pale yellow liquid), which was used directly in the next step without further purification.

Step 2

4-(2,3-dimethylphenoxy)-2-((2-fluoro-4-iodophenyl)amino)-N-(4-methoxybenzyl)-1-methyl-6-oxo-1,6-dihydropyridine-3-carboxamide The crude 5-(2,3-dimethylphenoxy)-1-(2-fluoro-4-iodophenyl)-3-(4-methoxybenzyl)-8-methylpyrido[2,3-d]pyrimidine-2,4,7(1H,3H,8H)-trione 18a (125 mg, 0.19 mmol) was dissolved in 6 mL of a mixture of tetrahydrofuran and water (V:V=4:1), followed by addition of lithium hydroxide (80 mg, 1.91 mmol). After stirring for 2 hours, the reaction solution was added with 50 mL of ethyl acetate. The organic phase was washed with 1 M sodium hydroxide solution (25 mL×3), dried over anhydrous sodium sulfate, filtered, and the filtrate was concentrated under reduced pressure to obtain the crude title compound 4-(2,3-dimethylphenoxy)-2-((2-fluoro-4-iodophenyl) amino)-N-(4-methoxybenzyl)-1-methyl-6-oxo-1,6-dihydropyridine-3-carboxamide 18b (130 mg, yellow oil), which was used directly in the next step without further purification.

Step 3

4-(2,3-dimethylphenoxy)-2-((2-fluoro-4-iodophenyl)amino)-1-methyl-6-oxo-1,6-dihydropyridine-3-carboxamide The crude 4-(2,3-dimethylphenoxy)-2-((2-fluoro-4-iodophenyl)amino)-N-(4-methoxybenzyl)-1-methyl-6-oxo-1,6-dihydropyridine-3-carboxamide 18b (130 mg, 0.19 mmol) was dissolved in 5 mL of anisole, followed by addition of aluminum chloride (127 mg, 0.95 mmol). The reaction solution was warmed up to 120° C. and stirred 1.5 hours, followed by addition of 10 mL of water and 1 mL of 1 M hydrochloric acid, and extracted with ethyl acetate (20 mL×3). The organic phase was dried over anhydrous sodium sulfate, and filtered. The filtrate was concentrated under reduced pressure, and the resulting residue was purified by preparative separation to obtain the title compound 4-(2,3-dimethylphenoxy)-2-((2-fluoro-4-iodophenyl)amino)-1-methyl-6-oxo-1,6-dihydropyridine-3-carboxamide 18 (26 mg, white solid), yield: 28.9%.

MS m/z (ESI): 506.0 [M−1]

$^1$H NMR (400 MHz, DMSO-$d_6$) δ 9.91 (s, 1H), 7.63-7.67 (m, 3H), 7.42-7.44 (d, 1H), 7.15-7.22 (m, 2H), 7.04-7.06 (d, 1H), 6.64-6.69 (t, 1H), 4.95 (s, 1H), 3.14 (s, 3H), 2.31 (s, 3H), 2.04 (s, 3H).

Example 19

4-(2-fluoro-3-methylphenoxy)-2-((2-fluoro-4-iodophenyl)amino)-1-methyl-6-oxo-1,6-dihydropyridine-3-carboxamide

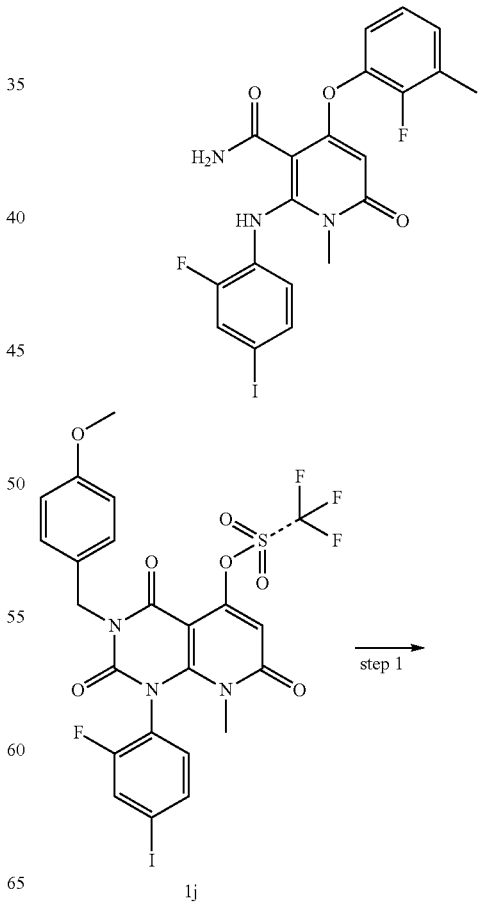

-continued

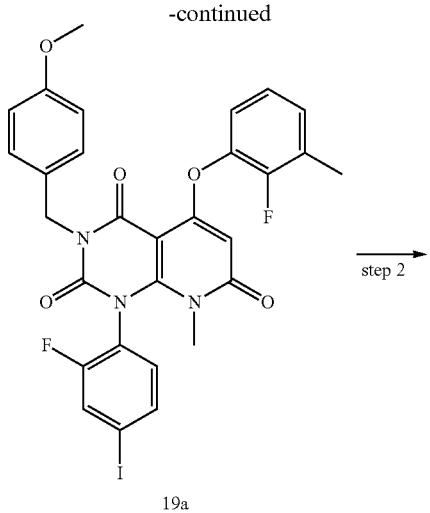

19a

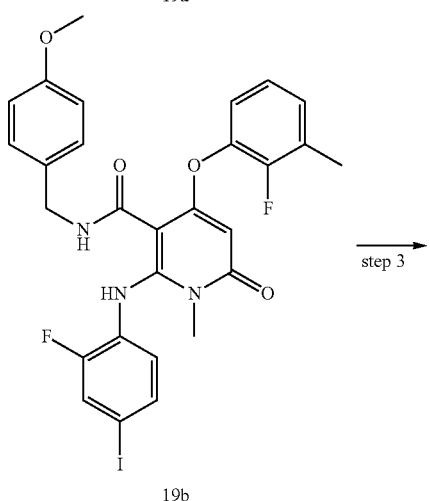

19b

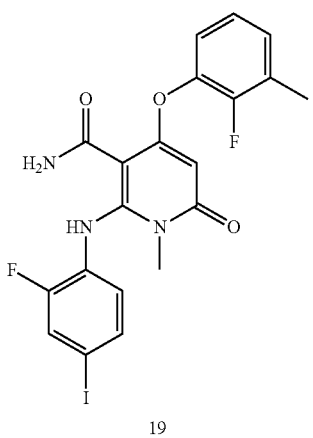

19

Step 1

5-(2-fluoro-3-methylphenoxy)-1-(2-fluoro-4-iodo-phenyl)-3-(4-methoxybenzyl)-8-methylpyrido[2,3-d]pyrimidine-2,4,7(1H,3H,8H)-trione 2-fluoro-3-methylphenol (30 mg, 0.24 mmol) was dissolved in 5 mL of tetrahydrofuran, followed by addition of sodium hydride (12 mg, 0.30 mmol). After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), warmed up to 60° C., and stirred for 1 hour. The reaction solution was concentrated under reduced pressure to obtain the crude title compound 5-(2-fluoro-3-methylphenoxy)-1-(2-fluoro-4-iodophenyl)-3-(4-methoxybenzyl)-8-methylpyrido[2,3-d]pyrimidine-2,4,7 (1H,3H,8H)-trione 19a (131 mg, pale yellow liquid), which was used directly in the next step without further purification.

MS m/z (ESI): 658.1 [M+1]

Step 2

4-(2-fluoro-3-methylphenoxy)-2-((2-fluoro-4-iodophenyl)amino)-N-(4-methoxybenzyl)-1-methyl-6-oxo-1,6-dihydropyridine-3-carboxamide The crude 5-(2-fluoro-3-methylphenoxy)-1-(2-fluoro-4-iodophenyl)-3-(4-methoxybenzyl)-8-methylpyrido[2,3-d] pyrimidine-2,4,7(1H,3H,8H)-trione 19a (131 mg, 0.20 mmol) was dissolved in 6 mL of a mixture of tetrahydrofuran and water (V:V=4:1), followed by addition of lithium hydroxide (168 mg, 4 mmol). The reaction solution was warmed up to 40° C. and stirred for 1 hour, followed by addition of 50 mL of ethyl acetate. The organic phase was washed with 1 M sodium hydroxide solution (25 mL×3), dried over anhydrous sodium sulfate, filtered, and the filtrate was concentrated under reduced pressure to obtain the crude title compound 4-(2-fluoro-3-methylphenoxy)-2-((2-fluoro-4-iodophenyl)amino)-N-(4-methoxybenzyl)-1-methyl-6-oxo-1,6-dihydropyridine-3-carboxamide 19b (126 mg, light brown solid), which was used directly in the next step without further purification.

MS m/z (ESI): 632.1 [M+1]

Step 3

4-(2-fluoro-3-methylphenoxy)-2-((2-fluoro-4-iodophenyl)amino)-1-methyl-6-oxo-1,6-dihydropyridine-3-carboxamide The crude 4-(2-fluoro-3-methylphenoxy)-2-((2-fluoro-4-iodophenyl)amino)-N-(4-methoxybenzyl)-1-methyl-6-oxo-1,6-dihydropyridine-3-carboxamide 19b (126 mg, 0.20 mmol) was dissolved in 5 mL of anisole, followed by addition of aluminum chloride (133 mg, 1 mmol). The reaction solution was warmed up to 120° C. and stirred for 1.5 hours, followed by addition of 10 mL of water and 1 mL of 1 M hydrochloric acid, and extracted with ethyl acetate (20 mL×3). The organic phase was dried over anhydrous sodium sulfate, and filtered. The filtrate was concentrated under reduced pressure, and the resulting residue was purified by preparative separation to obtain the title compound 4-(2-fluoro-3-methylphenoxy)-2-((2-fluoro-4-iodophenyl) amino)-1-methyl-6-oxo-1,6-dihydropyridine-3-carboxamide 19 (35 mg, gray-white solid), yield: 34.3%.

MS m/z (ESI): 512.1 [M+1]

$^1$H NMR (400 MHz, DMSO-$d_6$): δ 9.88 (s, 1H), 7.60-7.66 (m, 3H), 7.40-7.46 (m, 1H), 7.18-7.29 (m, 3H), 6.67 (t, 1H), 5.11 (s, 1H), 3.14 (s, 3H), 2.30 (s, 3H).

Example 20

4-(2,4-dimethylphenoxy)-2-((2-fluoro-4-iodophenyl)amino)-1-methyl-6-oxo-1,6-dihydropyridine-3-carboxamide

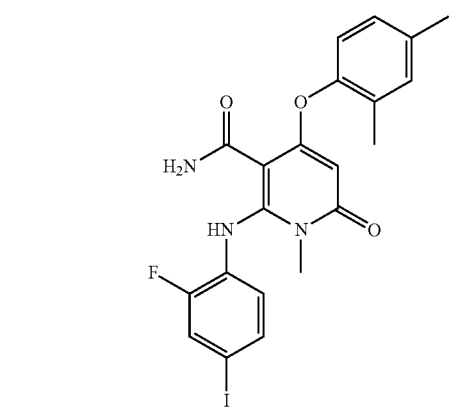

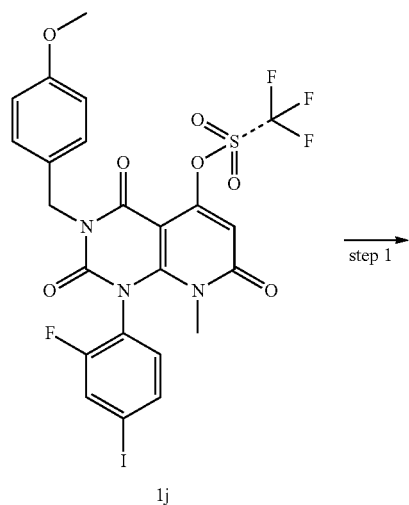
1j

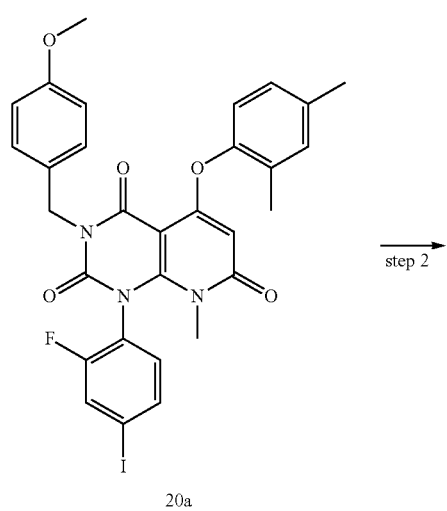
20a

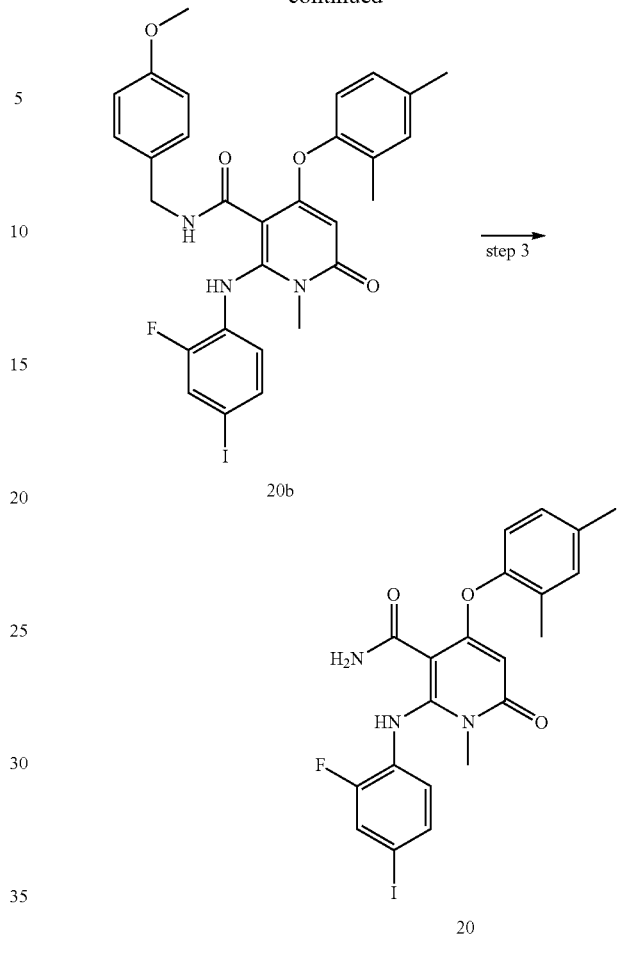
20b

20

Step 1

5-(2,4-dimethylphenoxy)-1-(2-fluoro-4-iodophenyl)-3-(4-methoxybenzyl)-8-methylpyrido[2,3-d]pyrimidine-2,4,7(1H,3H,8H)-trione 2,4-dimethyl-phenol (32 mg, 0.26 mmol) was dissolved in 5 mL of tetrahydrofuran, followed by addition of sodium hydride (16 mg, 0.40 mmol). After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), and stirred for 12 hours. The reaction solution was concentrated under reduced pressure to obtain the crude title compound 5-(2,4-dimethylphenoxy)-1-(2-fluoro-4-iodophenyl)-3-(4-methoxybenzyl)-8-methylpyrido[2,3-d]pyrimidine-2,4,7(1H,3H,8H)-trione 20a (130 mg, pale yellow liquid), which was used directly in the next step without further purification.

Step 2

4-(2,4-dimethylphenoxy)-2-((2-fluoro-4-iodophenyl)amino)-N-(4-methoxybenzyl)-1-methyl-6-oxo-1,6-dihydropyridine-3-carboxamide The crude 5-(2,4-dimethylphenoxy)-1-(2-fluoro-4-iodophenyl)-3-(4-methoxybenzyl)-8-methylpyrido[2,3-d]pyrimidine-2,4,7(1H,3H,8H)-trione 20a (130 mg, 0.20 mmol) was dissolved in 6 mL of a mixture of tetrahydrofuran and water (V:V=4:1), followed by addition of lithium hydroxide (42 mg, 1 mmol). After stirring for 4 hours, the reaction solution was added with 50 mL of ethyl acetate. The organic phase was washed with water (30 mL×1), 0.5 M hydrochloric acid (30 mL×1), and saturated sodium chloride solution (30 mL×1), successively, dried over anhydrous sodium sulfate, filtered, and the filtrate was concentrated under reduced pressure to obtain the crude title compound 4-(2,4-dimethylphenoxy)-2-((2-fluoro-4-iodophenyl)amino)-N-(4-methoxybenzyl)-1-methyl-6-oxo-1,6-dihydropyridine-3-carboxamide 20b (124 mg, reddish brown solid), which was used directly in the next step without further purification.

MS m/z (ESI): 628.1 [M+1]

Step 3

4-(2,4-dimethylphenoxy)-2-((2-fluoro-4-iodophenyl)amino)-1-methyl-6-oxo-1,6-dihydropyridine-3-carboxamide The crude 4-(2,4-dimethylphenoxy)-2-((2-fluoro-4-iodophenyl)amino)-N-(4-methoxybenzyl)-1-methyl-6-oxo-1,6-dihydropyridine-3-carboxamide 20b (124 mg, 0.20 mmol) was dissolved in 3 mL of anisole, followed by addition of aluminum chloride (133 mg, 1 mmol). The reaction solution was warmed up to 100° C. and stirred for 1 hour, followed by addition of 60 mL of dichloromethane. The organic phase was washed with water (50 mL×2) and saturated sodium chloride solution (50 mL×1), successively, dried over anhydrous sodium sulfate, and filtered. The filtrate was concentrated under reduced pressure, and the resulting residue was purified by preparative separation method to obtain the title compound 4-(2,4-dimethylphenoxy)-2-((2-fluoro-4-iodophenyl)amino)-1-methyl-6-oxo-1,6-dihydropyridine-3-carboxamide 20 (15 mg, white solid), yield: 31.4%.

MS m/z (ESI): 508.1 [M+1]

$^1$H NMR (400 MHz, DMSO-$d_6$): δ 10.0 (s, 1H), 7.61-7.66 (m, 3H), 7.41-7.44 (m, 1H), 7.17-7.18 (m, 1H), 7.07-7.14 (m, 2H), 6.64-6.68 (m, 1H), 4.96 (s, 1H), 3.13 (s, 3H), 2.31 (s, 3H), 2.10 (s, 3H).

Example 21

4-(2,6-dimethylphenoxy)-2-((2-fluoro-4-iodophenyl)amino)-1-methyl-6-oxo-1,6-dihydropyridine-3-carboxamide

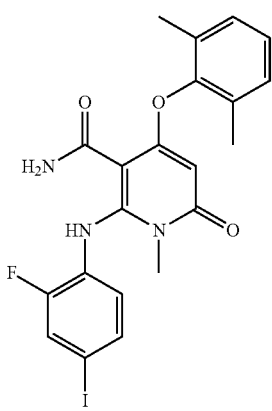

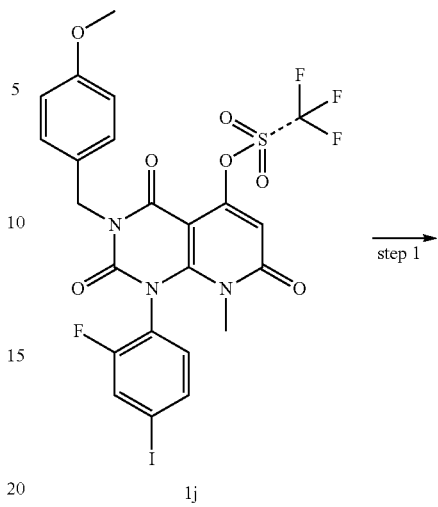

1j

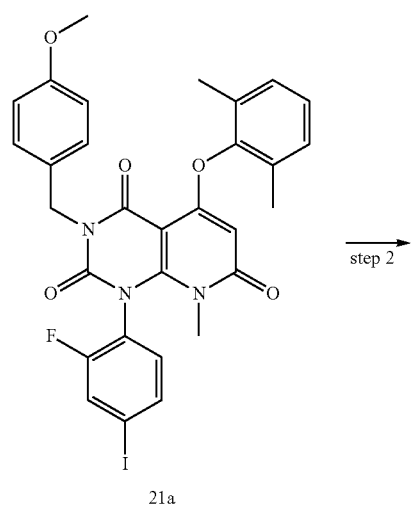

21a

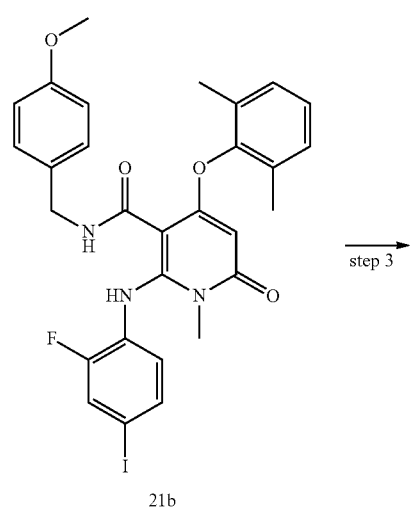

21b

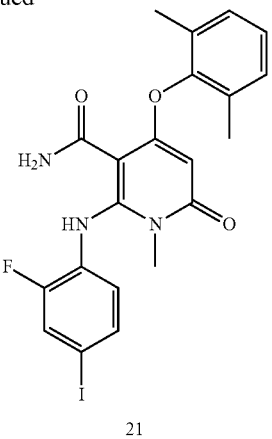

21

Step 1

5-(2,6-dimethylphenoxy)-1-(2-fluoro-4-iodophenyl)-3-(4-methoxybenzyl)-8-methylpyrido[2,3-d]pyrimidine-2,4,7(1H,3H,8H)-trione 2,6-dimethyl-phenol (32 mg, 0.26 mmol) was dissolved in 5 mL of tetrahydrofuran, followed by addition of sodium hydride (16 mg, 0.40 mmol). After stirring for 1.5 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), and stirred for 12 hours. The reaction solution was concentrated under reduced pressure to obtain the crude title compound 5-(2,6-dimethylphenoxy)-1-(2-fluoro-4-iodophenyl)-3-(4-methoxybenzyl)-8-methylpyrido[2,3-d]pyrimidine-2,4,7(1H,3H,8H)-trione 21a (130 mg, pale yellow liquid), which was used directly in the next step without further purification.

Step 2

4-(2,6-dimethylphenoxy)-2-((2-fluoro-4-iodophenyl)amino)-N-(4-methoxybenzyl)-1-methyl-6-oxo-1,6-dihydropyridine-3-carboxamide The crude 5-(2,6-dimethylphenoxy)-1-(2-fluoro-4-iodophenyl)-3-(4-methoxybenzyl)-8-methylpyrido[2,3-d]pyrimidine-2,4,7(1H,3H,8H)-trione 21a (130 mg, 0.20 mmol) was dissolved in 6 mL of a mixture of tetrahydrofuran and water (1 V:V=4:1), followed by addition of lithium hydroxide (42 mg, 1 mmol). After stirring for 4 hours, the reaction was added with 70 mL of dichloromethane. The organic phase was washed with water (30 mL×1) and saturated sodium chloride solution (30 mL×1), successively, dried over anhydrous sodium sulfate, filtered, and the filtrate was concentrated under reduced pressure to obtain the crude title compound 4-(2,6-dimethylphenoxy)-2-((2-fluoro-4-iodophenyl)amino)-N-(4-methoxybenzyl)-1-methyl-6-oxo-1,6-dihydropyridine-3-carboxamide 21b (125 mg, reddish brown solid), which was used directly in the next step without further purification.

MS m/z (ESI): 628.1 [M+1]

Step 3

4-(2,6-dimethylphenoxy)-2-((2-fluoro-4-iodophenyl)amino)-1-methyl-6-oxo-1,6-dihydropyridine-3-carboxamide The crude 4-(2,6-dimethylphenoxy)-2-((2-fluoro-4-iodophenyl)amino)-N-(4-methoxybenzyl)-1-methyl-6-oxo-1,6-dihydropyridine-3-carboxamide 21b (125 mg, 0.20 mmol) was dissolved in 3 mL of anisole, followed by addition of aluminum chloride (133 mg, 1 mmol). The reaction solution was warmed up to 100° C. and stirred for 1.5 hours, followed by addition of 60 mL of dichloromethane. The organic phase was washed with water (50 mL×2) and saturated sodium chloride solution (50 mL×1), successively, dried over anhydrous sodium sulfate, and filtered. The filtrate was concentrated under reduced pressure, and the resulting residue was purified by preparative separation to obtain the title compound 4-(2,6-dimethylphenoxy)-2-((2-fluoro-4-iodophenyl)amino)-1-methyl-6-oxo-1,6-dihydropyridine-3-carboxamide 21 (10 mg, white solid), yield: 9.9%.

MS m/z (ESI): 508.1 [M+1]

$^1$H NMR (400 MHz, DMSO-$d_6$): δ 10.33 (s, 1H), 7.62-7.67 (m, 3H), 7.42-7.44 (m, 1H), 7.16-7.21 (m, 3H), 6.69-6.74 (m, 1H), 4.88 (s, 1H), 3.12 (s, 3H), 2.13 (s, 6H).

Example 22

4-(4-fluoro-2-methylphenoxy)-2-((2-fluoro-4-iodophenyl)amino)-1-methyl-6-oxo-1,6-dihydropyridine-3-carboxamide

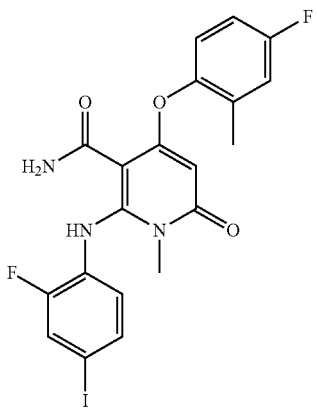

107

-continued

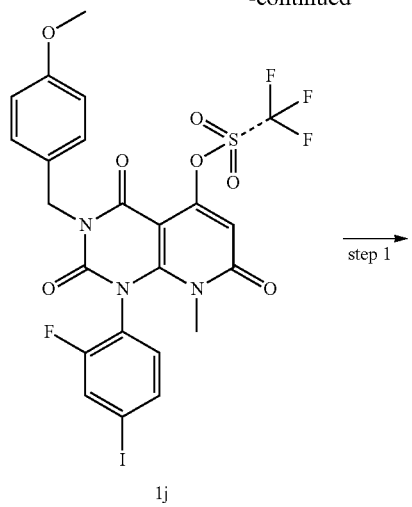

1j

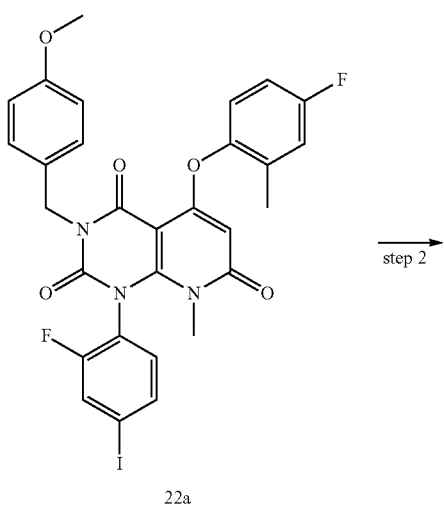

22a

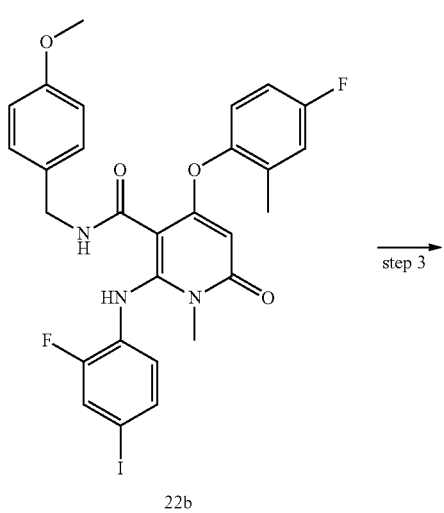

22b

108

-continued

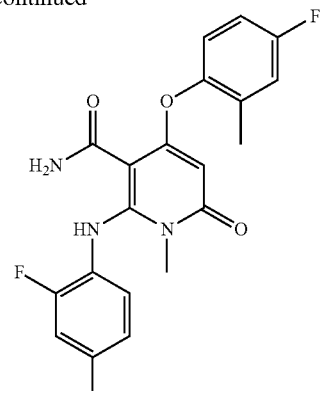

22

Step 1

5-(4-fluoro-2-methylphenoxy)-1-(2-fluoro-4-iodo-phenyl)-3-(4-methoxybenzyl)-8-methylpyrido[2,3-d]pyrimidine-2,4,7(1H,3H,8H)-trione 4-fluoro-2-methylphenol (24 mg, 0.19 mmol) was dissolved in 5 mL of tetrahydrofuran, followed by addition of sodium hydride (7 mg, 0.29 mmol). After stirring for 2 hours, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (130 mg, 0.19 mmol), and stirred for 12 hours. The reaction solution was concentrated under reduced pressure to obtain the crude title compound 5-(4-fluoro-2-methylphenoxy)-1-(2-fluoro-4-iodophenyl)-3-(4-methoxybenzyl)-8-methyl-pyrido[2,3-d]pyrimidine-2,4,7(1H,3H,8H)-trione 22a (124 mg, pale yellow liquid), which was used directly in the next step without further purification.

Step 2

4-(4-fluoro-2-methylphenoxy)-2-((2-fluoro-4-iodo-phenyl)amino)-N-(4-methoxybenzyl)-1-methyl-6-oxo-1,6-dihydropyridine-3-carboxamide The crude 5-(4-fluoro-2-methylphenoxy)-1-(2-fluoro-4-iodophenyl)-3-(4-methoxybenzyl)-8-methylpyrido[2,3-d]pyrimidine-2,4,7(1H,3H,8H)-trione 22a (124 mg, 0.19 mmol) was dissolved in 6 mL of a mixture of tetrahydrofuran and water (V:V=4:1), followed by addition of lithium hydroxide (80 mg, 1.91 mmol). After stirring for 2 hours, the reaction solution was added with 50 mL of ethyl acetate and 10 mL of water, dried over anhydrous sodium sulfate, filtered, and the filtrate was concentrated under reduced pressure to obtain the crude title compound 4-(4-fluoro-2-methylphenoxy)-2-((2-fluoro-4-iodophenyl)amino)-N-(4-methoxybenzyl)-1-methyl-6-oxo-1,6-dihydropyridine-3-carboxamide 22b (150 mg, yellow oil), which was used directly in the next step without further purification.

MS m/z (ESI): 630.1 [M−1]

Step 3

4-(4-fluoro-2-methylphenoxy)-2-((2-fluoro-4-iodo-phenyl)amino)-1-methyl-6-oxo-1,6-dihydropyridine-3-carboxamide The crude 4-(4-fluoro-2-methylphenoxy)-2-((2-fluoro-4-iodophenyl)amino)-N-(4-methoxybenzyl)-1-methyl-6-oxo- 1,6-dihydropyridine-3-carboxamide 22b (150 mg, 0.19 mmol) was dissolved in 5 mL of anisole, followed by addition of aluminum chloride (127 mg, 0.95 mmol). The reaction solution was warmed up to 120° C. and stirred for 1.5 hours, followed by addition of 20 mL of dichloromethane and 5 mL of water. The organic phase was dried over anhydrous sodium sulfate, and filtered. The filtrate was concentrated under reduced pressure, and the resulting residue was purified by preparative separation to obtain the title compound 4-(4-fluoro-2-methylphenoxy)-2-((2-fluoro-4-iodophenyl)amino)-1-methyl-6-oxo-1,6-dihydropyridine-3-carboxamide 22 (26 mg, white solid), yield: 26.6%.

MS m/z (ESI): 510.0 [M−1]

$^1$H NMR (400 MHz, DMSO-d$_6$) δ 9.94 (s, 1H), 7.63-7.67 (m, 3H), 7.42-7.45 (d, 1H), 7.26-7.30 (m, 2H), 7.16-7.20 (m, 1H), 6.64-6.70 (t, 1H), 4.99 (s, 1H), 3.15 (s, 3H), 2.15 (s, 3H).

Example 23

4-(2-methylphenoxy)-2-((2-fluoro-4-iodophenyl)amino)-1-methyl-6-oxo-1,6-dihydropyridine-3-carboxamide

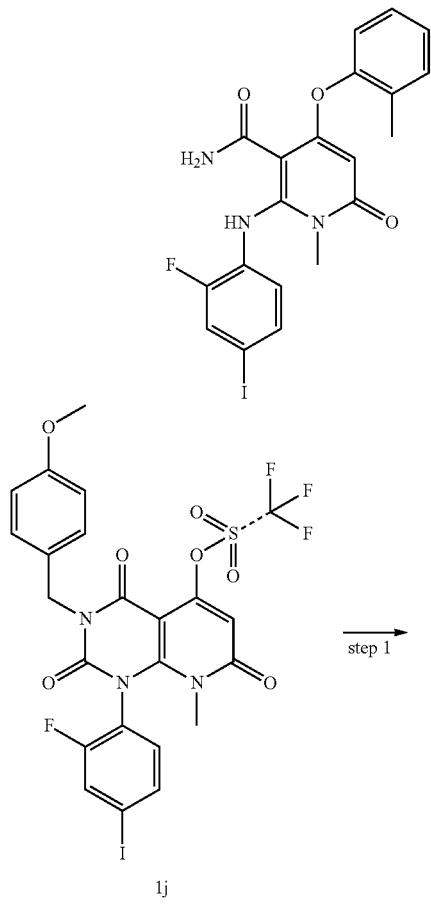

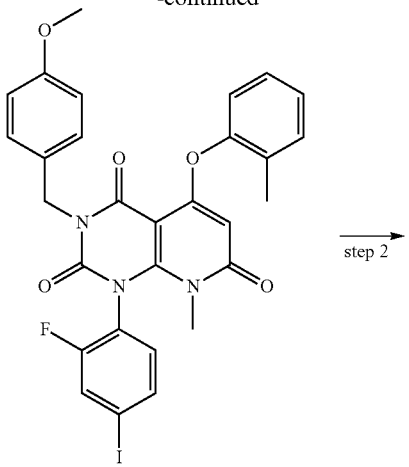

23a

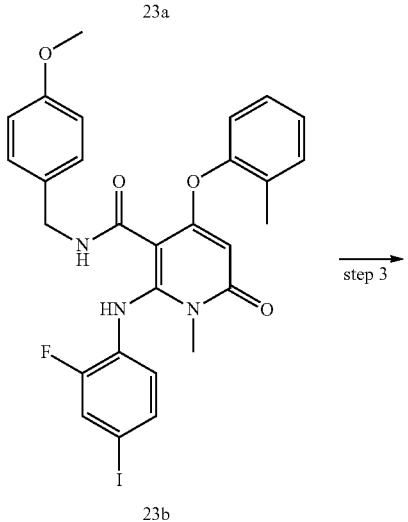

23b

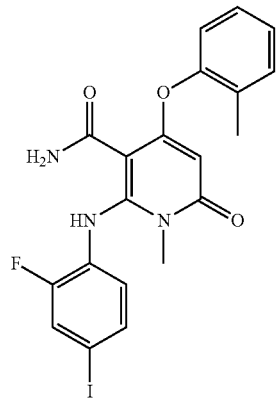

23

Step 1

5-(2-methylphenoxy)-1-(2-fluoro-4-iodophenyl)-3-(4-methoxybenzyl)-8-methylpyrido[2,3-d]pyrimidine-2,4,7(1H,3H,8H)-trione 2-methyl-phenol (21 mg, 0.19 mmol) was dissolved in 5 mL of tetrahydrofuran, followed by addition of sodium hydride (7 mg, 0.29 mmol). After stirring for 2 hours, the reaction solution was added with 1-(2-fluoro-4-iodophenyl)-

3-(4-methoxybenzyl)-8-methyl-2,4,7-trioxo-pyrido[2,3-d]pyrimidin-5-yl trifluoromethanesulfonate 1j (130 mg, 0.19 mmol), and stirred for 3 hours. The reaction solution was concentrated under reduced pressure to obtain the crude title compound 5-(2-methylphenoxy)-1-(2-fluoro-4-iodophenyl)-3-(4-methoxybenzyl)-8-methylpyrido[2,3-d]pyrimidine-2,4,7(1H,3H,8H)-trione 23a (122 mg, pale yellow liquid), which was used directly in the next step.

Step 2

4-(2-methylphenoxy)-2-((2-fluoro-4-iodophenyl)amino)-N-(4-methoxybenzyl)-1-methyl-6-oxo-1,6-dihydropyridine-3-carboxamide The crude 5-(2-methylphenoxy)-1-(2-fluoro-4-iodophenyl)-3-(4-methoxybenzyl)-8-methylpyrido[2,3-d]pyrimidine-2,4,7(1H,3H,8H)-trione 23a (122 mg, 0.19 mmol) was dissolved in 6 mL of a mixture of tetrahydrofuran and water (V:V=4:1), followed by addition of lithium hydroxide (80 mg, 1.91 mmol). After stirring for 2 hours, the reaction solution was added with 50 mL of ethyl acetate and 10 mL of water, dried over anhydrous sodium sulfate, filtered, and the filtrate was concentrated under reduced pressure to obtain the crude title compound 4-(2-methylphenoxy)-2-((2-fluoro-4-iodophenyl)amino)-N-(4-methoxybenzyl)-1-methyl-6-oxo-1,6-dihydropyridine-3-carboxamide 23b (140 mg, yellow oil), which was used directly in the next step without further purification.

Step 3

4-(2-methylphenoxy)-2-((2-fluoro-4-iodophenyl)amino)-1-methyl-6-oxo-1,6-dihydropyridine-3-carboxamide The crude 4-(2-methylphenoxy)-2-((2-fluoro-4-iodophenyl)amino)-N-(4-methoxybenzyl)-1-methyl-6-oxo-1,6-dihydropyridine-3-carboxamide 23b (150 mg, 0.19 mmol) was dissolved in 5 mL of anisole, followed by addition of aluminum chloride (127 mg, 0.95 mmol). The reaction solution was warmed up to 120° C. and stirred for 1.5 hours, followed by addition of 20 mL of dichloromethane and 5 mL of water. The organic phase was dried over anhydrous sodium sulfate, and filtered. The filtrate was concentrated under reduced pressure, and the resulting residue was purified by preparative separation to obtain the title compound 4-(2-methylphenoxy)-2-((2-fluoro-4-iodophenyl)amino)-1-methyl-6-oxo-1,6-dihydropyridine-3-carboxamide 23 (29 mg, white solid), yield: 30.9%.

MS m/z (ESI): 492.0 [M−1]

$^1$H NMR (400 MHz, DMSO-$d_6$) δ 10.00 (s, 1H), 7.64-7.67 (m, 3H), 7.21-7.45 (m, 5H), 6.65-6.70 (t, 1H), 4.97 (s, 1H), 3.14 (s, 3H), 2.15 (s, 3H).

Example 24

4-(3-hydroxy-2-methylphenoxy)-2-((2-fluoro-4-iodophenyl)amino)-1-methyl-6-oxo-1,6-dihydropyridine-3-carboxamide

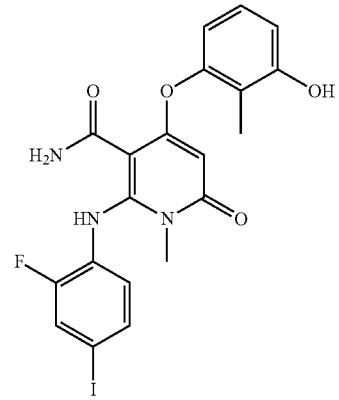

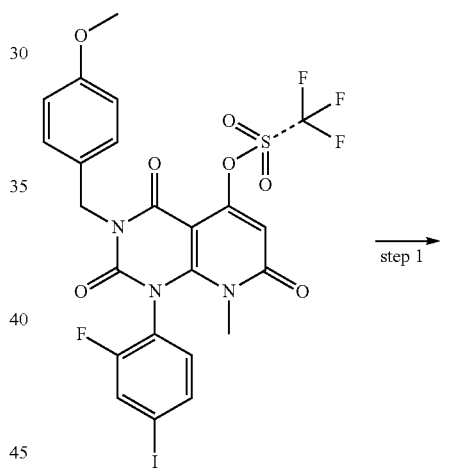

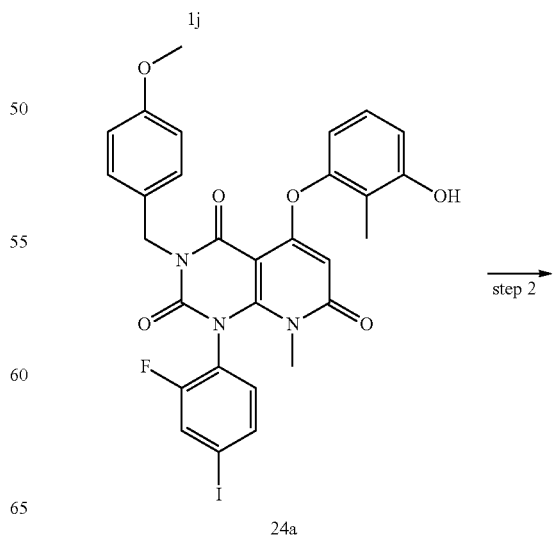

113

-continued

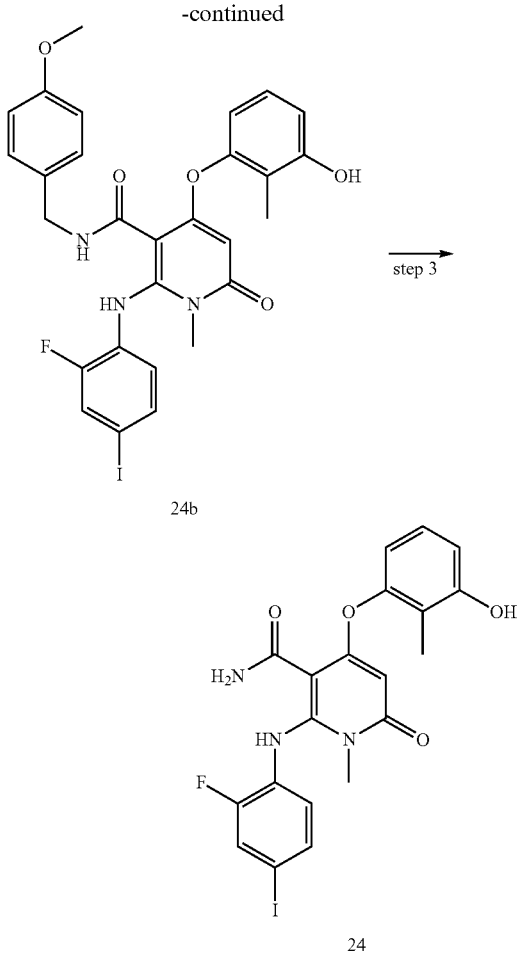

24b

24

Step 1

5-(3-hydroxy-2-methylphenoxy)-1-(2-fluoro-4-iodophenyl)-3-(4-methoxybenzyl)-8-methylpyrido[2,3-d]pyrimidine-2,4,7(1H,3H,8H)-trione 3-hydroxy-2-methylphenol (24 mg, 0.19 mmol) was dissolved in 5 mL of tetrahydrofuran, followed by addition of sodium hydride (7 mg, 0.29 mmol). After stirring for 2 hours, the reaction solution was added with 1-(2-fluoro-4-iodophenyl)-3-(4-methoxybenzyl)-8-methyl-2,4,7-trioxopyrido[2,3-d]pyrimidin-5-yl trifluoromethanesulfonate 1j (130 mg, 0.19 mmol), and stirred for 3 hours. The reaction solution was concentrated under reduced pressure to obtain the crude title compound 5-(3-hydroxy-2-methylphenoxy)-1-(2-fluoro-4-iodophenyl)-3-(4-methoxybenzyl)-8-methylpyrido[2,3-d]pyrimidine-2,4,7(1H,3H,8H)-trione 24a (125 mg, pale yellow liquid), which was used directly in the next step without further purification.

MS m/z (ESI): 656.0 [M+1]

Step 2

4-(3-hydroxy-2-methylphenoxy)-2-((2-fluoro-4-iodophenyl)amino)-N-(4-methoxybenzyl)-1-methyl-6-oxo-1,6-dihydropyridine-3-carboxamide The crude 5-(3-hydroxy-2-methylphenoxy)-1-(2-fluoro-4-iodophenyl)-3-(4-methoxybenzyl)-8-methylpyrido[2,3-d]pyrimidine-2,4,7(1H,3H,8H)-trione 24a (125 mg, 0.19 mmol) was dissolved in 6 mL of a mixture of tetrahydrofuran and water (V:V=4:1), followed by addition of lithium hydroxide (80 mg, 1.91 mmol). After stirring for 12 hours, the reaction solution was added with 50 mL of ethyl acetate and 10 mL of water, dried over anhydrous sodium sulfate, filtered, and the filtrate was concentrated under reduced pressure to obtain the crude title compound 4-(3-hydroxy-2-methylphenoxy)-2-((2-fluoro-4-iodophenyl)amino)-N-(4-methoxybenzyl)-1-methyl-6-oxo-1,6-dihydropyridine-3-carboxamide 24b (140 mg, brown solid), which was used directly in the next step without further purification.

MS m/z (ESI): 629.9 [M+1]

Step 3

4-(3-hydroxy-2-methylphenoxy)-2-((2-fluoro-4-iodophenyl)amino)-1-methyl-6-oxo-1,6-dihydropyridine-3-carboxamide The crude 4-(3-hydroxy-2-methylphenoxy)-2-((2-fluoro-4-iodophenyl)amino)-N-(4-methoxybenzyl)-1-methyl-6-oxo-1,6-dihydropyridine-3-carboxamide 24b (140 mg, 0.19 mmol) was dissolved in 5 mL of anisole, followed by addition of aluminum chloride (127 mg, 0.95 mmol). The reaction solution was warmed up to 100° C. and stirred for 3 hours, followed by addition of 20 mL of ethyl acetate and 5 mL of water. The organic phase was dried over anhydrous sodium sulfate, and filtered. The filtrate was concentrated under reduced pressure, and the resulting residue was purified by preparative separation to obtain the title compound 4-(3-hydroxy-2-methylphenoxy)-2-((2-fluoro-4-iodophenyl)amino)-1-methyl-6-oxo-1,6-dihydropyridine-3-carboxamide 24 (15 mg, gray solid), yield: 15.4%.

MS m/z (ESI): 508.1 [M−1]

$^1$H NMR (400 MHz, DMSO-$d_6$) δ 9.92 (s, 1H), 9.80 (s, 1H), 7.59-7.67 (m, 3H), 7.42-7.44 (d, 1H), 7.09-7.14 (t, 1H), 6.78-6.81 (d, 1H), 6.64-6.69 (m, 2H), 5.01 (s, 1H), 3.14 (s, 3H), 1.93 (s, 3H).

Example 25

4-(5-fluoro-2-methylphenoxy)-2-((2-fluoro-4-iodophenyl)amino)-1-methyl-6-oxo-1,6-dihydropyridine-3-carboxamide

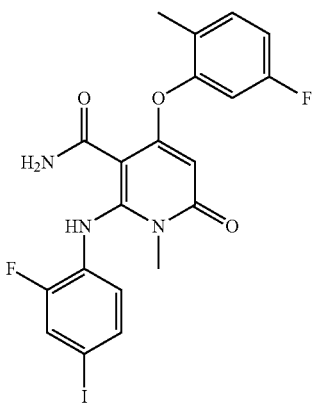

-continued

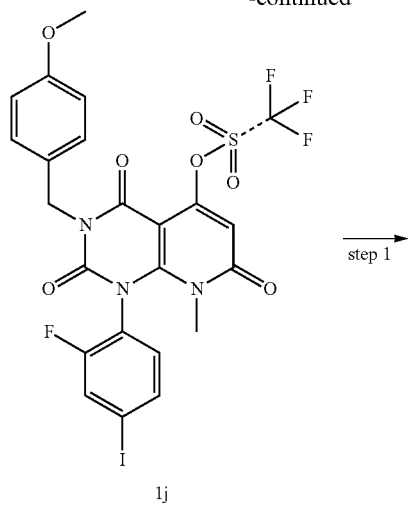

1j

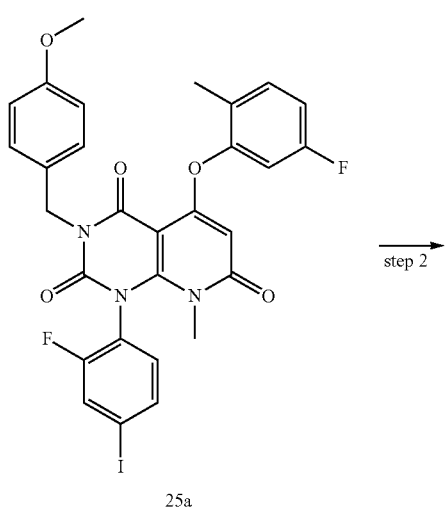

25a

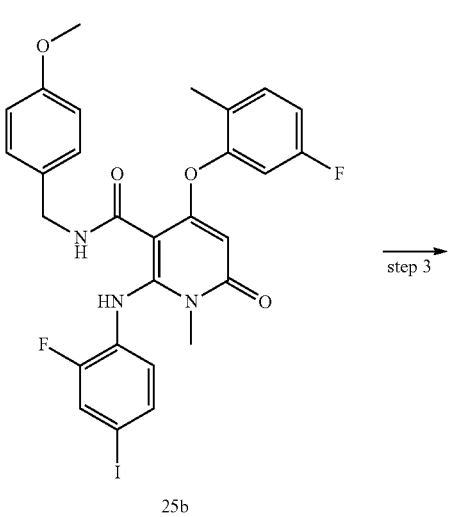

25b

-continued

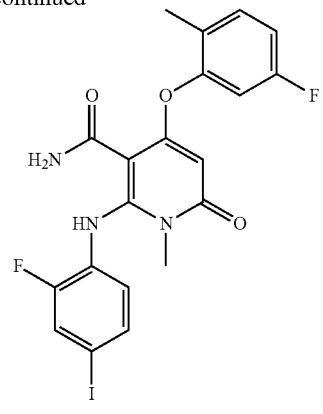

25

Step 1

5-(5-fluoro-2-methylphenoxy)-1-(2-fluoro-4-iodo-phenyl)-3-(4-methoxybenzyl)-8-methylpyrido[2,3-d]pyrimidine-2,4,7(1H,3H,8H)-trione 5-fluoro-2-methyl-phenol (33 mg, 0.26 mmol) was dissolved in 5 mL of tetrahydrofuran, followed by addition of sodium hydride (16 mg, 0.40 mmol). After stirring for 1 hour, the reaction was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), and stirred for 12 hours. The reaction solution was concentrated under reduced pressure to obtain the crude title compound 5-(5-fluoro-2-methylphenoxy)-1-(2-fluoro-4-iodophenyl)-3-(4-methoxybenzyl)-8-methylpyrido[2,3-d]pyrimidine-2,4,7(1H,3H,8H)-trione 25a (131 mg, pale yellow liquid), which was used directly in the next step without further purification.

Step 2

4-(5-fluoro-2-methylphenoxy)-2-((2-fluoro-4-iodo-phenyl)amino)-N-(4-methoxybenzyl)-1-methyl-6-oxo-1,6-dihydropyridine-3-carboxamide The crude 5-(5-fluoro-2-methylphenoxy)-1-(2-fluoro-4-iodophenyl)-3-(4-methoxybenzyl)-8-methylpyrido[2,3-d]pyrimidine-2,4,7(1H,3H,8H)-trione 25a (131 mg, 0.20 mmol) was dissolved in 6 mL of a mixture of tetrahydrofuran and water (V:V=4:1), followed by addition of lithium hydroxide (42 mg, 1 mmol). After stirring for 2 hours, the reaction solution was added with 60 mL of ethyl acetate. The organic phase was washed with water (30 mL×1) and saturated sodium chloride solution (30 mL×1), successively, dried over anhydrous sodium sulfate, filtered, and the filtrate was concentrated under reduced pressure to obtain the crude title compound 4-(5-fluoro-2-methylphenoxy)-2-((2-fluoro-4-iodophenyl)amino)-N-(4-methoxybenzyl)-1-methyl-6-oxo-1,6-dihydropyridine-3-carboxamide 25b (126 mg, brown solid), which was used directly in the next step without further purification.

MS m/z (ESI): 632.1 [M+1]

Step 3

4-(5-fluoro-2-methylphenoxy)-2-((2-fluoro-4-iodophenyl)amino)-1-methyl-6-oxo-1,6-dihydropyridine-3-carboxamide The crude 4-(5-fluoro-2-methylphenoxy)-2-((2-fluoro-4-iodophenyl)amino)-N-(4-methoxybenzyl)-1-methyl-6-oxo-1,6-dihydropyridine-3-carboxamide 25b (126 mg, 0.20 mmol) was dissolved in 3 mL of anisole, followed by addition of aluminum chloride (133 mg, 1 mmol). The reaction solution was warmed up to 100° C. and stirred for 1 hour, followed by addition of 40 mL of dichloromethane. The organic phase was washed with water (50 mL×2) and saturated sodium chloride solution (50 mL×1), successively, dried over anhydrous sodium sulfate, and filtered. The filtrate was concentrated under reduced pressure, and the resulting residue was purified by preparative separation to obtain the title compound 4-(5-fluoro-2-methylphenoxy)-2-((2-fluoro-4-iodophenyl)amino)-1-methyl-6-oxo-1,6-dihydropyridine-3-carboxamide 25 (10 mg, light brown solid), yield: 23.5%.

MS m/z (ESI): 512.1 [M+1]

$^1$H NMR (400 MHz, DMSO-d$_6$): δ 9.88 (s, 1H), 7.61-7.66 (m, 3H), 7.40-7.44 (m, 2H), 7.18-7.21 (m, 1H), 7.10-7.15 (m, 1H), 6.64-6.69 (m, 1H), 5.03 (s, 1H), 3.15 (s, 3H), 2.11 (s, 3H).

Example 26

5-fluoro-4-(3-fluoro-2-methylphenoxy)-2-((2-fluoro-4-iodophenyl)amino)-1-methyl-6-oxo-1,6-dihydropyridine-3-carboxamide

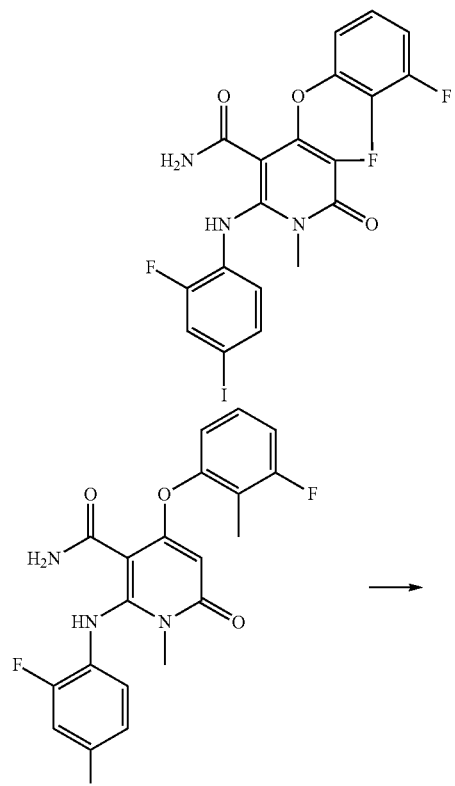

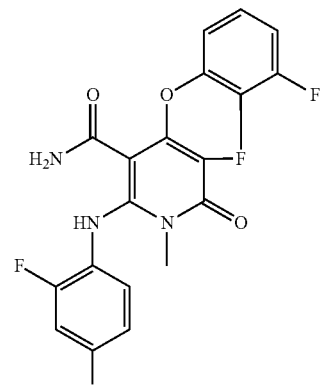

4-(3-fluoro-2-methylphenoxy)-2-((2-fluoro-4-iodophenyl)amino)-1-methyl-6-oxo-1,6-dihydropyridine-3-carboxamide 1 (10 mg, 0.02 mmol) was dissolved in 6 mL of dichloromethane. After cooling down to 0° C., the reaction solution was added with 5 mL of a solution of 1-chloromethyl-4-fluoro-1,4-diazoniabicyclo[2.2.2]octane bis(tetrafluoroborate) (11 mg, 0.03 mmol) in dichloromethane, warmed up to room temperature, and stirred for 12 hours. The reaction solution was concentrated under reduced pressure, and the resulting residue was purified by preparative separation to obtain the title compound 5-fluoro-4-(3-fluoro-2-methylphenoxy)-2-((2-fluoro-4-iodophenyl)amino)-1-methyl-6-oxo-1,6-dihydropyridine-3-carboxamide 26 (3 mg, reddish brown solid), yield: 30.0%.

MS m/z (ESI): 530.1 [M+1]

$^1$H NMR (400 MHz, DMSO-d$_6$): δ 8.68 (s, 1H), 7.54-7.60 (m, 2H), 7.44-7.46 (m, 1H), 7.35-7.37 (m, 1H), 7.14-7.20 (m, 1H), 6.93-6.97 (m, 1H), 6.76-6.78 (m, 1H), 6.62-6.66 (m, 1H), 3.33 (s, 3H), 2.21 (s, 3H).

Example 27

(R)—N-(2,3-dihydroxypropyl)-4-(3-fluoro-2-methylphenoxy)-2-((2-fluoro-4-iodophenyl) amino)-1-methyl-6-oxo-1,6-dihydropyridine-3-carboxamide

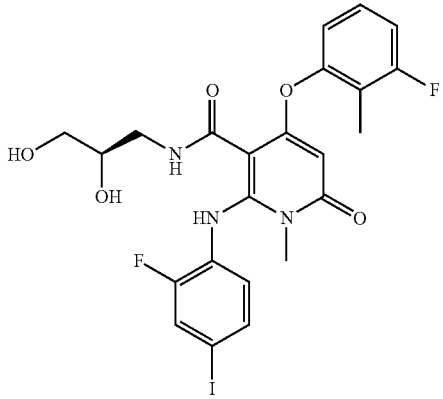

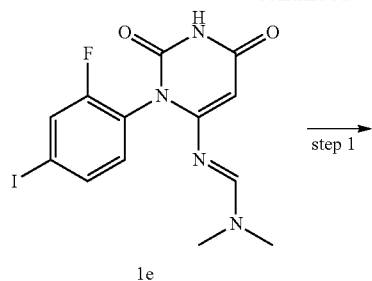
1e
→ step 1
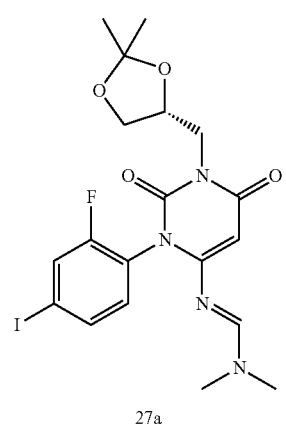
27a
→ step 2
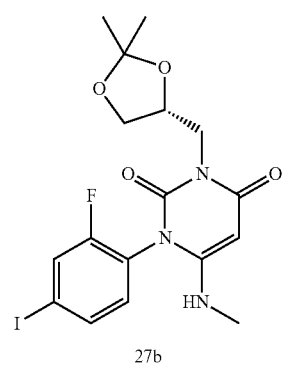
27b
→ step 3
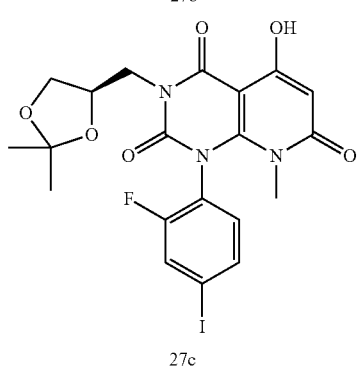
27c
→ step 4
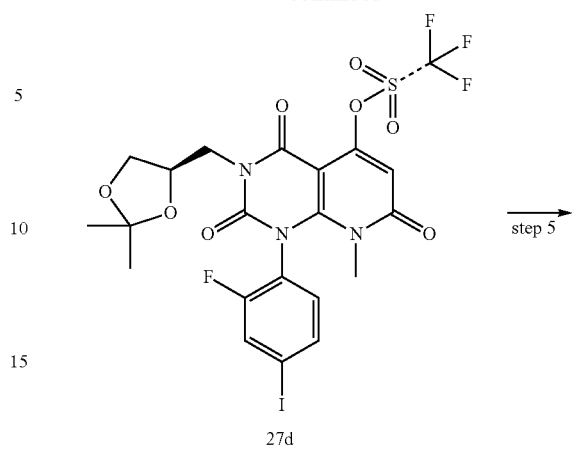
27d
→ step 5
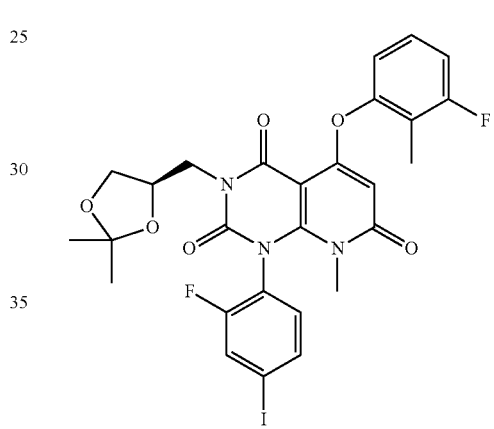
27e
→ step 6
27f
→ step 7

-continued

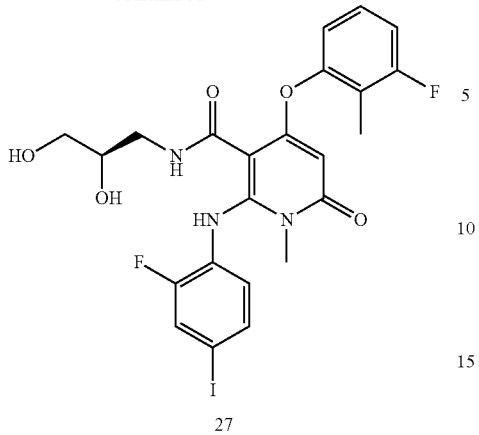

27

Step 1

(R,E)-N'-3-(2-fluoro-4-iodophenyl)-(1-((2,2-dimethyl-1,3-dioxolan-4-yl)methyl)-2,6-dioxo-1,2,3,6-tetrahydropyrimidin-4-yl)-N,N-dimethylformimidamide The crude (E)-N'-(3-(2-fluoro-4-iodophenyl)-2,6-dioxo-1,2,3,6-tetrahydropyrimidin-4-yl)-N,N-dimethylformimidamide 1e (3.30 g, 8.20 mmol), (R)-4-chloromethyl-2,2-dimethyl-1,3-dioxolane (2.47 g, 16.40 mmol), cesium carbonate (5.34 g, 16.40 mmol), and potassium iodide (200 mg, 1.20 mmol) were dissolved in 33 mL of N,N-dimethylformamide. The reaction solution was warmed up to 100° C. and stirred for 12 hours. After cooling down to room temperature, the reaction solution was added with 200 mL of ethyl acetate. The organic phase was washed with water (100 mL×3), dried over anhydrous sodium sulfate, filtered, and the filtrate concentrated under reduced pressure to obtain the crude title compound (R,E)-N'-3-(2-fluoro-4-iodophenyl)-(1-((2,2-dimethyl-1,3-dioxolan-4-yl)methyl)-2,6-dioxo-1,2,3,6-tetrahydropyrimidin-4-yl)-N,N-dimethylformimidamide 27a (3.56 g, dark brown solid), which was used directly in the next step without further purification.

MS m/z (ESI): 517.0 [M+1]

Step 2

(R)-3-((2,2-dimethyl-1,3-dioxolan-4-yl)methyl)-1-(2-fluoro-4-iodophenyl)-6-(methylamino)pyrimidine-2,4(1H,3H)-dione Sodium borohydride (391 mg, 10.34 mmol) was dissolved in 15 mL of a mixture of ethanol and tert-butanol (V:V=1:2). After cooling down to 0° C., the reaction solution was added with 15 mL of the crude (R,E)-N'-3-(2-fluoro-4-iodophenyl)-(1-((2,2-dimethyl-1,3-dioxolan-4-yl)methyl)-2,6-dioxo-1,2,3,6-tetrahydropyrimidin-4-yl)-N,N-dimethylformimidamide 27a (3.56 g, 6.90 mmol) in methanol, and stirred for 1 hour. The reaction solution was warmed up to room temperature and stirred for 12 hours. After cooling down to 0° C., the reaction solution was added with 100 mL of water, and the organic phase was washed with water (50 mL×3), dried over anhydrous sodium sulfate, filtered, and the filtrate was concentrated under reduced pressure to obtain the crude title compound (R)-3-((2,2-dimethyl-1,3-dioxolan-4-yl)methyl)-1-(2-fluoro-4-iodophenyl)-6-(methylamino)pyrimidine-2,4(1H,3H)-dione 27b (3.16 g, brown solid), which was used directly in the next step without further purification.

MS m/z (ESI): 476.0 [M+1]

Step 3

(R)-3-((2,2-dimethyl-1,3-dioxolan-4-yl)methyl)-1-(2-fluoro-4-iodophenyl)-5-hydroxy-8-methylpyrido[2,3-d]pyrimidine-2,4,7(1H,3H,8H)-trione The crude (R)-3-((2,2-dimethyl-1,3-dioxolan-4-yl)methyl)-1-(2-fluoro-4-iodophenyl)-6-(methylamino)pyrimidine-2,4(1H,3H)-dione 27b (3.16 g, 6.65 mmol) was dissolved in 35 mL of diethyl malonate. The reaction solution was stirred for 1 hour under reflux. The reaction solution was concentrated under reduced pressure, and the resulting residue was purified by silica gel column chromatography with eluent system B to obtain the title compound (R)-3-((2,2-dimethyl-1,3-dioxolan-4-yl)methyl)-1-(2-fluoro-4-iodophenyl)-5-hydroxy-8-methylpyrido[2,3-d]pyrimidine-2,4,7(1H,3H,8H)-trione 27c (356 mg, yellow solid), yield: 9.86%.

MS m/z (ESI): 544.0 [M+1]

Step 4

(R)-1-(2-fluoro-4-iodophenyl)-3-((2,2-dimethyl-1,3-dioxolan-4-yl)methyl)-8-methyl-2,4,7-trioxo-pyrido[2,3-d]pyrimidin-5-yl trifluoromethanesulfonate (R)-3-((2,2-dimethyl-1,3-dioxolan-4-yl)methyl)-1-(2-fluoro-4-iodophenyl)-5-hydroxy-8-methylpyrido[2,3-d]pyrimidine-2,4,7(1H,3H,8H)-trione 27c (356 mg, 0.66 mmol) was dissolved in 5 mL of dichloromethane, followed by addition of triethylamine (281 mg, 2.62 mmol). After cooling down to 0° C., the reaction solution was added with trifluoromethanesulfonic anhydride (370 mg, 1.31 mmol), warmed up to room temperature, and stirred for 12 hours. The reaction solution was concentrated under reduced pressure, and the resulting residue was purified by silica gel column chromatography with eluent system B to obtain the title compound (R)-1-(2-fluoro-4-iodophenyl)-3-((2,2-dimethyl-1,3-dioxolan-4-yl)methyl)-8-methyl-2,4,7-trioxo-pyrido[2,3-d]pyrimidin-5-yl trifluoromethanesulfonate 27d (150 mg, light yellow solid), yield: 33.9%.

MS m/z (ESI): 693.1 [M+18]

Step 5

(R)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7 (1H,3H,8H)-trione 3-fluoro-2-methylphenol (34 mg, 0.27 mmol) was dissolved in 5 mL of tetrahydrofuran, followed by addition of sodium hydride (13 mg, 0.33 mmol). After stirring for 2 hours, the reaction solution was added with (R)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7(1H,3H,8H)-trione 27d (150 mg, 0.22 mmol), and stirred for 12 hours. The reaction solution was concentrated under reduced pressure to obtain the crude title compound (R)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7(1H,3H,8H)-trione 27e (145 mg, pale yellow liquid), which was used directly in the next step without further purification.

Step 6

(R)-4-(3-fluoro-2-methylphenoxy)-2-((2-fluoro-4-iodophenyl)amino)-N-((2,2-dimethyl-1,3-dioxolan-4-yl)methyl)-1-methyl-6-oxo-1,6-dihydropyridine-3-carboxamide The crude (R)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7(1H,3H,8H)-trione 27e (145 mg, 0.22 mmol) was dissolved in 6 mL of a mixture of tetrahydrofuran and water (V:V=2:1), followed by addition of lithium hydroxide (186 mg, 4.44 mmol). The reaction solution was warmed up to 40° C. and stirred for 1 hour, followed by addition of 20 mL of ethyl acetate. The organic phase was washed with saturated sodium bicarbonate solution (10 mL×3) and water (20 mL×1), successively, dried over anhydrous sodium sulfate, filtered, and the filtrate was concentrated under reduced pressure to obtain the crude title compound (R)-4-(3-fluoro-2-methylphenoxy)-2-((2-fluoro-4-iodophenyl)amino)-N-((2,2-dimethyl-1,3-dioxolan-4-yl)methyl)-1-methyl-6-oxo-1,6-dihydropyridine-3-carboxamide 27f (139 mg, reddish brown solid), which was used directly in the next step without further purification.

MS m/z (ESI): 626.1 [M+1]

Step 7

(R)—N-(2,3-dihydroxypropyl)-4-(3-fluoro-2-methylphenoxy)-2-((2-fluoro-4-iodophenyl) amino)-1-methyl-6-oxo-1,6-dihydropyridine-3-carboxamide The crude (R)-4-(3-fluoro-2-methylphenoxy)-2-((2-fluoro-4-iodophenyl)amino)-N-((2,2-dimethyl-1,3-dioxolan-4-yl)methyl)-1-methyl-6-oxo-1,6-dihydropyridine-3-carboxamide 27f (139 mg, 0.22 mmol) was dissolved in 10 mL of tetrahydrofuran, followed by addition of 5 mL of 1 M hydrochloric acid. After stirring for 4 hours, the reaction solution was concentrated under reduced pressure, and the resulting residue was purified by preparative separation to obtain the title compound (R)—N-(2,3-dihydroxypropyl)-4-(3-fluoro-2-methylphenoxy)-2-((2-fluoro-4-iodophenyl) amino)-1-methyl-6-oxo-1,6-dihydropyridine-3-carboxamide 27 (70 mg, light brown solid), yield: 53.8%.

MS m/z (ESI): 586.2 [M+1]

$^1$H NMR (400 MHz, DMSO-d$_6$): δ 9.33 (s, 1H), 8.09 (t, 1H), 7.61 (d, 1H), 7.33-7.42 (m, 2H), 7.17 (t, 1H), 7.06 (d, 1H), 6.69 (t, 1H), 5.04 (s, 1H), 3.39-3.46 (m, 1H), 3.11-3.24 (m, 3H), 3.19 (s, 3H), 2.93-3.00 (m, 1H), 2.06 (s, 3H).

Example 28

(S)—N-(2,3-dihydroxypropyl)-4-(3-fluoro-2-methylphenoxy)-2-((2-fluoro-4-iodophenyl) amino)-1-methyl-6-oxo-1,6-dihydropyridine-3-carboxamide

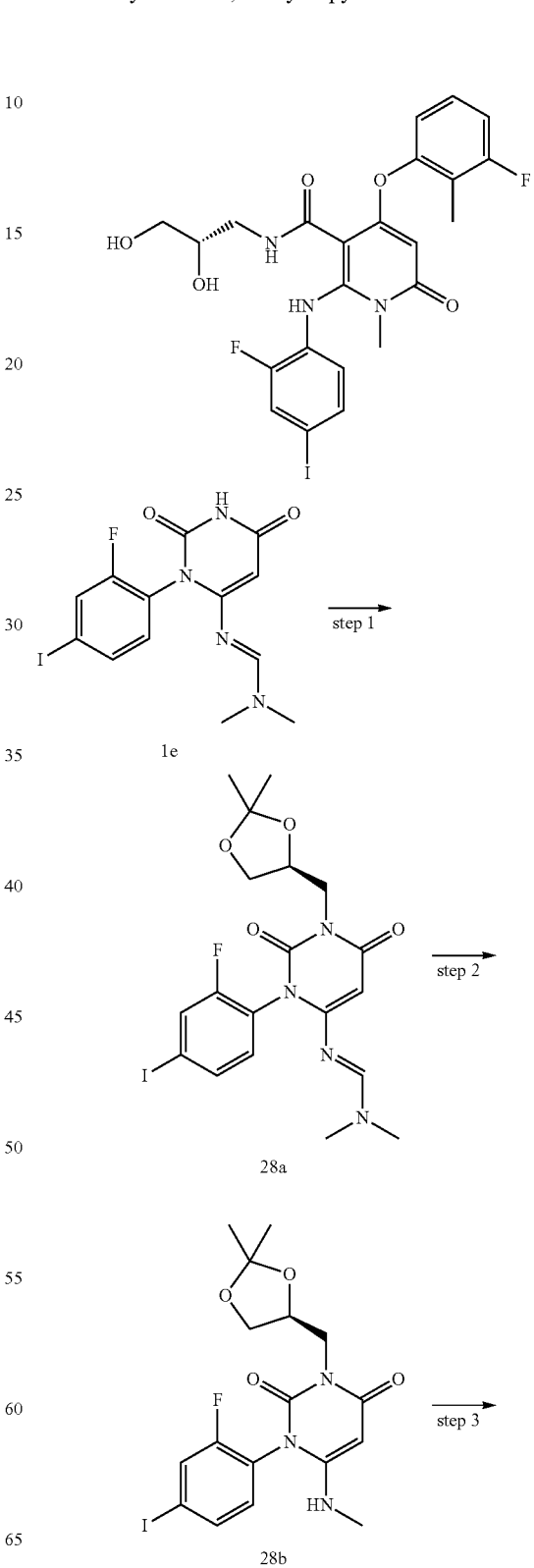

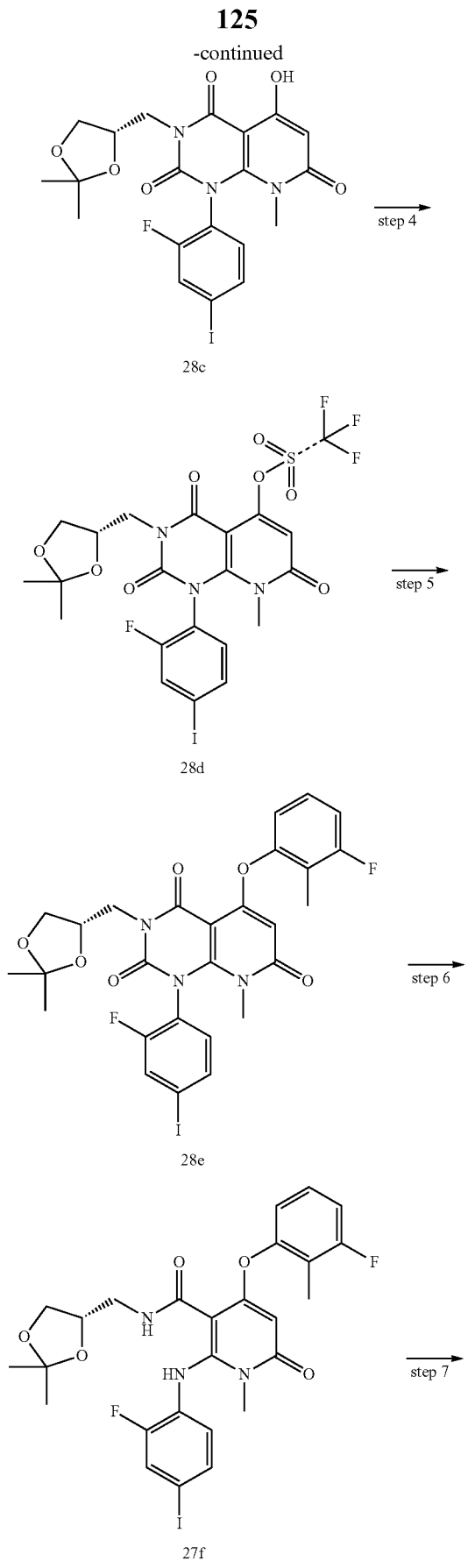

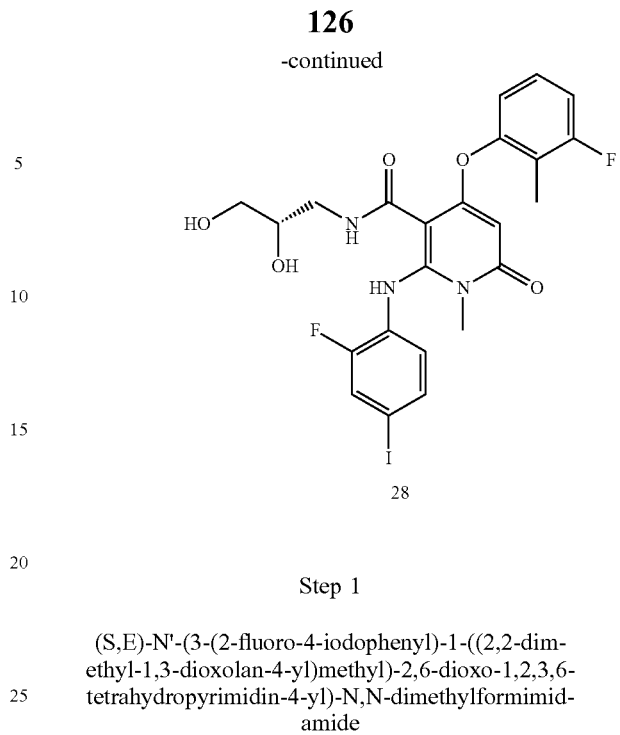

Step 1

(S,E)-N'-(3-(2-fluoro-4-iodophenyl)-1-((2,2-dimethyl-1,3-dioxolan-4-yl)methyl)-2,6-dioxo-1,2,3,6-tetrahydropyrimidin-4-yl)-N,N-dimethylformimidamide The crude (E)-N'-(3-(2-fluoro-4-iodophenyl)-2,6-dioxo-1,2,3,6-tetrahydro pyrimidin-4-yl)-N,N-dimethylformimidamide 1e (3.30 g, 8.20 mmol), (S)-4-chloro-2,2-dimethyl-1,3-dioxolane (2.47 g, 16.40 mmol), cesium carbonate (5.34 g, 16.40 mmol), and potassium iodide (200 mg, 1.20 mmol) were dissolved in 33 mL of N,N-dimethylformamide. The reaction solution was warmed up to 100° C. and stirred for 12 hours. After cooling down to room temperature, the reaction solution was added with 200 mL of ethyl acetate. The organic phase was washed with water (100 mL×3), dried over anhydrous sodium sulfate, filtered, and the filtrate was concentrated under reduced pressure to obtain the crude title compound (S,E)-N'-(3-(2-fluoro-4-iodophenyl)-1-((2,2-dimethyl-1,3-dioxolan-4-yl)methyl)-2,6-dioxo-1,2,3,6-tetrahydropyrimidin-4-yl)-N,N-dimethylformimidamide 28a (3.80 g, dark brown solid), which was used directly in the next step without further purification.

MS m/z (ESI): 517.0 [M+1]

Step 2

(S)-3-((2,2-dimethyl-1,3-dioxolan-4-yl)methyl)-1-(2-fluoro-4-iodophenyl)-6-(methylamino)pyrimidine-2,4(1H,3H)-dione Sodium borohydride (418 mg, 11.04 mmol) was dissolved in 15 mL of a mixture of ethanol and tert-butanol (V:V=1:2). After cooling down to 0° C., the reaction solution was added with the crude (S,E)-N'-(3-(2-fluoro-4-iodophenyl)-1-((2,2-dimethyl-1,3-dioxolan-4-yl)methyl)-2,6-dioxo-1,2,3,6-tetrahydropyrimidin-4-yl)-N,N-dimethylformimidamide 28a (3.80 g, 7.36 mmol), and stirred for 1 hour. After warming up to room temperature, the reaction solution was stirred for 12 hours, then cooled down to 0° C., followed by addition of 100 mL of water. The organic phase was washed with water (50 mL×3), dried over anhydrous sodium sulfate, filtered, and the filtrate was concentrated under reduced pressure to obtain the crude title compound (S)-3-((2,2-dimethyl-1,3-dioxolan-4-yl)methyl)-1-(2-fluoro-4-iodophenyl)-6-(methylamino)pyrimidine-2,4(1H,3H)-dione 28b (3.35 g, brown solid), which was used directly in the next step without further purification.

MS m/z (ESI): 476.1 [M+1]

Step 3

(S)-3-((2,2-dimethyl-1,3-dioxolan-4-yl)methyl)-1-(2-fluoro-4-iodophenyl)-5-hydroxy-8-methylpyrido[2,3-d]pyrimidine-2,4,7(1H,3H,8H)-trione The crude (S)-3-((2,2-dimethyl-1,3-dioxolan-4-yl)methyl)-1-(2-fluoro-4-iodophenyl)-6-(methylamino)pyrimidine-2,4(1H,3H)-dione 28b (3.35 g, 7.05 mmol) was dissolved in 35 mL of diethyl malonate. The reaction solution was stirred for 1 hour under reflux, then was concentrated under reduced pressure, and the resulting residue was purified by silica gel column chromatography with eluent system B to obtain the title compound (S)-3-((2,2-dimethyl-1,3-dioxolan-4-yl)methyl)-1-(2-fluoro-4-iodophenyl)-5-hydroxy-8-methylpyrido[2,3-d]pyrimidine-2,4,7(1H,3H,8H)-trione 28c (300 mg, yellow solid), yield: 7.83%.

MS m/z (ESI): 544.0 [M+1]

Step 4

(S)-1-(2-fluoro-4-iodophenyl)-3-((2,2-dimethyl-1,3-dioxolan-4-yl)methyl)-8-methyl-2,4,7-trioxo-pyrido[2,3-d]pyrimidin-5-yl trifluoromethanesulfonate (S)-3-((2,2-dimethyl-1,3-dioxolan-4-yl)methyl)-1-(2-fluoro-4-iodophenyl)-5-hydroxy-8-methylpyrido[2,3-d]pyrimidine-2,4,7(1H,3H,8H)-trione 28c (300 mg, 0.55 mmol) was dissolved in 5 mL of dichloromethane, followed by addition of 2,6-lutidine (237 mg, 2.21 mmol). After cooling down to 0° C., the reaction solution was added with trifluoromethanesulfonic anhydride (311 mg, 1.10 mmol), then warmed up to room temperature and stirred for 12 hours. The reaction solution was concentrated under reduced pressure, and the resulting residue was purified by silica gel column chromatography with eluent system B to obtain the title compound (S)-1-(2-fluoro-4-iodophenyl)-3-((2,2-dimethyl-1,3-dioxolan-4-yl)methyl)-8-methyl-2,4,7-trioxo-pyrido[2,3-d]pyrimidin-5-yl trifluoromethanesulfonate 28d (150 mg, light yellow solid), yield: 40.2%.

MS m/z (ESI): 676.1 [M+1]

Step 5

(S)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7(1H,3H,8H)-trione 3-fluoro-2-methylphenol (34 mg, 0.27 mmol) was dissolved in 5 mL of tetrahydrofuran, followed by addition of sodium hydride (13 mg, 0.33 mmol). After stirring for 2 hours, the reaction solution was added with (S)-1-(2-fluoro-4-iodophenyl)-3-((2,2-dimethyl-1,3-dioxolan-4-yl)methyl)-8-methyl-2,4,7-trioxo-pyrido[2,3-d]pyrimidin-5-yl trifluoromethanesulfonate 28d (150 mg, 0.22 mmol), then warmed up to 60° C. and stirred for 1 hour. The reaction solution was concentrated under reduced pressure to obtain the crude title compound (S)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7(1H,3H,8H)-trione 28e (145 mg, pale yellow liquid), which was used directly in the next step without further purification.

Step 6

(S)-4-(3-fluoro-2-methylphenoxy)-2-((2-fluoro-4-iodophenyl)amino)-N-((2,2-dimethyl-1,3-dioxolan-4-yl)methyl)-1-methyl-6-oxo-1,6-dihydropyridine-3-carboxamide The crude (S)-5-(3-fluoro-2-methylphenoxy)-1-(2-fluoro-4-iodophenyl)-3-((2,2-dimethyl-1,3-dioxolan-4-yl)methyl)-8-methylpyrido[2,3-d]pyrimidine-2,4,7(1H,3H,8H)-trione 28e (145 mg, 0.22 mmol) was dissolved in 6 mL of a mixture of tetrahydrofuran and water (V:V=2:1), followed by addition of lithium hydroxide (186 mg, 4.44 mmol). The reaction solution was warmed up to 40° C. and stirred for 1 hour, followed by addition of 20 mL of ethyl acetate. The organic phase was washed with saturated sodium bicarbonate solution (10 mL×3) and water (20 mL×1), successively, dried over anhydrous sodium sulfate, filtered, and the filtrate was concentrated under reduced pressure to obtain the crude title compound (S)-4-(3-fluoro-2-methylphenoxy)-2-((2-fluoro-4-iodophenyl)amino)-N-((2,2-dimethyl-1,3-dioxolan-4-yl)methyl)-1-methyl-6-oxo-1,6-dihydropyridine-3-carboxamide 28f (139 mg, light brown solid), which was used directly in the next step without further purification.

MS m/z (ESI): 626.2 [M+1]

Step 7

(S)—N-(2,3-dihydroxypropyl)-4-(3-fluoro-2-methylphenoxy)-2-((2-fluoro-4-iodophenyl) amino)-1-methyl-6-oxo-1,6-dihydropyridine-3-carboxamide The crude (S)-4-(3-fluoro-2-methylphenoxy)-2-((2-fluoro-4-iodophenyl)amino)-N-((2,2-dimethyl-1,3-dioxolan-4-yl)methyl)-1-methyl-6-oxo-1,6-dihydropyridine-3-carboxamide 28f (139 mg, 0.22 mmol) was dissolved in 10 mL of tetrahydrofuran, followed by addition of 5 mL of 1 M hydrochloric acid. After stirring for 2 hours, the reaction solution was concentrated under reduced pressure, and the resulting residue was purified by preparative separation to obtain the title compound (S)—N-(2,3-dihydroxypropyl)-4-(3-fluoro-2-methylphenoxy)-2-((2-fluoro-4-iodophenyl)amino)-1-methyl-6-oxo-1,6-dihydropyridine-3-carboxamide 28 (70 mg, light brown solid), yield: 53.8%.

MS m/z (ESI): 586.2 [M+1]

$^1$H NMR (400 MHz, DMSO-d$_6$): δ 9.33 (s, 1H), 8.09 (t, 1H), 7.61 (dd, 1H), 7.33-7.42 (m, 2H), 7.17 (t, 1H), 7.06 (d, 1H), 6.69 (t, 1H), 5.04 (s, 1H), 3.39-3.46 (m, 1H), 3.11-3.24 (m, 3H), 3.19 (s, 3H), 2.93-3.00 (m, 1H), 2.06 (s, 3H).

Example 29

2-((2-fluoro-4-iodophenyl)amino)-1-methyl-4-((2-methylpyridin-3-yl)oxy)-6-oxo-1,6-dihydropyridine-3-carboxamide

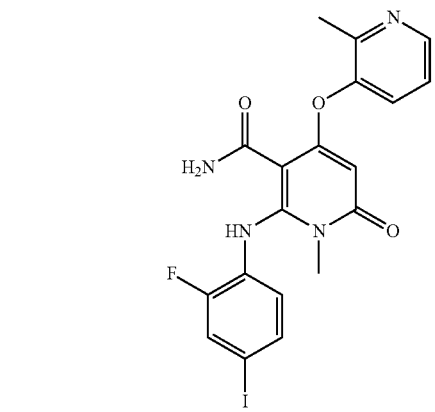

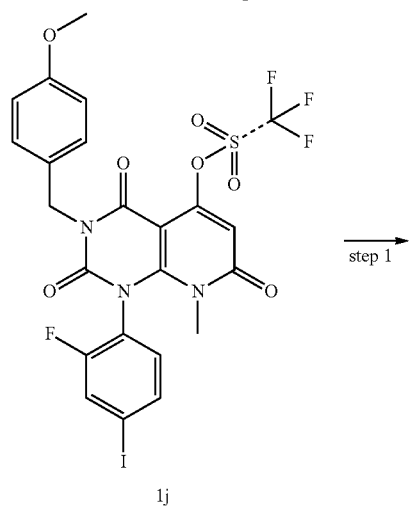
1j

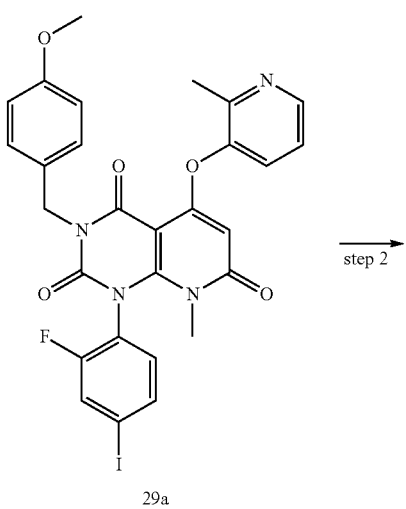
29a

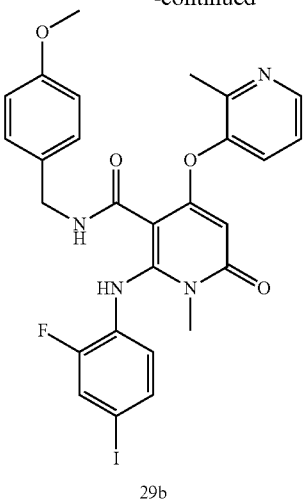
29b

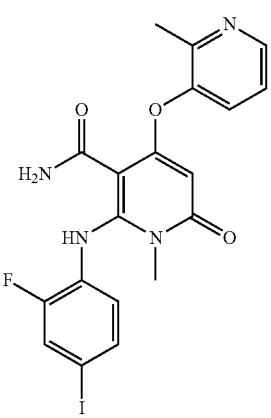
29

Step 1

5-((2-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione 2-methyl-3-hydroxy-pyridine (55 mg, 0.50 mmol) was dissolved in 5 mL of tetrahydrofuran, followed by addition of sodium hydride (24 mg, 0.60 mmol). After stirring for 1 hour, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), and stirred for 12 hours. The reaction solution was concentrated under reduced pressure to obtain the crude title compound 5-((2-methylpyridin-3-yl)oxy)-1-(2-fluoro-4-iodophenyl)-3-(4-methoxybenzyl)-8-methyl-pyrido[2,3-d]pyrimidine-2,4,7(1H,3H,8H)-trione 29a (128 mg, pale yellow liquid), which was used directly in the next step without further purification.

Step 2

4-((2-methylpyridin-3-yl)oxy)-2-((2-fluoro-4-iodophenyl)amino)-N-(4-methoxybenzyl)-1-methyl-6-oxo-1,6-dihydropyridine-3-carboxamide The crude 5-((2-methylpyridin-3-yl)oxy)-1-(2-fluoro-4-iodophenyl)-3-(4-methoxybenzyl)-8-methylpyrido[2,3-d]

pyrimidine-2,4,7(1H,3H,8H)-trione 29a (128 mg, 0.20 mmol) was dissolved in 6 mL of a mixture of tetrahydrofuran and water (V:V=5:1), followed by addition of lithium hydroxide (42 mg, 1 mmol). After stirring for 4 hours, the reaction solution was added with 50 mL of ethyl acetate and 10 mL of water. The aqueous phase was extracted with ethyl acetate (30 mL×3). The organic phases were combined, dried over anhydrous sodium sulfate, filtered, and the filtrate was concentrated under reduced pressure to obtain the crude title compound 4-((2-methylpyridin-3-yl)oxy)-2-((2-fluoro-4-iodophenyl)amino)-N-(4-methoxybenzyl)-1-methyl-6-oxo-1,6-dihydropyridine-3-carboxamide 29b (123 g, red-brown oil), which was used directly in the next step without further purification.

MS m/z (ESI): 615.1 [M+1]

Step 3

2-((2-fluoro-4-iodophenyl)amino)-1-methyl-4-((2-methylpyridin-3-yl)oxy)-6-oxo-1,6-dihydropyridine-3-carboxamide The crude 4-((2-methylpyridin-3-yl)oxy)-2-((2-fluoro-4-iodophenyl)amino)-N-(4-methoxybenzyl)-1-methyl-6-oxo-1,6-dihydropyridine-3-carboxamide 29b (123 mg, 0.20 mmol) was dissolved in 4 mL of anisole, followed by addition of aluminum chloride (133 mg, 1 mmol). The reaction solution was warmed up to 120° C. and stirred for 1 hour, followed by addition of 50 mL of ethyl acetate and 15 mL of water. The organic phase was washed with 1 M hydrochloric acid (25 mL×3), dried over anhydrous sodium sulfate, and filtered. The filtrate was concentrated under reduced pressure, and the resulting residue was purified by preparative separation to obtain the title compound 2-((2-fluoro-4-iodophenyl)amino)-1-methyl-4-((2-methylpyridin-3-yl)oxy)-6-oxo-1,6-dihydropyridine-3-carboxamide 29 (9 mg, light brown solid), yield: 9.1%.

MS m/z (ESI): 495.1 [M+1]

$^1$H NMR (400 MHz, DMSO-$d_6$): δ 9.89 (s, 1H), 8.43 (dd, 1H), 7.59-7.70 (m, 4H), 7.43 (dd, 1H), 7.38 (dd, 1H), 6.68 (t, 1H), 5.00 (s, 1H), 3.15 (s, 3H), 2.35 (s, 3H).

Example 30

2-((2-fluoro-4-iodophenyl)amino)-1-methyl-4-((5-methylpyridin-3-yl)oxy)-6-oxo-1,6-dihydropyridine-3-carboxamide

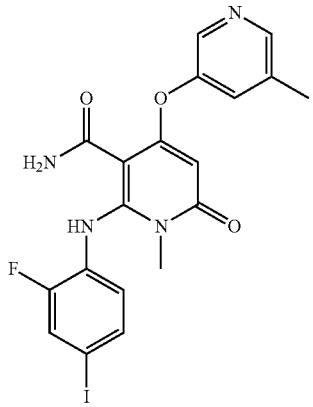

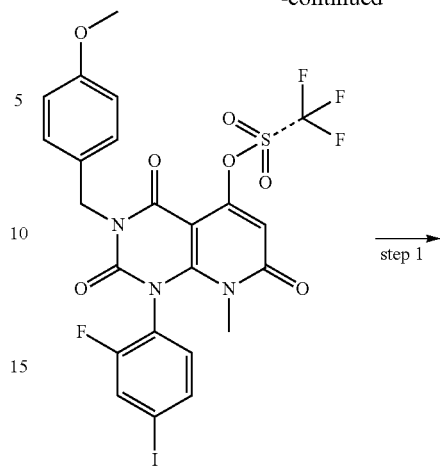

1j step 1

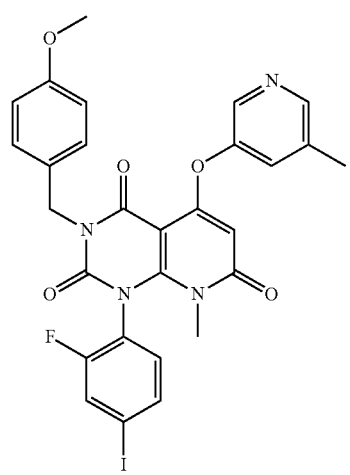

30a step 2

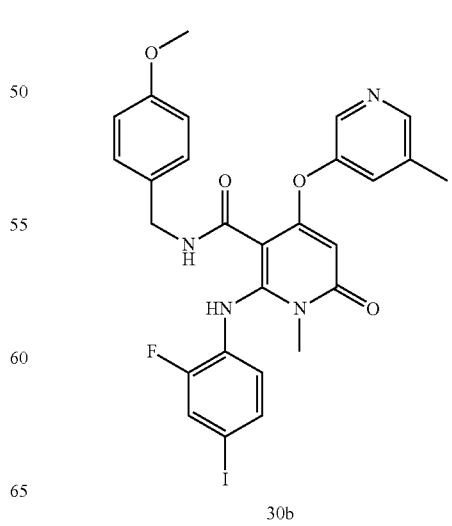

30b step 3

133

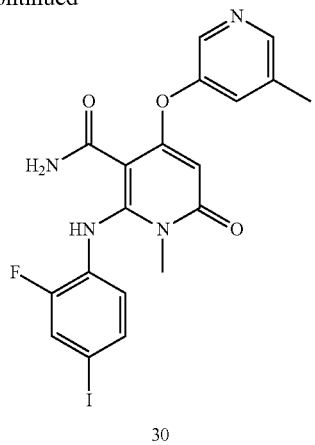

30

Step 1

5-((5-methylpyridin-3-yl)oxy)-1-(2-fluoro-4-iodo-phenyl)-3-(4-methoxybenzyl)-8-methylpyrido[2,3-d]pyrimidine-2,4,7(1H,3H,8H)-trione 5-methyl-3-hydroxy-pyridine (43 mg, 0.40 mmol) was dissolved in 5 mL of tetrahydrofuran, followed by addition of sodium hydride (16 mg, 0.40 mmol). After stirring for 1 hour, the reaction solution was added with 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (136 mg, 0.20 mmol), and stirred for 12 hours. The reaction solution was concentrated under reduced pressure to obtain the crude title compound 5-((5-methylpyridin-3-yl)oxy)-1-(2-fluoro-4-iodophenyl)-3-(4-methoxybenzyl)-8-methyl-pyrido[2,3-d]pyrimidine-2,4,7(1H,3H,8H)-trione 30a (128 mg, pale yellow liquid), which was used directly in the next step without further purification.

Step 2

4-((5-methylpyridin-3-yl)oxy)-2-((2-fluoro-4-iodo-phenyl)amino)-N-(4-methoxybenzyl)-1-methyl-6-oxo-1,6-dihydropyridine-3-carboxamide The crude 5-((5-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione 30a (128 mg, 0.20 mmol) was dissolved in 6 mL of a mixture of tetrahydrofuran and water (V:V=4:1), followed by addition of lithium hydroxide (42 mg, 1 mmol). After stirring for 3 hours, the reaction solution was added with 50 mL of ethyl acetate and 10 mL of water. The aqueous phase was extracted with ethyl acetate (30 mL×3). The organic phases were combined, washed with saturated sodium chloride solution (30 mL×3), dried over anhydrous sodium sulfate, filtered, and the filtrate was concentrated under reduced pressure to obtain the crude title compound 4-((5-methylpyridin-3-yl)oxy)-2-((2-fluoro-4-iodophenyl)amino)-N-(4-methoxybenzyl)-1-methyl-6-oxo-1,6-dihydropyridine-3-carb oxamide 30b (122 mg, brown oil), which was used directly in the next step without further purification.

MS m/z (ESI): 615.0 [M+1]

134

Step 3

2-((2-fluoro-4-iodophenyl)amino)-1-methyl-4-((5-methylpyridin-3-yl)oxy)-6-oxo-1,6-dihydropyridine-3-carboxamide The crude 4-((5-methylpyridin-3-yl)oxy)-2-((2-fluoro-4-iodophenyl)amino)-N-(4-methoxybenzyl)-1-methyl-6-oxo-1,6-dihydropyridine-3-carboxamide 30b (122 mg, 0.20 mmol) was dissolved in 4 mL of anisole, followed by addition of aluminum chloride (133 mg, 1 mmol). The reaction solution was warmed up to 100° C. and stirred for 4 hours, followed by addition of 50 mL of ethyl acetate and 15 mL of water. The organic phase was washed with water (25 mL×3), dried over anhydrous sodium sulfate, and filtered. The filtrate was concentrated under reduced pressure, and the resulting residue was purified by preparative separation method to obtain the title compound 2-((2-fluoro-4-iodophenyl)amino)-1-methyl-4-((5-methylpyridin-3-yl)oxy)-6-oxo-1,6-dihydropyridine-3-carboxamide 30 (18 mg, off-white solid), yield: 18.2%.

MS m/z (ESI): 495.1 [M+1]

$^1$H NMR (400 MHz, DMSO-d$_6$): δ 9.79 (s, 1H), 8.36-8.38 (m, 2H), 7.60-7.66 (m, 4H), 7.42-7.44 (m, 1H), 6.63-6.68 (m, 1H), 5.15 (s, 1H), 3.16 (s, 3H), 2.36 (s, 3H).

Example 31

2-((2-fluoro-4-iodophenyl)amino)-1-methyl-4-((6-methylpyridin-3-yl)oxy)-6-oxo-1,6-dihydropyridine-3-carboxamide

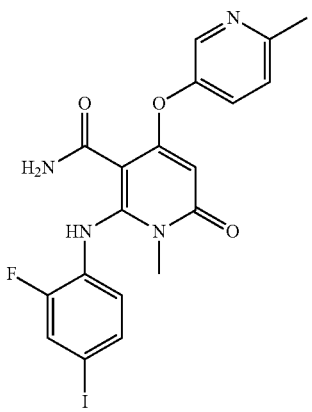

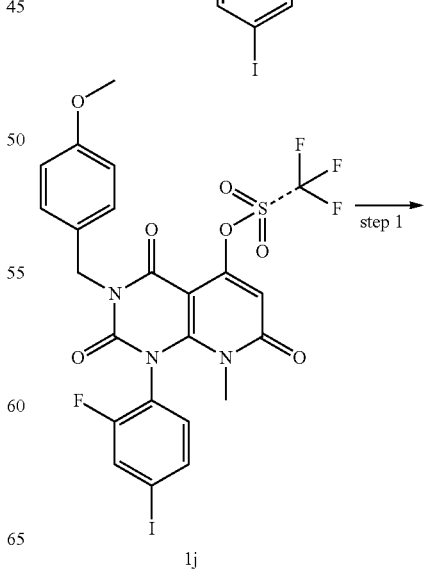

1j

135

-continued

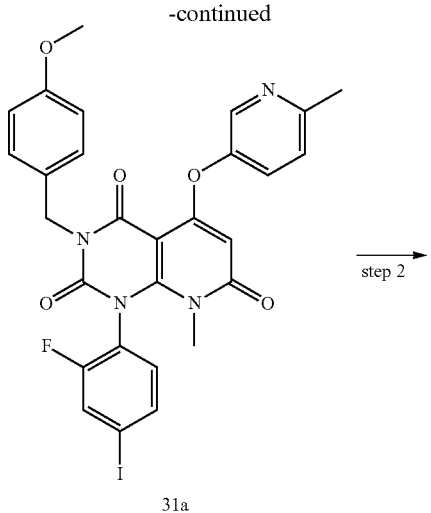

31a

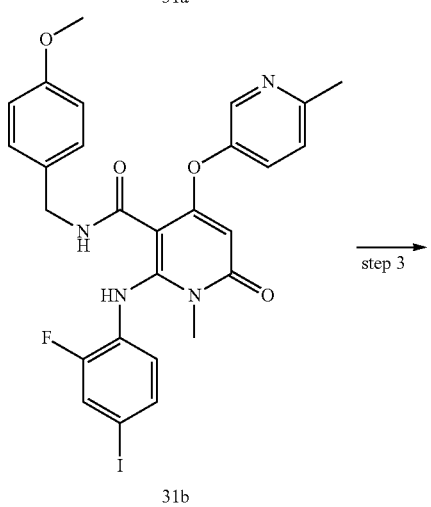

31b

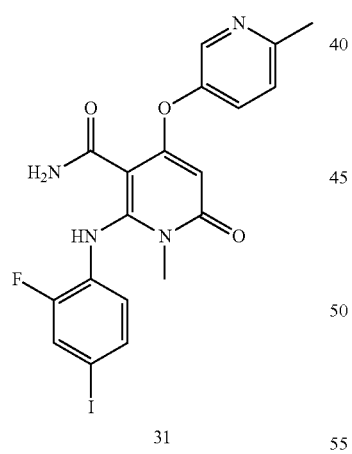

31

Step 1

5-((6-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione 6-methyl-3-hydroxy-pyridine (26 mg, 0.24 mmol) was dissolved in 5 mL of tetrahydrofuran, followed by addition of sodium hydride (12 mg, 0.30 mmol). After stirring for 2 hours, the reaction solution was added with 1-(2-fluoro-4-iodophenyl)-3-(4-methoxybenzyl)-8-methyl-2,4,7-trioxopyrido[2,3-d]pyrimidin-5-yl trifluoromethanesulfonate 1j (136 mg, 0.20 mmol), and warmed up to 60° C. and stirred for 1 hour. The reaction solution was concentrated under reduced pressure to obtain the crude title compound 5-((6-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione 31a (128 mg, pale yellow liquid), which was used directly in the next step without further purification.

MS m/z (ESI): 641.1 [M+1]

Step 2

4-((6-methylpyridin-3-yl)oxy)-2-((2-fluoro-4-iodophenyl)amino)-N-(4-methoxybenzyl)-1-methyl-6-oxo-1,6-dihydropyridine-3-carboxamide The crude 5-((6-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione 31a (128 mg, 0.20 mmol) was dissolved in 6 mL of a mixture of tetrahydrofuran and water (V:V=4:1), followed by addition of lithium hydroxide (168 mg, 4 mmol). The reaction solution was warmed up to 40° C. and stirred for 1 hour, followed by addition of 50 mL of ethyl acetate. The organic phase was washed with 1 M sodium hydroxide solution (30 mL×3), dried over anhydrous sodium sulfate, filtered, and the filtrate was concentrated under reduced pressure to obtain the crude title compound 4-((6-methylpyridin-3-yl)oxy)-2-((2-fluoro-4-iodophenyl)amino)-N-(4-methoxybenzyl)-1-methyl-6-oxo-1,6-dihydropyridine-3-carboxamide 31b (123 mg, brown oil), which was used directly in the next step without further purification.

MS m/z (ESI): 615.0 [M+1]

Step 3

2-((2-fluoro-4-iodophenyl)amino)-1-methyl-4-((6-methylpyridin-3-yl)oxy)-6-oxo-1,6-dihydropyridine-3-carboxamide The crude 4-((6-methylpyridin-3-yl)oxy)-2-((2-fluoro-4-iodophenyl)amino)-N-(4-methoxybenzyl)-1-methyl-6-oxo-1,6-dihydropyridine-3-carboxamide 31b (123 mg, 0.20 mmol) was dissolved in 5 mL of anisole, followed by addition of aluminum chloride (133 mg, 1 mmol). The reaction solution was warmed up to 120° C. and stirred for 4 hours, followed by addition of 50 mL of ethyl acetate and 15 mL of water. The organic phase was washed with water (25 mL×3), dried over anhydrous sodium sulfate, and filtered. The filtrate was concentrated under reduced pressure, and the resulting residue was purified by preparative separation to obtain the title compound 2-((2-fluoro-4-iodophenyl)amino)-1-methylpyridin-3-yl)oxy)-6-oxo-1,6-dihydropyridine-3-carboxamide 31 (30 mg, light brown solid), yield: 30.3%.

MS m/z (ESI): 495.0 [M+1]

$^1$H NMR (400 MHz, DMSO-$d_6$): δ 9.78 (s, 1H), 8.38-8.44 (m, 1H), 7.57-7.75 (m, 4H), 7.35-7.49 (m, 2H), 6.65 (t, 1H), 5.09 (s, 1H), 3.15 (s, 3H), 2.51 (s, 3H).

Example 32

2-((2-fluoro-4-iodophenyl)amino)-1-methyl-4-((2-methylpyridin-4-yl)oxy)-6-oxo-1,6-dihydropyridine-3-carboxamide

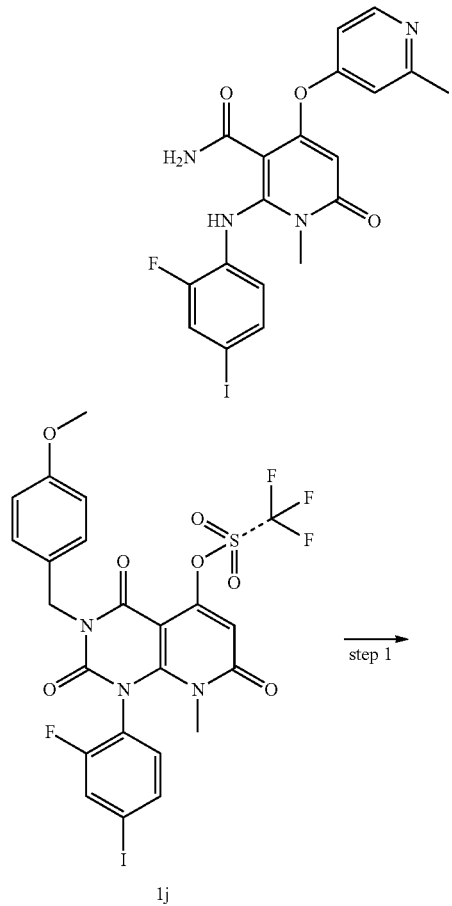

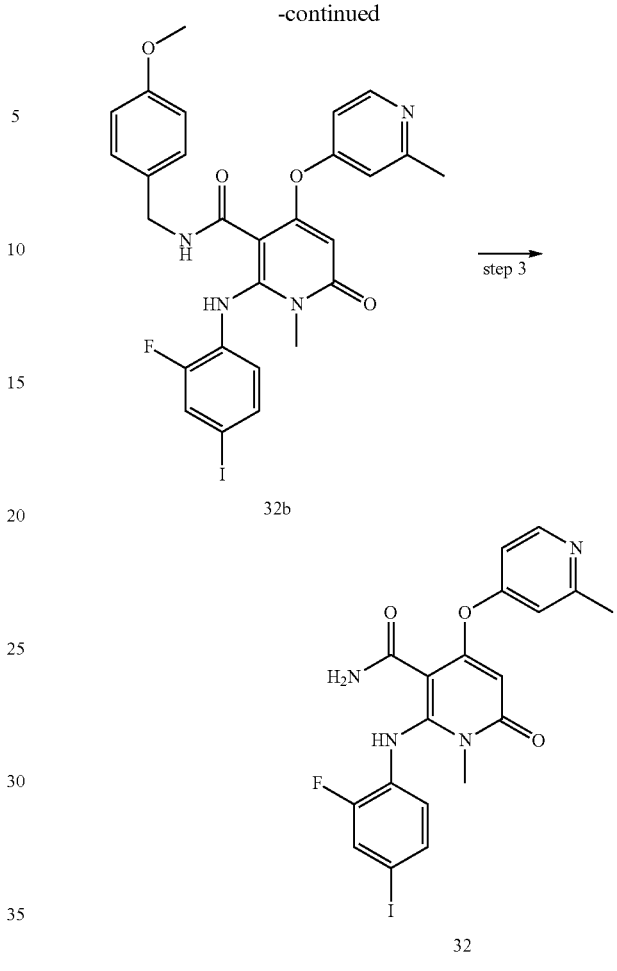

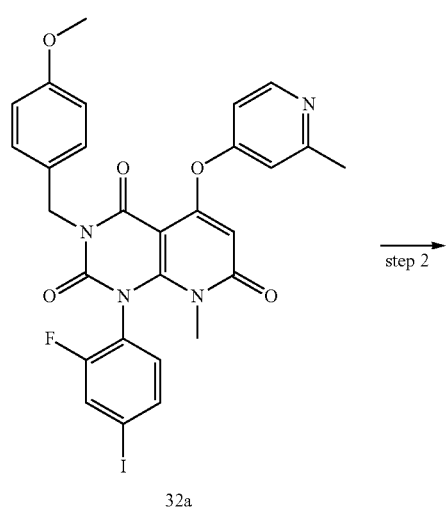

Step 1

5-((2-methylpyridin-4-yl)oxy)-1-(2-fluoro-4-iodophenyl)-3-(4-methoxybenzyl)-8-methylpyrido[2,3-d]pyrimidine-2,4,7(1H,3H,8H)-trione 2-methyl-4-hydroxy-pyridine (21 mg, 0.19 mmol) was dissolved in 10 mL of tetrahydrofuran, followed by addition of sodium hydride (7 mg, 0.29 mmol). After stirring for 2 hours, the reaction solution was added with 1-(2-fluoro-4-iodophenyl)-3-(4-methoxybenzyl)-8-methyl-2,4,7-trioxopyrido[2,3-d]pyrimidin-5-yl trifluoromethanesulfonate 1j (130 mg, 0.19 mmol). After stirring for 12 hours, the reaction solution was concentrated under reduced pressure to obtain the crude title compound 5-((2-methylpyridin-4-yl)oxy)-1-(2-fluoro-4-iodophenyl)-3-(4-methoxybenzyl)-8-methylpyrido[2,3-d]pyrimidine-2,4,7(1H,3H,8H)-trione 32a (122 mg, pale yellow liquid), which was used directly in the next step without further purification.

Step 2

4-((2-methylpyridin-4-yl)oxy)-2-((2-fluoro-4-iodophenyl)amino)-N-(4-methoxybenzyl)-1-methyl-6-oxo-1,6-dihydropyridine-3-carboxamide The crude 5-((2-methylpyridin-4-yl)oxy)-1-(2-fluoro-4-iodophenyl)-3-(4-methoxybenzyl)-8-methylpyrido[2,3-d]

pyrimidine-2,4,7(1H,3H,8H)-trione 32a (122 mg, 0.19 mmol) was dissolved in 6 mL of a mixture of tetrahydrofuran and water (V:V=4:1), followed by addition of lithium hydroxide (80 mg, 1.91 mmol). After stirring for 2 hours, the reaction solution was added with 50 mL of ethyl acetate and 10 mL of water. The aqueous phase was extracted with ethyl acetate (30 mL×3). The organic phases were combined, washed with saturated sodium chloride solution (30 mL×3), dried over anhydrous sodium sulfate, filtered, and the filtrate was concentrated under reduced pressure to obtain the crude title compound 4-((2-methylpyridin-4-yl)oxy)-2-((2-fluoro-4-iodophenyl)amino)-N-(4-methoxybenzyl)-1-methyl-6-oxo-1,6-dihydropyridine-3-carboxamide 32b (140 g, yellow oil), which was used directly in the next step without further purification.

Step 3

2-((2-fluoro-4-iodophenyl)amino)-1-methyl-4-((2-methylpyridin-4-yl)oxy)-6-oxo-1,6-dihydropyridine-3-carboxamide The crude 4-((2-methylpyridin-4-yl)oxy)-2-((2-fluoro-4-iodophenyl)amino)-N-(4-methoxybenzyl)-1-methyl-6-oxo-1,6-dihydropyridine-3-carboxamide 32b (140 mg, 0.19 mmol) was dissolved in 5 mL of anisole, followed by addition of aluminum chloride (127 mg, 0.96 mmol). The reaction solution was warmed up to 100° C. and stirred for 3 hours, followed by addition of 50 mL of ethyl acetate and 15 mL of water. The organic phase was washed with water (25 mL×3), dried over anhydrous sodium sulfate, and filtered. The filtrate was concentrated under reduced pressure, and the resulting residue was purified by preparative separation method to obtain the title compound 2-((2-fluoro-4-iodophenyl)amino)-1-methyl-4-((2-methylpyridin-4-yl)oxy)-6-oxo-1,6-dihydropyridine-3-carboxamide 32 (5 mg, yellow solid), yield: 5.3%.

MS m/z (ESI): 495.1 [M+1]

Example 33

2-((2-fluoro-4-iodophenyl)amino)-1-methyl-4-((4-methylpyridin-3-yl)oxy)-6-oxo-1,6-dihydropyridine-3-carboxamide

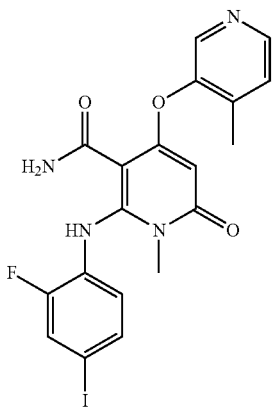

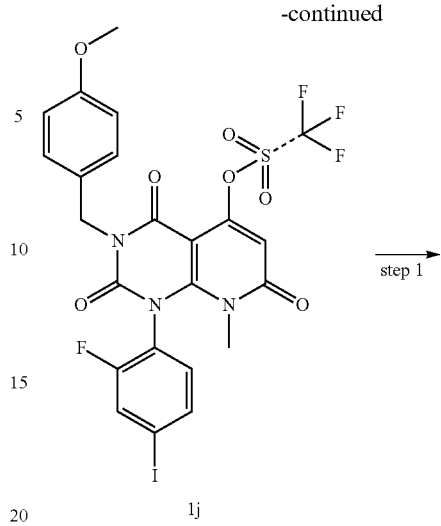

1j step 1

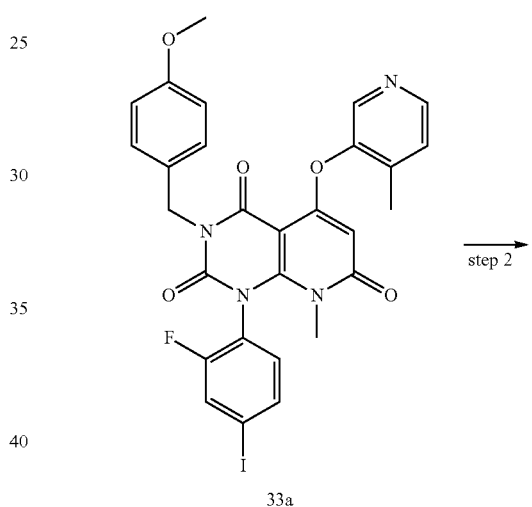

33a step 2

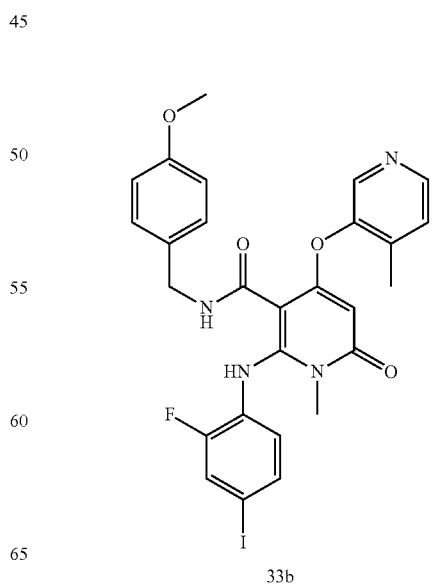

33b step 3

-continued

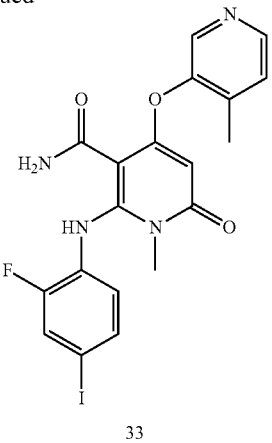

33

Step 1

5-((4-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione 4-methyl-3-hydroxy-pyridine (44 mg, 0.40 mmol) and 1-(2-fluoro-4-iodophenyl)-3-(4-methoxybenzyl)-8-methyl-2,4,7-trioxo-pyrido[2,3-d]pyrimidin-5-yl trifluoromethanesulfonate 1j (140 mg, 0.20 mmol) were dissolved in 5 mL of tetrahydrofuran, followed by addition of sodium hydride (24 mg, 0.60 mmol). After stirring for 1 hour, the reaction was added with, and stirred for 12 hours. The reaction solution was concentrated under reduced pressure to obtain the crude title compound 5-((4-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione 33a (128 mg, yellow liquid), which was used directly in the next step without further purification.

Step 2

4-((4-methylpyridin-3-yl)oxy)-2-((2-fluoro-4-iodophenyl)amino)-N-(4-methoxybenzyl)-1-methyl-6-oxo-1,6-dihydropyridine-3-carboxamide The crude 5-((4-methylpyridin-3-yl)oxy)-1-(2-fluoro-4-iodophenyl)-3-(4-methoxybenzyl)-8-methylpyrido[2,3-d]pyrimidine-2,4,7(1H,3H,8H)-trione 33a (128 mg, 0.20 mmol) was dissolved in 12 mL of a mixture of tetrahydrofuran and water (V:V=6:1), followed by addition of lithium hydroxide (84 mg, 2 mmol). After stirring for 2 hours, the reaction solution was added with 50 mL of ethyl acetate and 10 mL of water. The aqueous phase was extracted with ethyl acetate (30 mL×3). The organic phases were combined, washed with saturated sodium chloride solution (30 mL×3), dried over anhydrous sodium sulfate, filtered, and the filtrate was concentrated under reduced pressure to obtain the crude title compound 4-((4-methylpyridin-3-yl)oxy)-2-((2-fluoro-4-iodophenyl)amino)-N-(4-methoxybenzyl)-1-methyl-6-oxo-1,6-dihydropyridine-3-carboxamide 33b (122 g, yellow oil), which was used directly in the next step without further purification.

Step 3

2-((2-fluoro-4-iodophenyl)amino)-1-methyl-4-((4-methylpyridin-3-yl)oxy)-6-oxo-1,6-dihydropyridine-3-carboxamide The crude 4-((4-methylpyridin-3-yl)oxy)-2-((2-fluoro-4-iodophenyl)amino)-N-(4-methoxybenzyl)-1-methyl-6-oxo-1,6-dihydropyridine-3-carboxamide 33b (122 mg, 0.20 mmol) was dissolved in 5 mL of anisole, followed by addition of aluminum chloride (133 mg, 1 mmol). The reaction solution was warmed up to 100° C. and stirred for 12 hours, followed by addition of 50 mL of dichloromethane and 15 mL of water. The organic phase was washed with water (25 mL×3), dried over anhydrous sodium sulfate, and filtered. The filtrate was concentrated under reduced pressure, and the resulting residue was purified by preparative separation to obtain the title compound 2-((2-fluoro-4-iodophenyl)amino)-1-methyl-4-((4-methylpyridin-3-yl)oxy)-6-oxo-1,6-dihydropyridine-3-carboxamide 33 (31 mg, pale yellow solid), yield: 31.3%.

MS m/z (ESI): 495.1 [M+1]

$^1$H NMR (400 MHz, DMSO-$d_6$): δ 9.88 (s, 1H), 8.59 (s, 1H), 8.51-8.53 (d, 1H), 7.60-7.70 (m, 4H), 7.43-7.46 (dd, 1H), 6.68-6.73 (t, 1H), 5.14 (s, 1H), 3.17 (s, 3H), 2.27 (s, 3H).

Test Examples

Biological Evaluation

Test Example 1. Assay for Determining the Activity of the Compounds of the Present Invention on MEK1

MEK1 kinase activity was tested in vitro by the following method.

MEK kinase used in the assay: MEK1 (Recombinant Human Protein, Invitrogen, Catalog No. PV3093).

Kit used in the assay: Z'-LYTE™ Kinase Assay Kit-Ser/Thr 03 Peptide (Invitrogen, Catalog No. PV3176).

The following in vitro assay was used to determine the activity of the compounds of the present invention for inhibiting the proliferation of MEK kinase. The test compound was dissolved in dimethyl sulfoxide to the desired concentration. 1× Buffer A (Invitrogen, Catalog No. PV3189) was prepared, ATP was diluted with 1× Buffer A to obtain 400 μM ATP solution, appropriate amounts of Z'-LYTE™ Ser/Thr 03 Peptide (Invitrogen, Catalog No. PV3200), MEK kinase (MEK1) Enzymes and 1× Buffer A were mixed, and appropriate amounts of Z'-LYTE™ Ser/Thr 03 phosphoPeptide substrate (Invitrogen, Catalog No. PV3215) and 1× Buffer A were formulated into a mixture to be tested. The 4% DMSO solution of the test compound was prepared from 1× buffer and DMSO solution of the test compound. 2.5 μL DMSO solution of the test compound was added to a reaction well, and then 1× Buffer A, 2.5 μL of 400 μM ATP solution, 5 μL of enzyme and substrate mixture were added to become a 10 μL of reaction system. The reaction system was incubated for 4 hours at 37° C., and a mixture was prepared according to Reagent A: Buffer B=1:1024. 5 μL of a mixture of Reagent A (Invitrogen, Catalog No. PV3295) and Buffer B (Invitrogen, Catalog No. P3127) was added to a reaction well, the reaction system was incubated for 60 minutes at 25° C. The fluorescence was read by a NovoStar ELISA with excitation wavelength: 400 nm, and emission wavelength: 445 nm and 520 nm.

The activity of the compounds of the present invention: The above assay was used to determine the biochemical activity of the compounds of the present invention for inhibiting MEK kinase (MEK1). $IC_{50}$ values are shown in Table 1.

TABLE 1

Activity of the compounds of the present invention for inhibiting MEK kinase (MEK1)

| Example No. | $IC_{50}$/(nM) |
| --- | --- |
| 1 | 4.7 |
| 2 | 19.0 |
| 3 | 4.1 |
| 4 | 4.0 |
| 5 | 4.0 |
| 6 | 3.4 |
| 7 | 5.5 |
| 8 | 3.2 |
| 9 | 6.0 |
| 10 | 6.3 |
| 11 | 5.5 |
| 12 | 5.1 |
| 13 | 5.5 |
| 14 | 6.2 |
| 15 | 8.2 |
| 16 | 9.5 |
| 17 | 8.4 |
| 18 | 7.9 |
| 19 | 5.8 |
| 20 | 2.9 |
| 21 | 6.3 |
| 22 | 4.3 |
| 23 | 4.2 |
| 24 | 4.0 |
| 25 | 5.9 |
| 26 | 3.9 |
| 27 | 28.3 |
| 28 | 26.0 |
| 29 | 3.6 |
| 30 | 6.0 |
| 31 | 3.9 |
| 32 | 5.5 |
| 33 | 7.3 |

Conclusion: The compounds of the present invention had significant activity for inhibiting MEK1.

Test Example 2. Assay for Determining the Proliferation Inhibition Activity of the Compounds of the Present Invention on MEK2

MEK2 kinase activity was tested in vitro by the following method.

MEK kinase used in the assay:

MAP2K2 (MEK2) Recombinant Human Protein (Invitrogen, Catalog No. PV3615)

MAPK1 (ERK2) Recombinant Human Protein (Invitrogen, Catalog No. PV3314)

Kit used in the assay: Z'-LYTE™ Kinase Assay Kit-Ser/Thr 03 Peptide (Invitrogen, Catalog No. PV3176).

The following in vitro assay was used to determine the activity of the compounds of the present invention for inhibiting the proliferation of MEK kinase. The test compound was dissolved in dimethyl sulfoxide to the desired concentration. 1× Buffer A (Invitrogen, Catalog No. PV3189) was prepared, ATP was diluted with 1× Buffer A to obtain 400 μM ATP solution, appropriate amounts of Z'-LYTE™ Ser/Thr 03 Peptide (Invitrogen, Catalog No. PV3200), MEK kinase (MEK 2) enzymes, (ERK2) enzymes and 1× Buffer A were mixed, and appropriate amounts of Z'-LYTE™ Ser/Thr 03 phosphoPeptide substrate (Invitrogen, Catalog No. PV3215) and 1× Buffer A were formulated into a mixture to be tested. The 4% DMSO solution of the test compound was prepared from 1× buffer and DMSO solution of the test compound. 2.5 μL DMSO solution of the test compound was added to a reaction well, and then 2.5 μL of 400 μM ATP solution, 5 μL of enzyme and substrate mixture were added to become a 10 μL reaction system. The reaction system was incubated for 1.5 hours at 25° C., and a mixture was prepared according to Reagent A: Buffer B=1:1024. 5 μL of a mixture of Reagent A (Invitrogen, Catalog No. PV3295) and Buffer B (Invitrogen, Item No. P3127) was added to a reaction well, the reaction system was incubated for 60 minutes at 25° C., and then the fluorescence was read by a NovoStar ELISA with excitation wavelength: 400 nm, and emission wavelength: 445 nm and 520 nm.

The above assay was used to determine the biochemical activity of the compounds of the present invention for inhibiting MEK kinase (MEK2). $IC_{50}$ values are shown in Table 3.

TABLE 3

Activity of the compounds of the present invention for inhibiting MEK kinase (MEK2)

| Example No. | $IC_{50}$/(nM) |
| --- | --- |
| 1 | 108.3 |
| 3 | 19.8 |
| 22 | 120.8 |
| 29 | 216.8 |
| 31 | 350.9 |

Conclusion: The compounds of the present invention had significant activity for inhibiting MEK2.

Test Example 3. Assay for Determining the Proliferation Inhibition Activity of the Compounds of the Present Invention on Colo205

Cell line used in the assay: Colo205 (Cell Bank of the Chinese Academy of Sciences, Catalog No. TCHu102).

The following in vitro cell assay is to determine the activity of the compounds of the present invention for inhibiting the proliferation of human colon cancer cell, and the activity is expressed as $IC_{50}$. General programs of this kind of assay were as follows: First, the cell line to be tested (purchased from Cell Bank of the Chinese Academy of Sciences) was inoculated in a 96-well culture plate with a suitable cell concentration of 4000 cells/mL medium, and was cultured in a carbon dioxide incubator at 37° C., then grown overnight. The medium was replaced by new medium added with a series of concentrations (10000 nM, 1000 nM, 100 nM, 10 nM, 1 nM, 0.1 nM) of the test compound solutions. The plates were placed back in the incubator, and continuously cultured for 72 hours. After 72 hours, CCK8 (Cell Counting Kit-8, Catalog No.: CK04, purchased from colleagues chemical company) method was used to determine the proliferation inhibition activity of the test compounds. $IC_{50}$ values were calculated from the inhibition data of the test compounds at a series of different concentrations.

The above assay was used to determine the biochemical activity of the compounds of the present invention. $IC_{50}$ values are shown in Table 2.

TABLE 2

Proliferation inhibition activity of the compounds of
the present invention on Colo205 cell

| Example No. | $IC_{50}$/(nM) |
|---|---|
| 1 | 0.7 |
| 2 | 4.7 |
| 3 | 0.04 |
| 4 | 0.8 |
| 7 | 0.4 |
| 8 | 0.5 |
| 9 | 0.3 |
| 10 | 4.3 |
| 11 | 4.3 |
| 12 | 0.7 |
| 13 | 2.9 |
| 14 | 4.2 |
| 15 | 10.2 |
| 16 | 11.5 |
| 17 | 2.0 |
| 18 | 1.4 |
| 19 | 0.8 |
| 20 | 1.7 |
| 21 | 10.2 |
| 22 | 6.1 |
| 23 | 0.4 |
| 24 | 3.1 |
| 25 | 1.0 |
| 29 | 0.8 |
| 31 | 3.6 |
| 32 | 4 |

Conclusion: The compounds of the present invention had significant proliferation inhibition activity on Colo205 cell.

Test Example 4. Assay for Determining the Proliferation Inhibition Activity of the Compounds of the Present Invention on Human Colon Cancer Cell HCT116

The following in vitro cell assay was used to determine the activity of the compounds of the present invention for inhibiting the proliferation of human colon cancer cell, and the activity is expressed as $IC_{50}$.

Cell line which was used in the experiment: HCT116 (Cell Bank of the Chinese Academy of Sciences, Catalog No. TCHu99).

General programs of this kind of assay were as follows: First, the cell line to be tested was inoculated in a 384-well culture plate with a suitable cell concentration of 1000 cells/well, and was cultured in an incubator under the conditions of 37° C. and 5% $CO_2$, then grown overnight. The medium was replaced by new medium added with a series of concentrations (1000 nM, 250 nM, 62.50 nM, 15.63 nM, 3.91 nM, 0.98 nM, 0.24 nM, 0.06 nM, 0.015 nM, 0.004 nM) of the test compound solutions. The plates were placed back in the incubator, and continuously cultured for 72 hours. After 72 hours, CCK8 (Cell Counting Kit-8, Catalog No.: CK04, purchased from colleagues chemical company) method was used to determine the proliferation inhibition activity of the test compounds. $IC_{50}$ values were calculated from the inhibition data of the test compounds at a series of different concentrations.

The above assay was used to determine the biochemical activity of the compounds of the present invention. $IC_{50}$ values are shown in Table 4.

TABLE 4

Proliferation inhibition activity of the compounds of
the present invention on HCT116 cell

| Example No. | $IC_{50}$/(nM) |
|---|---|
| 1 | 8.6 |
| 3 | 0.06 |
| 22 | 10.3 |
| 29 | 8.9 |
| 31 | 36.4 |

Conclusion: The compounds of the present invention had significant proliferation inhibition activity on HCT116 cell.

In Vitro Evaluation for Inhibition Activity of the Compounds of the Present Invention on CYP Enzyme

Test Example 5. In Vitro Assay for Determining the Inhibition Activity of the Compounds of Example 1, Example 3, Example 4, Example 22, Example 29, Example 30 and Example 31 of the Present Invention on CYP Enzyme 1. Abstract Human liver microsome incubation system was used to reflect the activity of enzymes based on the amount of metabolites produced. Enzyme inhibition of the test compounds was investigated on CYP1A2, CYP2C9, CYP2C6, CYP3A4m, CYP3A4t and CYP2C19, and $IC_{50}$ values (a concentration of the test compound that is required for 50% inhibition of enzyme activity) were measured.

2. Protocol 2.1 Samples

Compounds of Example 1, Example 3, Example 4, Example 22, Example 29, Example 30 and Example 31.

2.2 Materials 2.2.1. Preparation of phosphate buffered saline (PBS)

18.303 g $K_2HPO_4$, 2.695 g $KH_2PO_4$, 11.175 g KCl and 372.2 mg EDTA were weighed and diluted with ultrapure water to 1000 mL to obtain phosphate buffered saline with pH 7.4 (EDTA is 1 mM, KCl is 0.15 M), and PBS was stored in the refrigerator at 4° C.

2.2.2. Weighing and Preparation of NADPH

Preparation of 40 mM NADPH solution: a standard sample of 100 mg of NADPH (MW=833.4 g/mol) was weighed and dissolved in 3 ml of PBS buffer, and then the solution was mixed uniformly.

2.2.3. Preparation of PBS Solution of Liver Microsomes

Preparation of a 0.25 mg/ml solution of liver microsomes: human liver microsomes (20 mg/ml) was diluted with PBS buffer to 0.25 mg/mL.

2.2.4. Preparation of the Reaction Solution of the Test Compound

The appropriate amount of test compound standard sample was weighed, and diluted with DMSO to 50 mM to obtain stock solution I. The stock solution I was diluted with PBS to 10 µM to obtain the reaction liquid which is to be used in incubation.

2.2.5. Preparation of CYP Probe Substrate and Selective Inhibitor

| | Probe substrate/Conc. | Positive control inhibitor/Conc. |
|---|---|---|
| 1A2 | Phenacetin/120 µM | β-Naphthoflavone/1 µM |
| 3A4-I | Midazolam/30 µM | Ketoconazole/3 µM |

-continued

| Probe substrate/Conc. | Positive control inhibitor/Conc. |
|---|---|
| 3A4-II Testosterone/900 μM | Ketoconazole/3 μM |
| 2C9 Diclofenac/40 μM | Sulfaphenazolum/30 μM |
| 2C19 (S)-Mephenytoin/300 μM | Ticlopidine/30 μM |
| 2D6 Dextromethorphan/40 μM | Quinidine/30 μM |

The final concentration of the above probe substrate and positive control inhibitors were prepared with PBS.

3. Process

The reaction mixture was prepared: 60 μL

| Reagents | Volume (uL) |
|---|---|
| Human liver microsomes (0.25 mg/ml) | 40 μL |
| Probe substrate | 10 μL |
| Test compound/positive control inhibitors | 10 μL |

The above mixture was preincubated for 5 minutes at 37° C., followed by addition of 40 μL of NADPH (2.5 mM, PBS formulation). The mixture solution was incubated for 20 minutes at 37° C. All incubated samples were set to double samples. 300 μL ice-cold acetonitrile was added to terminate the reaction. The reaction solution was added with 100 μl internal standard, mixed uniformly, and centrifuged for 10 minutes at 3500 rpm. The supernatant was transferred to the LC-MS/MS analysis.

4. Data Analysis

The activity of enzymes was reflected by the production amount of metabolites. Using a single point method, the formula was calculated as follows:

$$IC_{50} = C_0 \times \frac{100\% - \text{Inhibition rate at } C_0 \text{ concentration}}{\text{Inhibition rate at } C_0 \text{ concentration}}$$

[Assume Hill slope=1]

$C_0$=the concentration of test compound

According to the known literature: $IC_{50}>10$ μM belongs to weaker inhibition, $1$ μM$<IC_{50}<10$ μM belong to moderate inhibition, $IC_{50}<1$ μM belong to strong inhibition.

5. Results of In Vitro CYP Enzyme Inhibition

In vitro CYP enzyme inhibition results of the compounds of the invention were shown below.

| Example No. | IC$_{50}$/μM | | | | | |
|---|---|---|---|---|---|---|
| | CYP1A2 | CYP2C9 | CYP2C6 | CYP3A4m | CYP3A4t | CYP2C19 |
| 1 | >10 | >10 | >10 | >10 | >10 | >10 |
| 3 | >50 | >50 | >50 | >50 | >50 | >10 |
| 4 | >10 | >50 | >50 | >50 | >50 | >10 |
| 22 | >10 | >10 | >10 | >10 | >10 | >10 |
| 29 | >10 | >10 | >10 | >10 | >10 | >10 |
| 30 | >10 | >10 | >10 | >10 | >10 | >10 |
| 31 | >10 | >10 | >10 | >10 | >10 | >10 |

Preferred compounds of the present invention had weaker inhibition on CYP1A2, CYP2C9, CYP2C6, CYP3A4m, CYP3A4t and CYP2C19 enzymes. The compounds of the present invention thus had less likely drug metabolism interactions in clinical administration.

Pharmacokinetics Assay

Test Example 6. Pharmacokinetics Assay of the Compounds of Example 1, Example 22, Example 29 and Example 31 of the Present Invention 1. Abstract Sprague-Dawley (SD) rats were used as test animals. The compounds of Example 1, Example 22, Example 29 and Example 31 were administered intragastrically to rats to determine the drug concentration in plasma at different time points by a LC/MS/MS method. The pharmacokinetic behavior of the compounds of the present invention was studied and evaluated in rats.

2. Protocol 2.1 Samples

Compounds of Example 1, Example 22, Example 29 and Example 31.

2.2 Test Animals

16 Healthy adult SD rats, half male and half female, purchased from SINO-BRITSH SIPPR/BK LAB. ANIMAL LTD., CO, Certificate No.: SCXK (Shanghai) 2008-0016, were divided into four groups, with 4 rats in each group.

2.3 Preparation of the Test Compounds

The appropriate amounts of test compounds were weighed and mixed with 40 μL of tween 80 and 0.5% CMC-Na to prepare a 1 mg/mL suspension by an ultrasonic method.

2.4 Administration

After an overnight fast, 16 SD rats, half male and half female, were divided into 4 groups, with 4 rats in each group, and administered the test compounds intragastrically at a dose of 10 mg/kg, and an administration volume of 10 mL/kg.

3. Process

Blood samples (0.1 mL) were taken from the orbital sinus before administration, and at 0.5 h, 1 h, 2 h, 4 h, 6 h, 8 h, 11 h, 24 h and 48 h after administration, stored in heparinized tubes, and centrifuged for 10 minutes at 3,500 rpm to separate blood plasma. The plasma samples were stored at −20° C. The rats were fed 2 hours after administration.

The concentration of the test compounds in rat plasma after intragastrically administering the test compounds was analyzed by a LC-MS/MS method. The linearity range of the method is 1.00-2000 ng/ml, and the lower limit of quantification is 1.00 ng/ml. Plasma samples were analyzed after protein precipitation.

4. Results of Pharmacokinetic Parameters

Pharmacokinetic Parameters of the compounds of the present invention were shown as follows:

| Pharmacokinetics Assay (10 mg/kg) | | | | | | |
|---|---|---|---|---|---|---|
| Example No. | Plasma Conc. Cmax (ng/mL) | Area Under Curve AUC (ng/mL*h) | Half-Life T1/2 (h) | Mean Residence Time MRT (h) | Clearance CL/F (ml/min/kg) | Apparent Distribution Volume Vd (ml/kg) |
| 1 | 56.3 ± 15.6 | 642 ± 187 | 6.61 ± 1.66 | 10.5 ± 2.41 | 280 ± 94.6 | 163863 ± 87909 |
| 22 | 108 ± 38 | 1109 ± 746 | 7.18 ± 4.64 | 11.3 ± 6.7 | 224 ± 151 | 98789 ± 42165 |
| 29 | 1440 ± 396 | 6122 ± 3028 | 3.79 ± 0.76 | 3.79 ± 0.50 | 32.9 ± 15.5 | 11319 ± 6870 |
| 31 | 3372 ± 756 | 18126 ± 9974 | 4.12 ± 0.96 | 4.43 ± 0.96 | 11.6 ± 5.9 | 4483 ± 3051 |

Conclusion: The compounds of the present invention had good pharmacokinetic absorption and significant advantage of pharmacokinetic properties.

What is claimed is:

1. A compound of formula (I), or a tautomer, mesomer, racemate, enantiomer, or diastereomer thereof, or mixture thereof, or a pharmaceutically acceptable salt thereof:

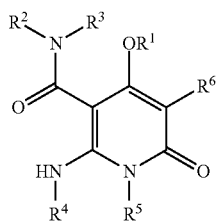

(I)

wherein:

$R^1$ is selected from the group consisting of cycloalkyl, heterocyclyl, aryl and heteroaryl, wherein the cycloalkyl, heterocyclyl, aryl and heteroaryl are each independently and optionally substituted with one or more groups selected from the group consisting of halogen, cyano, nitro, alkyl, haloalkyl, hydroxyalkyl, alkenyl, alkynyl, cycloalkyl, heterocyclyl, aryl, heteroaryl, —$OR^7$, —$C(O)OR^7$, —$OC(O)R^7$, —$O(CH_2)_n C(O)OR^7$, —$C(O)R^7$, —$C(O)NHR^7$, —$NHC(O)R^7$, —$NHC(O)OR^7$, —$NHS(O)_m R^7$, —$NR^8R^9$, —$OC(O)NR^8R^9$, and —$C(O)NR^8R^9$;

$R^2$ and $R^3$ are each independently selected from the group consisting of hydrogen and alkyl, wherein the alkyl is optionally substituted with one or more groups selected from the group consisting of halogen, cyano, nitro, alkenyl, alkynyl, heterocyclyl, aryl, heteroaryl, —$OR^7$, —$C(O)OR^7$, —$OC(O)R^7$, —$O(CH_2)_n C(O)OR^7$, —$C(O)R^7$, —$NHC(O)R^7$, —$NHC(O)OR^7$, —$NHS(O)_m R^7$, —$NR^8R^9$, —$OC(O)NR^8R^9$, and —$C(O)NR^8R^9$;

$R^4$ is selected from the group consisting of aryl and heteroaryl, wherein the aryl and heteroaryl are each independently and optionally substituted with one or more groups selected from the group consisting of halogen, cyano, hydroxy, nitro, alkyl, haloalkyl, hydroxyalkyl, alkenyl, alkynyl, heterocyclyl, aryl, heteroaryl, —$OR^7$, —$C(O)OR^7$, —$OC(O)R^7$, —$O(CH_2)_n C(O)OR^7$, —$C(O)R^7$, —$NHC(O)R^7$, —$NHC(O)OR^7$, —$NHS(O)_m R^7$, —$NR^8R^9$, —$OC(O)NR^8R^9$, and —$C(O)NR^8R^9$;

$R^5$ is selected from the group consisting of hydrogen, alkyl, alkenyl, and alkynyl, wherein the alkyl, alkenyl, and alkynyl are each independently and optionally substituted with one or more groups selected from the group consisting of halogen, hydroxy, alkoxy, cyano, and haloalkyl;

$R^6$ is selected from the group consisting of hydrogen, halogen and alkyl, wherein the alkyl is optionally substituted with one or more groups selected from the group consisting of halogen, hydroxy, cyano, nitro, alkoxy, cycloalkyl, heterocyclyl, aryl, and heteroaryl;

$R^7$ is selected from the group consisting of hydrogen, alkyl, cycloalkyl, heterocyclyl, aryl and heteroaryl, wherein the alkyl, cycloalkyl, heterocyclyl, aryl and heteroaryl are each independently and optionally substituted with one or more groups selected from the group consisting of alkyl, halogen, hydroxy, alkoxy, cycloalkyl, heterocyclyl, aryl, heteroaryl, carboxyl, and alkoxycarbonyl;

$R^8$ and $R^9$ are each independently selected from the group consisting of hydrogen, alkyl, cycloalkyl, heterocyclyl, aryl, and heteroaryl, wherein the alkyl, cycloalkyl, heterocyclyl, aryl, and heteroaryl are each independently and optionally substituted with one or more groups selected from the group consisting of alkyl, halogen, hydroxy, alkoxy, cycloalkyl, heterocyclyl, aryl, heteroaryl, carboxyl, and alkoxycarbonyl; or alternatively, $R^8$ and $R^9$ together with the nitrogen atom to which they are attached form a heterocyclyl, wherein the heterocyclyl contains one or more heteroatoms selected from the group consisting of N, O, and $S(O)_m$, and the heterocyclyl is optionally substituted with one or more groups selected from the group consisting of alkyl, halogen, hydroxy, alkoxy, cycloalkyl, heterocyclyl, aryl, heteroaryl, carboxyl, and alkoxycarbonyl;

m is 0, 1 or 2; and n is 0, 1 or 2.

2. The compound of formula (I), or the tautomer, mesomer, racemate, enantiomer, or diastereomer thereof, or mixture thereof, or the pharmaceutically acceptable salt thereof according to claim 1, wherein $R^1$ is selected from the group consisting of aryl and heteroaryl, wherein the aryl and heteroaryl are each optionally substituted with one or more groups selected from the group consisting of halogen, cyano, nitro, alkyl, haloalkyl, hydroxyalkyl, alkenyl, alkynyl, cycloalkyl, heterocyclyl, aryl, heteroaryl, —$OR^7$, —$C(O)OR^7$, —$OC(O)R^7$, —$O(CH_2)_n C(O)OR^7$, —$C(O)R^7$, —$C(O)NHR^7$, —$NHC(O)R^7$, —$NHC(O)OR^7$, —$NHS(O)_m R^7$, —$NR^8R^9$, —$OC(O)NR^8R^9$, and —$C(O)NR^8R^9$.

3. The compound of formula (I), or the tautomer, mesomer, racemate, enantiomer, or diastereomer thereof, or mixture thereof, or the pharmaceutically acceptable salt thereof according to claim 1, wherein $R^1$ is selected from the group consisting of phenyl and pyridyl, wherein the phenyl and pyridyl are each optionally substituted with one or more groups selected from the group consisting of alkyl, halogen, haloalkyl, —$C(O)NHR^7$, —$NHC(O)R^7$, —$NHC(O)OR^7$ and —$NHS(O)_m R^7$.

4. The compound of formula (I), or the tautomer, mesomer, racemate, enantiomer, or diastereomer thereof, or mixture thereof, or the pharmaceutically acceptable salt thereof according to claim 1, wherein $R^2$ is hydrogen, $R^3$ is selected from the group consisting of hydrogen and alkyl, wherein the alkyl is optionally substituted with one or more groups selected from the group consisting of halogen, cyano, nitro, alkenyl, alkynyl, heterocyclyl, aryl, heteroaryl, —C(O)OR$^7$, —OC(O)R$^7$, —O(CH$_2$)$_n$C(O)OR$^7$, —C(O)R$^7$, —NHC(O)R$^7$, —NHC(O)OR$^7$, —NHS(O)$_m$R$^7$, —NR$^8$R$^9$, —OC(O)NR$^8$R$^9$, and —C(O)NR$^8$R$^9$.

5. The compound of formula (I), or the tautomer, mesomer, racemate, enantiomer, or diastereomer thereof, or mixture thereof, or the pharmaceutically acceptable salt thereof according to claim 1, wherein $R^4$ is aryl, wherein the aryl is optionally substituted with one or more halogens.

6. The compound of formula (I), or the tautomer, mesomer, racemate, enantiomer, or diastereomer thereof, or mixture thereof, or the pharmaceutically acceptable salt thereof according to claim 1, wherein $R^5$ is alkyl, wherein the alkyl is optionally substituted with one or more groups selected from the group consisting of halogen, hydroxy, alkoxy, cyano, and haloalkyl.

7. The compound of formula (I), or the tautomer, mesomer, racemate, enantiomer, or diastereomer thereof, or mixture thereof, or the pharmaceutically acceptable salt thereof according to claim 1, wherein $R^6$ is selected from the group consisting of hydrogen and halogen.

8. The compound of formula (I), or the tautomer, mesomer, racemate, enantiomer, or diastereomer thereof, or mixture thereof, or the pharmaceutically acceptable salt thereof according to claim 1, being a compound of formula (II) or a tautomer, mesomer, racemate, enantiomer, or diastereomer thereof, or mixture thereof, or a pharmaceutically acceptable salt thereof:

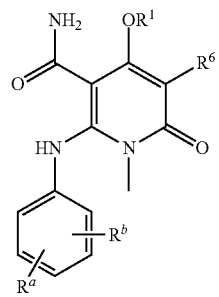

(II)

wherein $R^a$ and $R^b$ are each selected from the group consisting of hydrogen, halogen, alkyl, and haloalkyl;

$R^1$ is selected from the group consisting of phenyl and pyridinyl, wherein the phenyl and pyridyl are each optionally substituted with one or more groups selected from the group consisting of alkyl, halogen, haloalkyl, —OR$^7$, —C(O)NHR$^7$, —NHC(O)R$^7$, —NHC(O)OR$^7$, and —NHS(O)$_m$R$^7$;

$R^6$ is selected from the group consisting of hydrogen, halogen, and alkyl, wherein the alkyl is optionally substituted with one or more groups selected from the group consisting of halogen, hydroxy, cyano, nitro, alkoxy, cycloalkyl, heterocyclyl, aryl, and heteroaryl; and $R^7$ is selected from the group consisting of hydrogen, alkyl, cycloalkyl, heterocyclyl, aryl, and heteroaryl, wherein the alkyl, cycloalkyl, heterocyclyl, aryl and heteroaryl are each optionally substituted with one or more groups selected from the group consisting of alkyl, halogen, hydroxy, alkoxy, cycloalkyl, heterocyclyl, aryl, heteroaryl, carboxyl, and alkoxycarbonyl.

9. The compound of formula (I), or the tautomer, mesomer, racemate, enantiomer, or diastereomer thereof, or mixture thereof, or the pharmaceutically acceptable salt thereof according to claim 1, wherein $R^7$ is selected from the group consisting of hydrogen, alkyl, cycloalkyl, and heterocyclyl, wherein the alkyl is optionally substituted with one or more groups selected from the group consisting of halogen, hydroxy, and alkoxy.

10. A compound, or a tautomer, mesomer, racemate, enantiomer, or diastereomer thereof, or mixture thereof, or a pharmaceutically acceptable salt thereof, wherein the compound is selected from the group consisting of:

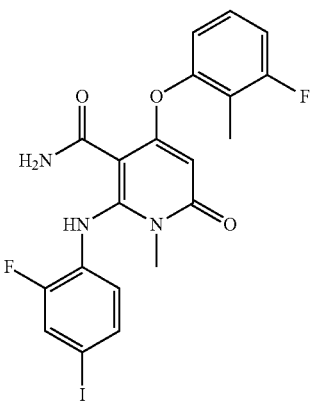

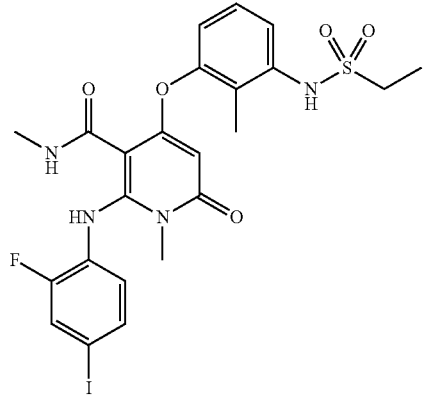

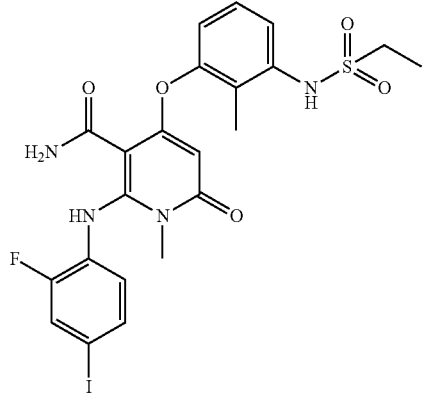

| 153 | 154 |
|---|---|
| -continued | -continued |
| 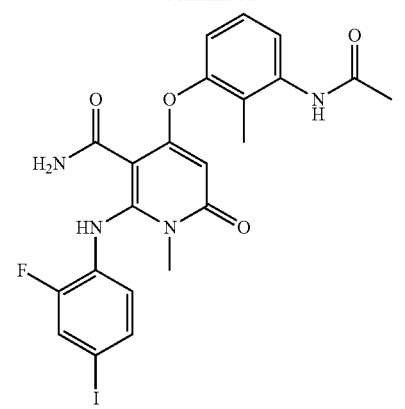 | 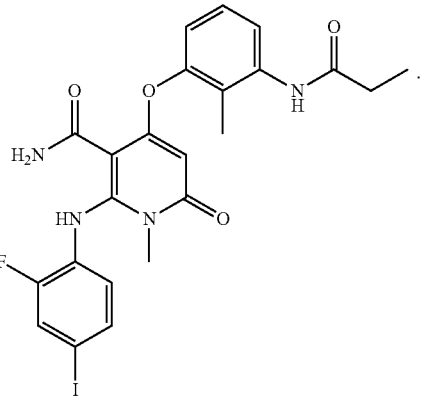 |
| 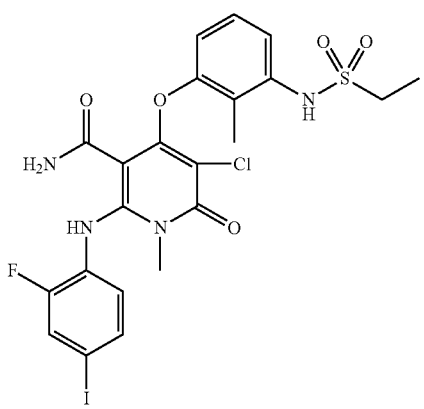 | 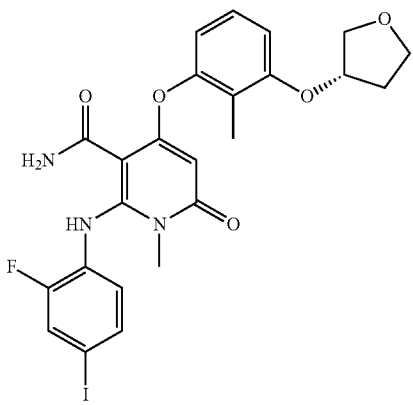 |
| 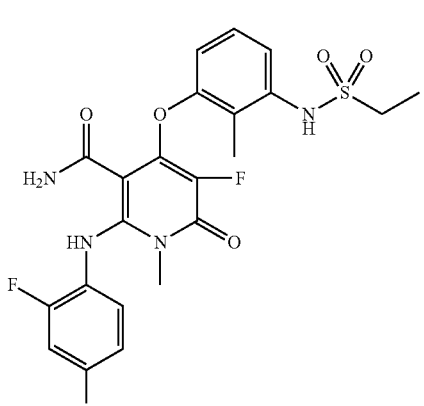 | 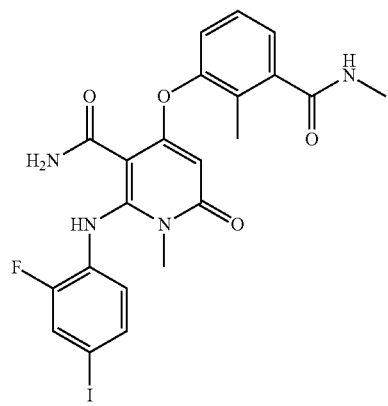 |
| 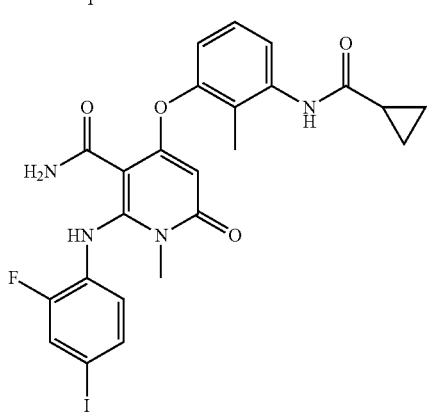 | 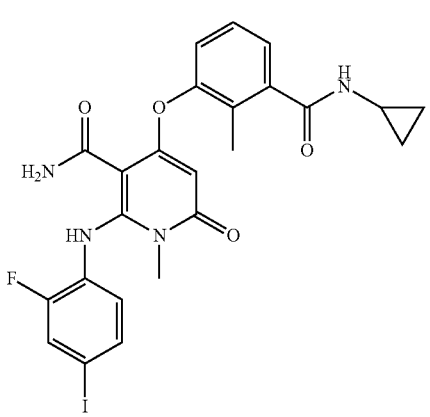 |

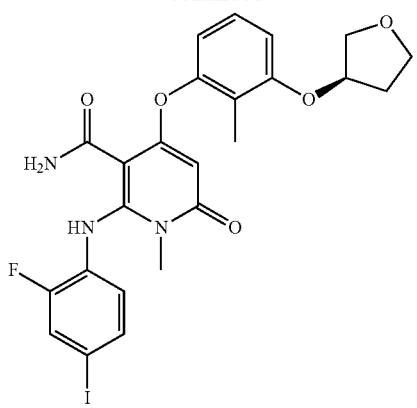
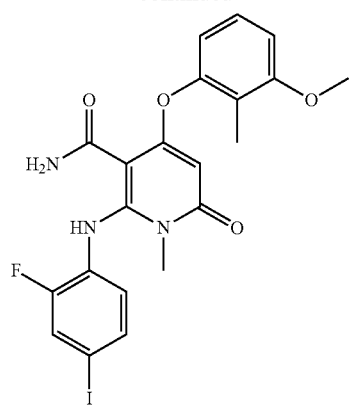
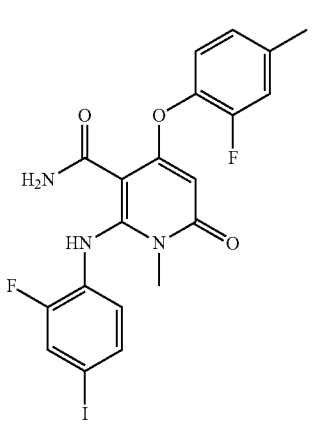
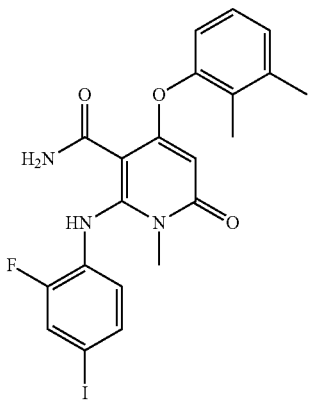
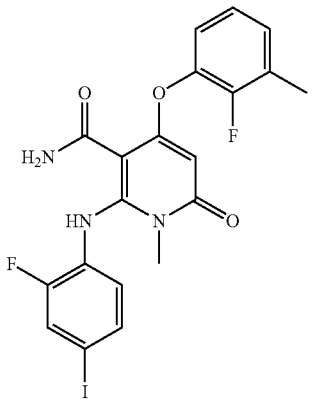

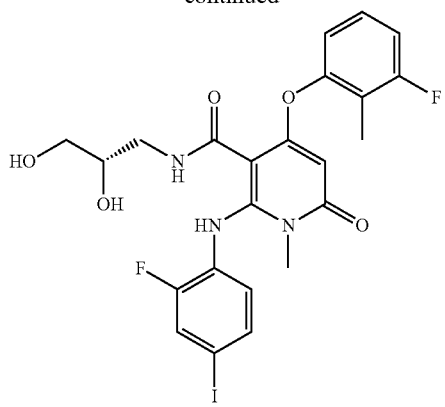

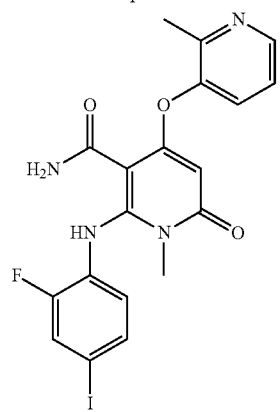

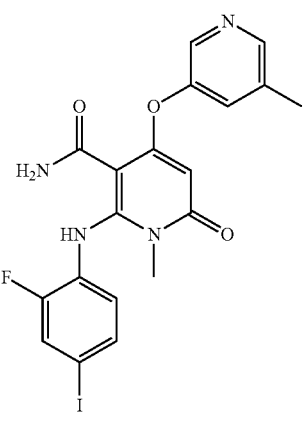

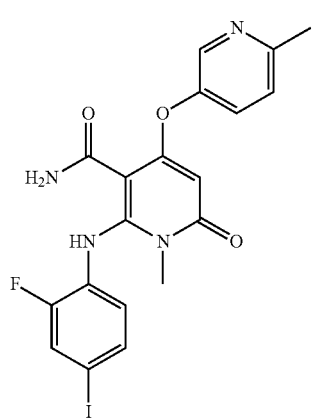

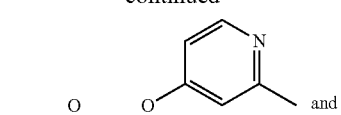

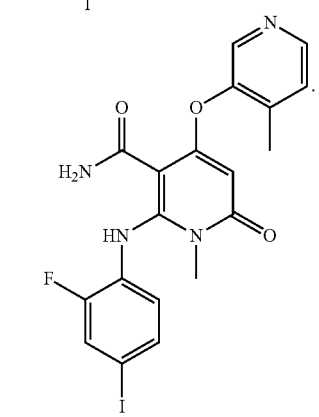

11. A process of preparing the compound of formula (I) according to claim 1, or the tautomer, mesomer, racemate, enantiomer, or diastereomer thereof, or mixture thereof, or the pharmaceutically acceptable salt thereof, comprising a step of:

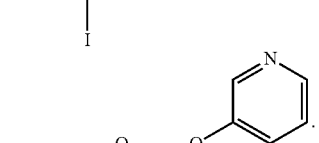

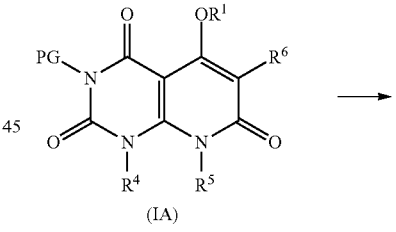

opening a ring of a compound of formula (IA) under an alkaline condition, and optionally removing the amino-protecting group PG to obtain the compound of formula (I);

Wherein:

PG is selected from the group consisting of alkyl and an amino-protecting group, wherein the alkyl and amino-protecting group are each optionally substituted with one or more groups selected from the group consisting of halogen, cyano, nitro, alkyl, cycloalkyl, heterocyclyl, aryl, heteroaryl, and —OR$^7$; and $R^7$ is selected from the group consisting of hydrogen, alkyl, cycloalkyl, heterocyclyl, aryl, and heteroaryl, wherein the alkyl, cycloalkyl, heterocyclyl, aryl, and heteroaryl are each optionally substituted with one or more groups selected from the group consisting of alkyl, halogen, hydroxy, alkoxy, cycloalkyl, heterocyclyl, aryl, heteroaryl, carboxyl, and alkoxycarbonyl.

12. A pharmaceutical composition comprising a therapeutically effective amount of the compound of formula (I), or the tautomer, mesomer, racemate, enantiomer, or diastereomer thereof, or mixture thereof, or the pharmaceutically acceptable salt thereof according to claim 1, and a pharmaceutically acceptable carrier, diluent, or excipient.

13. A method for inhibiting the activity of a mitogen-activated protein kinase kinase (MEK), comprising a step of administering to a subject in need thereof the pharmaceutical composition according to claim 12.

14. A method for treating cancer, comprising a step of administering to a subject in need thereof the pharmaceutical composition according to claim 12, wherein the cancer is selected from the group consisting of melanoma, glioblastoma, esophageal cancer, stomach cancer, liver cancer, pancreatic cancer, colorectal cancer, lung cancer, kidney cancer, breast cancer, ovarian cancer, prostate cancer, skin cancer, neuroblastoma, sarcoma, osteoma, osteosarcoma, seminoma, uterine cancer, head and neck cancer, multiple myeloma, malignant lymphoma, polycythemia vera, leukemia, thyroid cancer, ureter cancer, bladder cancer, gallbladder cancer, cholangiocarcinoma, and choriocarcinoma.

15. The method of claim 14, further comprising administering to the subject in need thereof one or more additional anticancer agents.

16. The method according to claim 14, wherein the cancer is colorectal cancer or lung cancer.

17. The process according to claim 11, wherein the amino-protecting group is benzyl.

18. A pharmaceutical composition comprising a therapeutically effective amount of the compound, or the tautomer, mesomer, racemate, enantiomer, or diastereomer thereof, or mixture thereof, or the pharmaceutically acceptable salt thereof according to claim 10, and a pharmaceutically acceptable carrier, diluent, or excipient.

19. A method for inhibiting the activity of a mitogen-activated protein kinase kinase (MEK), comprising a step of administering to a subject in need thereof the pharmaceutical composition according to claim 18.

20. A method for treating cancer, comprising a step of administering to a subject in need thereof the pharmaceutical composition according to claim 18, wherein the cancer is selected from the group consisting of melanoma, glioblastoma, esophageal cancer, stomach cancer, liver cancer, pancreatic cancer, colorectal cancer, lung cancer, kidney cancer, breast cancer, ovarian cancer, prostate cancer, skin cancer, neuroblastoma, sarcoma, osteoma, osteosarcoma, seminoma, uterine cancer, head and neck cancer, multiple myeloma, malignant lymphoma, polycythemia vera, leukemia, thyroid cancer, ureter cancer, bladder cancer, gallbladder cancer, cholangiocarcinoma, and choriocarcinoma.

21. The method of claim 20, further comprising administering to the subject in need thereof one or more additional anticancer agents.

22. The method according to claim 20, wherein the cancer is colorectal cancer or lung cancer.

* * * * *